United States Patent
Chen et al.

(10) Patent No.: US 11,999,713 B2
(45) Date of Patent: Jun. 4, 2024

(54) METHIONINE ADENOSYLTRANSFERASE 2a (MAT2A) INHIBITORS AND USES THEREOF

(71) Applicant: Insilico Medicine IP Limited, Hong Kong (HK)

(72) Inventors: Chiachun Chen, Shanghai (CN); Xiao Ding, Shanghai (CN); Xiaosong Liu, Shanghai (CN); Feng Ren, Shanghai (CN); Hailong Wang, Shanghai (CN)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

(21) Appl. No.: 18/509,658

(22) Filed: Nov. 15, 2023

(65) Prior Publication Data

US 2024/0132465 A1    Apr. 25, 2024

Related U.S. Application Data

(63) Continuation of application No. PCT/CN2022/126096, filed on Oct. 19, 2022.

(30) Foreign Application Priority Data

Oct. 20, 2021  (WO) ............... PCT/CN2021/125035
Sep. 1, 2022   (WO) ............... PCT/CN2022/116510

(51) Int. Cl.
  *C07D 401/04*   (2006.01)
  *C07D 239/95*   (2006.01)
  *C07D 403/04*   (2006.01)
  *C07D 471/04*   (2006.01)
  *C07D 487/04*   (2006.01)

(52) U.S. Cl.
  CPC ......... *C07D 401/04* (2013.01); *C07D 239/95* (2013.01); *C07D 403/04* (2013.01); *C07D 471/04* (2013.01); *C07D 487/04* (2013.01)

(58) Field of Classification Search
  CPC .. C07D 401/04; C07D 239/95; C07D 403/04; C07D 471/04; C07D 487/04
  See application file for complete search history.

(56) References Cited

FOREIGN PATENT DOCUMENTS

| CN | 111995587 A | 11/2020 |
|---|---|---|
| CN | 114650986 A | 6/2022 |
| CN | 114874207 A | 8/2022 |
| CN | 116239541 B | 7/2023 |
| CN | 116283800 B | 7/2023 |
| CN | 116478172 B | 9/2023 |
| WO | WO-0164679 A1 | 9/2001 |
| WO | WO-02102793 A2 | 12/2002 |
| WO | WO-2006098969 A2 | 9/2006 |
| WO | WO-2006124490 A2 | 11/2006 |
| WO | WO-2008011032 A1 | 1/2008 |
| WO | WO-2008060476 A2 | 5/2008 |
| WO | WO-2010149786 A1 | 12/2010 |
| WO | WO-2014079232 A1 | 5/2014 |
| WO | WO-2018215798 A1 | 11/2018 |
| WO | WO-2019191470 A1 | 10/2019 |
| WO | WO-2020123395 A1 | 6/2020 |
| WO | WO-2020139991 A1 | 7/2020 |
| WO | WO-2020139992 A1 | 7/2020 |
| WO | WO-2020243376 A1 | 12/2020 |
| WO | WO-2021081212 A1 | 4/2021 |
| WO | WO-2021139775 A1 | 7/2021 |
| WO | WO-2021252678 A1 | 12/2021 |
| WO | WO-2021252679 A1 | 12/2021 |
| WO | WO-2021252680 A1 | 12/2021 |
| WO | WO-2021252681 A1 | 12/2021 |
| WO | WO-2021254529 A1 | 12/2021 |
| WO | WO-2021259815 A1 | 12/2021 |
| WO | WO-2022052924 A1 | 3/2022 |
| WO | WO-2022053022 A1 | 3/2022 |
| WO | WO-2022063128 A1 | 3/2022 |
| WO | WO-2022078403 A1 | 4/2022 |
| WO | WO-2022127847 A1 | 6/2022 |
| WO | WO-2022206730 A1 | 10/2022 |
| WO | WO-2023066283 A1 | 4/2023 |

OTHER PUBLICATIONS

De Fusco; J. Med. Chem. 2021, 64, 10, 6814-6826. https://doi.org/10.1021/acs.jmedchem.1c00067 (Year: 2021).*
Konteatis; J. Med. Chem. 2021, 64, 4430-4449. https://doi.org/10.1021/acs.jmedchem.0c01895 (Year: 2021).*
PCT/CN2022/126096 International Search Report and Written Opinion dated Dec. 15, 2022.

* cited by examiner

*Primary Examiner* — Daniel R Carcanague
(74) *Attorney, Agent, or Firm* — WILSON SONSINI GOODRICH & ROSATI

(57) ABSTRACT

Described herein are MAT2A inhibitors and pharmaceutical compositions comprising said inhibitors. The subject compounds and compositions are useful for the treatment of a disease or disorder associated with MAT2A.

20 Claims, No Drawings

METHIONINE ADENOSYLTRANSFERASE 2a (MAT2A) INHIBITORS AND USES THEREOF

CROSS-REFERENCE

This application is a continuation of International Application No. PCT/CN2022/126096, filed Oct. 19, 2022, which claims the benefit of International Application No. PCT/CN2021/125035, filed Oct. 20, 2021 and International Application No. PCT/CN2022/116510, filed Sep. 1, 2022; which are incorporated herein by reference in their entirety.

BACKGROUND

Methionine adenosyltransferase 2a (MAT2A) plays an important role in metabolism and epigenetics. Despite its broad cellular role, inhibition of MAT2A has been shown to result in a selective anti-proliferative effect in cancers with deletion of a separate metabolic gene, methylthioadenosine phosphorylase ("MTAP"). MTAP deficiency occurs frequently in both solid tumors and hematologic malignancies. As such, compounds that inhibit MAT2A are potential agents for treating MTAP-deleted cancers.

SUMMARY

Disclosed herein is a compound of Formula (I) or Formula (II), or a pharmaceutically acceptable salt or solvate thereof:

Formula (I)

Formula (II)

wherein:

is selected from $C_{3-6}$cycloalkyl, $C_{2-9}$heterocycloalkyl, $C_{6-10}$aryl, and $C_{1-10}$heteroaryl;

$Z^1$ is $CR^7$ or N;
$Z^2$ is $CR^9$ or N;
$Z^3$ is $CR^6$ or N;
$Z^4$ is $CR^{6}a$ or N;
X is selected from —N($R^4$)—, —O—, and —C($R^5$)($R^{5a}$)—;
Y is selected from —N($R^{4a}$)—, —O—, and —C($R^5$)($R^{5a}$)—;
$R^1$ is selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —N($R^{10}$)($R^{11}$), —C(O)$OR^{10}$, —OC(O)N($R^{10}$)($R^{11}$), —N($R^{12}$)C(O)N($R^{10}$)($R^{11}$), —N($R^{12}$)C(O)$OR^{13}$, —N($R^{12}$)S(O)$_2R^{13}$, —C(O)$R^{13}$, —S(O)$R^{13}$, —OC(O)$R^{13}$, —C(O)N($R^{10}$)($R^{11}$), —C(O)C(O)N($R^{10}$)($R^{11}$), —N($R^{12}$)C(O)$R^{13}$, —S(O)$_2R^{13}$, —S(O)$_2$N($R^{10}$)($R^{11}$)—, —N=S(=O)($R^{13}$)$_2$, —S(=O)(=NH)N($R^{10}$)($R^{11}$), —S(=O)(=NH)C($R^{10}$)($R^{11}$), —S(=O)(=N$R^{13}$)$R^{13}$, —CH$_2$C(O)N($R^{10}$)($R^{11}$), —CH$_2$N($R^{12}$)C(O)$R^{13}$, —CH$_2$S(O)$_2R^{13}$, —CH$_2$S(O)$_2$N($R^{10}$)($R^{11}$), —Si($C_{1-6}$alkyl)$_3$, and —P(O)($R^{10}$)$_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15a}$;
$R^{1a}$ and $R^{1b}$ are independently selected from hydrogen, halogen, $C_{1-6}$alkyl, $C_{1-6}$haloalkyl, $C_{2-6}$ alkenyl, $C_{2-6}$alkynyl, $C_{3-6}$cycloalkyl, $C_{2-9}$heterocycloalkyl, $C_{6-10}$aryl, and $C_{1-9}$heteroaryl; wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15a}$;
each $R^2$ and each $R^3$ are each independently selected from hydrogen, halogen, oxo, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —N($R^{10}$)($R^{11}$), —C(O)$OR^{10}$, —OC(O)N($R^{10}$)($R^{11}$), —N($R^{12}$)C(O)N($R^{10}$)($R^{11}$), —N($R^{12}$)C(O)$OR^{13}$, —N($R^{12}$)S(O)$_2R^{13}$, —C(O)$R^{13}$, —S(O)$R^{13}$, —OC(O)$R^{13}$, —C(O)N($R^{10}$)($R^{11}$), —C(O)C(O)N($R^{10}$)($R^{11}$), —N($R^{12}$)C(O)$R^{13}$, —S(O)$_2R^{13}$, —S(O)$_2$N($R^{10}$)($R^{11}$)—, —N=S(=O)($R^{13}$)$_2$, —S(=O)(=NH)N($R^{10}$)($R^{11}$), —S(=O)(=NH)C($R^{10}$)($R^{11}$), —S(=O)(=N$R^{13}$)$R^{13}$, —CH$_2$C(O)N($R^{10}$)($R^{11}$), —CH$_2$N($R^{12}$)C(O)$R^{13}$, —CH$_2$S(O)$_2R^{13}$, —CH$_2$S(O)$_2$N($R^{10}$)($R^{11}$), —Si($C_{1-6}$alkyl)$_3$, and —P(O)($R^{10}$)$_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$; or $R^2$ and $R^3$, together with the carbon to which they are attached, form a $C_{3-6}$cycloalkyl or $C_{2-9}$heterocycloalkyl;
$R^4$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; or $R^4$ and an $R^3$ are combined to form a $C_{2-9}$heterocycloalkyl optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{4a}$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; or $R^{4a}$ and an $R^3$ are combined to form a $C_{2-9}$heterocycloalkyl optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^5$ and $R^{5a}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N{=}S({=}O)(R^{13})_2$, —$S({=}O)({=}NH)N(R^{10})(R^{11})$, —$S({=}O)({=}NH)C(R^{10})(R^{11})$, —$S({=}O)({=}NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; or $R^5$ and an $R^3$ are combined to form a $C_{3-6}$cycloalkyl, $C_{2-9}$heterocycloalkyl, $C_{6-10}$aryl, or $C_{2-9}$heteroaryl, wherein $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^6$, $R^7$, $R^8$, and $R^9$ are independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N{=}S({=}O)(R^{13})_2$, —$S({=}O)({=}NH)N(R^{10})(R^{11})$, —$S({=}O)({=}NH)C(R^{10})(R^{11})$, —$S({=}O)({=}NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15c}$;

$R^{6a}$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N{=}S({=}O)(R^{13})_2$, —$S({=}O)({=}NH)N(R^{10})(R^{11})$, —$S({=}O)({=}NH)C(R^{10})(R^{11})$, —$S({=}O)({=}NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, and $C_{1-9}$heteroaryl are optionally substituted with one, two, or three groups selected from $R^{15c}$;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl; or $R^{10}$ and $R^{11}$, together with the nitrogen to which they are attached, form a $C_{2-9}$heterocycloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{14}$ is independently selected from halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N{=}S({=}O)(R^{13})_2$, —$S({=}O)({=}NH)N(R^{10})(R^{11})$, —$S({=}O)({=}NH)C(R^{10})(R^{11})$, —$S({=}O)({=}NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15d}$;

each $R^{15a}$, $R^{15b}$, $R^{15c}$, and $R^{15d}$ are each independently selected from halogen, oxo, —CN, $C_{1-6}$alkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N{=}S({=}O)(R^{13})_2$, —$S({=}O)({=}NH)N(R^{10})(R^{11})$, —$S({=}O)({=}NH)C(R^{10})(R^{11})$, —$S({=}O)({=}NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$ and —$P(O)(R^{10})_2$;

m is 0, 1, 2, 3, 4, or 5; and
n is 0, 1, 2, 3, 4, 5, or 6.

In some embodiments is a compound, or a pharmaceutically acceptable salt or solvate thereof, having the structure of Formula (I):

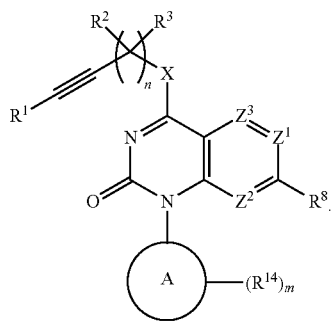

Formula (I)

In some embodiments is a compound of Formula (I), or a pharmaceutically acceptable salt or solvate thereof, wherein $Z^3$ is $CR^6$. In some embodiments is a compound of Formula (I), or a pharmaceutically acceptable salt or solvate thereof, wherein $R^6$ is selected from hydrogen, halogen, —CN, $C_{1-6}$alkyl, $C_{1-6}$haloalkyl, —$OR^{10}$, and —$N(R^{10})(R^{11})$. In some embodiments is a compound of Formula (I), or a pharmaceutically acceptable salt or solvate thereof, wherein $R^6$ is selected from hydrogen and —$OR^{10}$ and $R^{10}$ is $C_{1-6}$alkyl. In some embodiments is a compound of Formula (I), or a pharmaceutically acceptable salt or solvate thereof, wherein $R^6$ is hydrogen. In some embodiments is a compound of Formula (I), or a pharmaceutically acceptable salt or solvate thereof, wherein $Z^3$ is N. In some embodiments is a compound of Formula (I), or a pharmaceutically acceptable salt or solvate thereof, wherein X is —$N(R^4)$—. In some embodiments is a compound of Formula (I), or a pharmaceutically acceptable salt or solvate thereof, wherein $R^4$ is hydrogen or $C_{1-6}$alkyl. In some embodiments is a compound of Formula (I), or a pharmaceutically acceptable salt or solvate thereof, wherein $R^4$ is hydrogen. In some embodiments is a compound of Formula (I), or a pharmaceutically acceptable salt or solvate thereof, wherein X is —$N(R^4)$— and $R^4$ and an $R^3$ are combined to form a $C_{2-9}$heterocycloalkyl optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

In some embodiments is a compound, or a pharmaceutically acceptable salt or solvate thereof, having the structure of Formula (II):

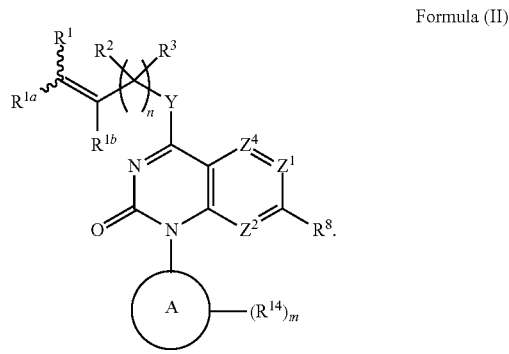

Formula (II)

In some embodiments is a compound of Formula (II), or a pharmaceutically acceptable salt or solvate thereof, wherein $Z^4$ is $CR^{6a}$. In some embodiments is a compound of Formula (II), or a pharmaceutically acceptable salt or solvate thereof, wherein $R^{6a}$ is selected from hydrogen, halogen, —CN, $C_{1-6}$alkyl, $C_{1-6}$haloalkyl, —$OR^{10}$, and —$N(R^{10})(R^{11})$. In some embodiments is a compound of Formula (II), or a pharmaceutically acceptable salt or solvate thereof, wherein $R^{6a}$ is selected from hydrogen and —$OR^{10}$ and $R^{10}$ is $C_{1-6}$alkyl. In some embodiments is a compound of Formula (II), or a pharmaceutically acceptable salt or solvate thereof, wherein $R^{6a}$ is hydrogen. In some embodiments is a compound of Formula (II), or a pharmaceutically acceptable salt or solvate thereof, wherein $Z^4$ is N. In some embodiments is a compound of Formula (II), or a pharmaceutically acceptable salt or solvate thereof, wherein $R^{1a}$ and $R^{1b}$ are independently selected from hydrogen and $C_{1-6}$alkyl optionally substituted with one, two, or three groups selected from $R^{1a}$. In some embodiments is a compound of Formula (II), or a pharmaceutically acceptable salt or solvate thereof, wherein $R^{1a}$ and $R^{1b}$ are independently selected from hydrogen and unsubstituted $C_{1-6}$alkyl. In some embodiments is a compound of Formula (II), or a pharmaceutically acceptable salt or solvate thereof, wherein $R^{1a}$ and $R^{1b}$ are hydrogen. In some embodiments is a compound of Formula (II), or a pharmaceutically acceptable salt or solvate thereof, wherein Y is —$N(R^{4a})$—. In some embodiments is a compound of Formula (II), or a pharmaceutically acceptable salt or solvate thereof, wherein $R^{4a}$ is hydrogen or $C_{1-6}$alkyl. In some embodiments is a compound of Formula (II), or a pharmaceutically acceptable salt or solvate thereof, wherein $R^{4a}$ is hydrogen.

In some embodiments is a compound of Formula (I), (Ib), or (II), or a pharmaceutically acceptable salt or solvate thereof, wherein each $R^2$ is independently selected from hydrogen and $C_{1-6}$alkyl. In some embodiments is a compound of Formula (I), (Ib), or (II), or a pharmaceutically acceptable salt or solvate thereof, wherein each $R^2$ is hydrogen. In some embodiments is a compound of Formula (I), (Ib), or (II), or a pharmaceutically acceptable salt or solvate thereof, wherein each $R^3$ is independently selected from hydrogen and $C_{1-6}$alkyl. In some embodiments is a compound of Formula (I), (Ib), or (II), or a pharmaceutically acceptable salt or solvate thereof, wherein each $R^3$ is hydrogen. In some embodiments is a compound of Formula (I), (Ib), or (II), or a pharmaceutically acceptable salt or solvate thereof, wherein $R^2$ and $R^3$, together with the carbon to which they are attached, form a $C_{3-6}$cycloalkyl. In some embodiments is a compound of Formula (I) or (II), or a pharmaceutically acceptable salt or solvate thereof, wherein n is 1, 2, or 3. In some embodiments is a compound of Formula (I) or (II), or a pharmaceutically acceptable salt or solvate thereof, wherein n is 1. In some embodiments is a compound of Formula (I) or (II), or a pharmaceutically acceptable salt or solvate thereof, wherein $Z^1$ is $CR^7$. In some embodiments is a compound of Formula (I) or (II), or a pharmaceutically acceptable salt or solvate thereof, wherein $R^7$ is hydrogen, halogen, —CN, $C_{1-6}$alkyl, $C_{1-6}$haloalkyl, —OR$^{10}$, or —N(R$^{10}$)(R$^{11}$). In some embodiments is a compound of Formula (I) or (II), or a pharmaceutically acceptable salt or solvate thereof, wherein $R^7$ is hydrogen, halogen, $C_{1-6}$alkyl, or $C_{1-6}$haloalkyl. In some embodiments is a compound of Formula (I) or (II), or a pharmaceutically acceptable salt or solvate thereof, wherein $R^7$ is hydrogen. In some embodiments is a compound of Formula (I) or (II), or a pharmaceutically acceptable salt or solvate thereof, wherein $Z^1$ is N. In some embodiments is a compound of Formula (I) or (II), or a pharmaceutically acceptable salt or solvate thereof, wherein $Z^2$ is $CR^9$. In some embodiments is a compound of Formula (I) or (II), or a pharmaceutically acceptable salt or solvate thereof, wherein $R^9$ is hydrogen, halogen, —CN, $C_{1-6}$alkyl, $C_{1-6}$haloalkyl, —OR$^{10}$, or —N(R$^{10}$)(R$^{11}$). In some embodiments is a compound of Formula (I) or (II), or a pharmaceutically acceptable salt or solvate thereof, wherein $R^9$ is hydrogen, halogen, $C_{1-6}$alkyl, or $C_{1-6}$haloalkyl. In some embodiments is a compound of Formula (I) or (II), or a pharmaceutically acceptable salt or solvate thereof, wherein $R^9$ is hydrogen. In some embodiments is a compound of Formula (I) or (II), or a pharmaceutically acceptable salt or solvate thereof, wherein $Z^2$ is N.

In some embodiments is a compound, or a pharmaceutically acceptable salt or solvate thereof, having the structure of Formula (Ia):

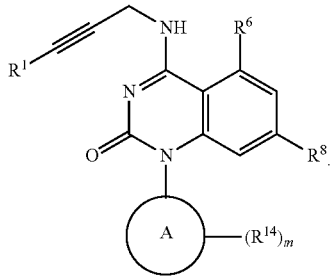

Formula (Ia)

In some embodiments is a compound, or a pharmaceutically acceptable salt or solvate thereof, having the structure of Formula (Ib):

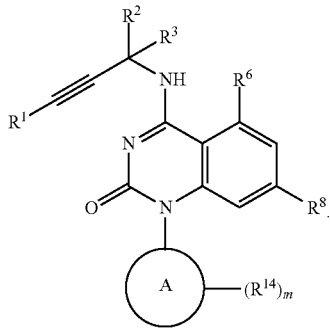

Formula (Ib)

In some embodiments is a compound, or a pharmaceutically acceptable salt or solvate thereof, having the structure of Formula (IIa):

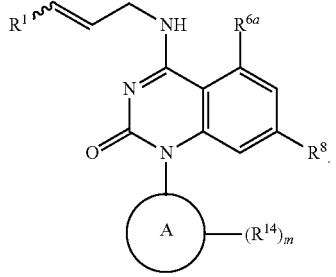

Formula (IIa)

In some embodiments is a compound of Formula (I), (Ia), (II), or (IIa), or a pharmaceutically acceptable salt or solvate thereof, wherein

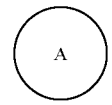

is $C_{1-10}$heteroaryl. In some embodiments is a compound of Formula (I), (Ia), (II), or (IIa), or a pharmaceutically acceptable salt or solvate thereof, wherein

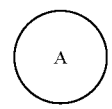

is $C_{1-10}$heteroaryl selected from pyridyl, pyrimidyl, pyrazinyl, and pyridazinyl. In some embodiments is a compound of Formula (I), (Ia), (II), or (IIa), or a pharmaceutically acceptable salt or solvate thereof, wherein

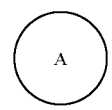

is pyridyl. In some embodiments is a compound of Formula (I), (Ia), (II), or (IIa), or a pharmaceutically acceptable salt or solvate thereof, wherein

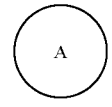

is phenyl. In some embodiments is a compound of Formula (I), (Ia), (II), or (IIa), or a pharmaceutically acceptable salt or solvate thereof, wherein each $R^{14}$ is independently selected from halogen, $C_{1-6}$alkyl, $C_{1-6}$haloalkyl, —OR$^{10}$, and —N(R$^{10}$)(R$^{11}$). In some embodiments is a compound of Formula (I), (Ia), (II), or (IIa), or a pharmaceutically acceptable salt or solvate thereof, wherein each $R^{14}$ is independently selected from halogen and $C_{1-6}$alkyl. In some embodiments is a compound of Formula (I), (Ia), (II), or (IIa), or a pharmaceutically acceptable salt or solvate thereof, wherein each $R^{14}$ is independently selected from halogen. In some embodiments is a compound of Formula (I), (Ia), (II), or (IIa), or a pharmaceutically acceptable salt or solvate thereof, wherein m is 1 In some embodiments is a compound of Formula (I), (Ia), (II), or (IIa), or a pharmaceutically acceptable salt or solvate thereof, wherein m is 0. In some embodiments is a compound of Formula (I), (Ia), (II), or (IIa), or a pharmaceutically acceptable salt or solvate thereof, wherein $R^8$ is hydrogen, halogen, —CN, $C_{1-6}$alkyl, $C_{1-6}$haloalkyl, —$OR^{10}$, or $C_{3-6}$cycloalkyl. In some embodiments is a compound of Formula (I), (Ia), (II), or (IIa), or a pharmaceutically acceptable salt or solvate thereof, wherein $R^8$ is hydrogen, halogen or $C_{1-6}$haloalkyl. In some embodiments is a compound of Formula (I), (Ia), (II), or (IIa), or a pharmaceutically acceptable salt or solvate thereof, wherein $R^8$ is halogen. In some embodiments is a compound of Formula (I), (Ia), (II), or (IIa), or a pharmaceutically acceptable salt or solvate thereof, wherein $R^1$ is selected from hydrogen, $C_{1-6}$alkyl, $C_{1-6}$haloalkyl, $C_{3-6}$cycloalkyl, $C_{2-9}$heterocycloalkyl, and $C_{1-9}$heteroaryl, wherein $C_{1-6}$alkyl, $C_{3-6}$cycloalkyl, $C_{2-9}$heterocycloalkyl, and $C_{1-9}$heteroaryl are optionally substituted with one, two, or three groups selected from $R^{11}$. In some embodiments is a compound of Formula (I), (Ia), (II), or (IIa), or a pharmaceutically acceptable salt or solvate thereof, wherein $R^1$ is selected from hydrogen and unsubstituted $C_{3-6}$cycloalkyl. In some embodiments is a compound of Formula (I), (Ia), (II), or (IIa), or a pharmaceutically acceptable salt or solvate thereof, wherein $R^1$ is unsubstituted $C_{3-6}$cycloalkyl. In some embodiments is a compound of Formula (I), (Ia), (II), or (IIa), or a pharmaceutically acceptable salt or solvate thereof, wherein $R^1$ is unsubstituted cyclopropyl. In some embodiments is a compound of Formula (I), (Ia), (II), or (IIa), or a pharmaceutically acceptable salt or solvate thereof, wherein $R^1$ is hydrogen.

In some embodiments is a pharmaceutical composition comprising a compound of Formula (I), (Ia), (II), or (IIa), or a pharmaceutically acceptable salt or solvate thereof, and at least one pharmaceutically acceptable excipient.

In some embodiments is a method of treating cancer in a mammal in need thereof, comprising administering to the mammal a compound of Formula (I), (Ia), (II), or (IIa), or a pharmaceutically acceptable salt or solvate thereof. In some embodiments is a method of treating cancer in a mammal in need thereof, comprising administering to the mammal a compound of Formula (I), (Ia), (II), or (IIa), or a pharmaceutically acceptable salt or solvate thereof, wherein the cancer is a MTAP-deleted cancer. In some embodiments is a method of treating cancer in a mammal in need thereof, comprising administering to the mammal a compound of Formula (I), (Ia), (II), or (IIa), or a pharmaceutically acceptable salt or solvate thereof, wherein the cancer is selected from liver cancer, colon cancer, pancreatic cancer, prostate cancer, lung cancer, breast cancer, and T cell leukemia.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO₂. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH₂), 1-propenyl (—CH₂CH=CH₂), isopropenyl [—C(CH₃)=CH₂], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH₂, or —NO₂. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH₂, or —NO₂. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH₂, or —NO₂. In some embodiments, the alkylene is optionally substituted with halogen, —CN, —OH, or —OMe. In some embodiments, the alkylene is optionally substituted with halogen.

"Alkoxy" refers to a radical of the formula —ORa where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH₂, or —NO₂. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF₃, —OH, —OMe, —NH₂, or —NO₂. In some embodiments, the aryl is optionally substituted with halogen, methyl, ethyl, —CN, —CF₃, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms ($C_3$-$C_{15}$ fully saturated cycloalkyl or $C_3$-$C_{15}$ cycloalkenyl), from three to ten carbon atoms ($C_3$-$C_{10}$ fully saturated cycloalkyl or $C_3$-$C_{10}$ cycloalkenyl), from three to eight carbon atoms ($C_3$-$C_8$ fully saturated cycloalkyl or $C_3$-$C_5$ cycloalkenyl), from three to six carbon atoms ($C_3$-$C_6$ fully saturated cycloalkyl or $C_3$-$C_6$ cycloalkenyl), from three to five carbon atoms ($C_3$-$C_5$ fully saturated cycloalkyl or $C_3$-$C_5$ cycloalkenyl), or three to four carbon atoms ($C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ fully saturated heterocycloalkyl or C$_2$-C$_{15}$ heterocycloalkenyl), from two to ten carbon atoms (C$_2$-C$_{10}$ fully saturated heterocycloalkyl or C$_2$-C$_{10}$ heterocycloalkenyl), from two to eight carbon atoms (C$_2$-C$_8$ fully saturated heterocycloalkyl or C$_2$-C$_8$ heterocycloalkenyl), from two to seven carbon atoms (C$_2$-C$_7$ fully saturated heterocycloalkyl or C$_2$-C$_7$ heterocycloalkenyl), from two to six carbon atoms (C$_2$-C$_6$ fully saturated heterocycloalkyl or C$_2$-C$_6$ heterocycloalkenyl), from two to five carbon atoms (C$_2$-C$_5$ fully saturated heterocycloalkyl or C$_2$-C$_5$ heterocycloalkenyl), or two to four carbon atoms (C$_2$-C$_4$ fully saturated heterocycloalkyl or C$_2$-C$_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered fully saturated heterocycloalkyl. In some embodiments, the heterocycloalkyl is a 3- to 7-membered fully saturated heterocycloalkyl. In some embodiments, the heterocycloalkyl is a 3- to 6-membered fully saturated heterocycloalkyl. In some embodiments, the heterocycloalkyl is a 4- to 6-membered fully saturated heterocycloalkyl. In some embodiments, the heterocycloalkyl is a 5- to 6-membered fully saturated heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

Compounds

Described herein are compounds of Formula (I), (Ia), (II), and (IIa), or a pharmaceutically acceptable salt or solvate thereof, useful in the treatment of a disease or disorder associated with MAT2A inhibition. In some embodiments, the compounds of Formula (I), (Ia), (II), and (IIa), or a pharmaceutically acceptable salt or solvate thereof, are useful in the treatment of cancer. In some embodiments, the cancer is selected from liver cancer, colon cancer, pancreatic cancer, prostate cancer, lung cancer, breast cancer, and T cell leukemia.

In some embodiments disclosed herein is a compound of Formula (I), or a pharmaceutically acceptable salt or solvate thereof:

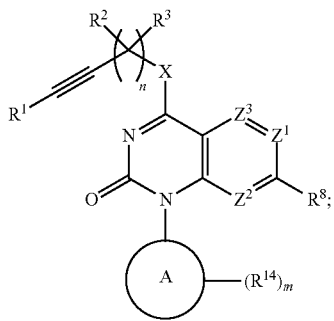

Formula (I)

wherein:

is selected from $C_{3-6}$cycloalkyl, $C_{2-9}$heterocycloalkyl, $C_{6-10}$aryl, and $C_{1-10}$heteroaryl;

$Z^1$ is $CR^7$ or N;

$Z^2$ is $CR^9$ or N;

$Z^3$ is $CR^6$ or N;

X is selected from $-N(R^4)-$, $-O-$, and $-C(R^5)(R^{5a})-$;

$R^1$ is selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $-N=S(=O)(R^{13})_2$, $-S(=O)(=NH)N(R^{10})(R^{11})$, $-S(=O)(=NH)C(R^{10})(R^{11})$, $-S(=O)(=NR^{13})R^{13}$, $-CH_2C(O)N(R^{10})(R^{11})$, $-CH_2N(R^{12})C(O)R^{13}$, $-CH_2S(O)_2R^{13}$, $-CH_2S(O)_2N(R^{10})(R^{11})$, $-Si(C_{1-6}alkyl)_3$, and $-P(O)(R^{10})_2$, wherein $C_{1-6}$alkyl, $C_{2-6}$ alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15a}$;

each $R^2$ and each $R^3$ are each independently selected from hydrogen, halogen, oxo, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $-N=S(=O)(R^{13})_2$, $-S(=O)(=NH)N(R^{10})(R^{11})$, $-S(=O)(=NH)C(R^{10})(R^{11})$, $-S(=O)(=NR^{13})R^{13}$, $-CH_2C(O)N(R^{10})(R^{11})$, $-CH_2N(R^{12})C(O)R^{13}$, $-CH_2S(O)_2R^{13}$, $-CH_2S(O)_2N(R^{10})(R^{11})$, $-Si(C_{1-6}alkyl)_3$, and $-P(O)(R^{10})_2$, wherein $C_{1-6}$alkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl are optionally substituted with one, two, or three groups selected from $R^{15b}$; or $R^2$ and $R^3$, together with the carbon to which they are attached, form a $C_{3-6}$cycloalkyl or $C_{2-9}$heterocycloalkyl;

$R^4$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; or $R^4$ and an $R^3$ are combined to form a $C_{2-9}$heterocycloalkyl optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^5$ and $R^{6a}$ are independently selected from hydrogen, halogen, $C_{1-6}$alkyl, $C_{1-6}$haloalkyl, $C_{2-6}$ alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $-N=S(=O)(R^{13})_2$, $-S(=O)(=NH)N(R^{10})(R^{11})$, $-S(=O)(=NH)C(R^{10})(R^{11})$, $-S(=O)(=NR^{13})R^{13}$, $-CH_2C(O)N(R^{10})(R^{11})$, $-CH_2N(R^{12})C(O)R^{13}$, $-CH_2S(O)_2R^{13}$, $-CH_2S(O)_2N(R^{10})(R^{11})$, $-Si(C_{1-6}alkyl)_3$, and $-P(O)(R^{10})_2$, wherein $C_{1-6}$alkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; or $R^5$ and an $R^3$ are combined to form a $C_{3-6}$cycloalkyl, $C_{2-9}$heterocycloalkyl, $C_{6-10}$aryl, or $C_{2-9}$heteroaryl, wherein $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^6$, $R^7$, $R^8$, and $R^9$ are independently selected from hydrogen, halogen, $-CN$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $-N=S(=O)(R^{13})_2$, $-S(=O)(=NH)N(R^{10})(R^{11})$, $-S(=O)(=NH)C(R^{10})(R^{11})$, $-S(=O)(=NR^{13})R^{13}$, $-CH_2C(O)N(R^{10})(R^{11})$, $-CH_2N(R^{12})C(O)R^{13}$, $-CH_2S(O)_2R^{13}$, $-CH_2S(O)_2N(R^{10})(R^{11})$, $-Si(C_{1-6}alkyl)_3$, and $-P(O)(R^{10})_2$, wherein $C_{1-6}$alkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl are optionally substituted with one, two, or three groups selected from $R^{15c}$;

each $R^{10}$ is independently selected from hydrogen, $C_{1-6}$alkyl, $C_{1-6}$haloalkyl, $C_{2-6}$alkenyl, $C_{2-6}$ alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl; or $R^{10}$ and $R^{11}$, together with the nitrogen to which they are attached, form a $C_{2-9}$heterocycloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{14}$ is independently selected from halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$ alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15d}$;

each $R^{15a}$, $R^{15b}$, $R^{15c}$, and $R^{15d}$ are each independently selected from halogen, oxo, —CN, $C_{1-6}$alkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$ heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$ and —$P(O)(R^{10})_2$;

m is 0, 1, 2, 3, 4, or 5; and n is 0, 1, 2, 3, 4, 5, or 6.

In some embodiments of a compound of Formula (I), or a pharmaceutically acceptable salt or solvate thereof, X is —$N(R^4)$—. In some embodiments of Formula (II), or a pharmaceutically acceptable salt or solvate thereof, X is —$N(R^4)$— and $R^4$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (I), or a pharmaceutically acceptable salt or solvate thereof, X is —$N(R^4)$— and $R^4$ is hydrogen or $C_{1-6}$alkyl. In some embodiments of a compound of Formula (I), or a pharmaceutically acceptable salt or solvate thereof, X is —$N(R^4)$— and $R^4$ is hydrogen. In some embodiments of a compound of Formula (I), or a pharmaceutically acceptable salt or solvate thereof, X is —$N(R^4)$— and $R^4$ is $C_{1-6}$alkyl. In some embodiments of a compound of Formula (I), or a pharmaceutically acceptable salt or solvate thereof, X is —$N(R^4)$— and $R^4$ is —$CH_3$. In some embodiments of a compound of Formula (I), or a pharmaceutically acceptable salt or solvate thereof, X is —$N(R^4)$— and $R^4$ and an $R^3$ are combined to form a $C_{2-9}$heterocycloalkyl optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (I), or a pharmaceutically acceptable salt or solvate thereof, X is —$N(R^4)$— and $R^4$ and an $R^3$ are combined to form a $C_{2-9}$heterocycloalkyl optionally substituted with one, two, or three groups selected from halogen, hydroxy, $C_{1-6}$alkyl, $C_{1-6}$haloalkyl, and $C_{1-6}$alkoxy. In some embodiments of a compound of Formula (I), or a pharmaceutically acceptable salt or solvate thereof, X is —$N(R^4)$— and $R^4$ and an $R^3$ are combined to form a piperidinyl, piperazinyl, pyrrolidinyl, or azetidinyl ring optionally substituted with one, two, or three groups selected from halogen, hydroxy, $C_{1-6}$alkyl, $C_{1-6}$haloalkyl, and $C_{1-6}$alkoxy. In some embodiments of a compound of Formula (I), or a pharmaceutically acceptable salt or solvate thereof, X is —$N(R^4)$— and $R^4$ and an $R^3$ are combined to form an unsubstituted piperidinyl, piperazinyl, pyrrolidinyl, or azetidinyl ring.

In some embodiments of a compound of Formula (I), or a pharmaceutically acceptable salt or solvate thereof, X is —O—.

In some embodiments of a compound of Formula (I), or a pharmaceutically acceptable salt or solvate thereof, X is —$C(R^5)(R^{5a})$—. In some embodiments of a compound of Formula (I), or a pharmaceutically acceptable salt or solvate thereof, X is —$C(R^5)(R^{5a})$— and $R^5$ and $R^{5a}$ are independently selected from hydrogen and $C_{1-6}$alkyl. In some embodiments of a compound of Formula (I), or a pharmaceutically acceptable salt or solvate thereof, X is —$C(R^5)(R^{5a})$— and $R^5$ and $R^{5a}$ are hydrogen. In some embodiments of a compound of Formula (I), or a pharmaceutically acceptable salt or solvate thereof, X is —$C(R^5)(R^{5a})$— and $R^5$ and $R^{5a}$ are $C_{1-6}$alkyl. In some embodiments of Formula (I), or a pharmaceutically acceptable salt or solvate thereof, X is —$C(R^5)(R^{5a})$—, $R^5$ is hydrogen, and $R^{5a}$ is $C_{1-6}$alkyl.

In some embodiments of a compound of Formula (I) or (Ib), or a pharmaceutically acceptable salt or solvate thereof, each $R^2$ is independently selected from hydrogen and $C_{1-6}$alkyl. In some embodiments of a compound of Formula (I) or (Ib), or a pharmaceutically acceptable salt or solvate thereof, each $R^2$ is hydrogen. In some embodiments of a compound of Formula (I) or (Ib), or a pharmaceutically acceptable salt or solvate thereof, each $R^3$ is independently selected from hydrogen and $C_{1-6}$alkyl. In some embodiments of a compound of Formula (I) or (Ib), or a pharmaceutically acceptable salt or solvate thereof, each $R^3$ is hydrogen. In some embodiments of a compound of Formula (I) or (Ib), or a pharmaceutically acceptable salt or solvate thereof, each $R^2$ and $R^3$, together with the carbon to which they are attached, form a $C_{3-6}$cycloalkyl. In some embodiments of a compound of Formula (I) or (Ib), or a pharmaceutically acceptable salt or solvate thereof, each $R^2$ and $R^3$, together with the carbon to which they are attached, form a cyclopropyl ring. In some embodiments of a compound of Formula (I) or (Ib), or a pharmaceutically acceptable salt or solvate thereof, each $R^2$ and $R^3$, together with the carbon to which they are attached, form a cyclobutyl ring. In some embodiments of a compound of Formula (I) or (Ib), or a pharmaceutically acceptable salt or solvate thereof, each $R^2$ and $R^3$, together with the carbon to which they are attached, form a cyclopentyl ring. In some embodiments of a compound of Formula (I) or (Ib), or a pharmaceutically acceptable salt or solvate thereof, each $R^2$ and $R^3$, together with the carbon to which they are attached, form a cyclohexyl ring.

In some embodiments of a compound of Formula (I), or a pharmaceutically acceptable salt or solvate thereof, n is 1, 2, or 3. In some embodiments of a compound of Formula (I), or a pharmaceutically acceptable salt or solvate thereof, n is 1. In some embodiments of a compound of Formula (I), or a pharmaceutically acceptable salt or solvate thereof, n is 2. In some embodiments of a compound of Formula (I), or a pharmaceutically acceptable salt or solvate thereof, n is 3. In some embodiments of a compound of Formula (I), or a pharmaceutically acceptable salt or solvate thereof, n is 4. In some embodiments of a compound of Formula (I), or a pharmaceutically acceptable salt or solvate thereof, n is 5. In some embodiments of a compound of Formula (I), or a pharmaceutically acceptable salt or solvate thereof, n is 6.

In some embodiments of a compound of Formula (I), or a pharmaceutically acceptable salt or solvate thereof, $Z^1$ is $CR^7$. In some embodiments of a compound of Formula (I), or a pharmaceutically acceptable salt or solvate thereof, $Z^1$ is $CR^7$ and $R^7$ is hydrogen, halogen, —CN, $C_{1-6}$alkyl, $C_{1-6}$haloalkyl, —$OR^{10}$, or —$N(R^{10})(R^{11})$. In some embodiments of a compound of Formula (I), or a pharmaceutically acceptable salt or solvate thereof, $Z^1$ is $CR^7$ and $R^7$ is hydrogen, halogen, $C_{1-6}$alkyl, or $C_{1-6}$haloalkyl. In some embodiments of a compound of Formula (I), or a pharmaceutically acceptable salt or solvate thereof, $Z^1$ is $CR^7$ and $R^7$ is hydrogen.

In some embodiments of a compound of Formula (I), or a pharmaceutically acceptable salt or solvate thereof, $Z^1$ is N.

In some embodiments of a compound of Formula (I), or a pharmaceutically acceptable salt or solvate thereof, $Z^2$ is $CR^9$. In some embodiments of a compound of Formula (I), or a pharmaceutically acceptable salt or solvate thereof, $Z^2$ is $CR^9$ and $R^9$ is hydrogen, halogen, —CN, $C_{1-6}$alkyl, $C_{1-6}$haloalkyl, —$OR^{10}$, or —$N(R^{10})(R^{11})$. In some embodiments of a compound of Formula (I), or a pharmaceutically acceptable salt or solvate thereof, $Z^2$ is $CR^9$ and $R^9$ is hydrogen, halogen, $C_{1-6}$alkyl, or $C_{1-6}$haloalkyl. In some embodiments of a compound of Formula (I), or a pharmaceutically acceptable salt or solvate thereof, $Z^2$ is $CR^9$ and $R^9$ is hydrogen.

In some embodiments of a compound of Formula (I), or a pharmaceutically acceptable salt or solvate thereof, $Z^2$ is N.

In some embodiments of a compound of Formula (I), or a pharmaceutically acceptable salt or solvate thereof, $Z^3$ is $CR^6$. In some embodiments of a compound of Formula (I), or a pharmaceutically acceptable salt or solvate thereof, $Z^3$ is $CR^6$ and $R^6$ is selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R'sc$.

In some embodiments of a compound of Formula (I), or a pharmaceutically acceptable salt or solvate thereof, $Z^3$ is $CR^6$ and $R^6$ is selected from hydrogen, halogen, —CN, $C_{1-6}$alkyl, $C_{1-6}$haloalkyl, —$OR^{10}$, and —$N(R^{10})(R^{11})$. In some embodiments of a compound of Formula (I), or a pharmaceutically acceptable salt or solvate thereof, $Z^3$ is $CR^6$ and $R^6$ is selected from hydrogen and —$OR^{10}$ and $R^{10}$ is $C_{1-6}$alkyl. In some embodiments of a compound of Formula (I), or a pharmaceutically acceptable salt or solvate thereof, $Z^3$ is $CR^6$ and $R^6$ is hydrogen.

In some embodiments of a compound of Formula (I), or a pharmaceutically acceptable salt or solvate thereof, $Z^3$ is N.

In some embodiments of a compound of Formula (I), or a pharmaceutically acceptable salt or solvate thereof,

is $C_{1-10}$heteroaryl. In some embodiments of a compound of Formula (I), or a pharmaceutically acceptable salt or solvate thereof,

is $C_{1-10}$heteroaryl selected from pyridyl, pyrimidyl, pyrazinyl, and pyridazinyl. In some embodiments of a compound of Formula (I), or a pharmaceutically acceptable salt or solvate thereof,

is 5 or 6 membered heteroaryl. In some embodiments of a compound of Formula (I), or a pharmaceutically acceptable salt or solvate thereof,

is 5 membered heteroaryl. In some embodiments of a compound of Formula (I), or a pharmaceutically acceptable salt or solvate thereof,

is 6 membered heteroaryl. In some embodiments of a compound of Formula (I), or a pharmaceutically acceptable salt or solvate thereof, (A)

is pyridyl. In some embodiments of a compound of Formula (I), or a pharmaceutically acceptable salt or solvate thereof, (A)

is pyrimidyl. In some embodiments of a compound of Formula (I), or a pharmaceutically acceptable salt or solvate thereof, (A)

is pyrazinyl. In some embodiments of a compound of Formula (I), or a pharmaceutically acceptable salt or solvate thereof, (A)

is pyridazinyl.

In some embodiments of a compound of Formula (I), or a pharmaceutically acceptable salt or solvate thereof, (A)

is $C_{6-10}$aryl. In some embodiments of a compound of Formula (I), or a pharmaceutically acceptable salt or solvate thereof, (A)

is phenyl.

In some embodiments of a compound of Formula (I), or a pharmaceutically acceptable salt or solvate thereof, (A)

is $C_{2-9}$heterocycloalkyl.

In some embodiments of a compound of Formula (I), or a pharmaceutically acceptable salt or solvate thereof, (A)

is $C_{3-6}$cycloalkyl.

In some embodiments of a compound of Formula (I), or a pharmaceutically acceptable salt or solvate thereof, each $R^{14}$ is independently selected from halogen, $C_{1-6}$alkyl, $C_{1-6}$haloalkyl, —$OR^{10}$, and —$N(R^{10})(R^{11})$. In some embodiments of a compound of Formula (I), or a pharmaceutically acceptable salt or solvate thereof, each $R^{14}$ is independently selected from halogen and $C_{1-6}$alkyl. In some embodiments of a compound of Formula (I), or a pharmaceutically acceptable salt or solvate thereof, each $R^{14}$ is independently selected from halogen. In some embodiments of a compound of Formula (I), or a pharmaceutically acceptable salt or solvate thereof, each $R^{14}$ is independently selected from $C_{1-6}$alkyl.

In some embodiments of a compound of Formula (I), or a pharmaceutically acceptable salt or solvate thereof, m is 0, 1, or 2. In some embodiments of a compound of Formula (I), or a pharmaceutically acceptable salt or solvate thereof, m is 0 or 1. In some embodiments of a compound of Formula (I), or a pharmaceutically acceptable salt or solvate thereof, m is 0. In some embodiments of a compound of Formula (I), or a pharmaceutically acceptable salt or solvate thereof, m is 1. In some embodiments of a compound of Formula (I), or a pharmaceutically acceptable salt or solvate thereof, m is 2. In some embodiments of a compound of Formula (I), or a pharmaceutically acceptable salt or solvate thereof, m is 3.

In some embodiments of a compound of Formula (I), or a pharmaceutically acceptable salt or solvate thereof, $R^8$ is selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R'sc$.

In some embodiments of a compound of Formula (I), or a pharmaceutically acceptable salt or solvate thereof, $R^8$ is hydrogen, halogen, —CN, $C_{1-6}$alkyl, $C_{1-6}$haloalkyl, —$OR^{10}$, or $C_{3-6}$cycloalkyl. In some embodiments of a compound of Formula (I), or a pharmaceutically acceptable salt or solvate thereof, $R^8$ is hydrogen, halogen, or $C_{1-6}$haloalkyl. In some embodiments of a compound of Formula (I), or a pharmaceutically acceptable salt or solvate thereof, $R^8$ is hydrogen. In some embodiments of a compound of Formula (I), or a pharmaceutically acceptable salt or solvate thereof, $R^8$ is halogen. In some embodiments of a compound of Formula (I), or a pharmaceutically acceptable salt or solvate thereof, $R^8$ is $C_{1-6}$haloalkyl. In some embodiments of a compound of Formula (I), or a pharmaceutically acceptable salt or solvate thereof, $R^8$ is —$CF_3$. In some embodiments of a compound of Formula (I), or a pharmaceutically acceptable salt or solvate thereof, $R^8$ is $C_{1-6}$alkyl. In some embodiments of a compound of Formula (I), or a pharmaceutically acceptable salt or solvate thereof, $R^8$ is —CH$_3$. In some embodiments of a compound of Formula (I), or a pharmaceutically acceptable salt or solvate thereof, $R^8$ is C$_{3-6}$cycloalkyl. In some embodiments of a compound of Formula (I), or a pharmaceutically acceptable salt or solvate thereof, $R^8$ is cyclopropyl. In some embodiments of a compound of Formula (I), or a pharmaceutically acceptable salt or solvate thereof, $R^8$ is —CN.

In some embodiments of a compound of Formula (I), or a pharmaceutically acceptable salt or solvate thereof, $R^1$ is selected from hydrogen, C$_{1-6}$alkyl, C$_{1-6}$haloalkyl, C$_{3-6}$cycloalkyl, C$_{2-9}$heterocycloalkyl, and C$_{1-9}$heteroaryl, wherein C$_{1-6}$alkyl, C$_{3-6}$cycloalkyl, C$_{2-9}$heterocycloalkyl, and C$_{1-9}$heteroaryl are optionally substituted with one, two, or three groups selected from $R^{15}$.

In some embodiments of a compound of Formula (I), or a pharmaceutically acceptable salt or solvate thereof, $R^1$ is hydrogen.

In some embodiments of a compound of Formula (I), or a pharmaceutically acceptable salt or solvate thereof, $R^1$ is C$_{1-6}$alkyl optionally substituted with one, two, or three groups selected from $R^{15a}$. In some embodiments of a compound of Formula (I), or a pharmaceutically acceptable salt or solvate thereof, $R^1$ is C$_{1-6}$alkyl optionally substituted with one, two, or three groups selected from C$_{2-9}$ heterocycloalkyl, C$_{1-9}$heteroaryl, —OR$^{10}$, and —N(R$^{10}$)(R$^{11}$). In some embodiments of a compound of Formula (I), or a pharmaceutically acceptable salt or solvate thereof, $R^1$ is C$_{1-6}$alkyl substituted with one group selected from C$_{2-9}$heterocycloalkyl, C$_{1-9}$heteroaryl, —OR$^{10}$, and —N(R$^{10}$)(R$^{11}$). In some embodiments of a compound of Formula (I), or a pharmaceutically acceptable salt or solvate thereof, $R^1$ is C$_{1-6}$alkyl substituted with one group selected from C$_{2-9}$heterocycloalkyl, C$_{1-9}$heteroaryl, —OR$^{10}$, and —N(R$^{10}$)(R$^{11}$) and R$^{10}$ and R$^{11}$ are independently selected from hydrogen and C$_{1-6}$alkyl. In some embodiments of a compound of Formula (I), or a pharmaceutically acceptable salt or solvate thereof, $R^1$ is unsubstituted C$_{1-6}$alkyl.

In some embodiments of a compound of Formula (I), or a pharmaceutically acceptable salt or solvate thereof, $R^1$ is C$_{3-6}$cycloalkyl optionally substituted with one, two, or three groups selected from $R^{15a}$. In some embodiments of a compound of Formula (I), or a pharmaceutically acceptable salt or solvate thereof, $R^1$ is C$_{3-6}$cycloalkyl substituted with one, two, or three groups selected from C$_{1-6}$alkyl, —OR$^{10}$, and —N(R$^{10}$)(R$^{11}$). In some embodiments of a compound of Formula (I), or a pharmaceutically acceptable salt or solvate thereof, $R^1$ is C$_{3-6}$cycloalkyl substituted with one group selected from —OR$^{10}$ and —N(R$^{10}$)(R$^{11}$) R$^{10}$ and R$^{11}$ are independently selected from hydrogen and C$_{1-6}$alkyl. In some embodiments of a compound of Formula (I), or a pharmaceutically acceptable salt or solvate thereof, $R^1$ is unsubstituted C$_{3-6}$cycloalkyl. In some embodiments of a compound of Formula (I), or a pharmaceutically acceptable salt or solvate thereof, $R^1$ is unsubstituted cyclopropyl. In some embodiments of a compound of Formula (I), or a pharmaceutically acceptable salt or solvate thereof, $R^1$ is unsubstituted cyclobutyl.

In some embodiments of a compound of Formula (I), or a pharmaceutically acceptable salt or solvate thereof, $R^1$ is C$_{1-6}$haloalkyl.

In some embodiments of a compound of Formula (I), or a pharmaceutically acceptable salt or solvate thereof, $R^1$ is C$_{2-9}$heterocycloalkyl optionally substituted with one, two, or three groups selected from $R^{15a}$. In some embodiments of a compound of Formula (I), or a pharmaceutically acceptable salt or solvate thereof, $R^1$ is C$_{2-9}$ heterocycloalkyl optionally substituted with one, two, or three groups selected from C$_{1-6}$alkyl, —OR$^{10}$, and —N(R$^{10}$)(R$^{11}$). In some embodiments of a compound of Formula (I), or a pharmaceutically acceptable salt or solvate thereof, $R^1$ is unsubstituted C$_{2-9}$ heterocycloalkyl.

In some embodiments of a compound of Formula (I), or a pharmaceutically acceptable salt or solvate thereof, $R^1$ is C$_{1-9}$heteroaryl optionally substituted with one, two, or three groups selected from $R^{15a}$. In some embodiments of a compound of Formula (I), or a pharmaceutically acceptable salt or solvate thereof, $R^1$ is C$_{1-9}$heteroaryl optionally substituted with one, two, or three groups selected from C$_{1-6}$alkyl, —OR$^{10}$, and —N(R$^{10}$)(R$^{11}$). In some embodiments of a compound of Formula (I), or a pharmaceutically acceptable salt or solvate thereof, $R^1$ is unsubstituted C$_{1-9}$heteroaryl.

In some embodiments disclosed herein is a compound of Formula (Ia), or a pharmaceutically acceptable salt or solvate thereof:

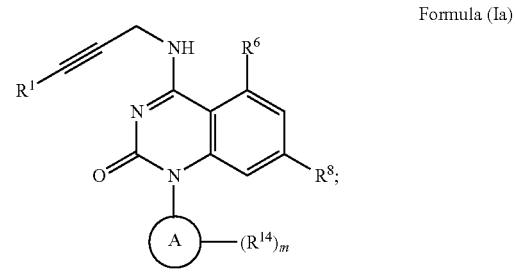

Formula (Ia)

wherein:

Ⓐ is selected from C$_{3-6}$cycloalkyl, C$_{2-9}$heterocycloalkyl, C$_{6-10}$aryl, and C$_{1-10}$heteroaryl;

R$^1$ is selected from hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from $R^{15a}$;

R$^6$ and R$^8$ are independently selected from hydrogen, halogen, —CN, C$_{1-6}$alkyl, C$_{1-6}$haloalkyl, C$_{2-6}$ alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl are optionally substituted with one, two, or three groups selected from R$^{15c}$;

each R$^{10}$ is independently selected from hydrogen, C$_{1-6}$alkyl, C$_{1-6}$haloalkyl, C$_{2-6}$alkenyl, C$_{2-6}$ alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl; or R$^{10}$ and R$^{11}$, together with the nitrogen to which they are attached, form a C$_{2-9}$heterocycloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{14}$ is independently selected from halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15d}$;

each R$^{15a}$, R$^{15c}$, and R$^{15d}$ are each independently selected from halogen, oxo, —CN, C$_{1-6}$alkyl, C$_{2-6}$ alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$ heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$) and —P(O)(R$^{10}$)$_2$; and m is 0, 1, 2, 3, 4, or 5.

In some embodiments disclosed herein is a compound of Formula (Ia), or a pharmaceutically acceptable salt or solvate thereof:

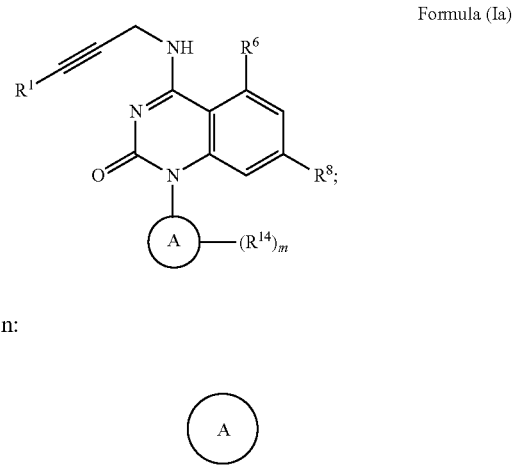

Formula (Ia)

wherein:

A is selected from C$_{3-6}$cycloalkyl, C$_{2-9}$heterocycloalkyl, C$_{6-10}$aryl, and C$_{1-10}$heteroaryl;

R$^1$ is selected from hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15a}$;

R$^6$ and R$^8$ are independently selected from halogen, —CN, C$_{1-6}$alkyl, C$_{1-6}$haloalkyl, C$_{2-6}$alkenyl, C$_{2-6}$ alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N $(R^{10})(R^{11})$, —C(O)C(O)N$(R^{10})(R^{11})$, —N$(R^{12})$C(O)R$^{13}$, —S(O)$_2$R$^{13}$, —S(O)$_2$N$(R^{10})(R^{11})$—, —N=S(=O)$(R^{13})_2$, —S(=O)(=NH)N$(R^{10})(R^{11})$, —S(=O)(=NH)C$(R^{10})(R^{11})$, —S(=O)(=NR$^{13}$)R$^{13}$, —CH$_2$C(O)N$(R^{10})(R^{11})$, —CH$_2$N$(R^{12})$C(O)R$^{13}$, —CH$_2$S(O)$_2$R$^{13}$, —CH$_2$S(O)$_2$N$(R^{10})(R^{11})$, —Si(C$_{1-6}$alkyl)$_3$, and —P(O)$(R^{10})_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15c}$;

each R$^{10}$ is independently selected from hydrogen, C$_{1-6}$alkyl, C$_{1-6}$haloalkyl, C$_{2-6}$alkenyl, C$_{2-6}$ alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl; or R$^{10}$ and R$^{11}$, together with the nitrogen to which they are attached, form a C$_{2-9}$heterocycloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{14}$ is independently selected from halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N$(R^{10})(R^{11})$, —C(O)OR$^{10}$, —OC(O)N$(R^{10})(R^{11})$, —N$(R^{12})$C(O)N$(R^{10})(R^{11})$, —N$(R^{12})$C(O)OR$^{13}$, —N$(R^{12})$S(O)$_2$R$^{13}$, —C(O)R$^{13}$, —S(O)R$^{13}$, —OC(O)R$^{13}$, —C(O)N$(R^{10})(R^{11})$, —C(O)C(O)N$(R^{10})(R^{11})$, —N$(R^{12})$C(O)R$^{13}$, —S(O)$_2$R$^{13}$, —S(O)$_2$N$(R^{10})(R^{11})$—, —N=S(=O)$(R^{13})_2$, —S(=O)(=NH)N$(R^{10})(R^{11})$, —S(=O)(=NH)C$(R^{10})(R^{11})$, —S(=O)(=NR$^{13}$)R$^{13}$, —CH$_2$C(O)N$(R^{10})(R^{11})$, —CH$_2$N$(R^{12})$C(O)R$^{13}$, —CH$_2$S(O)$_2$R$^{13}$, —CH$_2$S(O)$_2$N$(R^{10})(R^{11})$, —Si(C$_{1-6}$alkyl)$_3$, and —P(O)$(R^{10})_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15d}$;

each R$^{15a}$, R$^{15c}$, and R$^{15d}$ are each independently selected from halogen, oxo, —CN, C$_{1-6}$alkyl, C$_{2-6}$ alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$ heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —SF$_5$, —N$(R^{10})(R^{11})$, —C(O)OR$^{10}$, —OC(O)N$(R^{10})(R^{11})$, —N$(R^{12})$C(O)N$(R^{10})(R^{11})$, —N$(R^{12})$C(O)OR$^{13}$, —N$(R^{12})$S(O)$_2$R$^{13}$, —C(O)R$^{13}$, —S(O)R$^{13}$, —OC(O)R$^{13}$, —C(O)N$(R^{10})(R^{11})$, —C(O)C(O)N$(R^{10})(R^{11})$, —N$(R^{12})$C(O)R$^{13}$, —S(O)$_2$R$^{13}$, —S(O)$_2$N$(R^{10})(R^{11})$—, —N=S(=O)$(R^{13})_2$, —S(=O)(=NH)N$(R^{10})(R^{11})$, —S(=O)(=NH)C$(R^{10})(R^{11})$, —S(=O)(=NR$^{13}$)R$^{13}$, —CH$_2$C(O)N$(R^{10})(R^{11})$, —CH$_2$N$(R^{12})$C(O)R$^{13}$, —CH$_2$S(O)$_2$R$^{13}$, —CH$_2$S(O)$_2$N$(R^{10})(R^{11})$, —Si(C$_{1-6}$alkyl)$_3$, and —P(O)$(R^{10})_2$, wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —SF$_5$, —N$(R^{10})(R^{11})$, —C(O)OR$^{10}$, —OC(O)N$(R^{10})(R^{11})$, —N$(R^{12})$C(O)N$(R^{10})(R^{11})$, —N$(R^{12})$C(O)OR$^{13}$, —N$(R^{12})$S(O)$_2$R$^{13}$, —C(O)R$^{13}$, —S(O)R$^{13}$, —OC(O)R$^{13}$, —C(O)N$(R^{10})(R^{11})$, —C(O)C(O)N$(R^{10})(R^{11})$, —N$(R^{12})$C(O)R$^{13}$, —S(O)$_2$R$^{13}$, —S(O)$_2$N$(R^{10})(R^{11})$—, —N=S(=O)$(R^{13})_2$, —S(=O)(=NH)N$(R^{10})(R^{11})$, —S(=O)(=NH)C$(R^{10})(R^{11})$, —S(=O)(=NR$^{13}$)R$^{13}$, —CH$_2$C(O)N$(R^{10})(R^{11})$, —CH$_2$N$(R^{12})$C(O)R$^{13}$, —CH$_2$S(O)$_2$R$^{13}$, —CH$_2$S(O)$_2$N$(R^{10})(R^{11})$ and —P(O)$(R^{10})_2$; and m is 0, 1, 2, 3, 4, or 5.

In some embodiments disclosed herein is a compound of Formula (Ib), or a pharmaceutically acceptable salt or solvate thereof:

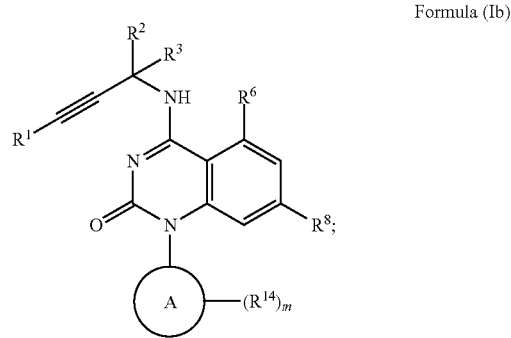

Formula (Ib)

wherein:

A is selected from C$_{3-6}$cycloalkyl, C$_{2-9}$heterocycloalkyl, C$_{6-10}$aryl, and C$_{1-10}$heteroaryl;

R$^1$ is selected from hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N$(R^{10})(R^{11})$, —C(O)OR$^{10}$, —OC(O)N$(R^{10})(R^{11})$, —N$(R^{12})$C(O)N$(R^{10})(R^{11})$, —N$(R^{12})$C(O)OR$^{13}$, —N$(R^{12})$S(O)$_2$R$^{13}$, —C(O)R$^{13}$, —S(O)R$^{13}$, —OC(O)R$^{13}$, —C(O)N$(R^{10})(R^{11})$, —C(O)C(O)N$(R^{10})(R^{11})$, —N$(R^{12})$C(O)R$^{13}$, —S(O)$_2$R$^{13}$, —S(O)$_2$N$(R^{10})(R^{11})$—, —N=S(=O)$(R^{13})_2$, —S(=O)(=NH)N$(R^{10})(R^{11})$, —S(=O)(=NH)C$(R^{10})(R^{11})$, —S(=O)(=NR$^{13}$)R$^{13}$, —CH$_2$C(O)N$(R^{10})(R^{11})$, —CH$_2$N$(R^{12})$C(O)R$^{13}$, —CH$_2$S(O)$_2$R$^{13}$, —CH$_2$S(O)$_2$N$(R^{10})(R^{11})$, —Si(C$_{1-6}$alkyl)$_3$, and —P(O)$(R^{10})_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15a}$;

each R$^2$ and each R$^3$ are each independently selected from hydrogen, halogen, oxo, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15b}$; or R$^2$ and R$^3$, together with the carbon to which they are attached, form a C$_{3-6}$cycloalkyl or C$_{2-9}$heterocycloalkyl;

R$^6$ and R$^8$ are independently selected from halogen, —CN, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^3$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15c}$;

each R$^{10}$ is independently selected from hydrogen, C$_{1-6}$alkyl, C$_{1-6}$haloalkyl, C$_{2-6}$alkenyl, C$_{2-6}$ alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$ alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl; or R$^{10}$ and R$^{11}$, together with the nitrogen to which they are attached, form a C$_{2-9}$heterocycloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{14}$ is independently selected from halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15a}$;

each R$^{15a}$, R$^{15c}$, and R$^{15d}$ are each independently selected from halogen, oxo, —CN, C$_{1-6}$alkyl, C$_{2-6}$ alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$ heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$) and —P(O)(R$^{10}$)$_2$; and m is 0, 1, 2, 3, 4, or 5.

In some embodiments disclosed herein is a compound of Formula (Ib), or a pharmaceutically acceptable salt or solvate thereof:

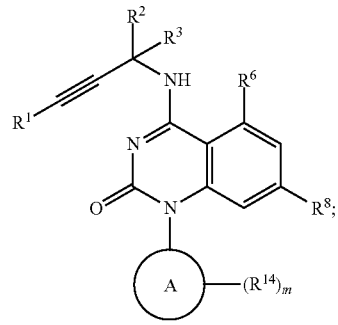

Formula (Ib)

wherein:

is selected from $C_{3-6}$cycloalkyl, $C_{2-9}$heterocycloalkyl, $C_{6-10}$aryl, and $C_{1-10}$heteroaryl;

$R^1$ is selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15a}$;

each $R^2$ and each $R^3$ are each independently selected from hydrogen, halogen, oxo, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^3$)$_2$, —S(=O)(=NH)N(R$^{10}$)(R$^{11}$), —S(=O)(=NH)C(R$^{10}$)(R$^{11}$), —S(=O)(=NR$^3$)R$^3$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$; or $R^2$ and $R^3$, together with the carbon to which they are attached, form a $C_{3-6}$cycloalkyl or $C_{2-9}$heterocycloalkyl;

$R^6$ and $R^8$ are independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15c}$;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl; or $R^{10}$ and $R^{11}$, together with the nitrogen to which they are attached, form a $C_{2-9}$heterocycloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{14}$ is independently selected from halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15d}$;

each $R^{15a}$, $R^{15c}$, and $R^{15d}$ are each independently selected from halogen, oxo, —CN, $C_{1-6}$alkyl, $C_{2-6}$alkenyl, $C_{2-6}$alkynyl, $C_{3-10}$cycloalkyl, —CH$_2$—C$_{3-6}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, $C_{1-9}$heteroaryl, —CH$_2$—C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein $C_{1-6}$alkyl, $C_{2-6}$alkenyl, $C_{2-6}$alkynyl, $C_{3-6}$cycloalkyl, —CH$_2$—C$_{3-10}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, —CH$_2$—C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$) and —P(O)(R$^{10}$)$_2$; and m is 0, 1, 2, 3, 4, or 5.

In some embodiments of a compound of Formula (Ia) or (Ib), or a pharmaceutically acceptable salt or solvate thereof, $R^6$ and $R^8$ are independently selected from halogen, —CN, $C_{1-6}$alkyl, $C_{1-6}$haloalkyl, $C_{3-6}$cycloalkyl, $C_{2-9}$heterocycloalkyl, —OR$^{10}$, and —N(R$^{10}$)(R$^{11}$), wherein $C_{1-6}$alkyl, $C_{3-6}$cycloalkyl, and $C_{2-9}$heterocycloalkyl are optionally substituted with one, two, or three groups selected from R$^{15c}$.

In some embodiments of a compound of Formula (Ia) or (Ib), or a pharmaceutically acceptable salt or solvate thereof, $R^6$ is selected from hydrogen, halogen, —CN, $C_{1-6}$alkyl, $C_{1-6}$haloalkyl, —OR$^{10}$, and —N(R$^{10}$)(R$^{11}$). In some embodiments of a compound of Formula (Ia) or (Ib), or a pharmaceutically acceptable salt or solvate thereof, $R^6$ is selected from hydrogen and —OR$^{10}$ and R$^{10}$ is $C_{1-6}$alkyl. In some embodiments of a compound of Formula (Ia) or (Ib), or a pharmaceutically acceptable salt or solvate thereof, $R^6$ is hydrogen.

In some embodiments of a compound of Formula (Ia) or (Ib), or a pharmaceutically acceptable salt or solvate thereof,

is $C_{1-10}$heteroaryl. In some embodiments of a compound of Formula (Ia) or (Ib), or a pharmaceutically acceptable salt or solvate thereof,

is $C_{1-10}$heteroaryl selected from pyridyl, pyrimidyl, pyrazinyl, and pyridazinyl. In some embodiments of a compound of Formula (Ia) or (Ib), or a pharmaceutically acceptable salt or solvate thereof,

is 5 or 6 membered heteroaryl. In some embodiments of a compound of Formula (Ia) or (Ib), or a pharmaceutically acceptable salt or solvate thereof,

is 5 membered heteroaryl. In some embodiments of a compound of Formula (Ia) or (Ib), or a pharmaceutically acceptable salt or solvate thereof,

is 6 membered heteroaryl. In some embodiments of a compound of Formula (Ia) or (Ib), or a pharmaceutically acceptable salt or solvate thereof,

is pyridyl. In some embodiments of a compound of Formula (Ia) or (Ib), or a pharmaceutically acceptable salt or solvate thereof,

is pyrimidyl. In some embodiments of a compound of Formula (Ia) or (Ib), or a pharmaceutically acceptable salt or solvate thereof,

is pyrazinyl. In some embodiments of a compound of Formula (Ia) or (Ib), or a pharmaceutically acceptable salt or solvate thereof,

is pyridazinyl.

In some embodiments of a compound of Formula (Ia) or (Ib), or a pharmaceutically acceptable salt or solvate thereof,

is $C_{6-10}$aryl. In some embodiments of a compound of Formula (Ia) or (Ib), or a pharmaceutically acceptable salt or solvate thereof,

is phenyl.

In some embodiments of a compound of Formula (Ia) or (Ib), or a pharmaceutically acceptable salt or solvate thereof,

is $C_{2-9}$heterocycloalkyl.

In some embodiments of a compound of Formula (Ia) or (Ib), or a pharmaceutically acceptable salt or solvate thereof, Ⓐ is $C_{3-6}$cycloalkyl.

In some embodiments of a compound of Formula (Ia) or (Ib), or a pharmaceutically acceptable salt or solvate thereof, each $R^{14}$ is independently selected from halogen, $C_{1-6}$alkyl, $C_{1-6}$haloalkyl, —$OR^{10}$, and —$N(R^{10})(R^{11})$. In some embodiments of a compound of Formula (Ia) or (Ib), or a pharmaceutically acceptable salt or solvate thereof, each $R^{14}$ is independently selected from halogen and $C_{1-6}$alkyl. In some embodiments of a compound of Formula (Ia) or (Ib), or a pharmaceutically acceptable salt or solvate thereof, each $R^{14}$ is independently selected from halogen. In some embodiments of a compound of Formula (Ia) or (Ib), or a pharmaceutically acceptable salt or solvate thereof, each $R^{14}$ is independently selected from $C_{1-6}$alkyl.

In some embodiments of a compound of Formula (Ia) or (Ib), or a pharmaceutically acceptable salt or solvate thereof, m is 0, 1, or 2. In some embodiments of a compound of Formula (Ia) or (Ib), or a pharmaceutically acceptable salt or solvate thereof, m is 0 or 1. In some embodiments of a compound of Formula (Ia) or (Ib), or a pharmaceutically acceptable salt or solvate thereof, m is 0. In some embodiments of a compound of Formula (Ia) or (Ib), or a pharmaceutically acceptable salt or solvate thereof, m is 1. In some embodiments of a compound of Formula (Ia) or (Ib), or a pharmaceutically acceptable salt or solvate thereof, m is 2. In some embodiments of a compound of Formula (Ia) or (Ib), or a pharmaceutically acceptable salt or solvate thereof, m is 3.

In some embodiments of a compound of Formula (Ia) or (Ib), or a pharmaceutically acceptable salt or solvate thereof, $R^8$ is hydrogen, halogen, —CN, $C_{1-6}$alkyl, $C_{1-6}$haloalkyl, —$OR^{10}$, or $C_{3-6}$cycloalkyl. In some embodiments of a compound of Formula (Ia) or (Ib), or a pharmaceutically acceptable salt or solvate thereof, $R^8$ is hydrogen, halogen, or $C_{1-6}$haloalkyl. In some embodiments of a compound of Formula (Ia) or (Ib), or a pharmaceutically acceptable salt or solvate thereof, $R^8$ is hydrogen. In some embodiments of a compound of Formula (Ia) or (Ib), or a pharmaceutically acceptable salt or solvate thereof, $R^8$ is halogen. In some embodiments of a compound of Formula (Ia) or (Ib), or a pharmaceutically acceptable salt or solvate thereof, $R^8$ is $C_{1-6}$haloalkyl. In some embodiments of a compound of Formula (Ia) or (Ib), or a pharmaceutically acceptable salt or solvate thereof, $R^8$ is —$CF_3$. In some embodiments of a compound of Formula (Ia) or (Ib), or a pharmaceutically acceptable salt or solvate thereof, $R^8$ is $C_{1-6}$alkyl. In some embodiments of a compound of Formula (Ia) or (Ib), or a pharmaceutically acceptable salt or solvate thereof, $R^8$ is —$CH_3$. In some embodiments of a compound of Formula (Ia) or (Ib), or a pharmaceutically acceptable salt or solvate thereof, $R^8$ is $C_{3-6}$cycloalkyl. In some embodiments of a compound of Formula (Ia) or (Ib), or a pharmaceutically acceptable salt or solvate thereof, $R^8$ is cyclopropyl. In some embodiments of a compound of Formula (Ia) or (Ib), or a pharmaceutically acceptable salt or solvate thereof, $R^8$ is —CN.

In some embodiments of a compound of Formula (Ia) or (Ib), or a pharmaceutically acceptable salt or solvate thereof, $R^1$ is selected from hydrogen, $C_{1-6}$alkyl, $C_{1-6}$haloalkyl, $C_{3-6}$cycloalkyl, $C_{2-9}$heterocycloalkyl, and $C_{1-9}$heteroaryl, wherein $C_{1-6}$alkyl, $C_{3-6}$cycloalkyl, $C_{2-9}$ heterocycloalkyl, and $C_{1-9}$heteroaryl are optionally substituted with one, two, or three groups selected from $R^{15a}$;

In some embodiments of a compound of Formula (Ia) or (Ib), or a pharmaceutically acceptable salt or solvate thereof, $R^1$ is hydrogen.

In some embodiments of a compound of Formula (Ia) or (Ib), or a pharmaceutically acceptable salt or solvate thereof, $R^1$ is $C_{1-6}$alkyl optionally substituted with one, two, or three groups selected from $R^{15a}$. In some embodiments of a compound of Formula (Ia) or (Ib), or a pharmaceutically acceptable salt or solvate thereof, $R^1$ is $C_{1-6}$alkyl optionally substituted with one, two, or three groups selected from $C_{2-9}$heterocycloalkyl, $C_{1-9}$heteroaryl, —$OR^{10}$, and —$N(R^{10})(R^{11})$. In some embodiments of a compound of Formula (Ia) or (Ib), or a pharmaceutically acceptable salt or solvate thereof, $R^1$ is $C_{1-6}$alkyl substituted with one group selected from $C_{2-9}$heterocycloalkyl, $C_{1-9}$heteroaryl, —$OR^{10}$, and —$N(R^{10})(R^{11})$. In some embodiments of a compound of Formula (Ia) or (Ib), or a pharmaceutically acceptable salt or solvate thereof, $R^1$ is $C_{1-6}$alkyl substituted with one group selected from $C_{2-9}$heterocycloalkyl, $C_{1-9}$heteroaryl, —$OR^{10}$, and —$N(R^{10})(R^{11})$ and $R^{10}$ and $R^{11}$ are independently selected from hydrogen and $C_{1-6}$alkyl. In some embodiments of a compound of Formula (Ia) or (Ib), or a pharmaceutically acceptable salt or solvate thereof, $R^1$ is unsubstituted $C_{1-6}$alkyl.

In some embodiments of a compound of Formula (Ia) or (Ib), or a pharmaceutically acceptable salt or solvate thereof, $R^1$ is $C_{3-6}$cycloalkyl optionally substituted with one, two, or three groups selected from $R^{15a}$. In some embodiments of a compound of Formula (Ia) or (Ib), or a pharmaceutically acceptable salt or solvate thereof, $R^1$ is $C_{3-6}$cycloalkyl substituted with one, two, or three groups selected from $C_{1-6}$alkyl, —$OR^{10}$, and —$N(R^{10})(R^{11})$. In some embodiments of a compound of Formula (Ia) or (Ib), or a pharmaceutically acceptable salt or solvate thereof, $R^1$ is $C_{3-6}$cycloalkyl substituted with one group selected from —$OR^{10}$ and —$N(R^{10})(R^{11})$ $R^{10}$ and $R^{11}$ are independently selected from hydrogen and $C_{1-6}$alkyl. In some embodiments of a compound of Formula (Ia) or (Ib), or a pharmaceutically acceptable salt or solvate thereof, $R^1$ is unsubstituted $C_{3-6}$cycloalkyl. In some embodiments of a compound of Formula (Ia) or (Ib), or a pharmaceutically acceptable salt or solvate thereof, $R^1$ is unsubstituted cyclopropyl. In some embodiments of a compound of Formula (Ia) or (Ib), or a pharmaceutically acceptable salt or solvate thereof, $R^1$ is unsubstituted cyclobutyl.

In some embodiments of a compound of Formula (Ia) or (Ib), or a pharmaceutically acceptable salt or solvate thereof, $R^1$ is $C_{1-6}$haloalkyl.

In some embodiments of a compound of Formula (Ia) or (Ib), or a pharmaceutically acceptable salt or solvate thereof, $R^1$ is $C_{2-9}$heterocycloalkyl optionally substituted with one, two, or three groups selected from $R^{15a}$. In some embodiments of a compound of Formula (Ia) or (Ib), or a pharmaceutically acceptable salt or solvate thereof, $R^1$ is $C_{2-9}$heterocycloalkyl optionally substituted with one, two, or three groups selected from $C_{1-6}$alkyl, —$OR^{10}$, and —$N(R^{10})(R^{11})$. In some embodiments of a compound of Formula (Ia) or (Ib), or a pharmaceutically acceptable salt or solvate thereof, $R^1$ is unsubstituted $C_{2-9}$heterocycloalkyl.

In some embodiments of a compound of Formula (Ia) or (Ib), or a pharmaceutically acceptable salt or solvate thereof, $R^1$ is $C_{1-9}$heteroaryl optionally substituted with one, two, or three groups selected from $R^{15a}$. In some embodiments of a compound of Formula (Ia) or (Ib), or a pharmaceutically acceptable salt or solvate thereof, $R^1$ is $C_{1-9}$heteroaryl optionally substituted with one, two, or three groups selected from C$_{1-6}$alkyl, —OR$^{10}$, and —N(R$^{10}$)(R$^{11}$). In some embodiments of a compound of Formula (Ia) or (Ib), or a pharmaceutically acceptable salt or solvate thereof, R$^1$ is unsubstituted C$_{1-9}$heteroaryl.

In some embodiments disclosed herein is a compound of Formula (II), or a pharmaceutically acceptable salt or solvate thereof:

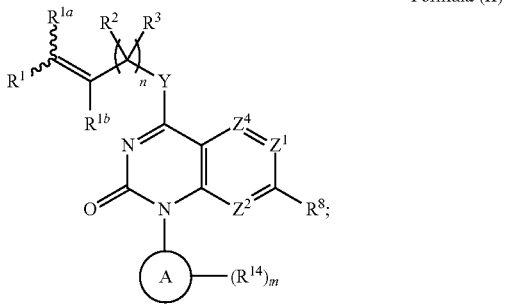

Formula (II)

wherein:

is selected from C$_{3-6}$cycloalkyl, C$_{2-9}$heterocycloalkyl, C$_{6-10}$aryl, and C$_{1-10}$heteroaryl;

Z$^1$ is CR$^7$ or N;

Z$^2$ is CR$^9$ or N;

Z$^4$ is CR$^6$a or N;

Y is selected from —N(R$^{4a}$)—, —O—, and —C(R$_5$)(R$^{5a}$)—;

R$^1$ is selected from hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15a}$;

R$^{1a}$ and R$^{1b}$ are independently selected from hydrogen, halogen, C$_{1-6}$alkyl, C$_{1-6}$haloalkyl, C$_{2-6}$ alkenyl, C$_{2-6}$alkynyl, C$_{3-6}$cycloalkyl, C$_{2-9}$heterocycloalkyl, C$_{6-10}$aryl, and C$_{1-9}$heteroaryl; wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15a}$;

each R$^2$ and each R$^3$ are each independently selected from hydrogen, halogen, oxo, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl are optionally substituted with one, two, or three groups selected from R$^{15b}$; or R$^2$ and R$^3$, together with the carbon to which they are attached, form a C$_{3-6}$cycloalkyl or C$_{2-9}$heterocycloalkyl;

R$^{4a}$ is selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl; or R$^{4a}$ and an R$^3$ are combined to form a C$_{2-9}$heterocycloalkyl optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

R$^5$ and R$^{5a}$ are independently selected from hydrogen, halogen, C$_{1-6}$alkyl, C$_{1-6}$haloalkyl, C$_{2-6}$ alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl; or R$^5$ and an R$^3$ are combined to form a C$_{3-6}$cycloalkyl, C$_{2-9}$heterocycloalkyl, C$_{6-10}$aryl, or C$_{2-9}$heteroaryl, wherein C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

R$^{6a}$ is selected from hydrogen, halogen, —CN, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)

(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$heterocycloalkyl, and C$_{1-9}$heteroaryl are optionally substituted with one, two, or three groups selected from R$^{15c}$;

R$^7$, R$^8$, and R$^9$ are independently selected from hydrogen, halogen, —CN, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15c}$;

each R$^{10}$ is independently selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl; or R$^{10}$ and R$^{11}$, together with the nitrogen to which they are attached, form a C$_{2-9}$heterocycloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{14}$ is independently selected from halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$), —Si(C$_{1-6}$alkyl)$_3$, and —P(O)(R$^{10}$)$_2$, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15d}$;

each R$^{15a}$, R$^{15b}$, R$^{15c}$, and R$^{15d}$ are each independently selected from halogen, oxo, —CN, C$_{1-6}$alkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$ heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, —N=S(=O)(R$^{13}$)$_2$, —S(=O)(=NH)N(R$^{10}$)(R$^{11}$), —S(=O)(=NH)C(R$^{10}$)(R$^{11}$), —S(=O)(=NR$^{13}$)R$^{13}$, —CH$_2$C(O)N(R$^{10}$)(R$^{11}$), —CH$_2$N(R$^{12}$)C(O)R$^{13}$, —CH$_2$S(O)$_2$R$^{13}$, —CH$_2$S(O)$_2$N(R$^{10}$)(R$^{11}$) and —P(O)(R$^{10}$)$_2$;

m is 0, 1, 2, 3, 4, or 5; and n is 0, 1, 2, 3, 4, 5, or 6.

In some embodiments of a compound of Formula (II), or a pharmaceutically acceptable salt or solvate thereof, Y is —N(R$^{4a}$)—. In some embodiments of a compound of Formula (II), or a pharmaceutically acceptable salt or solvate thereof, Y is —N(R$^{4a}$)— and R$^{4a}$ is selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl. In some embodiments of a compound of Formula (II), or a pharmaceutically acceptable salt or solvate thereof, Y is —N(R$^{4a}$)— and R$^{4a}$ is hydrogen or C$_{1-6}$alkyl. In some embodiments of a compound of Formula (II), or a pharmaceutically acceptable salt or solvate thereof, Y is —N(R$^{4a}$)— and R$^{4a}$ is hydrogen. In some embodiments of a compound of Formula (II), or a pharmaceutically acceptable salt or solvate thereof, Y is —N(R$^{4a}$)— and R$^{4a}$ is C$_{1-6}$alkyl. In some embodiments of a compound of Formula (II), or a pharmaceutically acceptable salt or solvate thereof, Y is —N(R$^{4a}$)— and R$^{4a}$ is —CH$_3$.

In some embodiments of a compound of Formula (II), or a pharmaceutically acceptable salt or solvate thereof, Y is —O—.

In some embodiments of a compound of Formula (II), or a pharmaceutically acceptable salt or solvate thereof, Y is —C(R$^5$)(R$^{5a}$)—. In some embodiments of a compound of Formula (II), or a pharmaceutically acceptable salt or solvate thereof, Y is —C(R$^5$)(R$^{5a}$)— and R$^5$ and R$^{5a}$ are independently selected from hydrogen and C$_{1-6}$alkyl. In some embodiments of a compound of Formula (II), or a pharmaceutically acceptable salt or solvate thereof, Y is —C(R$^5$)(R$^{5a}$)— and R$^5$ and R$^{5a}$ are hydrogen. In some embodiments of a compound of Formula (II), or a pharmaceutically acceptable salt or solvate thereof, Y is —C(R$^5$)(R$^{5a}$)— and R$^5$ and R$^{5a}$ are C$_{1-6}$alkyl. In some embodiments of a compound of Formula (II), or a pharmaceutically acceptable salt or solvate thereof, Y is —C(R$^5$)(R$^{5a}$)—, R$^5$ is hydrogen, and R$^{5a}$ is C$_{1-6}$alkyl.

In some embodiments of a compound of Formula (II), or a pharmaceutically acceptable salt or solvate thereof, each R$^2$ is independently selected from hydrogen and C$_{1-6}$alkyl. In some embodiments of a compound of Formula (II), or a pharmaceutically acceptable salt or solvate thereof, each R$^2$ is hydrogen. In some embodiments of a compound of Formula (II), or a pharmaceutically acceptable salt or solvate thereof, each R$^3$ is independently selected from hydrogen and C$_{1-6}$alkyl. In some embodiments of a compound of Formula (II), or a pharmaceutically acceptable salt or solvate thereof, each R$^3$ is hydrogen. In some embodiments of a compound of Formula (II), or a pharmaceutically acceptable salt or solvate thereof, each R$^2$ and R$^3$, together with the carbon to which they are attached, form a C$_{3-6}$cycloalkyl. In some embodiments of a compound of Formula (II), or a pharmaceutically acceptable salt or solvate thereof, each R$^2$ and R$^3$, together with the carbon to which they are attached, form a cyclopropyl ring. In some embodiments of a compound of Formula (II), or a pharmaceutically acceptable salt or solvate thereof, each R$^2$ and R$^3$, together with the carbon to which they are attached, form a cyclobutyl ring. In some embodiments of a compound of Formula (II), or a pharmaceutically acceptable salt or solvate thereof, each R$^2$ and R$^3$, together with the carbon to which they are attached, form a cyclopentyl ring. In some embodiments of a compound of Formula (II), or a pharmaceutically acceptable salt or solvate thereof, each R$^2$ and R$^3$, together with the carbon to which they are attached, form a cyclohexyl ring.

In some embodiments of a compound of Formula (II), or a pharmaceutically acceptable salt or solvate thereof, n is 1, 2, or 3. In some embodiments of a compound of Formula (II), or a pharmaceutically acceptable salt or solvate thereof, n is 1. In some embodiments of a compound of Formula (II), or a pharmaceutically acceptable salt or solvate thereof, n is 2. In some embodiments of a compound of Formula (II), or a pharmaceutically acceptable salt or solvate thereof, n is 3. In some embodiments of a compound of Formula (II), or a pharmaceutically acceptable salt or solvate thereof, n is 4. In some embodiments of a compound of Formula (II), or a pharmaceutically acceptable salt or solvate thereof, n is 5. In some embodiments of a compound of Formula (II), or a pharmaceutically acceptable salt or solvate thereof, n is 6.

In some embodiments of a compound of Formula (II), or a pharmaceutically acceptable salt or solvate thereof, Z$^1$ is CR$^7$. In some embodiments of a compound of Formula (II), or a pharmaceutically acceptable salt or solvate thereof, Z$^1$ is CR$^7$ and R$^7$ is hydrogen, halogen, —CN, C$_{1-6}$alkyl, C$_{1-6}$haloalkyl, —OR$^{10}$, or —N(R$^{10}$)(R$^{11}$). In some embodiments of a compound of Formula (II), or a pharmaceutically acceptable salt or solvate thereof, Z$^1$ is CR$^7$ and R$^7$ is hydrogen, halogen, C$_{1-6}$alkyl, or C$_{1-6}$haloalkyl. In some embodiments of a compound of Formula (II), or a pharmaceutically acceptable salt or solvate thereof, Z$^1$ is CR$^7$ and R$^7$ is hydrogen.

In some embodiments of a compound of Formula (II), or a pharmaceutically acceptable salt or solvate thereof, Z$^1$ is N.

In some embodiments of a compound of Formula (II), or a pharmaceutically acceptable salt or solvate thereof, Z$^2$ is CR$^9$. In some embodiments of a compound of Formula (II), or a pharmaceutically acceptable salt or solvate thereof, Z$^2$ is CR$^9$ and R$^9$ is hydrogen, halogen, —CN, C$_{1-6}$alkyl, C$_{1-6}$haloalkyl, —OR$^{10}$, or —N(R$^{10}$)(R$^{11}$). In some embodiments of a compound of Formula (II), or a pharmaceutically acceptable salt or solvate thereof, Z$^2$ is CR$^9$ and R$^9$ is hydrogen, halogen, C$_{1-6}$alkyl, or C$_{1-6}$haloalkyl. In some embodiments of a compound of Formula (II), or a pharmaceutically acceptable salt or solvate thereof, Z$^2$ is CR$^9$ and R$^9$ is hydrogen.

In some embodiments of a compound of Formula (II), or a pharmaceutically acceptable salt or solvate thereof, Z$^2$ is N.

In some embodiments of a compound of Formula (II), or a pharmaceutically acceptable salt or solvate thereof, Z$^4$ is CR$^{6a}$. In some embodiments of a compound of Formula (II), or a pharmaceutically acceptable salt or solvate thereof, Z$^4$ is CR$^{6a}$ and R$^{6a}$ is selected from hydrogen, halogen, —CN, C$_{1-6}$alkyl, C$_{1-6}$haloalkyl, —OR$^{10}$, and —N(R$^{10}$)(R$^{11}$). In some embodiments of a compound of Formula (II), or a pharmaceutically acceptable salt or solvate thereof, Z$^4$ is CR$^{6a}$ and R$^{6a}$ is selected from hydrogen and —OR$^{10}$ and R$^{10}$ is C$_{1-6}$alkyl. In some embodiments of a compound of Formula (II), or a pharmaceutically acceptable salt or solvate thereof, Z$^4$ is CR$^{6a}$ and R$^{6a}$ is hydrogen.

In some embodiments of a compound of Formula (II), or a pharmaceutically acceptable salt or solvate thereof, Z$^4$ is N.

In some embodiments of a compound of Formula (II), or a pharmaceutically acceptable salt or solvate thereof, (A)

is C$_{1-10}$heteroaryl. In some embodiments of a compound of Formula (II), or a pharmaceutically acceptable salt or solvate thereof, (A)

is C$_{1-10}$heteroaryl selected from pyridyl, pyrimidyl, pyrazinyl, and pyridazinyl. In some embodiments of a compound of Formula (II), or a pharmaceutically acceptable salt or solvate thereof, (A)

is 5 or 6 membered heteroaryl. In some embodiments of a compound of Formula (II), or a pharmaceutically acceptable salt or solvate thereof, (A)

is 5 membered heteroaryl. In some embodiments of a compound of Formula (II), or a pharmaceutically acceptable salt or solvate thereof, (A)

is 6 membered heteroaryl. In some embodiments of a compound of Formula (II), or a pharmaceutically acceptable salt or solvate thereof, (A)

is pyridyl. In some embodiments of a compound of Formula (II), or a pharmaceutically acceptable salt or solvate thereof, (A)

is pyrimidyl. In some embodiments of a compound of Formula (II), or a pharmaceutically acceptable salt or solvate thereof, (A)

is pyrazinyl. In some embodiments of a compound of Formula (II), or a pharmaceutically acceptable salt or solvate thereof, (A)

is pyridazinyl.

In some embodiments of a compound of Formula (II), or a pharmaceutically acceptable salt or solvate thereof, (A)

is $C_{6-10}$aryl. In some embodiments of a compound of Formula (II), or a pharmaceutically acceptable salt or solvate thereof, (A)

is phenyl.

In some embodiments of a compound of Formula (II), or a pharmaceutically acceptable salt or solvate thereof, (A)

is $C_{2-9}$heterocycloalkyl.

In some embodiments of a compound of Formula (II), or a pharmaceutically acceptable salt or solvate thereof, (A)

is $C_{3-6}$cycloalkyl.

In some embodiments of a compound of Formula (II), or a pharmaceutically acceptable salt or solvate thereof, each $R^{14}$ is independently selected from halogen, $C_{1-6}$alkyl, $C_{1-6}$haloalkyl, —$OR^{10}$, and —$N(R^{10})(R^{11})$. In some embodiments of a compound of Formula (II), or a pharmaceutically acceptable salt or solvate thereof, each $R^{14}$ is independently selected from halogen and $C_{1-6}$alkyl. In some embodiments of a compound of Formula (II), or a pharmaceutically acceptable salt or solvate thereof, each $R^{14}$ is independently selected from halogen.

In some embodiments of a compound of Formula (II), or a pharmaceutically acceptable salt or solvate thereof, m is 0, 1, or 2. In some embodiments of a compound of Formula (II), or a pharmaceutically acceptable salt or solvate thereof, m is 0 or 1. In some embodiments of a compound of Formula (II), or a pharmaceutically acceptable salt or solvate thereof, m is 0. In some embodiments of a compound of Formula (II), or a pharmaceutically acceptable salt or solvate thereof, m is 1. In some embodiments of a compound of Formula (II), or a pharmaceutically acceptable salt or solvate thereof, m is 2. In some embodiments of a compound of Formula (II), or a pharmaceutically acceptable salt or solvate thereof, m is 3.

In some embodiments of a compound of Formula (II), or a pharmaceutically acceptable salt or solvate thereof, $R^8$ is hydrogen, halogen, —CN, $C_{1-6}$alkyl, $C_{1-6}$haloalkyl, —$OR^{10}$, or $C_{3-6}$cycloalkyl. In some embodiments of a compound of Formula (II), or a pharmaceutically acceptable salt or solvate thereof, $R^8$ is hydrogen, halogen, or $C_{1-6}$haloalkyl. In some embodiments of a compound of Formula (II), or a pharmaceutically acceptable salt or solvate thereof, $R^8$ is hydrogen. In some embodiments of a compound of Formula (II), or a pharmaceutically acceptable salt or solvate thereof, $R^8$ is halogen. In some embodiments of a compound of Formula (II), or a pharmaceutically acceptable salt or solvate thereof, $R^8$ is $C_{1-6}$haloalkyl. In some embodiments of a compound of Formula (II), or a pharmaceutically acceptable salt or solvate thereof, $R^8$ is —$CF_3$. In some embodiments of a compound of Formula (II), or a pharmaceutically acceptable salt or solvate thereof, $R^8$ is $C_{1-6}$alkyl. In some embodiments of a compound of Formula (II), or a pharmaceutically acceptable salt or solvate thereof, $R^8$ is —$CH_3$. In some embodiments of a compound of Formula (II), or a pharmaceutically acceptable salt or solvate thereof, $R^8$ is $C_{3-6}$cycloalkyl. In some embodiments of a compound of Formula (II), or a pharmaceutically acceptable salt or solvate thereof, $R^8$ is cyclopropyl. In some embodiments of a compound of Formula (II), or a pharmaceutically acceptable salt or solvate thereof, $R^8$ is —CN.

In some embodiments of a compound of Formula (II), or a pharmaceutically acceptable salt or solvate thereof, $R^{1b}$ is hydrogen.

In some embodiments of a compound of Formula (II), or a pharmaceutically acceptable salt or solvate thereof, $R^{1b}$ is hydrogen.

In some embodiments of a compound of Formula (II), or a pharmaceutically acceptable salt or solvate thereof, $R^1$ is selected from hydrogen, $C_{1-6}$alkyl, $C_{1-6}$haloalkyl, $C_{3-6}$cycloalkyl, $C_{2-9}$ heterocycloalkyl, and $C_{1-9}$heteroaryl, wherein $C_{1-6}$alkyl, $C_{3-6}$cycloalkyl, $C_{2-9}$heterocycloalkyl, and $C_{1-9}$heteroaryl are optionally substituted with one, two, or three groups selected from $R^{15a}$;

In some embodiments of a compound of Formula (II), or a pharmaceutically acceptable salt or solvate thereof, $R^1$ is hydrogen.

In some embodiments of a compound of Formula (II), or a pharmaceutically acceptable salt or solvate thereof, $R^1$ is $C_{1-6}$alkyl optionally substituted with one, two, or three groups selected from $R^{15a}$. In some embodiments of a compound of Formula (II), or a pharmaceutically acceptable salt or solvate thereof, $R^1$ is $C_{1-6}$alkyl optionally substituted with one, two, or three groups selected from $C_{2-9}$ heterocycloalkyl, $C_{1-9}$heteroaryl, $-OR^{10}$, and $-N(R^{10})(R^{11})$. In some embodiments of a compound of Formula (II), or a pharmaceutically acceptable salt or solvate thereof, $R^1$ is $C_{1-6}$alkyl substituted with one group selected from $C_{2-9}$heterocycloalkyl, $C_{1-9}$heteroaryl, $-OR^{10}$, and $-N(R^{10})(R^{11})$. In some embodiments of a compound of Formula (II), or a pharmaceutically acceptable salt or solvate thereof, $R^1$ is $C_{1-6}$alkyl substituted with one group selected from $C_{2-9}$heterocycloalkyl, $C_{1-9}$heteroaryl, $-OR^{10}$, and $-N(R^{10})(R^{11})$ and $R^{10}$ and $R^{11}$ are independently selected from hydrogen and $C_{1-6}$alkyl. In some embodiments of a compound of Formula (II), or a pharmaceutically acceptable salt or solvate thereof, $R^1$ is unsubstituted $C_{1-6}$alkyl.

In some embodiments of a compound of Formula (II), or a pharmaceutically acceptable salt or solvate thereof, $R^1$ is $C_{3-6}$cycloalkyl optionally substituted with one, two, or three groups selected from $R^{15a}$. In some embodiments of a compound of Formula (II), or a pharmaceutically acceptable salt or solvate thereof, $R^1$ is $C_{3-6}$cycloalkyl substituted with one, two, or three groups selected from $C_{1-6}$alkyl, $-OR^{10}$, and $-N(R^{10})(R^{11})$. In some embodiments of a compound of Formula (II), or a pharmaceutically acceptable salt or solvate thereof, $R^1$ is $C_{3-6}$cycloalkyl substituted with one group selected from $-OR^{10}$ and $-N(R^{10})(R^{11})$ $R^{10}$ and $R^{11}$ are independently selected from hydrogen and $C_{1-6}$alkyl. In some embodiments of a compound of Formula (II), or a pharmaceutically acceptable salt or solvate thereof, $R^1$ is unsubstituted $C_{3-6}$cycloalkyl. In some embodiments of a compound of Formula (II), or a pharmaceutically acceptable salt or solvate thereof, $R^1$ is unsubstituted cyclopropyl. In some embodiments of a compound of Formula (II), or a pharmaceutically acceptable salt or solvate thereof, $R^1$ is unsubstituted cyclobutyl.

In some embodiments of a compound of Formula (II), or a pharmaceutically acceptable salt or solvate thereof, $R^1$ is $C_{1-6}$haloalkyl.

In some embodiments of a compound of Formula (II), or a pharmaceutically acceptable salt or solvate thereof, $R^1$ is $C_{2-9}$heterocycloalkyl optionally substituted with one, two, or three groups selected from $R^{15a}$. In some embodiments of a compound of Formula (II), or a pharmaceutically acceptable salt or solvate thereof, $R^1$ is $C_{2-9}$heterocycloalkyl optionally substituted with one, two, or three groups selected from $C_{1-6}$alkyl, $-OR^{10}$, and $-N(R^{10})(R^{11})$. In some embodiments of a compound of Formula (II), or a pharmaceutically acceptable salt or solvate thereof, $R^1$ is unsubstituted $C_{2-9}$ heterocycloalkyl.

In some embodiments of a compound of Formula (II), or a pharmaceutically acceptable salt or solvate thereof, $R^1$ is $C_{1-9}$heteroaryl optionally substituted from $R^{15a}$. In some embodiments of a compound of Formula (II), or a pharmaceutically acceptable salt or solvate thereof, $R^1$ is $C_{1-9}$heteroaryl optionally substituted with one, two, or three groups selected from $C_{1-6}$alkyl, $-OR^{10}$, and $-N(R^{10})(R^{11})$. In some embodiments of a compound of Formula (II), or a pharmaceutically acceptable salt or solvate thereof, $R^1$ is unsubstituted $C_{1-9}$heteroaryl.

In some embodiments disclosed herein is a compound of Formula (IIa), or a pharmaceutically acceptable salt or solvate thereof:

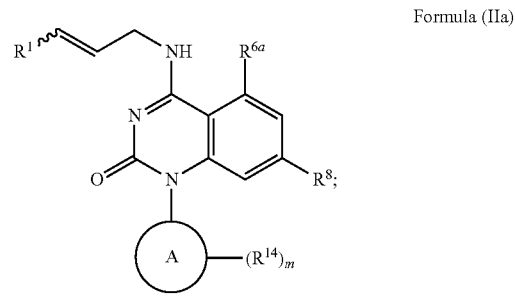

Formula (IIa)

wherein:

is selected from $C_{3-6}$cycloalkyl, $C_{2-9}$heterocycloalkyl, $C_{6-10}$aryl, and $C_{1-10}$heteroaryl;

$R^1$ is selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $-N=S(=O)(R^{13})_2$, $-S(=O)(=NH)N(R^{10})(R^{11})$, $-S(=O)(=NH)C(R^{10})(R^{11})$, $-S(=O)(=NR^{13})R^{13}$, $-CH_2C(O)N(R^{10})(R^{11})$, $-CH_2N(R^{12})C(O)R^{13}$, $-CH_2S(O)_2R^{13}$, $-CH_2S(O)_2N(R^{10})(R^{11})$, $-Si(C_{1-6}alkyl)_3$, and $-P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15a}$;

$R^{6a}$ is selected from hydrogen, halogen, $-CN$, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $-N=S(=O)(R^{13})_2$, $-S(=O)(=NH)N(R^{10})(R^{11})$, $-S(=O)(=NH)C(R^{10})(R^{11})$, $-S(=O)(=NR^{13})R^{13}$, $-CH_2C(O)N(R^{10})(R^{11})$, $-CH_2N(R^{12})C(O)R^{13}$, $-CH_2S(O)_2R^{13}$, $-CH_2S(O)_2N(R^{10})(R^{11})$, $-Si(C_{1-6}alkyl)_3$, and $-P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, and $C_{1-9}$heteroaryl are optionally substituted with one, two, or three groups selected from $R^{15c}$;

$R^{10}$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15c}$;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl; or $R^{10}$ and $R^{11}$, together with the nitrogen to which they are attached, form a $C_{2-9}$heterocycloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$ heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{14}$ is independently selected from halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15a}$;

each $R^{15a}$, $R^{15c}$, and $R^{15d}$ are each independently selected from halogen, oxo, —CN, $C_{1-6}$alkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$, —$Si(C_{1-6}alkyl)_3$, and —$P(O)(R^{10})_2$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, —$N=S(=O)(R^{13})_2$, —$S(=O)(=NH)N(R^{10})(R^{11})$, —$S(=O)(=NH)C(R^{10})(R^{11})$, —$S(=O)(=NR^{13})R^{13}$, —$CH_2C(O)N(R^{10})(R^{11})$, —$CH_2N(R^{12})C(O)R^{13}$, —$CH_2S(O)_2R^{13}$, —$CH_2S(O)_2N(R^{10})(R^{11})$ and —$P(O)(R^{10})_2$; and m is 0, 1, 2, 3, 4, or 5.

In some embodiments of a compound of Formula (IIa), or a pharmaceutically acceptable salt or solvate thereof, $R^{6a}$ is selected from hydrogen, halogen, —CN, $C_{1-6}$alkyl, $C_{1-6}$haloalkyl, —$OR^{10}$, and —$N(R^{10})(R^{11})$. In some embodiments of a compound of Formula (IIa), or a pharmaceutically acceptable salt or solvate thereof, $R^{6a}$ is selected from hydrogen and —$OR^{10}$ and $R^{10}$ is $C_{1-6}$alkyl. In some embodiments of a compound of Formula (IIa), or a pharmaceutically acceptable salt or solvate thereof, $R^{6a}$ is hydrogen.

In some embodiments of a compound of Formula (IIa), or a pharmaceutically acceptable

salt or solvate thereof, is $C_{1-10}$heteroaryl. In some embodiments of a compound of Formula (IIa), or a pharmaceutically acceptable salt or solvate thereof,

is $C_{1-10}$heteroaryl selected from pyridyl, pyrimidyl, pyrazinyl, and pyridazinyl. In some embodiments of a compound of Formula (IIa), or a pharmaceutically acceptable salt or solvate thereof,

is pyridyl. In some embodiments of a compound of Formula (IIa), or a pharmaceutically acceptable salt or solvate thereof,

is pyrimidyl. In some embodiments of a compound of Formula (IIa), or a pharmaceutically acceptable salt or solvate thereof,

is pyrazinyl. In some embodiments of a compound of Formula (IIa), or a pharmaceutically acceptable salt or solvate thereof,

is pyridazinyl.

In some embodiments of a compound of Formula (IIa), or a pharmaceutically acceptable salt or solvate thereof,

is $C_{6-10}$aryl. In some embodiments of a compound of Formula (IIa), or a pharmaceutically acceptable salt or solvate thereof,

is phenyl.

In some embodiments of a compound of Formula (IIa), or a pharmaceutically acceptable salt or solvate thereof,

is $C_{2-9}$heterocycloalkyl.

In some embodiments of a compound of Formula (IIa), or a pharmaceutically acceptable salt or solvate thereof,

is $C_{3-6}$cycloalkyl.

In some embodiments of a compound of Formula (IIa), or a pharmaceutically acceptable salt or solvate thereof, each $R^{14}$ is independently selected from halogen, $C_{1-6}$alkyl, $C_{1-6}$haloalkyl, —$OR^{10}$, and —$N(R^{10})(R^{11})$. In some embodiments of a compound of Formula (IIa), or a pharmaceutically acceptable salt or solvate thereof, each $R^{14}$ is independently selected from halogen and $C_{1-6}$alkyl. In some embodiments of a compound of Formula (IIa), or a pharmaceutically acceptable salt or solvate thereof, each $R^{14}$ is independently selected from halogen.

In some embodiments of a compound of Formula (IIa), or a pharmaceutically acceptable salt or solvate thereof, m is 0, 1, or 2. In some embodiments of a compound of Formula (IIa), or a pharmaceutically acceptable salt or solvate thereof, m is 0 or 1. In some embodiments of a compound of Formula (IIa), or a pharmaceutically acceptable salt or solvate thereof, m is 0. In some embodiments of a compound of Formula (IIa), or a pharmaceutically acceptable salt or solvate thereof, m is 1. In some embodiments of a compound of Formula (IIa), or a pharmaceutically acceptable salt or solvate thereof, m is 2. In some embodiments of a compound of Formula (IIa), or a pharmaceutically acceptable salt or solvate thereof, m is 3.

In some embodiments of a compound of Formula (IIa), or a pharmaceutically acceptable salt or solvate thereof, $R^8$ is hydrogen, halogen, —CN, $C_{1-6}$alkyl, $C_{1-6}$haloalkyl, —$OR^{10}$, or $C_{3-6}$cycloalkyl. In some embodiments of a compound of Formula (IIa), or a pharmaceutically acceptable salt or solvate thereof, $R^8$ is hydrogen, halogen, or $C_{1-6}$haloalkyl. In some embodiments of a compound of Formula (IIa), or a pharmaceutically acceptable salt or solvate thereof, $R^8$ is hydrogen. In some embodiments of a compound of Formula (IIa), or a pharmaceutically acceptable salt or solvate thereof, $R^8$ is halogen. In some embodiments of a compound of Formula (IIa), or a pharmaceutically acceptable salt or solvate thereof, $R^8$ is $C_{1-6}$haloalkyl. In some embodiments of a compound of Formula (IIa), or a pharmaceutically acceptable salt or solvate thereof, $R^8$ is —$CF_3$. In some embodiments of a compound of Formula (IIa), or a pharmaceutically acceptable salt or solvate thereof, $R^8$ is $C_{1-6}$alkyl. In some embodiments of a compound of Formula (IIa), or a pharmaceutically acceptable salt or solvate thereof, $R^8$ is —$CH_3$. In some embodiments of a compound of Formula (IIa), or a pharmaceutically acceptable salt or solvate thereof, $R^8$ is $C_{3-6}$cycloalkyl. In some embodiments of a compound of Formula (IIa), or a pharmaceutically acceptable salt or solvate thereof, $R^8$ is cyclopropyl. In some embodiments of a compound of Formula (IIa), or a pharmaceutically acceptable salt or solvate thereof, $R^8$ is —CN.

In some embodiments of a compound of Formula (IIa), or a pharmaceutically acceptable salt or solvate thereof, $R^1$ is selected from hydrogen, $C_{1-6}$alkyl, $C_{1-6}$haloalkyl, $C_{3-6}$cycloalkyl, $C_{2-9}$ heterocycloalkyl, and $C_{1-9}$heteroaryl, wherein $C_{1-6}$alkyl, $C_{3-6}$cycloalkyl, $C_{2-9}$heterocycloalkyl, and $C_{1-9}$heteroaryl are optionally substituted with one, two, or three groups selected from $R^{15a}$;

In some embodiments of a compound of Formula (IIa), or a pharmaceutically acceptable salt or solvate thereof, $R^1$ is hydrogen.

In some embodiments of a compound of Formula (IIa), or a pharmaceutically acceptable salt or solvate thereof, $R^1$ is $C_{1-6}$alkyl optionally substituted with one, two, or three groups selected from $R^{15a}$. In some embodiments of a compound of Formula (IIa), or a pharmaceutically acceptable salt or solvate thereof, $R^1$ is $C_{1-6}$alkyl optionally substituted with one, two, or three groups selected from $C_{2-9}$heterocycloalkyl, $C_{1-9}$heteroaryl, —$OR^{10}$, and —$N(R^{10})(R^{11})$. In some embodiments of a compound of Formula (IIa), or a pharmaceutically acceptable salt or solvate thereof, $R^1$ is $C_{1-6}$alkyl substituted with one group selected from $C_{2-9}$heterocycloalkyl, C$_{1-9}$heteroaryl, —OR$^{10}$, and —N(R$^{10}$)(R$^{11}$). In some embodiments of a compound of Formula (IIa), or a pharmaceutically acceptable salt or solvate thereof, R$^1$ is C$_{1-6}$alkyl substituted with one group selected from C$_{2-9}$heterocycloalkyl, C$_{1-9}$heteroaryl, —OR$^{10}$, and —N(R$^{10}$)(R$^{11}$) and R$^{10}$ and R$^{11}$ are independently selected from hydrogen and C$_{1-6}$alkyl. In some embodiments of a compound of Formula (IIa), or a pharmaceutically acceptable salt or solvate thereof, R$^1$ is unsubstituted C$_{1-6}$alkyl.

In some embodiments of a compound of Formula (IIa), or a pharmaceutically acceptable salt or solvate thereof, R$^1$ is C$_{3-6}$cycloalkyl optionally substituted with one, two, or three groups selected from R$^{15a}$. In some embodiments of a compound of Formula (IIa), or a pharmaceutically acceptable salt or solvate thereof, R$^1$ is C$_{3-6}$cycloalkyl substituted with one, two, or three groups selected from C$_{1-6}$alkyl, —OR$^{10}$, and —N(R$^{10}$)(R$^{11}$). In some embodiments of a compound of Formula (IIa), or a pharmaceutically acceptable salt or solvate thereof, R$^1$ is C$_{3-6}$cycloalkyl substituted with one group selected from —OR$^{10}$ and —N(R$^{10}$)(R$^{11}$) R$^{10}$ and R$^{11}$ are independently selected from hydrogen and C$_{1-6}$alkyl. In some embodiments of a compound of Formula (IIa), or a pharmaceutically acceptable salt or solvate thereof, R$^1$ is unsubstituted C$_{3-6}$cycloalkyl. In some embodiments of a compound of Formula (IIa), or a pharmaceutically acceptable salt or solvate thereof, R$^1$ is unsubstituted cyclopropyl. In some embodiments of a compound of Formula (IIa), or a pharmaceutically acceptable salt or solvate thereof, R$^1$ is unsubstituted cyclobutyl.

In some embodiments of a compound of Formula (IIa), or a pharmaceutically acceptable salt or solvate thereof, R$^1$ is C$_{1-6}$haloalkyl.

In some embodiments of a compound of Formula (IIa), or a pharmaceutically acceptable salt or solvate thereof, R$^1$ is C$_{2-9}$heterocycloalkyl optionally substituted with one, two, or three groups selected from R$^{15a}$. In some embodiments of a compound of Formula (IIa), or a pharmaceutically acceptable salt or solvate thereof, R$^1$ is C$_{2-9}$heterocycloalkyl optionally substituted with one, two, or three groups selected from C$_{1-6}$alkyl, —OR$^{10}$, and —N(R$^{10}$)(R$^{11}$). In some embodiments of a compound of Formula (IIa), or a pharmaceutically acceptable salt or solvate thereof, R$^1$ is unsubstituted C$_{2-9}$ heterocycloalkyl.

In some embodiments of a compound of Formula (IIa), or a pharmaceutically acceptable salt or solvate thereof, R$^1$ is C$_{1-9}$heteroaryl optionally substituted with one, two, or three groups selected from R$^{15a}$. In some embodiments of a compound of Formula (IIa), or a pharmaceutically acceptable salt or solvate thereof, R$^1$ is C$_{1-9}$heteroaryl optionally substituted with one, two, or three groups selected from C$_{1-6}$alkyl, —OR$^{10}$, and —N(R$^{10}$)(R$^{11}$). In some embodiments of a compound of Formula (IIa), or a pharmaceutically acceptable salt or solvate thereof, R$^1$ is unsubstituted C$_{1-9}$heteroaryl.

Any combination of the groups described above for the various variables is contemplated herein. Throughout the specification, groups and substituents thereof are chosen by one skilled in the field to provide stable moieties and compounds.

In some embodiments is a compound, or a pharmaceutically acceptable salt or solvate thereof, selected from a compound found in table 1.

TABLE 1

| Example # | Structure |
|---|---|
| 1 | 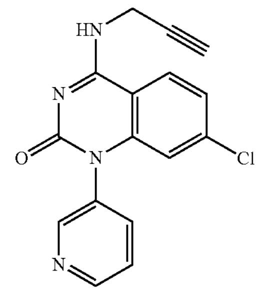 [SMILES: C#CCNc1nc(=O)n(-c2cccnc2)c2cc(Cl)ccc12] |
| 2 | 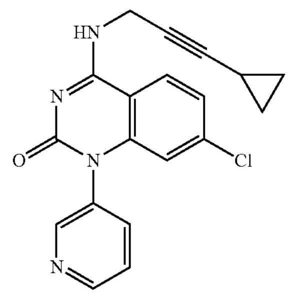 [SMILES: O=c1nc(NCC#CC2CC2)c2ccc(Cl)cc2n1-c1cccnc1] |
| 3 | 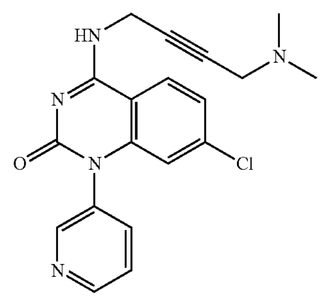 [SMILES: CN(C)CC#CCNc1nc(=O)n(-c2cccnc2)c2cc(Cl)ccc12] |
| 4 | 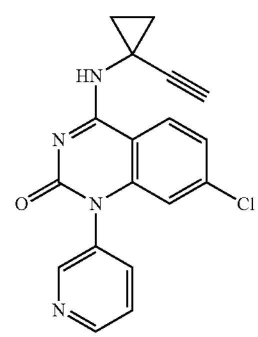 [SMILES: C#CC1(Nc2nc(=O)n(-c3cccnc3)c3cc(Cl)ccc23)CC1] |
| 5 | 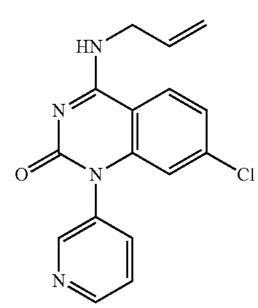 [SMILES: C=CCNc1nc(=O)n(-c2cccnc2)c2cc(Cl)ccc12] |

TABLE 1-continued

| Example # | Structure |
|---|---|
| 6 | 4-(pent-4-yn-1-ylamino)-7-chloro-1-(pyridin-3-yl)quinazolin-2(1H)-one |
| 7 | 4-(prop-2-yn-1-ylamino)-7-(trifluoromethyl)-1-(pyridin-3-yl)quinazolin-2(1H)-one |
| 8 | 4-(but-3-yn-1-ylamino)-7-chloro-1-(2-chlorophenyl)quinazolin-2(1H)-one |
| 9 | 4-(prop-2-yn-1-yloxy)-7-chloro-1-(pyridin-3-yl)quinazolin-2(1H)-one |
| 10 | 4-(prop-2-yn-1-ylamino)-7-chloro-1-(2-chlorophenyl)quinazolin-2(1H)-one |
| 11 | 4-(3-ethynylpiperidin-1-yl)-7-chloro-1-(2-chlorophenyl)quinazolin-2(1H)-one |
| 12 | 4-(3-ethynyl-3-hydroxyazetidin-1-yl)-7-chloro-1-(2-chlorophenyl)quinazolin-2(1H)-one |
| 13 | 4-(4-ethynylpiperidin-1-yl)-7-chloro-1-(2-chlorophenyl)quinazolin-2(1H)-one |
| 14 | 4-((4-morpholinobut-2-yn-1-yl)amino)-7-(trifluoromethyl)-1-(pyridin-3-yl)quinazolin-2(1H)-one |

TABLE 1-continued
| Example # | Structure |
|---|---|
| 15 | 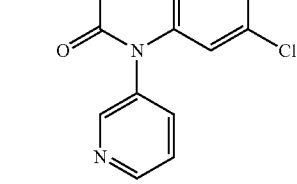 |
| 16 | 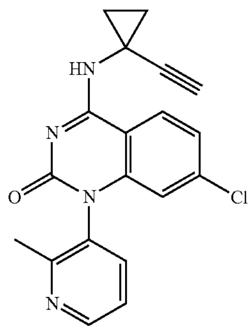 [SMILES: C#CC1(Nc2nc(=O)n(-c3cccnc3C)c3cc(Cl)ccc23)CC1] |
| 17 | 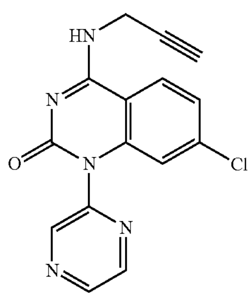 [SMILES: C#CCNc1nc(=O)n(-c2cnccn2)c2cc(Cl)ccc12] |
| 18 | 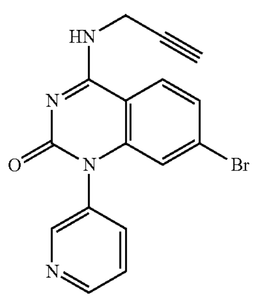 [SMILES: C#CCNc1nc(=O)n(-c2cccnc2)c2cc(Br)ccc12] |
| 19 | 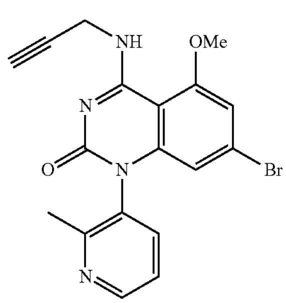 [SMILES: C#CCNc1nc(=O)n(-c2cccnc2C)c2cc(Br)cc(OC)c12] |
TABLE 1-continued
| Example # | Structure |
|---|---|
| 20 | 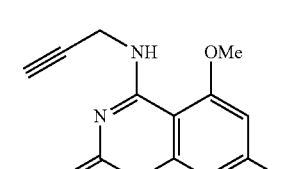 |
| 21 | 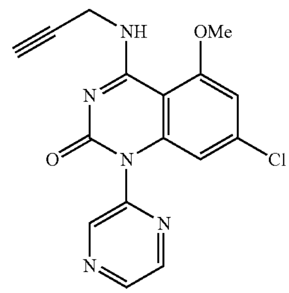 [SMILES: C#CCNc1nc(=O)n(-c2cnccn2)c2cc(Cl)cc(OC)c12] |
| 22 | 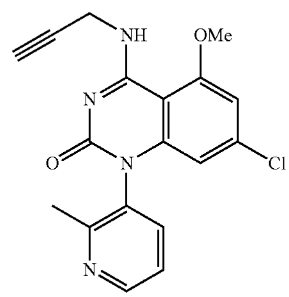 [SMILES: C#CCNc1nc(=O)n(-c2cccnc2C)c2cc(Cl)cc(OC)c12] |
| 23 | 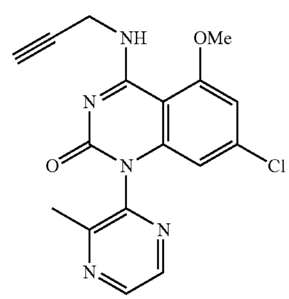 [SMILES: C#CCNc1nc(=O)n(-c2nccnc2C)c2cc(Cl)cc(OC)c12] |
| 24 | 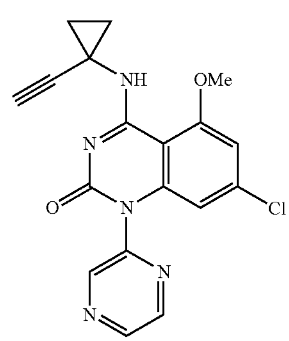 [SMILES: C#CC1(Nc2nc(=O)n(-c3cnccn3)c3cc(Cl)cc(OC)c23)CC1] |

TABLE 1-continued
| Example # | Structure |
|---|---|
| 25 | 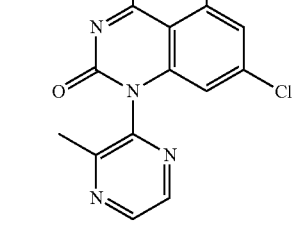 |
| 26 | 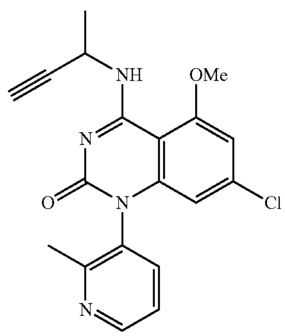 [SMILES: C#CC(C)Nc1nc(=O)n(-c2cccnc2C)c2cc(Cl)cc(OC)c12] |
| 27 | 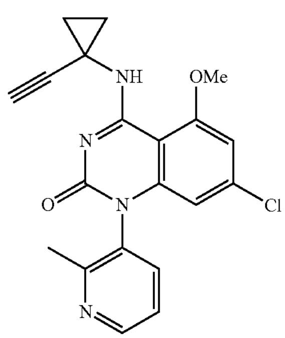 [SMILES: C#CC1(Nc2nc(=O)n(-c3cccnc3C)c3cc(Cl)cc(OC)c23)CC1] |
| 28 | 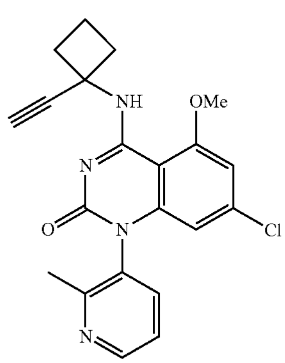 [SMILES: C#CC1(Nc2nc(=O)n(-c3cccnc3C)c3cc(Cl)cc(OC)c23)CCC1] |
| 29 | 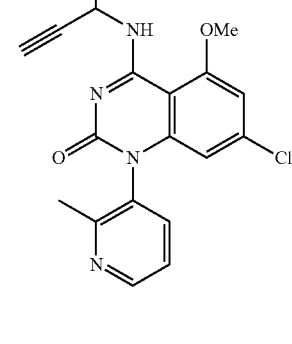 |
| 30 | 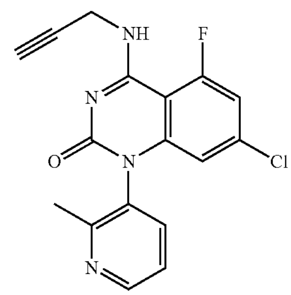 [SMILES: C#CCNc1nc(=O)n(-c2cccnc2C)c2cc(Cl)cc(F)c12] |
| 31 | 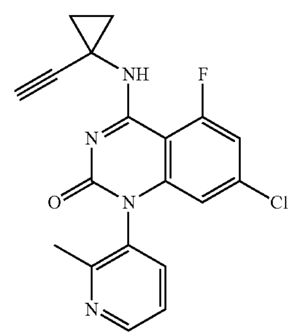 [SMILES: C#CC1(Nc2nc(=O)n(-c3cccnc3C)c3cc(Cl)cc(F)c23)CC1] |
| 32 | 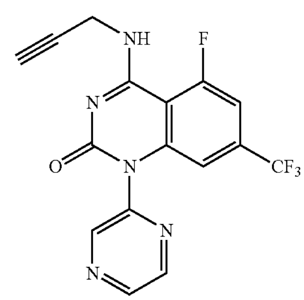 [SMILES: C#CCNc1nc(=O)n(-c2cnccn2)c2cc(C(F)(F)F)cc(F)c12] |
| 33 | 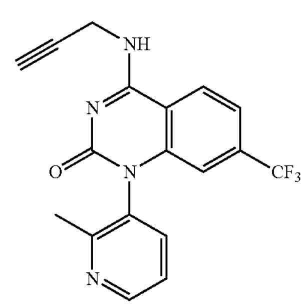 [SMILES: C#CCNc1nc(=O)n(-c2cccnc2C)c2cc(C(F)(F)F)ccc12] |

TABLE 1-continued

| Example # | Structure |
|---|---|
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |

TABLE 1-continued
| Example # | Structure |
|---|---|
| 43 | 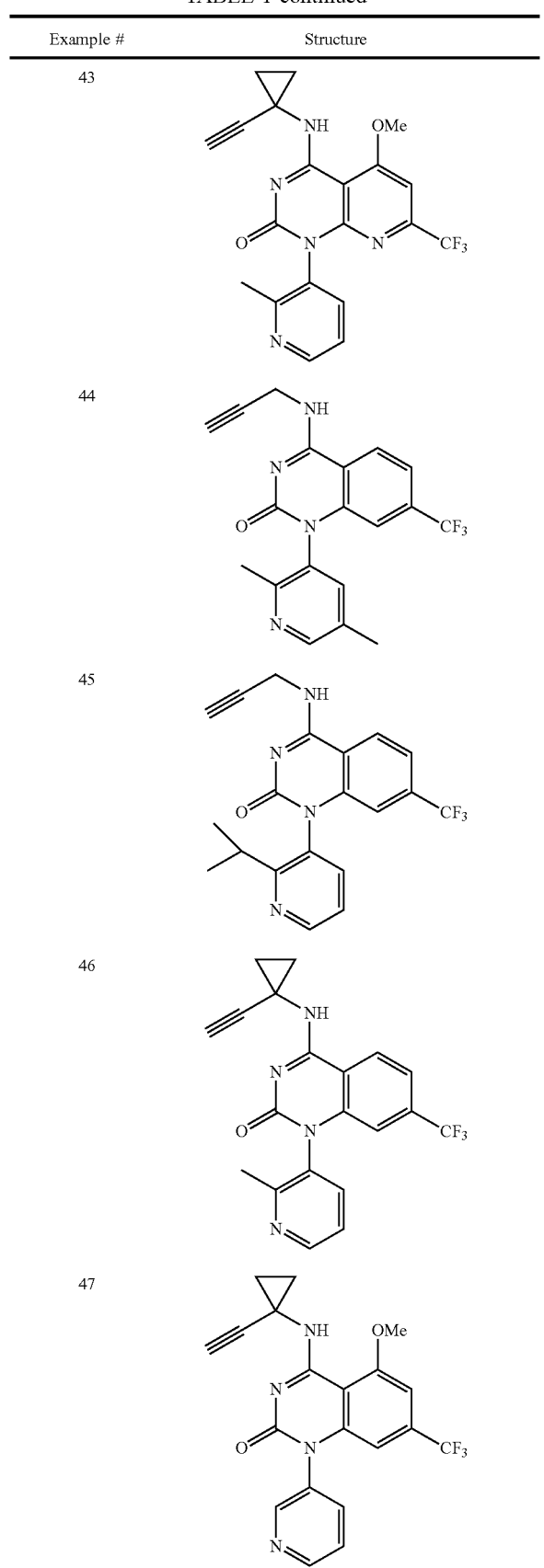 |
| 44 | 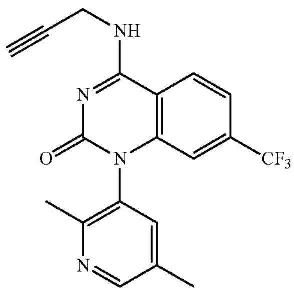 [SMILES: C#CCNc1nc(=O)n(-c2cc(C)cnc2C)c2cc(C(F)(F)F)ccc12] |
| 45 | 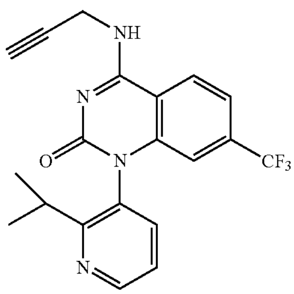 [SMILES: C#CCNc1nc(=O)n(-c2cccnc2C(C)C)c2cc(C(F)(F)F)ccc12] |
| 46 | 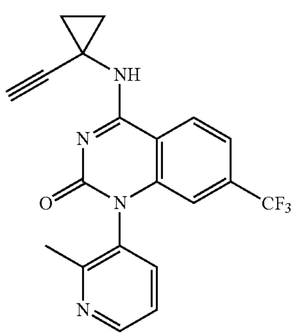 [SMILES: C#CC1(Nc2nc(=O)n(-c3cccnc3C)c3cc(C(F)(F)F)ccc23)CC1] |
| 47 | 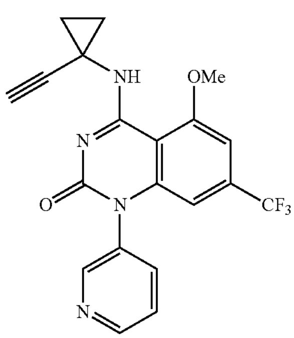 [SMILES: C#CC1(Nc2nc(=O)n(-c3cccnc3)c3cc(C(F)(F)F)cc(OC)c23)CC1] |
TABLE 1-continued
| Example # | Structure |
|---|---|
| 48 | 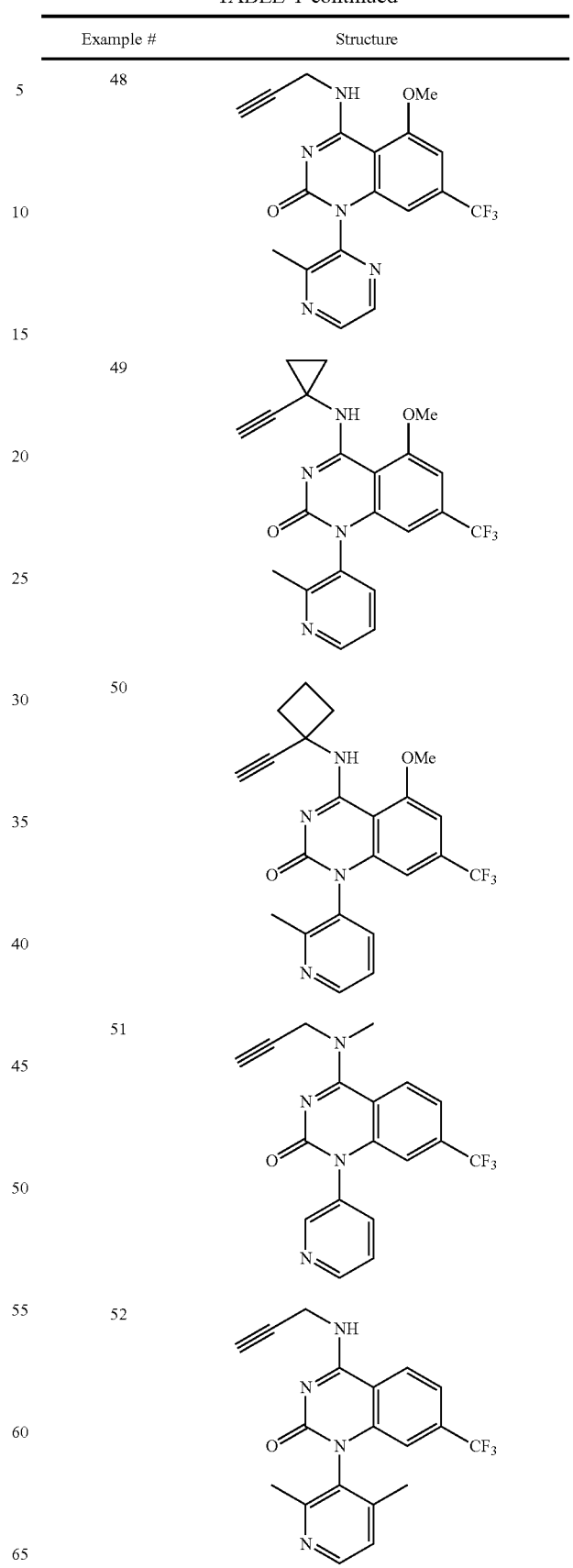 |
| 49 | 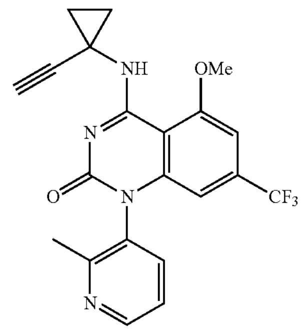 [SMILES: C#CC1(Nc2nc(=O)n(-c3cccnc3C)c3cc(C(F)(F)F)cc(OC)c23)CC1] |
| 50 | 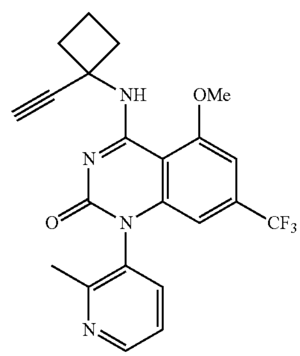 [SMILES: C#CC1(Nc2nc(=O)n(-c3cccnc3C)c3cc(C(F)(F)F)cc(OC)c23)CCC1] |
| 51 | 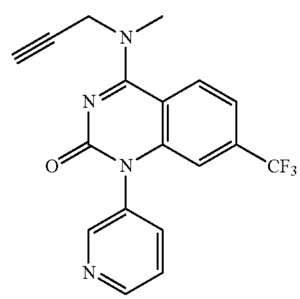 [SMILES: C#CCN(C)c1nc(=O)n(-c2cccnc2)c2cc(C(F)(F)F)ccc12] |
| 52 | 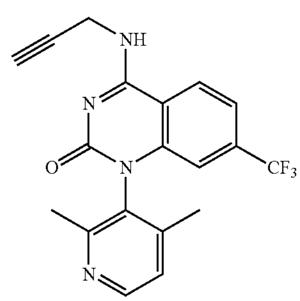 [SMILES: C#CCNc1nc(=O)n(-c2c(C)ccnc2C)c2cc(C(F)(F)F)ccc12] |

TABLE 1-continued

| Example # | Structure |
|---|---|
| 53 | (structure) |
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |

TABLE 1-continued

| Example # | Structure |
|---|---|
| 63 | (4-(prop-2-yn-1-ylamino)-7-(trifluoromethyl)pyrido[2,3-d]pyrimidin-2(1H)-one, N1-pyridazin-3-yl) |
| 64 | (4-(but-3-yn-2-ylamino)-7-(trifluoromethyl)quinazolin-2(1H)-one, N1-pyridin-3-yl) |
| 65 | (4-(but-3-yn-2-ylamino)-7-chloro-5-methoxyquinazolin-2(1H)-one, N1-pyridin-3-yl) |
| 66 | (4-((1-ethynylcyclopropyl)amino)-7-chloro-5-methoxyquinazolin-2(1H)-one, N1-pyridin-3-yl) |
| 67 | (4-((1-ethynylcyclopropyl)amino)-7-(trifluoromethyl)quinazolin-2(1H)-one, N1-pyridin-3-yl) |
| 68 | (4-((1-ethynylcyclopropyl)amino)-7-(trifluoromethyl)pyrido[2,3-d]pyrimidin-2(1H)-one, N1-pyridin-3-yl) |
| 69 | (4-((1-ethynylcyclopropyl)amino)-7-(trifluoromethyl)quinazolin-2(1H)-one, N1-pyrazin-2-yl) |
| 70 | (4-((1-ethynylcyclopropyl)amino)-7-(trifluoromethyl)pyrido[2,3-d]pyrimidin-2(1H)-one, N1-pyridazin-3-yl) |

TABLE 1-continued

| Example # | Structure |
|---|---|
| 71 | 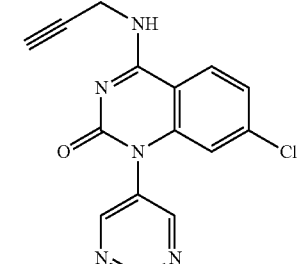 |
| 72 | 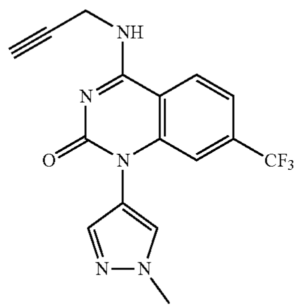 [SMILES: C#CCNc1nc(=O)n(-c2cnn(C)c2)c2cc(C(F)(F)F)ccc12] |
| 73 | 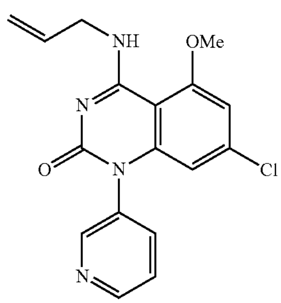 [SMILES: C=CCNc1nc(=O)n(-c2cccnc2)c2cc(Cl)cc(OC)c12] |
| 74 | 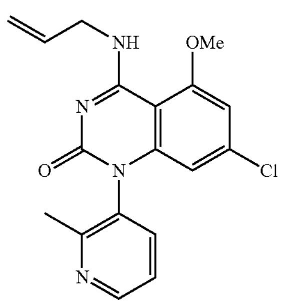 [SMILES: C=CCNc1nc(=O)n(-c2cccnc2C)c2cc(Cl)cc(OC)c12] |
| 75 | 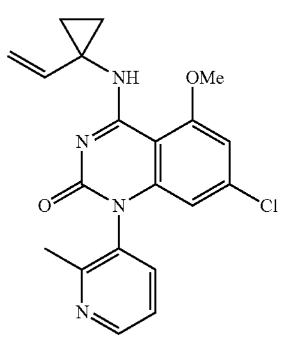 [SMILES: C=CC1(Nc2nc(=O)n(-c3cccnc3C)c3cc(Cl)cc(OC)c23)CC1] |
| 76 | |
| 77 | |
| 78 | |
| 79 | |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^2$H (D), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability.

In some embodiments, the abundance of deuterium in each of the substituents disclosed herein is independently at least 1%, at least 10%, at least 20%, at least 30%, at least 40%, at least 50%, at least 60%, at least 70%, at least 80%, at least 90%, or 100% of a total number of hydrogen and deuterium. In some embodiments, one or more of the substituents disclosed herein comprise deuterium at a percentage higher than the natural abundance of deuterium. In some embodiments, one or more hydrogens are replaced with one or more deuteriums in one or more of the substituents disclosed herein.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+$ $(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein is a method of treating a disease in which inhibition of MAT2A is beneficial, the method comprising administering a compound of Formula (I), (Ia), (Ib), (II), and (IIa) disclosed herein, or a pharmaceutically acceptable salt or solvate thereof. In some embodiments, the method comprises administering a pharmaceutical composition comprising a compound of Formula (I), (Ia), (Ib), (II), and (IIa) disclosed herein, or a pharmaceutically acceptable salt or solvate thereof.

Disclosed herein is a method of treating a disease or disorder associated with MAT2A, the method comprising administering to the subject a compound of Formula (I), (Ia), (Ib), (II), and (IIa) disclosed herein, or a pharmaceutically acceptable salt or solvate thereof. In some embodiments, the method comprises administering a pharmaceutical composition comprising a compound of Formula (I), (Ia), (Ib), (II), and (IIa) disclosed herein, or a pharmaceutically acceptable salt or solvate thereof.

Disclosed herein is a method of treating cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating cancer in a subject, the method comprising administering to the subject a compound of Formula (I), (Ia), (Ib), (II), and (IIa) disclosed herein, or a pharmaceutically acceptable salt or solvate thereof, wherein the cancer is selected from liver cancer, colon cancer, pancreatic cancer, prostate cancer, lung cancer, breast cancer, and T cell leukemia. In some embodiments is a method of treating liver cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating colon cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating pancreatic cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating prostate cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating lung cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating breast cancer in a subject, the method comprising administering to the subject a compound of Formula (I), (Ia), (Ib), (II), and (IIa) disclosed herein, or a pharmaceutically acceptable salt or solvate thereof. In some embodiments is a method of treating T cell leukemia in a subject the method comprising administering to the subject a compound of Formula (I), (Ia), (Ib), (II), and (IIa) disclosed herein, or a pharmaceutically acceptable salt or solvate thereof Dosing In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound of Formula (I), (Ia), (Ib), (II), and (IIa) described herein, or a pharmaceutically acceptable salt or solvate thereof, and at least one pharmaceutically acceptable excipient. In some embodiments is a pharmaceutical compositions comprising a compound of Formula (I) described herein, or a pharmaceutically acceptable salt or solvate thereof, and at least one pharmaceutically acceptable excipient. In some embodiments is a pharmaceutical compositions comprising a compound of Formula (Ia) described herein, or a pharmaceutically acceptable salt or solvate thereof, and at least one pharmaceutically acceptable excipient. In some embodiments is a pharmaceutical compositions comprising a compound of Formula (Ib) described herein, or a pharmaceutically acceptable salt or solvate thereof, and at least one pharmaceutically acceptable excipient. In some embodiments is a pharmaceutical compositions comprising a compound of Formula (II) described herein, or a pharmaceutically acceptable salt or solvate thereof, and at least one pharmaceutically acceptable excipient. In some embodiments is a pharmaceutical compositions comprising a compound of Formula (IIa) described herein, or a pharmaceutically acceptable salt or solvate thereof, and at least one pharmaceutically acceptable excipient.

Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt or solvate thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt or solvate thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

EXAMPLES

The following examples are provided for illustrative purposes only and not to limit the scope of the claims provided herein.

As used above, and throughout the description of the invention, the following abbreviations, unless otherwise indicated, shall be understood to have the following meanings:

| | |
|---|---|
| ACN or MeCN | acetonitrile |
| AcOH | acetic acid |
| Ac | acetyl |
| Bn | benzyl |
| BOC or Boc | tert-butyl carbamate |
| i-Bu | iso-butyl |
| t-Bu | tert-butyl |
| CDI | 1,1-carbonyldiimidazole |
| DBU | 1,8-diazabicyclo[5.4.0]undec-7-ene |
| DCE | dichloroethane (ClCH$_2$CH$_2$Cl) |
| DCM | dichloromethane (CH$_2$Cl$_2$) |
| DIBAL—H | diisobutylaluminum hydride |
| DIPEA or DIEA | diisopropylethylamine |
| DMAP | 4-(N,N-dimethylamino)pyridine |
| DME | 1,2-dimethoxyethane |
| DMF | N,N-dimethylformamide |
| DMA | N,N-dimethylacetamide |
| DMPU | N,N'-dimethylpropyleneurea |
| DMSO | dimethylsulfoxide |
| DPPA | diphenyl phosphoryl azide |
| Dppf or dppf | 1,1'-bis(diphenylphosphino)ferrocene |
| EDC or EDCI | N-(3-dimethylaminopropyl)-N'-ethylcarbodiimide hydrochloride |
| eq | equivalent(s) |
| Et | ethyl |
| Et$_2$O | diethyl ether |
| EtOH | ethanol |
| EtOAc | ethyl acetate |
| HATU | 1-[bis(dimethylamino)methylene]-1H-1,2,3-triazolo[4,5-b]pyridinium 3-oxid hexafluorophosphate |
| HOBt | 1-hydroxybenzotriazole |
| HPLC | high performance liquid chromatography |
| KOAc | potassium acetate |
| KOtBu | potassium tert-butoxide |
| KHMDS | potassium bis(trimethylsilyl)amide |
| NaHMDS | sodium bis(trimethylsilyl)amide |
| LiHMDS | lithium bis(trimethylsilyl)amide |
| LAH/LiAlH4 | lithium aluminum anhydride |
| LCMS | liquid chromatography mass spectrometry |
| Me | methyl |
| MeOH | methanol |
| MS | mass spectroscopy |
| MTBE | methyl tert-butyl ether |
| NBS | N-bromosuccinimide |
| NMP | N-methyl-pyrrolidin-2-one |
| NMR | nuclear magnetic resonance |
| PE | petroleum ether |
| Ph | phenyl |
| iPr/i-Pr | iso-propyl |
| PyAOP | 7-Azabenzotriazol-1-yloxy)tripyrrolidinophosphonium hexafluorophosphate |
| RP-HPLC | reverse-phase high-pressure liquid chromatography |
| rt | room temperature |
| SEM | 2-(trimethylsilyl)ethoxymethyl |
| TBS | tert-butyldimethylsilyl |
| TEA | triethylamine |
| TFA | trifluoroacetic acid |
| THF | tetrahydrofuran |
| TLC | thin layer chromatography |
| TMS | trimethylsilyl |

Intermediate A: Synthesis of 7-chloro-4-hydroxy-5-methoxy-1-(pyridin-3-yl)quinazolin-2(1H)-one

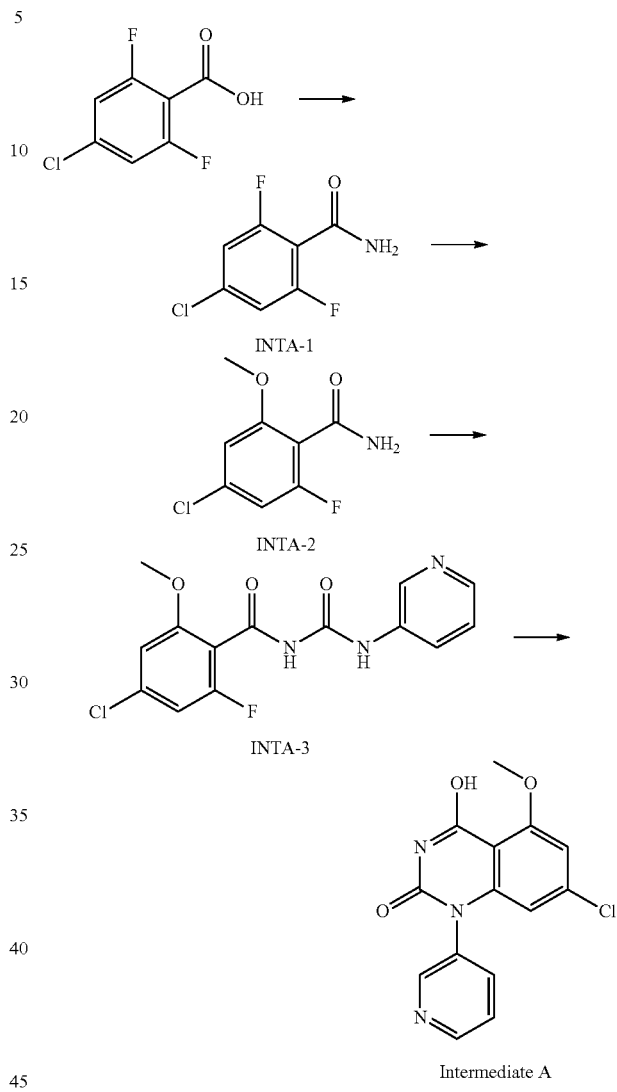

Step 1: A solution of 4-chloro-2, 6-difluorobenzoic acid (23.0 g, 119.45 mmol) in SOCl$_2$ (100 mL) was stirred at 80° C. for 3 hrs. The mixture was concentrated under reduced pressure and the residue was dissolved in dioxane (60 mL) and then NH$_4$OH (60 mL) was added at 0° C. dropwise. The mixture was then stirred at 25° C. for 0.5 h and concentrated, diluted with water while stirring until a white solid was precipitated. The solid was filtered, washed with water, and dried to afford compound INTA-1 (15.0 g, 65.6% yield). $^1$H NMR (400 MHz, DMSO-d$_6$) δ 8.17 (brs, 1H), 7.92 (brs, 1H), 7.49-7.42 (m, 2H).

Step 2: To a stirred suspension of compound INTA-1 (5.0 g, 26.10 mmol) in MeOH (50 mL) was added sodium methanolate (1.6 g, 28.71 mmol) at room temperature and the mixture was stirred at 60° C. for 5 hrs. The reaction was concentrated, diluted with water while stirring until a white solid was precipitated. Then the solid was collected, washed with water, and dried to afford compound INTA-2 (5.0 g, 94.1% yield). LCMS: 204.0 [M+H]$^+$.

Step 3: To a stirred suspension of compound INTA-2 (11.0 g, 54.0 mmol) in DCE (100 mL) was added oxalyl dichloride (7.54 g, 59.4 mmol). The suspension was heated to 80° C. for 1 h. The mixture was allowed to cool to 25° C., then pyridin-3-amine (10.2 g, 108 mmol) was added. The mixture was stirred at 25° C. for 0.5 h and then concentrated. The crude was triturated with MeOH (100 mL) at 25° C. for 30 min to give compound INTA-3 (16.0 g, 89.6% yield). LC-MS: 324.1 [M+H]⁺.

Step 4: To a solution of compound INTA-3 (10.0 g, 30.9 mmol) in THF (100 mL) was added dropwise KHMDS (1.0 M, 67.9 mL) at −20° C. The mixture was quenched with NH₄Cl (200.0 mL), then filtered and the residue was concentrated to give compound Intermediate A (5.50 g, 55.7% yield). LC-MS: 304.1 [M+H]⁺. ¹H NMR: (400 MHz, DMSO-d₆) δ 11.54 (brs, 1H), 8.74 (dd, J=4.8, 1.6 Hz, 1H), 8.64 (d, J=2.0 Hz, 1H), 8.02-7.86 (m, 1H), 7.68-7.64 (m, 1H), 6.96 (s, 1H), 5.86 (s, 1H), 3.90 (s, 3H).

Intermediate B: Synthesis of 7-chloro-4-hydroxy-5-methoxy-1-(2-methylpyridin-3-yl)quinazolin-2(1H)-one

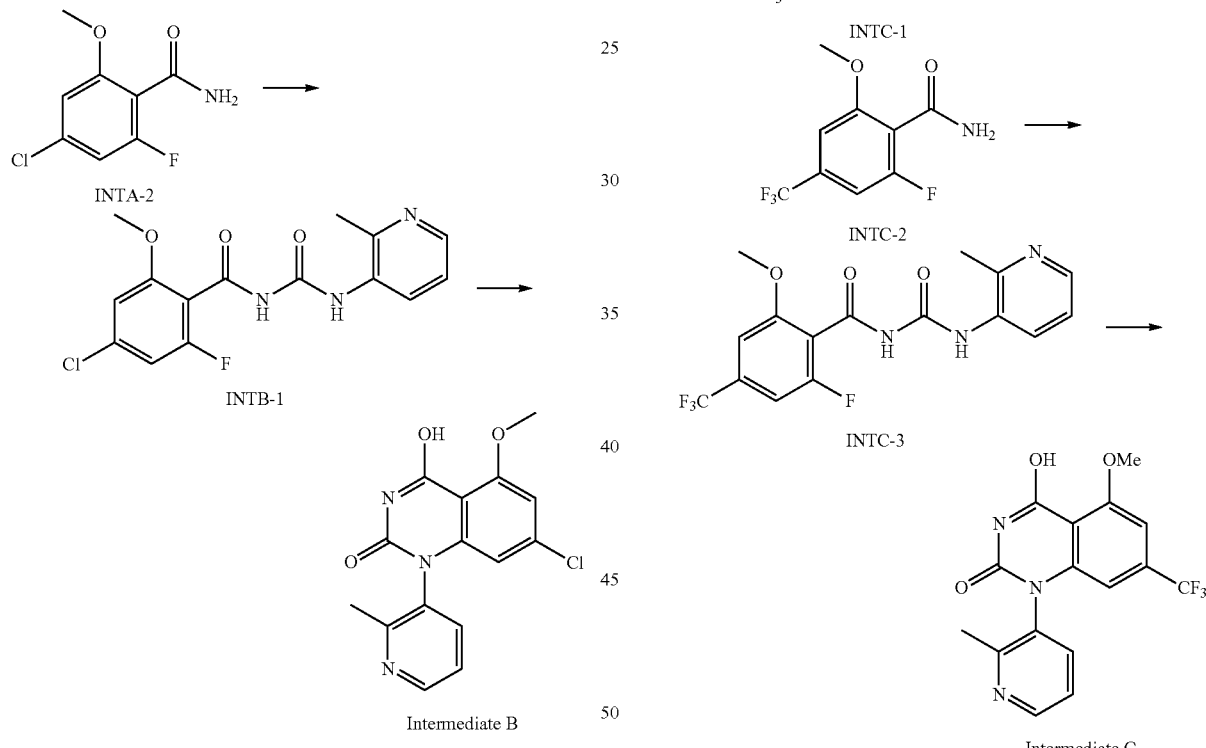

Intermediate C: Synthesis of 4-hydroxy-5-methoxy-1-(2-methylpyridin-3-yl)-7-(trifluoromethyl)quinazolin-2(1H)-one

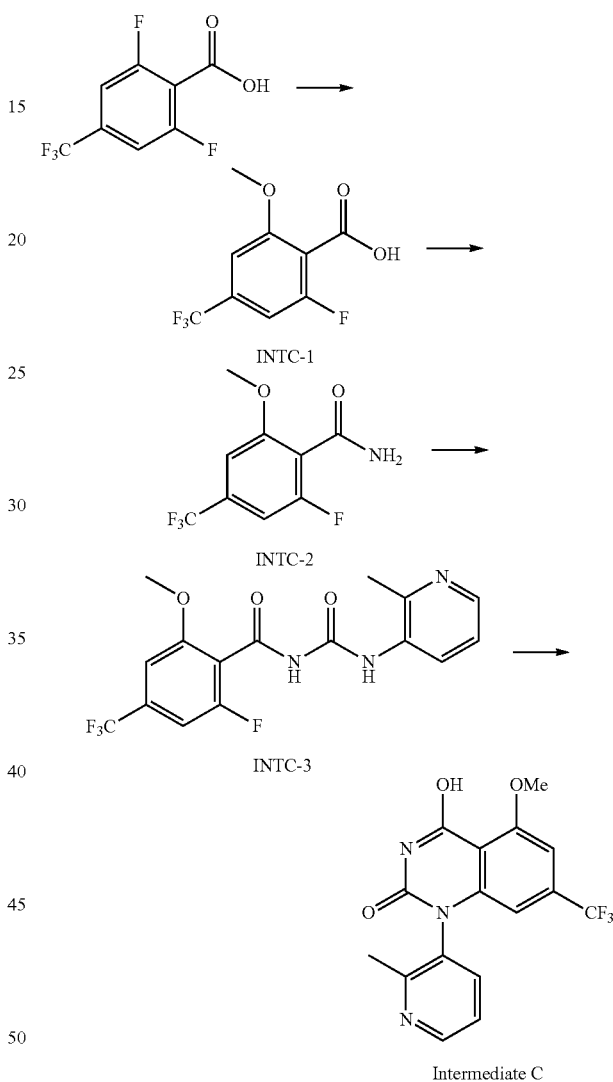

Step 1: To a solution of compound INTA-2 (6.0 g, 29.47 mmol) in DCE (100 mL) was added oxalyl dichloride (4.1 g, 32.42 mmol) at room temperature. The mixture was stirred at 80° C. for 1 h and then cooled to room temperature. 2-Methylpyridin-3-amine (6.4 g, 58.94 mmol) was added and the mixture was stirred at room temperature for another 1 h, then cooled to 0° C. The precipitate formed was collected by filtration, washed with water, and dried to afford compound INTB-1 (6.2 g, 62.3% yield). LCMS: 338.1 [M+H]⁺.

Step 2: To a solution of compound INTB-1 (500.0 mg, 1.48 mmol) in THF (10 mL) was added KHMDS (3.3 mL, 3.26 mmol, 1.0 M in THF) at −20° C., then the mixture was allowed to stir at room temperature for 7 hrs. The mixture was concentrated, diluted with water, and adjust pH to 6~7 with aqueous 4.0 M HCl. The precipitate was collected by filtration, washed with water, and dried to afford compound Intermediate B (400.0 mg, 85.8% yield). LCMS: 318.1 [M+H]⁺.

Step 1: To a solution of sodium methanolate (358.0 mg, 6.63 mmol) in MeOH (5 mL) were added 2,6-difluoro-4-(trifluoromethyl)benzoic acid (500.0 mg, 2.21 mmol), and the reaction was stirred at 80° C. for 2 hrs. The mixture was then cooled to room temperature and concentrated The residue was diluted with water (10 mL), adjusted pH to 2~3 with aqueous 6.0 M HCl and the mixture was extracted with DCM (15.0 mL×3), the organic layer was washed by brine, dried, and concentrated to afford compound INTC-1 (215.0 mg, 40.8% yield). ¹H NMR (400 MHz, DMSO-d₆) δ 7.37 (d, J=8.8 Hz, 1H), 7.28 (s, 1H), 3.92 (s, 3H).

Step 2: Compound INTC-1 (380.0 mg, 1.59 mmol) was mixed in SOCl₂ (6.0 mL), and then the resulting solution was heated at 80° C. for 2 hrs. The solution was then cooled to room temperature and concentrated to remove excess SOCl$_2$. The residue was taken up in dioxane (6.0 mL), treated with NH$_4$OH (40% w/w, 6.0 mL). The resulting solution was stirred at 0° C. to room temperature for 1 h. The mixture was concentrated under reduced pressure and diluted with water. Then the solid product formed was collected and washed with water and dried to afford compound INTC-2 (230 mg, 60.8% yield). $^1$H NMR (400 MHz, DMSO-d$_6$) δ 7.96 (s, 1H), 7.71 (s, 1H), 7.31 (dd, J=8.8 Hz, 0.4 Hz, 1H), 7.23 (s, 1H), 3.89 (s, 3H).

Step 3: To a stirred suspension of compound INTC-2 (230 mg, 0.97 mmol) in dichloroethane (5 mL) at room temperature was added oxalyl dichloride (135 mg, 1.07 mmol). The resultant suspension was heated to 80° C. for 1 h. The mixture was cooled to room temperature, 2-methylpyridin-3-amine (209.8 mg, 1.94 mmol) was added. The mixture was stirred at room temperature for 16 hrs. The precipitate was collected, washed with water, and dried to afford compound INTC-3 (120 mg, 33.3% yield). LCMS: 372.0 [M+H]$^+$.

Step 4: KHMDS (0.47 mL, 0.47 mmol, 1.0 M in THF) was added to a mixture of compound INTC-3 (80.0 mg, 0.21 mmol) in THF (3.0 mL) at −20° C., and the resulting mixture was allowed to warm to room temperature over 1 h. The mixture was concentrated, diluted with water, and adjusted pH to 6~7 with aqueous 4.0 M HCl. The precipitate was collected, washed with water, and dried to afford compound Intermediate C (60.0 mg, 79.2% yield). $^1$H NMR (400 MHz, DMSO-d$_6$) δ 11.71 (s, 1H), 8.66 (dd, J=4.8 Hz, 1.6 Hz, 1H), 7.88 (dd, J=8.0 Hz, 1.6 Hz, 1H), 7.52 (dd, J=7.6 Hz, 4.8 Hz, 1H), 7.15 (s, 1H), 5.98 (s, 1H), 3.98 (s, 3H), 2.25 (s, 3H).

Example 1: Synthesis of 7-chloro-4-(prop-2-yn-1-ylamino)-1-(pyridin-3-yl)quinazolin-2(1H)-one

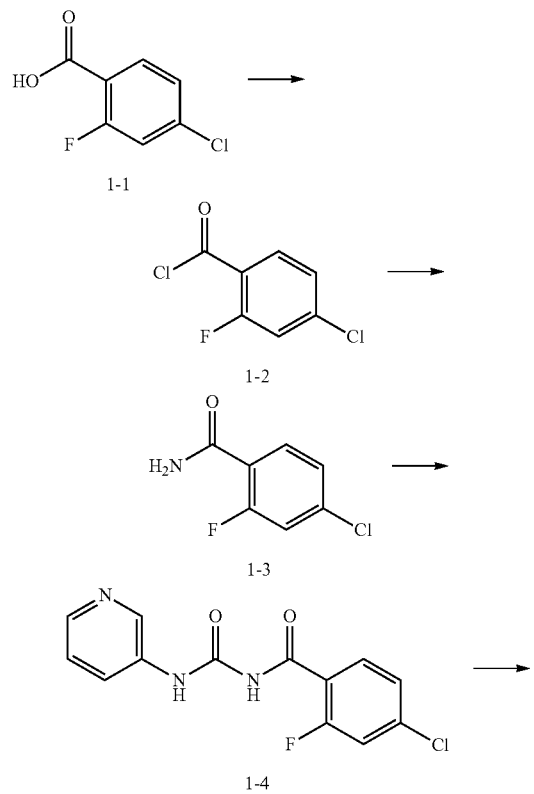

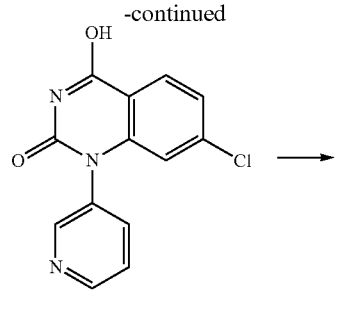

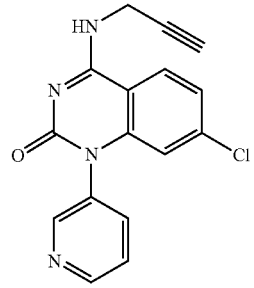

Example 1

Steps 1 and 2: 4-Chloro-2-fluorobenzoic acid (10.0 g, 57.29 mmol) was dissolved in SOCl$_2$ (20.0 mL), and then the resulting solution was heated at 70° C. for 2 hrs. The solution was then cooled to room temperature. Excess SOCl$_2$ was removed under vacuum, and the residue was taken up in dioxane (30.0 mL), and treated with NH$_4$OH (40%, 30.0 mL). The resulting solution was stirred at 0° C. to room temperature for 1 h. The mixture was concentrated under reduced pressure and diluted with water while stirring until a white solid was precipitated. The solid was removed by filtration, washed with water (50.0 mL) and dried under vacuum to afford compound 1-3 (7.80 g, 78% yield) as a white solid. LCMS: Rt: 1.250 min; MS m/z (ESI): 174.0 [M+H]$^+$.

Step 3: To a stirred of compound 1-3 (7.80 g, 44.94 mmol) in dichloroethane (60.0 mL) at r.t. was added oxalyl dichloride (6.37 g, 49.43 mmol). The resultant suspension was heated to 80° C. for 1 h and then cooled to room temperature. Pyridin-3-amine (8.2 mL, 89.88 mmol) was added to the reaction mixture. The resulting mixture was stirred at r.t. for 30 min, then cooled to 0° C. for 10 min. The precipitate was collected by filtration, washed with water (60.0 mL), and dried under vacuum to afford compound 1-4 (12.6 g, 95% yield).

Step 4: KHMDS (21.5 mL, 94.39 mmol, 2.2 eq) was added to a stirred solution of compound 1-4 (12.6 g, 42.90 mmol) in THF (100.0 mL) at −20° C., and the resulting mixture was warmed to r.t. over 3 h. The reaction mixture was then diluted with EtOAc (40.0 mL) and washed with saturated aqueous ammonium chloride. The organic layer was dried over Na$_2$SO$_4$, filtered, and concentrated in vacuo. The residue was further sonicated in DCM (15.0 mL). The resulting solid was collected by filtration and dried in vacuo to obtain compound 1-5 (10.0 g, 85% yield). LCMS: Rt: 1.077 min; MS m/z (ESI): 274.0 [M+H]$^+$. $^1$H NMR (400 MHz, DMSO-d$_6$) δ 11.92 (s, 1H), 8.76 (dd, J=4.8, 1.2 Hz, 1H), 8.68 (d, J=2.0 Hz, 1H), 8.06 (d, J=8.4 Hz, 1H), 7.99-7.97 (m, 1H), 7.70-7.67 (dd, J=4.2, 1.6 Hz, 1H), 7.35 (dd, J=4.8 Hz, 1H), 6.39 (d, J=1.6 Hz, 1H).

Step 5: A mixture of compound 1-5 (100.0 mg, 0.37 mmol), prop-2-yn-1-amine (121.0 mg, 2.19 mmol), PyAOP (286.0 mg, 0.55 mmol) and DBU (280.0 mg, 1.83 mmol) in DMF (2.0 mL) was stirred at r.t. for 8 h. Water (20.0 mL) was added to the resulting mixture. The organic layer was separated, and the aqueous layer was extracted with EtOAc (50.0 mL×3). The combined organic layers were washed with water and brine. The organic solution was dried over Na$_2$SO$_4$, filtered, concentrated, and purified by prep TLC (dichloromethane:methanol=20:1) to give a crude adduct which was further purified by a prep-HPLC to give Example 1 (8.6 mg, 8% yield). LCMS: Rt: 1.255 min; MS m/z (ESI): 311.1 [M+H]$^+$. $^1$H NMR (400 MHz, DMSO-d$_6$) δ 9.08 (dd, J=4.8, 4.8 Hz 1H), 8.72 (dd, J=4.8, 1.2 Hz, 1H), 8.57 (d, J=2.0 Hz, 1H), 8.20 (d, J=8.8 Hz, 1H), 7.87 (d, J=8.8 Hz, 1H), 7.64 (dd, J=8.0, 3.2 Hz, 1H), 7.33 (dd, J=8.8, 1.6 Hz, 1H), 6.37 (d, J=2.0 Hz, 1H), 4.32 (dd, J=4.8, 2.0 Hz, 2H), 3.22 (s, 1H).

Example 2: Synthesis of 7-chloro-4-((3-cyclopropylprop-2-yn-1-yl)amino)-1-(pyridin-3-yl)quinazolin-2(1H)-one

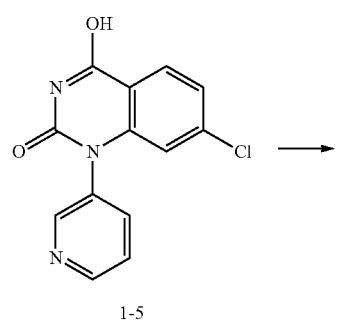

1-5

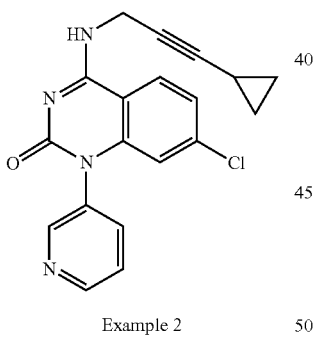

Example 2

A mixture of compound 1-5 (100.0 mg, 0.37 mmol, 1.0 eq), 3-cyclopropylprop-2-yn-1-amine hydrochloride (96.0 mg, 0.73 mmol), PyAOP (286 mg, 0.55 mmol), DBU (340.0 mg, 2.19 mmol) and DMAP (23 mg, 0.18 mmol) in DMF (2.0 mL) was stirred at r.t. for 16 hrs. Water (20.0 mL) was added to the resulting solution. The aqueous phase was extracted with EtOAc (50.0 mL×3). The combined organic layer was washed with water, brine, dried over Na$_2$SO$_4$, filtered, concentrated, and purified by prep TLC (dichloromethane:methanol=20:1) to yield a crude adduct. The crude was further purified by prep-HPLC to give Example 2 (16.6 mg, 13% yield). LCMS: Rt: 1.450 min; MS m/z (ESI): 351.1 [M+H]$^+$. $^1$H NMR (400 MHz, DMSO-d$_6$) δ 8.99 (t, J=5.2 Hz, 1H), 8.71 (d, J=3.6 Hz, 1H), 8.56 (s, 1H), 8.20 (d, J=8.8 Hz, 1H), 7.88-7.85 (m, 1H), 7.64 (dd, J=8.0, 4.8 Hz, 1H), 7.30 (dd, J=8.8, 2.0 Hz, 1H), 6.36 (d, J=1.6 Hz, 1H), 4.28 (dd, J=4.8, 1.6 Hz, 2H), 1.35-1.32 (m, 1H), 0.79-0.74 (m, 2H), 0.62-0.58 (m, 2H).

Example 3: Synthesis of 7-chloro-4-((4-(dimethylamino)but-2-yn-1-yl)amino)-1-(pyridin-3-yl)quinazolin-2(1H)-one

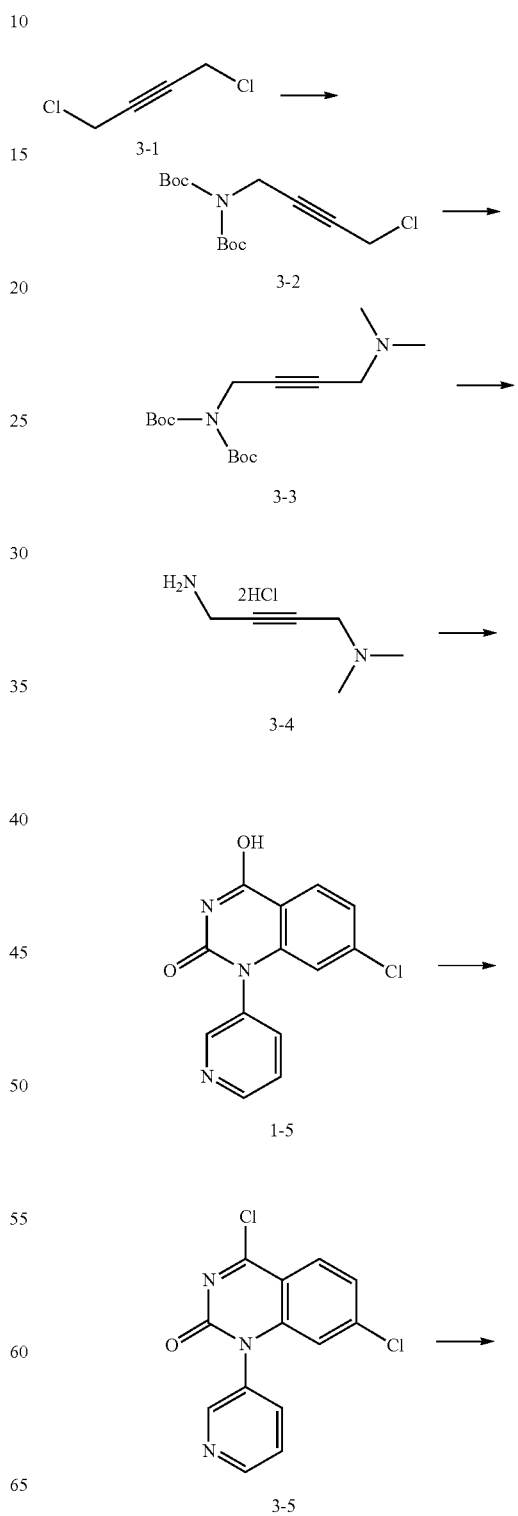

-continued

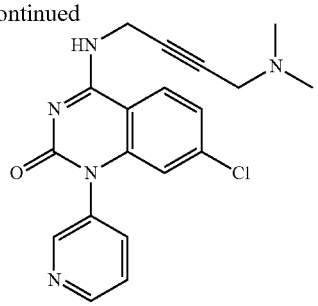

Example 3

Step 1: To a stirred solution of di-tert-butyl iminodicarbonate (3.54 g, 16.3 mmol,) in DMF (50.0 mL) at 0° C., was added NaH (60%, 585 mg, 24.4 mmol). The cold bath was removed, and additional DMF (70.0 mL) was added for 15 min. 1,4-dichlorobut-2-yne (4.00 g, 32.5 mmol) was then added, and the resulting mixture was stirred at r.t. for 2 hrs. The reaction mixture was poured into a cold LiCl (5% aq, 500.0 mL) solution and extracted with EtOAc (100.0 mL×3). The combined organic layer was washed with water, brine, dried over $Na_2SO_4$, filtered, and concentrated under reduced pressure to give a crude residue. The residue was purified by gel column chromatography (petroleum ether: ethyl acetate=10:1) to give compound 3-2 (960.0 mg, 10% yield) as a clear oil. $^1$H NMR (400 MHz, DMSO-$d_6$) δ 4.46 (s, 2H), 4.34 (s, 2H), 1.46 (s, 18H).

Step 2: To a stirred solution of 3-2 (300.0 mg, 0.99 mmol) in THF (3.0 mL) was added dimethylamine (2.0 M in THF) (2.0 mL, 1.98 mmol) at 0° C. The resulting mixture was stirred at room temperature for 16 h. The reaction was diluted with ethyl acetate (5.0 mL) and water (5.0 mL). The aqueous layer was extracted with ethyl acetate (50.0 mL×3). The combined organic layer was washed with water, brine, dried over $Na_2SO_4$, filtered, and concentrated in vacuo to afford 3-3 (200.0 mg, 0.64 mmol, 65% yield) as a clear oil. $^1$H NMR (400 MHz, DMSO-$d_6$) δ 4.28 (s, 2H), 3.19 (s, 2H), 2.14 (s, 6H), 1.45 (s, 18H).

Step 3: To a stirred solution of 3-3 (200.0 mg, 0.64 mmol) in DCM (3.0 mL) and MeOH (3.0 mL) were added HCl solution (3.0 mL, 3.0 M in EtOAc), and the reaction was stirred at room temperature for 1.5 hrs. The resulting reaction was concentrated in vacuum to give 3-4 (105.0 mg, 89% yield) which was used in next step without further purification.

Steps 4 and 5: To a stirred solution of 1-5 (100.0 mg, 0.37 mmol) in toluene (1.0 mL) was added DIPEA (472.0 mg, 3.65 mmol) and $POCl_3$ (280.0 mg, 1.83 mmol) at 0° C. The resulting suspension was heated to 100° C. for 2 hrs and then cooled to room temperature. A solution of 3-4 (105.0 mg, 0.57 mmol) and DIPEA (0.24 mL, 1.46 mmol) in NMP (1.0 mL) was added. The mixture was stirred at r.t. for 16 hrs. Water (20.0 mL) was added and the mixture was extracted by EtOAc (20.0 mL×3). The water layer was concentrated and purified by prep-HPLC to give residue. The residue was further purified by prep-TLC (petroleum ether: ethyl acetate=10:1) to give Example 3 (6.4 mg, 5% yield). LCMS: Rt: 0.895 min; MS m/z (ESI): 368.1 [M+H]$^+$. $^1$H NMR (400 MHz, DMSO-$d_6$) δ 8.76 (dd, J=4.8, 1.6 Hz, 1H), 8.58 (d, J=2.4 Hz, 1H), 8.29 (d, J=8.8 Hz, 1H), 7.91 (s, 1H), 7.71-7.68 (m, 1H), 7.56-7.53 (m, 1H), 7.19 (dd, J=8.0, 4.2 Hz, 1H), 6.50 (d, J=2.0 Hz, 1H), 4.54 (s, 2H), 3.78 (s, 2H), 2.86 (s, 6H).

Example 4: Synthesis of 7-chloro-4-((1-ethynylcyclopropyl)amino)-1-(pyridin-3-yl)quinazolin-2(1H)-one

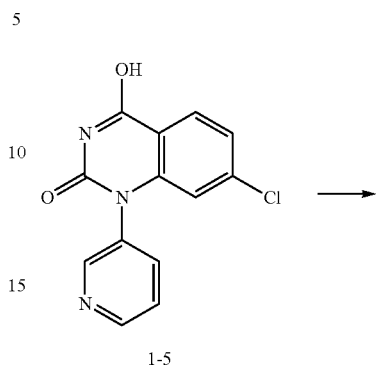

1-5

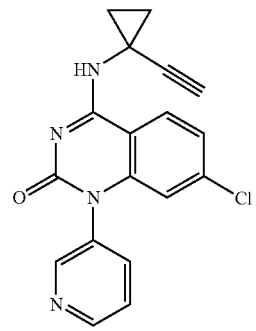

Example 4

To a solution of 1-5 (100.0 mg, 0.37 mmol) in toluene (1.0 mL) was added DIPEA (472 mg, 3.65 mmol) and $POCl_3$ (280.0 mg, 1.83 mmol) at 0° C. The resulting mixture was heated to 100° C. for 2 hrs and then cooled to room temperature. A solution of 1-ethynylcyclopropan-1-amine hydrochloride (43.0 mg, 0.73 mmol) and DIPEA (0.24 mL, 1.46 mmol) in NMP (0.5 mL) was added. The mixture was stirred at r.t. for 16 hrs. Water (20.0 mL) was added to the resulting mixture. The aqueous layer was extracted with EtOAc (20.0 mL×3). The combined organic layer was washed with brine, dried over $Na_2SO_4$, filtered, concentrated, and purified by prep TLC (petroleum ether: EtOAc=1:1) to give a residue. This residue was purified by prep-HPLC to give Example 4 (6.4 mg, 5% yield). LCMS: Rt: 5.747 min; MS m/z (ESI): 337.0 [M+H]$^+$. $^1$H NMR (400 MHz, DMSO-$d_6$) δ 9.13 (s, 1H), 8.72 (dd, J=4.8, 1.2 Hz, 1H), 8.58 (d, J=2.4 Hz, 1H), 8.16 (d, J=8.4 Hz, 1H), 7.90-7.87 (m, 1H), 7.65 (dd, J=8.0, 4.8 Hz, 1H), 7.31 (dd, J=8.4, 1.6 Hz, 1H), 6.36 (d, J=1.6 Hz, 1H), 3.05 (s, 1H), 1.32-1.20 (m, 4H).

Example 5: Synthesis of 4-(allylamino)-7-chloro-1-(pyridin-3-yl)quinazolin-2(1H)-one

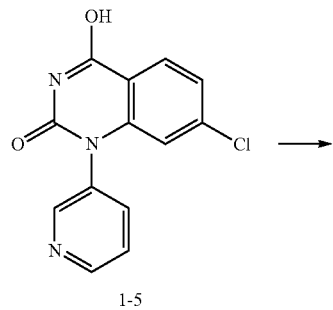

1-5

Example 6: Synthesis of 7-chloro-4-(pent-4-yn-1-ylamino)-1-(pyridin-3-yl)quinazolin-2(1H)-one

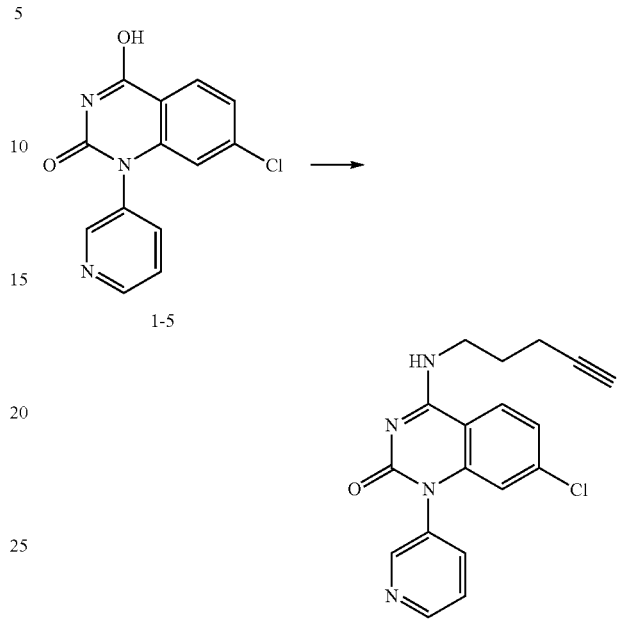

1-5

Example 6

To a mixture of A-5 (100.0 mg, 0.37 mmol), pent-4-yn-1-amine hydrochloride (87.4 mg, 0.73 mmol), PyAOP (286.0 mg, 0.55 mmol) and DBU (334.0 mg, 2.19 mmol) in DMF (2.0 mL) was stirred at r.t. for 3 hrs. Water (20.0 mL) was added, and the aqueous was extracted with EtOAc (50.0 mL×3). The combined organic layer was washed with water, brine, dried over $Na_2SO_4$, filtered, concentrated, and purified by prep TLC to give Example 6 (7.8 mg, 6% yield). LCMS: Rt: 1.360 min; MS m/z (ESI): 339.1 [M+H]$^+$. $^1$H NMR (400 MHz, MeOD) δ 8.73 (d, J=3.6 Hz, 1H), 8.56 (d, J=1.6 Hz, 1H), 8.06 (d, J=8.4 Hz, 1H), 7.88 (d, J=8.4 Hz, 1H), 7.70 (dd, J=8.0, 5.2 Hz, 1H), 7.28 (dd, J=8.8, 2.0 Hz, 1H), 6.52 (d, J=1.6 Hz, 1H), 3.73 (t, J=7.2 Hz, 2H), 2.35-2.25 (m, 2.0 Hz, 2H), 1.99-1.94 (m, 1H), 1.35-1.28 (m, 2H).

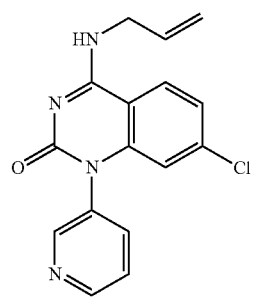

Example 5

To a solution of A-5 (100.0 mg, 0.37 mmol) in toluene (1.0 mL) was added DIPEA (472.0 mg, 3.65 mmol) and POCl$_3$ (280.0 mg, 1.83 mmol) at 0° C. The resulting mixture was heated to 100° C. for 2 hrs and then cooled to room temperature. DIPEA (236.0 mg, 1.83 mmol) and a solution of prop-2-en-1-amine (68.0 mg, 0.73 mmol) in NMP (0.5 mL) was added to the resulting solution. The mixture was further stirred at 50° C. for 2 hrs. Water (15.0 mL) was added, and the pH was adjusted to 8-9 by adding aqueous $Na_2CO_3$. The resulting aqueous solution was extracted with EtOAc (50.0 mL×3), and the combined organic layer was washed with brine, dried over $Na_2SO_4$, filtered, concentrated, and purified by prep TLC to give a residue. The residue was purified by prep-HPLC to give Example 5 (6.2 mg, 5% yield over two steps). LCMS: Rt: 1.057 min; MS m/z (ESI): 313.1 [M+H]$^+$. $^1$H NMR (400 MHz, DMSO-d$_6$) δ 8.86 (t, J=4.4 Hz, 1H), 8.70 (d, J=3.6 Hz, 1H), 8.55 (d, J=1.2 Hz, 1H), 8.24 (d, J=8.4 Hz, 1H), 7.85 (d, J=8.0 Hz, 1H), 7.65-7.62 (m, 1H), 7.32 (d, J=8.4 Hz, 1H), 6.36 (s, 1H), 6.04-5.95 (m, 1H), 5.27-5.15 (m, 2H), 4.17 (s, 2H).

Example 7: Synthesis of 4-(prop-2-yn-1-ylamino)-1-(pyridin-3-yl)-7-(trifluoromethyl)quinazolin-2(1H)-one

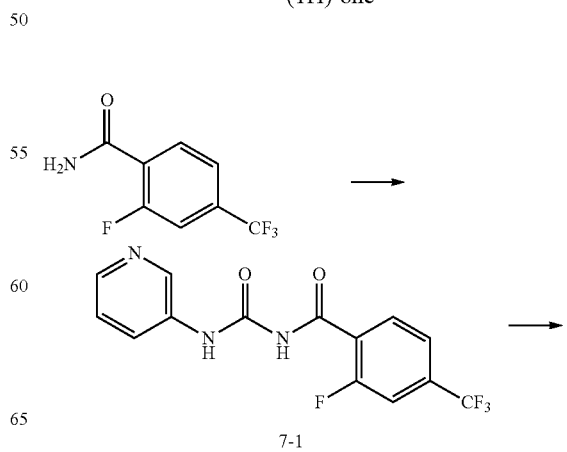

7-1

-continued

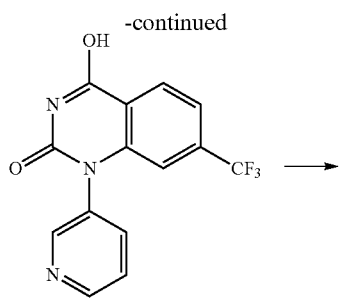

7-2

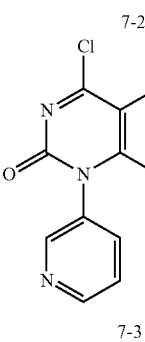

7-3

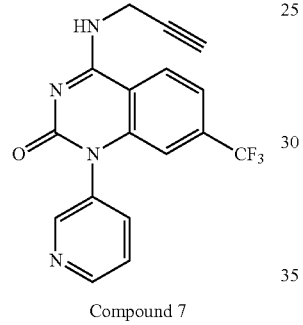

Compound 7

Step 1: To a stirred solution of 2-fluoro-4-(trifluoromethyl)benzamide (2.00 g, 9.66 mmol) in dichloroethane (15.0 mL) at r.t. was added oxalyl dichloride (1.37 g, 10.62 mmol). The resulting solution was heated at 80° C. for 1 h. The reaction mixture was cooled to r.t. Pyridin-3-amine (1.82 g, 19.31 mmol) was added and the mixture was stirred at r.t. for 30 min, then cooled to 0° C. The resulting solution was further stirred for 10 min. A precipitate was collected by filtration, washed with water, and dried under vacuum to afford 7-1 (2.70 g, 86% yield). LCMS: Rt: 1.390 min; MS m/z (ESI): 328.1 [M+H]+.

Step 2: LiHMDS (1.5 mL, 6.72 mmol) was added to a mixture of 7-1 (1.00 g, 3.06 mmol) in THF (10.0 mL) at −20° C., and the resulting mixture was allowed to warm to r.t. over 2 hrs. The reaction mixture was then diluted with EtOAc (30.0 mL) and washed with saturated aqueous ammonium chloride. The organic layer was dried over Na$_2$SO$_4$, filtered, and concentrated in vacuo. The residue was further sonicated in water, collected by filtration, and dried in vacuo to give 7-2 (600.0 mg, 64% yield). LCMS: Rt: 1.405 min; MS m/z (ESI): 308.1 [M+H]+.

Steps 3 and 4: To a stirred solution of 7-2 (100.0 mg, 0.33 mmol) in toluene (1.0 mL) was added DIPEA (0.55 mL, 3.30 mmol) and POCl$_3$ (0.15 mL, 1.65 mmol) at 0° C. The resulting mixture was heated at 100° C. for 2 hrs. After cooling to r.t., a solution of prop-2-yn-1-amine (37 mg, 0.66 mmol) and DIPEA (0.27 mL, 1.65 mmol) in NMP (0.5 mL) was added. The mixture was stirred at r.t. for 16 hrs. Water (20.0 mL) was added, and the aqueous layer was extracted with EtOAc (20.0 mL×3). The combined organic layers were washed with brine, dried over Na$_2$SO$_4$, filtered, concentrated, and purified by prep TLC (EtOAc:methanol=30:1) to give (Example 7) (21.0 mg, 19% yield). LCMS: Rt: 1.177 min; MS m/z (ESI): 345.1 [M+H]+. $^1$H NMR (400 MHz, DMSO-d$_6$) δ 9.27 (t, J=5.2 Hz, 1H), 8.74 (d, J=4.4 Hz, 1H), 8.61 (d, J=2.0 Hz, 1H), 8.42 (d, J=8.4 Hz, 1H), 7.91 (d, J=6.8 Hz, 1H), 8.68-8.62 (m, 2H), 6.58 (s, 1H), 4.36-4.34 (m, 2H), 3.24 (t, J=4.4 Hz, 1H). $^{19}$F NMR (376 MHz, DMSO-d$_6$) −62.11.

Example 8: Synthesis of 4-(but-3-yn-1-ylamino)-7-chloro-1-(2-chlorophenyl)quinazolin-2(1H)-one

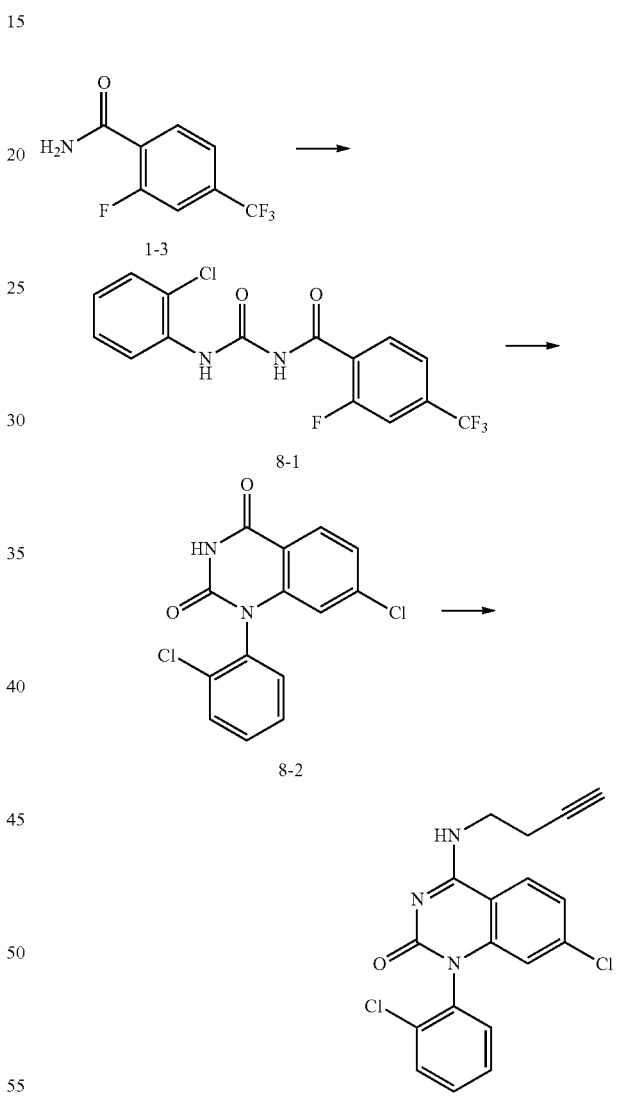

Step 1: To a solution of 1-3 (10.0 g, 57.80 mmol) in anhydrous THF (100.0 mL) was added (COCl)$_2$ (11.01 g, 86.70 mmol) at 0° C. The resulting solution was stirred at 80° C. for 1 h. The reaction mixture was concentrated The crude was dissolved in THF (150.0 mL). 2-Chloroaniline (11.01 g, 86.70 mmol) was added to the resulting mixture and stirred for 1 h. The resulting precipitated solid was filtered and washed with H$_2$O (100.0 mL) to give 8-1 (13.0 g, 69% yield). $^1$H NMR (400 MHz, DMSO-d$_6$) δ 11.35 (s, 1H), 10.96 (s, 1H), 8.24 (d, J=5.8 Hz, 1H), 7.73 (d, J=7.9 Hz, 1H), 7.61 (d, J=12.9 Hz, 1H), 7.52 (d, J=7.2 Hz, 1H), 7.45-7.39 (m, 1H), 7.39-7.31 (m, 1H), 7.13 (s, 1H).

Step 2: To a solution of 8-1 (14.0 g, 42.8 mmol) in anhydrous THF (150.0 mL) was added KHMDS (128.0 mL, 128 mmol). The resulting solution was stirred at 70° C. for 1 h. The reaction mixture was quenched with H$_2$O (100.0 mL) and the aqueous layer was acidified by adding 3.0 M HCl solution to pH=7. The aqueous was extracted with ethyl acetate (100.0 mL×3). The combined organic layer was dried over MgSO$_4$, and concentrated to give 8-2 (7.3 g, yield: 56% yield). LCMS: Rt: 982 min; MS m/z (ESI): 307.0 [M+H]$^+$. $^1$H NMR (400 MHz, DMSO-d$_6$) δ 11.96 (s, 1H), 8.08 (m, 1H), 7.75 (s, 1H), 7.66-7.56 (m, 3H), 7.36 (d, J=8.8 Hz, 1H), 6.24 (s, 1H).

Step 3: A mixture of 8-2 (40.0 mg, 0.13 mmol), but-3-yn-1-amine hydrochloride (21.0 mg, 0.20 mmol), PyAOP (102.0 mg, 0.20 mmol) and TEA (66.0 mg, 0.65 mmol) in DMF (0.5 mL) was stirred at r.t. for 2 hrs. Water (10.0 mL) was added, the aqueous layer was extracted with EtOAc (10.0 mL×3). The combined organic layer was washed with brine, dried over Na$_2$SO$_4$, filtered, concentrated, and purified by prep TLC to give Example 8 (2.3 mg, 5% yield). LCMS: Rt: 1.705 min; MS m/z (ESI): 358.0 [M+H]$^+$. $^1$H NMR (400 MHz, DMSO-d$_6$) δ 8.88 (t, J=5.2 Hz, 1H), 8.20 (d, J=8.4 Hz, 1H), 7.76-7.73 (m, 1H), 7.59-7.56 (m, 2H), 7.53-7.52 (m, 1H), 7.36-7.33 (m, 1H), 6.22 (d, J=3.2 Hz, 1H), 3.65-3.60 (m, 2H), 2.91 (t, J=2.6 Hz, 1H), 2.60-2.56 (m, 2H).

Example 9: Synthesis of 7-chloro-4-(prop-2-yn-1-yloxy)-1-(pyridin-3-yl)quinazolin-2(1H)-one (Compound 9)

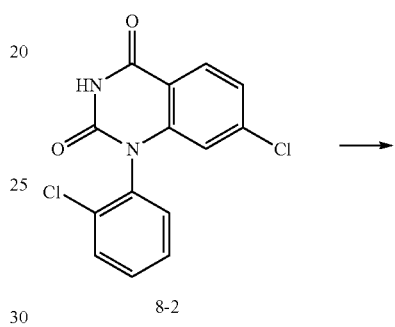

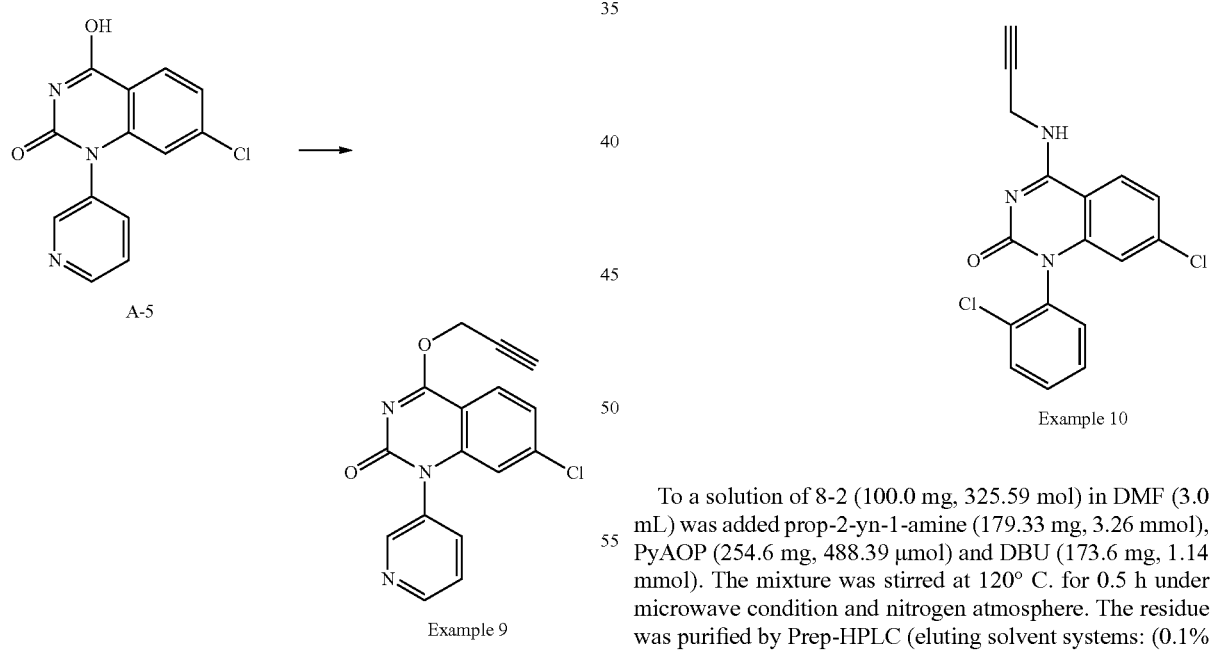

To a solution of A-5 (100.0 mg, 0.37 mmol) in toluene (1.0 mL) was added DIPEA (472 mg, 3.65 mmol) and POCl$_3$ (280.0 mg, 1.83 mmol) at 0° C. The resulting mixture was heated to 100° C. for 2 hrs and then cooled to room temperature. A solution of prop-2-yn-1-ol (82.0 mg, 1.46 mmol) and t-BuOK (123.0 mg, 1.10 mmol) in THF (0.5 mL) was added. The reaction mixture was stirred at r.t. for 30 min, and at 80° C. for 16 hrs. After cooling to r.t., water (20.0 mL) was added to the resulting mixture. The aqueous solution was extracted with EtOAc (30.0 mL×3). The combined organic layer was washed with brine, dried over Na$_2$SO$_4$, filtered, concentrated, and purified by prep-HPLC to give Compound 9 (2.1 mg, 2% yield over two steps). LCMS: Rt: 1.287 min; MS m/z (ESI): 312.1 [M+H]$^+$. $^1$H NMR (400 MHz, MeOD-d$_4$) δ 8.81-8.80 (m, 1H), 8.65 (s, 1H), 8.16-8.14 (dd, J=8.8, 2.0 Hz, 1H), 7.99-7.97 (dd, J=8.0, 1.2 Hz, 1H), 7.79-7.75 (m, 1H), 7.42-7.40 (m, 1H), 6.67 (s, 1H), 4.61 (s, 2H), 3.15 (s, 1H).

Example 10: Synthesis of 7-chloro-1-(2-chlorophenyl)-4-(prop-2-yn-1-ylamino)quinazolin-2(1H)-one

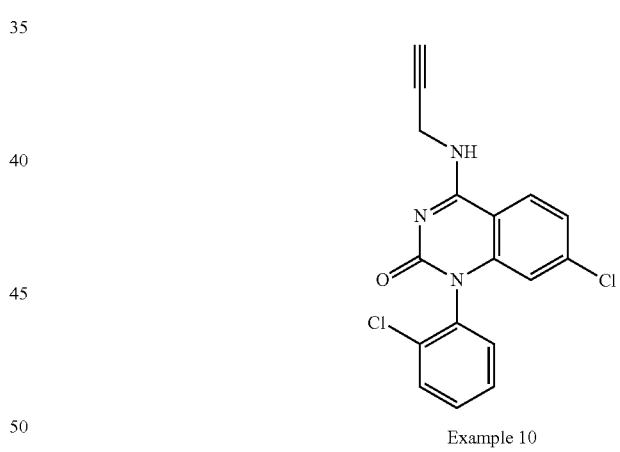

To a solution of 8-2 (100.0 mg, 325.59 mol) in DMF (3.0 mL) was added prop-2-yn-1-amine (179.33 mg, 3.26 mmol), PyAOP (254.6 mg, 488.39 μmol) and DBU (173.6 mg, 1.14 mmol). The mixture was stirred at 120° C. for 0.5 h under microwave condition and nitrogen atmosphere. The residue was purified by Prep-HPLC (eluting solvent systems: (0.1% FA) H$_2$O-MeCN, column: Xbridge C18 250 mm*19 mm, begin gradient (%):37, end gradient (%):58, gradient time (min): 15, flow rate (mL/min): 20) to afford (Example 10 (15.7 mg, 14% yield). LCMS: Rt: 2.420 min; MS m/z (ESI): 344.10 [M+H]$^+$. $^1$H NMR (400 MHz, DMSO-d$_6$) δ 9.06 (t, J=5.4 Hz, 1H), 8.18 (d, J=8.7 Hz, 1H), 7.76-7.68 (m, 1H), 7.57-7.48 (m, 3H), 7.31 (d, J=10.7 Hz, 1H), 6.20 (s, 1H), 4.29 (dd, J=10.3, 2.7 Hz, 2H), 3.19 (t, J=2.5 Hz, 1H).

Example 11: Synthesis of 7-chloro-1-(2-chlorophenyl)-4-(3-ethynylpiperidin-1-yl)quinazolin-2(1H)-one N

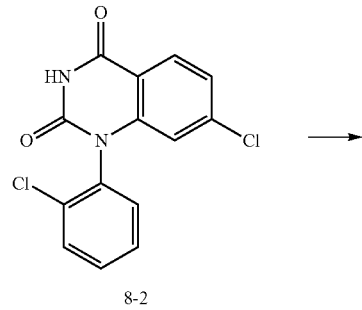

8-2

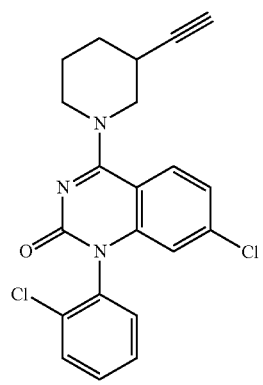

Example 11

To a solution of 8-2 (100.0 mg, 325.59 mol) in DMF (3.0 mL) was added 3-ethynylpiperidine hydrochloride salt (89.2 mg, 488.39 μmol), PyAOP (254.6 mg, 488.39 mol) and DBU (247.84 mg, 1.63 mmol). The mixture was stirred at 120° C. for 0.5 h under microwave condition and nitrogen atmosphere. The residue was purified by Prep-HPLC to afford (Example 11) (39.2 mg, 30% yield). LCMS: Rt: 2.756 min; MS m/z (ESI): 398.20 [M+H]+. $^1$H NMR (400 MHz, DMSO-$d_6$) δ 7.89 (dd, J=8.7, 5.6 Hz, 1H), 7.75-7.68 (m, 1H), 7.59-7.45 (m, 3H), 7.25 (d, J=10.8 Hz, 1H), 6.25 (d, J=4.8 Hz, 1H), 4.12-3.94 (m, 1H), 3.78 (d, J=15.3 Hz, 1H), 3.69-3.47 (m, 2H), 3.01 (d, J=19.3 Hz, 1H), 2.79 (s, 1H), 2.02-1.80 (m, 2H), 1.76-1.56 (m, 2H).

Example 12: Synthesis of 7-chloro-1-(2-chlorophenyl)-4-(3-ethynyl-3-hydroxyazetidin-1-yl)quinazolin-2(1H)-one

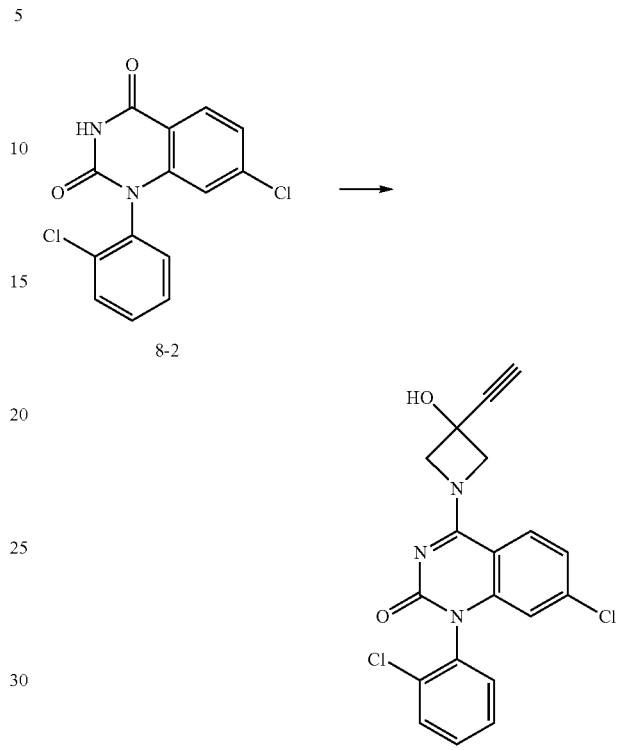

Example 12

To a solution of 8-2 (100.0 mg, 325.59 mol) in DMF (3.0 mL) was added 3-ethynylazetidin-3-ol trifluoroacetic acid salt (102.64 mg, 488.39 mol), PyAOP (254.6 mg, 488.39 mol) and DBU (247.84 mg, 1.63 mmol). The mixture was stirred at 120° C. for 0.5 h under microwave condition and nitrogen atmosphere. The residue was purified by prep-HPLC to afford Example 12 (15.7 mg, 13% yield). LCMS: Rt: 2.359 min; MS m/z (ESI): 386.10 [M+H]+. $^1$H NMR (400 MHz, DMSO-$d_6$) δ 7.82 (d, J=8.8 Hz, 1H), 7.71 (dd, J=6.1, 3.4 Hz, 1H), 7.56-7.52 (m, 2H), 7.49-7.44 (m, 1H), 7.19 (dd, J=8.7, 2.1 Hz, 1H), 6.78 (s, 1H), 6.21 (d, J=2.0 Hz, 1H), 5.21-4.04 (m, 4H), 3.75 (s, 1H).

Example 13: Synthesis of 7-chloro-1-(2-chlorophenyl)-4-(4-ethynylpiperidin-1-yl)quinazolin-2(1H)-one

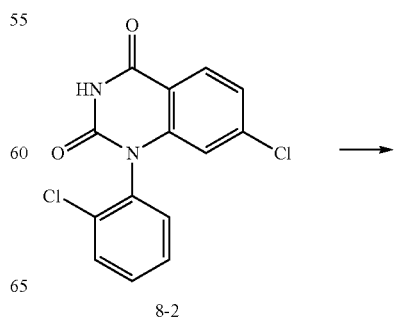

8-2

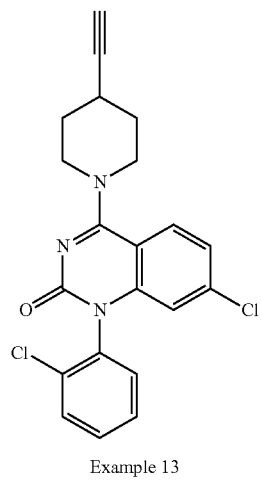

Example 13

To a solution of 8-2 (100.0 mg, 325.59 μmol) in DMF (3.0 mL) was added 4-ethynylpiperidine hydrochloride salt (71.12 mg, 488.39 μmol), PyAOP (254.6 mg, 488.39 mol) and DBU (247.84 mg, 1.63 mmol). The mixture was stirred at 120° C. for 0.5 h under microwave condition and nitrogen atmosphere. The residue was purified by prep-HPLC to afford Example 13) (28.6 mg, 22% yield). LCMS: Rt: 2.736 min; MS m/z (ESI): 398.10 [M+H]+. 1H NMR (400 MHz, DMSO-d6) δ 7.84 (d, J=8.7 Hz, 1H), 7.76-7.68 (m, 1H), 7.58-7.46 (m, 3H), 7.22 (dd, J=8.7, 2.1 Hz, 1H), 6.24 (d, J=2.0 Hz, 1H), 4.04-3.93 (m, 2H), 3.58-3.42 (m, 2H), 3.01 (d, J=2.4 Hz, 1H), 2.80 (d, J=9.7 Hz, 1H), 1.95 (d, J=10.7 Hz, 2H), 1.69 (dd, J=16.6, 3.9 Hz, 2H).

Example 14: Synthesis of 4-((4-morpholinobut-2-yn-1-yl)amino)-1-(pyridin-3-yl)-7-(trifluoromethyl)quinazolin-2(1H)-one

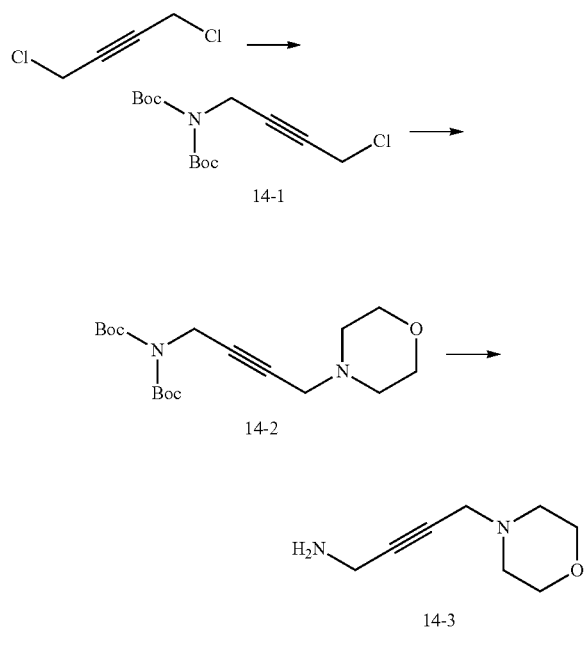

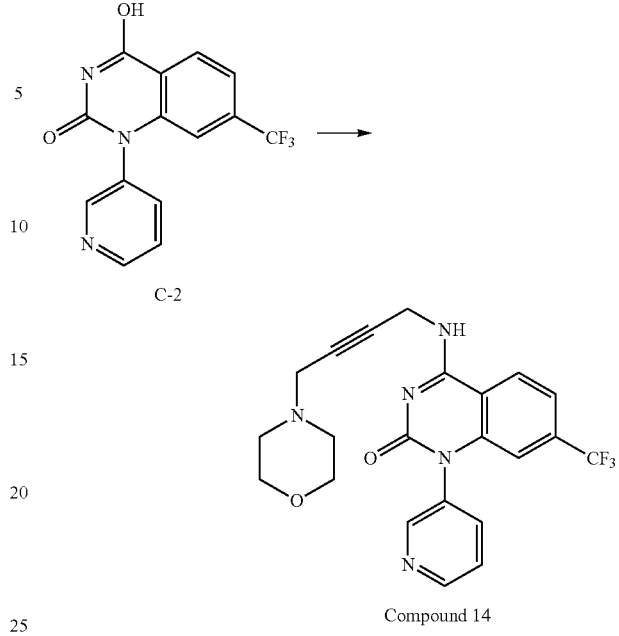

Compound 14

Step 1: To a solution of di-tert-butyl iminodicarbonate (4.4 g, 20.33 mmol) in DMF (50 mL) at 0° C. was added NaH (1.2 g, 30.49 mmol, 60% oil dispersion). The cold bath was removed, and more DMF (50 mL) was added. After stirring for 15 min, 1,4-dichlorobut-2-yne (5.0 g, 40.66 mmol) was quickly added and the mixture was stirred at room temperature for 2 hrs. The mixture was poured into a cold solution of LiCl (5% aq, 500 mL) and extracted with EtOAc (100 mL×3). The combined organic layers were washed with water, brine, dried by Na2SO4 and concentrated. The residue was purified by gel column chromatography to afford compound 14-1 (1.7 g, 13.8% yield). 1H NMR (400 MHz, DMSO-d6) δ 4.46 (s, 2H), 4.34 (s, 2H), 1.46 (s, 18H).

Step 2: To a solution of morpholine (732.0 mg, 8.40 mmol) and compound 14-1 (1.7 g, 5.60 mmol) in MeCN (30 mL) was added K2CO3 (1.6 g, 11.20 mmol) at room temperature Then the mixture was stirred at 60° C. for 4 hrs. The reaction mixture was cooled to room temperature and filtered, washed with EA, the filtrate was concentrated and purified by gel column chromatography to afford compound 14-2 (1.1 g, 55.4% yield). 1H NMR (400 MHz, DMSO-d6) δ 4.28 (s, 2H), 3.56 (t, J=4.4 Hz, 4H), 3.26 (s, 2H), 2.41 (t, J=4.8 Hz, 4H), 1.46 (s, 18H).

Step 3: To a solution of compound 14-2 (1.1 g, 3.10 mmol) in DCM (10 mL) and MeOH (5 mL) was added HCl (3.0 mL, 3M in EtOAC) at 0° C., then the reaction was stirred at room temperature for 5 hrs. The mixture was concentrated to afford compound 14-3 (600.0 mg, 85.2% yield). 1H NMR (400 MHz, DMSO-d6) δ 8.64 (s, 3H), 4.16 (s, 2H), 3.96-3.83 (m, 6H), 3.20-3.45 (m, 4H). Step 4: To a stirred solution of compound C-2 (100.0 mg, 0.33 mmol) in toluene (1 mL) was added DIEA (420.7 mg, 3.25 mmol) and POCl3 (249.0 mg, 1.63 mmol) at 0° C. The resultant suspension was heated to 100° C. for 2 hrs, and then cooled to room temperature. A mixture of DIEA (252.5 mg, 1.95 mmol) and compound 14-3 (300.0 mg, 1.30 mmol) in MeCN (1.5 mL) was added to the reaction at 0° C. Then the mixture was stirred at room temperature for 16 hrs and concentrated. The residue was purified by column chromatography to afford compound 14. LCMS: 444.1 [M+H]+. 1H NMR (400 MHz, DMSO-d6) δ 9.28 (t, J=5.2 Hz, 1H), 8.73 (dd, J=4.8 Hz, 1.6 Hz, 1H), 8.60 (d, J=2.0 Hz, 1H), 8.43 (d, J=8.4 Hz, 1H), 7.92-7.89 (m, 1H), 7.68-7.61 (m, 2H), 6.58 (s, 1H), 4.40 (dd, J=3.2 Hz, 2.0 Hz, 2H), 3.57 (t, J=4.8 Hz, 4H), 3.28 (s, 2H), 2.33 (t, J=2.0 Hz, 4H)

TABLE 2

Compounds in Table 2 below were prepared in accordance with the synthetic sequence in step 4 for Example 14 using the corresponding starting materials

| Example | Structure | MW: [M + H]+ | 1H NMR |
|---|---|---|---|
| 51 | 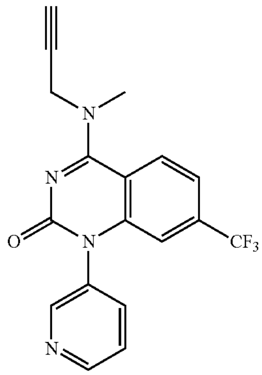 [SMILES: C#CCN(C)c1nc(=O)n(-c2cccnc2)c2cc(C(F)(F)F)ccc12] | 359.1 | 1H NMR (400 MHz, DMSO-d6) δ 8.74 (dd, J = 4.8 Hz, 1.6 Hz, 1H), 8.61 (d, J = 2.0 Hz, 1H), 8.28 (d, J = 8.4 Hz, 1H), 7.94-7.88 (m, 1H), 7.67 (dd, J = 8.0 Hz, 4.8 Hz, 1H), 7.56 (dd, J = 8.8 Hz, 1.2 Hz, 1H), 6.62 (s, 1H), 4.52 (d, J = 2.0 Hz, 2H), 3.47 (t, J = 2.4 Hz, 1H), 3.40 (s, 3H). |
| 64 | 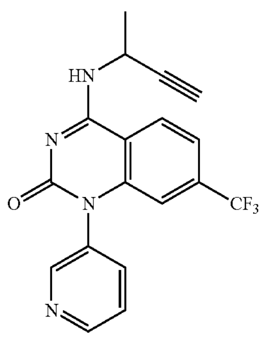 [SMILES: C#CC(C)Nc1nc(=O)n(-c2cccnc2)c2cc(C(F)(F)F)ccc12] | 359.1 | 1H NMR (400 MHz, DMSO-d6) δ 9.08 (d, J = 8.0 Hz 1H), 8.73 (d, J = 4.0 Hz, 1H), 8.61 (s, 1H), 8.53 (d, J = 8.4 Hz, 1H), 7.90 (d, J = 4.4 Hz, 1H), 7.68-7.62 (m, 2H), 6.57 (s, 1H), 5.31-5.26 (m, 1H), 3.27 (s, 1H), 1.53 (d, J = 6.8 Hz, 3H). |
| 67 | 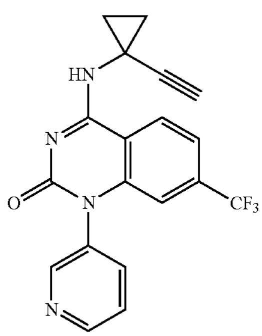 [SMILES: C#CC1(Nc2nc(=O)n(-c3cccnc3)c3cc(C(F)(F)F)ccc23)CC1] | 371.1 | 1H NMR (400 MHz, DMSO-d6) δ 9.31 (s, 1H), 8.74 (dd, J = 4.8 Hz, 1.2 Hz, 1H), 8.62 (d, J = 2.0 Hz, 1H), 8.38 (d, J = 8.4 Hz, 1H), 7.93 (dd, J = 6.4 Hz, 2.0 Hz, 1H), 7.67 (dd, J = 8.0 Hz, 4.8 Hz, 1H), 7.59 (d, J = 8.0 Hz, 1H), 6.56 (s, 1H), 3.07 (s, 1H), 1.34-1.31 (m, 1H), 1.25-1.22 (m, 1H). |
| 76 | 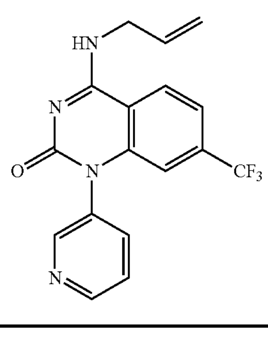 | 347.1 | 1H NMR (400 MHz, DMSO-d6) δ 9.09 (t, J = 4.0 Hz, 1H), 8.74 (dd, J = 4.8 Hz, 1.2 Hz, 1H), 8.61 (d, J = 2.0 Hz, 1H), 8.46 (d, J = 8.4 Hz , 1H), 7.94-7.91 (m, 1H), 7.68 (dd, J = 8.0 Hz, 4.8 Hz, 1H), 7.62 (d, J = 7.6 Hz, 1H), 6.59 (s, 1H), 6.06-5.96 (m, 1H), 5.28-5.16 (m, 2H), 4.20 (s, 2H). |

Example 15: Synthesis of 7-chloro-1-(2-methylpyridin-3-yl)-4-(prop-2-yn-1-ylamino)quinazolin-2(1H)-one

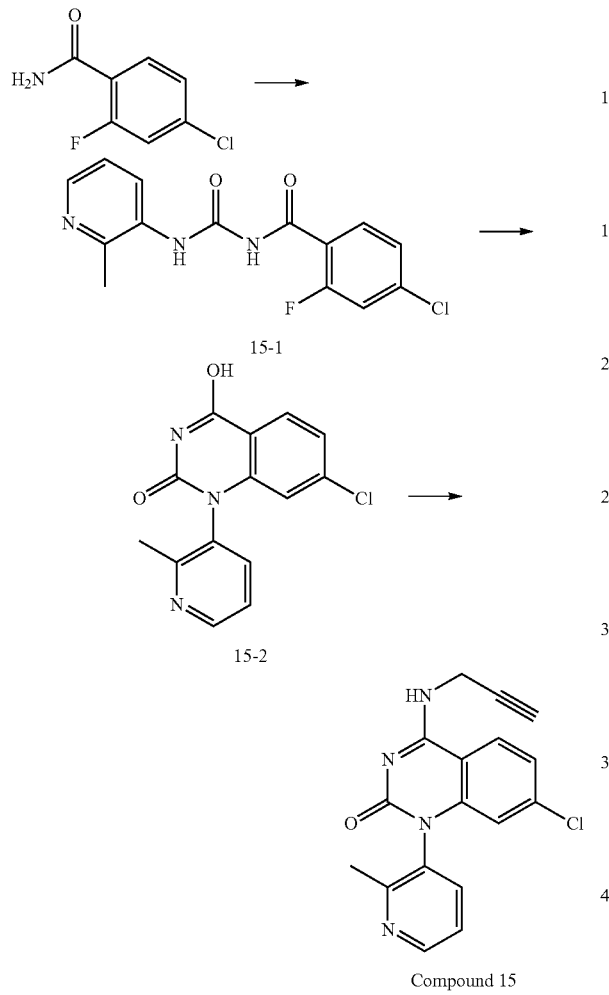

Compound 15

Step 1: To a stirred suspension of 4-chloro-2-fluorobenzamide (500.0 mg, 2.88 mmol) in dichloroethane (15 mL) at room temperature was added oxalyl dichloride (402.0 mg, 3.17 mmol). The resultant suspension was heated to 80° C. for 1 h. The mixture was cooled to room temperature, 2-methylpyridin-3-amine (623.0 mg, 5.76 mmol) was added. The mixture was stirred at room temperature for 1 h, then cooled to 0° C. The precipitate was collected by filtration, washed with water, and dried to afford compound 15-1. LCMS: 308.1 [M+H]⁺.

Step 2: KHMDS (3.9 mL, 3.93 mmol, 1.0 M in THF) was added to a mixture of compound 15-1 (550.0 mg, 1.79 mmol) in THF (10 mL) at −20° C., and the resulting mixture was warmed to room temperature over 3 hrs. The mixture was concentrated, diluted with water, and adjusted pH value to 6~7 with aqueous 4.0 M HCl. The precipitate was collected by filtration, washed with water, and dried to afford compound 15-2. LCMS: 288.1 [M+H]⁺.

Steps 3: To a stirred suspension of compound 15-2 (100.0 mg, 0.35 mmol) in toluene (3 mL) was added DIPEA (450.0 mg, 3.48 mmol) and POCl$_3$ (266.0 mg, 1.74 mmol) at 0° C. The suspension was heated at 100° C. for 2 hrs, then cooled to room temperature. A mixture of DIPEA (225.0 mg, 1.74 mmol) and prop-2-yn-1-amine (192.0 mg, 3.48 mmol) in NMP (2 mL) was added. The mixture was stirred at 50° C. for 1 h and concentrated. The residue was diluted with DCM (20 mL) and water (20 mL), extracted with DCM (20 mL×3), the combined organic phases were washed with water (50 mL×3), brine, dried over anhydrous Na$_2$SO$_4$ and concentrated. The residue was purified by prep-TLC to afford compound 15. LCMS: 325.1 [M+H]⁺. ¹H NMR (400 MHz, DMSO-d$_6$) δ 9.11 (t, J=5.6 Hz, 1H), 8.61 (m, 1H), 8.23 (d, J=8.8 Hz, 1H), 7.74 (dd, J=8.0 Hz, 1.6 Hz), 7.49-7.44 (m, 1H), 7.35 (dd, J=8.8 Hz, 2.0 Hz, 1H), 6.28 (d, J=2.0 Hz, 1H), 4.42-4.24 (m, 2H), 3.23 (s, 1H), 2.17 (s, 3H).

Example 16: Synthesis of 7-chloro-4-((1-ethynylcyclopropyl)amino)-1-(2-methylpyridin-3-yl)quinazolin-2(1H)-one

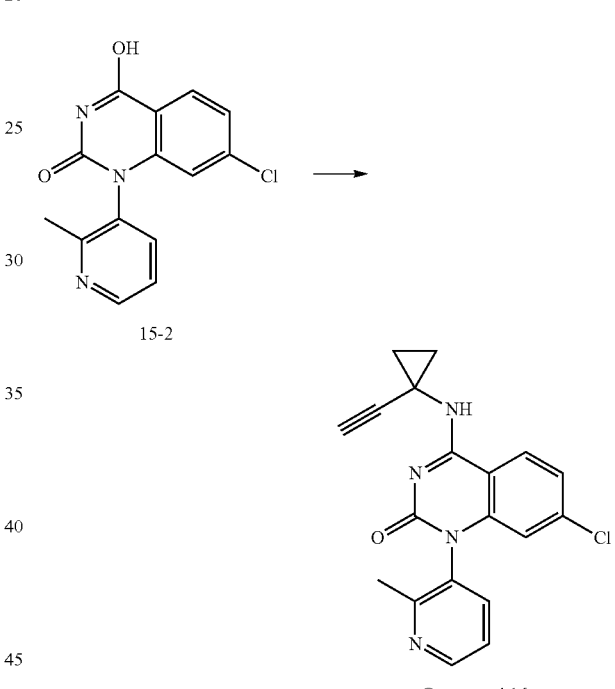

Compound 16

To a stirred suspension of compound 15-2 (110.0 mg, 0.38 mmol) in toluene (2.0 mL) was added DIPEA (494.0 mg, 3.82 mmol) and POCl$_3$ (293.0 mg, 1.91 mmol) at 0° C. The resultant suspension was heated to 100° C. for 2 hrs, then cooled to room temperature. A mixture of DIPEA (494.0 mg, 3.82 mmol) and 1-ethynylcyclopropan-1-amine hydrochloride (269.0 mg, 2.29 mmol) in NMP (0.5 mL) was added and the mixture was stirred at room temperature for 16 hrs. The mixture was diluted with DCM (5 mL) and water (15 mL), extracted with DCM (10 mL×3), the combined organic phases were washed with water (10 mL×3), brine, dried over Na$_2$SO$_4$ and concentrated. The residue was purified by gel column chromatography to afford compound 16 (80.4 mg, 60.0% yield). LCMS: 351.0 [M+H]⁺. ¹H NMR (400 MHz, DMSO-d$_6$) δ 9.13 (s, 1H), 8.61 (d, J=4.0 Hz, 1H), 8.20 (d, J=8.8 Hz, 1H), 7.77 (d, J=7.2 Hz, 1H), 7.49-7.45 (m, 1H), 7.33 (d, J=7.6 Hz, 1H), 6.27 (s, 1H), 3.05 (s, 1H), 2.17 (s, 3H), 1.32-1.20 (m, 4H).

Example 17: Synthesis of 7-chloro-4-(prop-2-yn-1-ylamino)-1-(pyrazin-2-yl)quinazolin-2(1H)-one

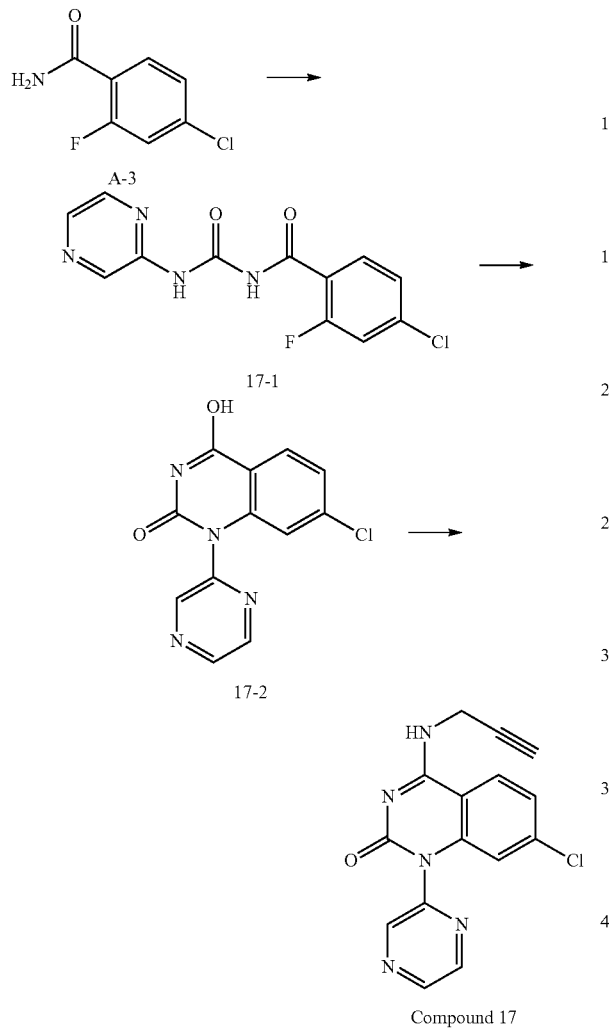

Step 1: To a solution of compound A-3 (1.0 g, 5.76 mmol) in DCE (15 mL) was added oxalyl dichloride (805.0 mg, 6.34 mmol) at room temperature, the reaction was stirred at 80° C. for 1 h. After cooling to room temperature, pyrazin-2-amine (1.1 g, 11.52 mmol) was added and the precipitate formed. The mixture was stirred at room temperature for another 1 h and the precipitate was collected by filtration, washed with water, and dried to afford compound 17-1 (1.3 g, 76.4% yield). LCMS: 295.1 [M+H]⁺.

Step 2: To a solution of compound 17-1 (800.0 mg, 2.71 mmol) in DMF (8 mL) was added KHMDS (6.0 mL, 5.97 mmol, 1M in THF) at −20° C., then the mixture was stirred at room temperature for 16 hrs. The reaction was diluted with water (80 mL) and adjusted pH to 6~7 with aqueous 4M HCl. The precipitate was collected by filtration, washed with water, and dried to afford compound 17-2 (520 mg, 69.7% yield). LCMS: 275.0 [M+H]⁺.

Step 3: To a solution of compound 17-2 (100.0 mg, 0.36 mmol) in toluene (1 mL) was added POCl₃ (279.0 mg, 1.82 mmol) and DIEA (470.5 mg, 3.64 mmol). The suspension was heated to 100° C. for 2 hrs, then cooled to room temperature. A mixture of prop-2-yn-1-amine (100.3 mg, 1.82 mmol) and DIEA (235.3 mg, 1.82 mmol) in NMP (1 mL) was added and the resulting mixture was stirred at room temperature for 16 hrs. The mixture was concentrated, the residue was diluted with DCM (20 mL) and water (20 mL), extracted by DCM (20 mL×3), the combined organic phases were washed with water (50 mL×3), brine, dried over anhydrous Na₂SO₄ and concentrated. The residue was purified by prep-HPLC to provide compound 17 LCMS: 312.1 [M+H]. ¹H NMR (400 MHz, CD₃OD) δ 8.81-8.76 (m, 3H), 8.08 (d, J=8.8 Hz, 1H), 7.32 (dd, J=8.8 Hz, 1.6 Hz, 1H), 6.20 (d, J=2.0 Hz, 1H), 4.45 (d, J=2.4 Hz, 2H), 2.68 (t, J=2.4 Hz, 1H).

Example 18: Synthesis of 7-bromo-4-(prop-2-yn-1-ylamino)-1-(pyridin-3-yl)quinazolin-2(1H)-one

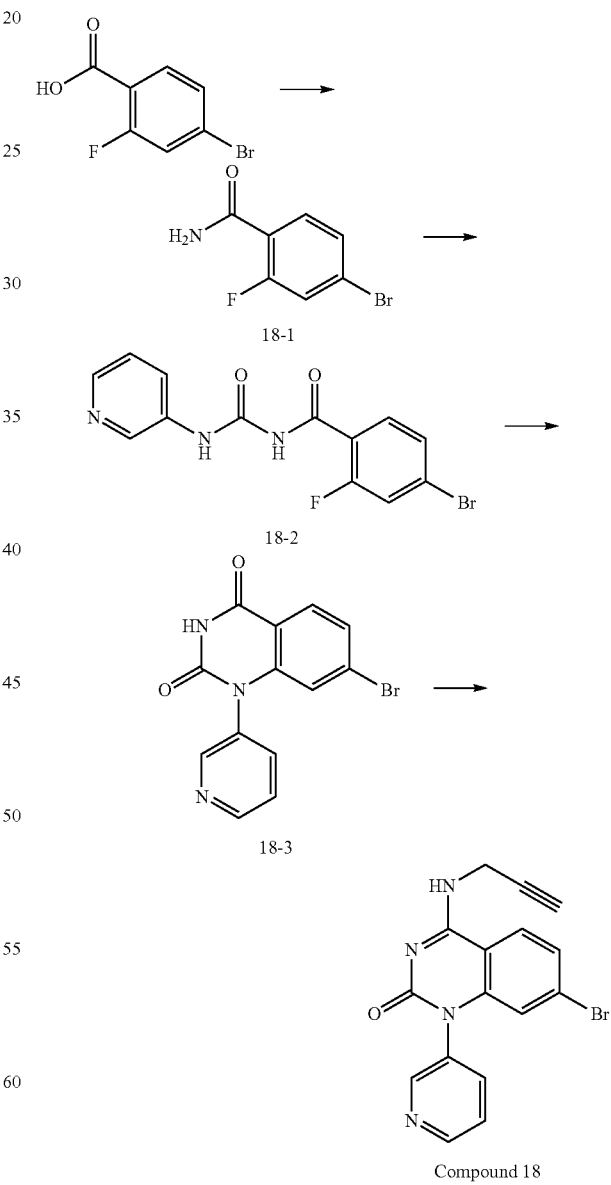

Step 1: To a solution of 4-bromo-2-fluorobenzoic acid (30.0 g, 137.7 mmol) in anhydrous THF (300 mL) was added oxalyl chloride (26.25 g, 206.7 mmol) and DMF (0.5 mL). The mixture was stirred at room temperature for 1 h and concentrated. The crude was dissolved in DCM (50 mL) and was added to a solution of ammonia (93.6 mL, 1.37 mol) in MeOH (200 mL) dropwise. The mixture was stirred at room temperature for 1 h and concentrated, dried to afford compound 18-1. LCMS: 217.9 [M+H]$^+$.

Step 2: To a solution of compound 18-1 (2.0 g, 9.17 mmol) in anhydrous THF (40 mL) was added dropwise (COCl)$_2$ (1.75 g, 13.76 mmol) at 0° C. The solution was stirred at 80° C. for 1 h and then concentrated. The crude was diluted with THF (30 mL) and pyridin-3-amine (950.0 mg, 10.1 mmol) was added dropwise. The mixture was filtered, and the precipitated solid was washed to afford compound 18-2. LCMS: 337.9 [M+H]$^+$.

Step 3: To a solution compound 18-2 (1.7 g, 5.03 mmol) in anhydrous THF (20 mL) was added KHMDS (20.0 mL, 20.1 mmol). The resulting solution was stirred at 70° C. for 1 h. The mixture was diluted with H$_2$O (40 mL) and the aqueous layer was acidified by 3.0 M HCl solution to pH=8. The mixture was filtered, and the filtrate was washed with THF (20 mL×2) to give compound 18-3. LCMS: 317.8 [M+H]$^+$. $^1$H NMR (400 MHz, DMSO-d$_6$) δ 11.89 (s, 1H), 8.68 (d, 2H), 8.02-7.85 (m, 2H), 7.72-7.57 (m, 1H), 7.51-7.37 (m, 1H), 6.48 (s, 1H).

Step 4: To a stirred solution of compound 18-3 (100.0 mg, 0.32 mmol) in DMF (1 mL) was added prop-2-yn-1-amine (35.0 mg, 0.63 mmol), PyAOP (246.0 mg, 0.47 mmol) and DBU (144.0 mg, 0.94 mmol). The suspension was stirred at room temperature for 1 h. Water (15.0 mL) was added and the mixture was extracted with DCM (10 mL×3). The organic layer was washed by brine, dried by Na$_2$SO$_4$, filtered, concentrated, and purified by prep-HPLC to afford compound 18. LCMS: 355.0 [M+H]$^+$. $^1$H NMR (400 MHz, DMSO-d$_6$) δ 9.09 (s, 1H), 8.71 (d, 1H), 8.57 (d, 1H), 8.11 (d, 1H), 7.88 (m, 1H), 7.66 (m, 1H), 7.46 (d, 1H), 6.51 (d, 1H), 4.32 (s, 2H), 3.23-3.21 (m, 1H).

Example 19: Synthesis of 7-bromo-5-methoxy-1-(2-methylpyridin-3-yl)-4-(prop-2-yn-1-ylamino)quinazolin-2(1H)-one

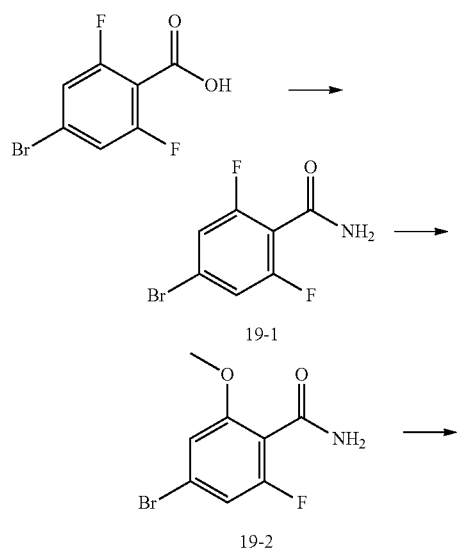

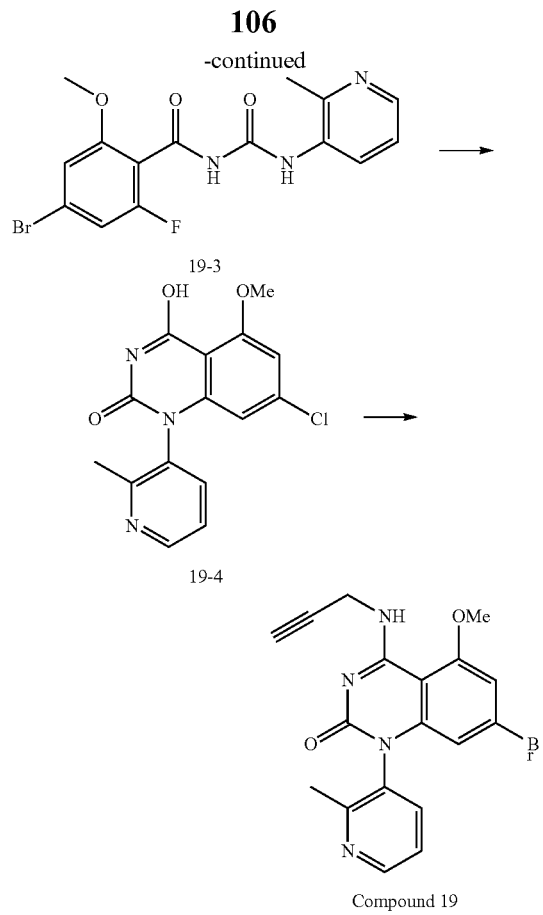

Compound 19

Step 1: 4-bromo-2,6-difluorobenzoic acid (3.0 g, 12.66 mmol) was mixed in SOCl$_2$ (25.0 mL), and then the resulting solution was heated at 80° C. for 2 hrs. The solution was cooled to room temperature and then concentrated. The residue was dissolved in dioxane (15 mL), treated with NH$_4$OH (40%) (15.0 mL). The resulting mixture was stirred 0° C. to room temperature for 1 h and concentrated. Water was added while stirring until a white solid was precipitated. Then the solid product was filtered and washed to give compound 19-1 (2.7 g, 83.7% yield). LCMS: 235.9 [M+H]$^+$.

Step 2: To a solution of sodium methanolate (50.5 mg, 0.93 mmol) in MeOH (4 mL) were added compound 19-1 (200 mg, 0.85 mmol), and the reaction was stirred at 80° C. for 6 hrs. The mixture was then cooled to room temperature and concentrated to give compound 19-2 (200 mg, 94.7% yield). LCMS: 248.0 [M+H]$^+$.

Step 3: To a stirred suspension of compound 19-2 (200.0 mg, 0.80 mmol) in dichloroethane (4 mL) at room temperature was added oxalyl chloride (112.0 mg, 0.88 mmol). The resultant suspension was heated to 80° C. for 1 h. The mixture was cooled to room temperature, 2-methylpyridin-3-amine (174.0 mg, 1.61 mmol) was added. The resultant reaction was stirred at room temperature for 20 min, then cooled to 0° C. The mixture was stirred at room temperature for 16 hrs. The precipitate was collected, washed, and dried to afford compound 19-3 (200.0 mg, 58.4% yield). LCMS: 381.9 [M+H]$^+$.

Step 4: NaH (50.0 mg, 1.25 mmol, 60% dispersion) was added to a mixture of compound 19-3 (160.0 mg, 0.42 mmol) in THF (5 mL) at −20° C., and the resulting mixture was warm to room temperature, then stirred for 2 hrs. The mixture was poured into ice-water (3 mL), adjusted pH to 6~7 with aqueous 4M HCl. The precipitate was collected by filtration, washed with water, and dried to afford compound 19-4 (120 mg, 71.2% yield). LCMS: 362.0 [M+H]$^+$.

Steps 5: To a stirred suspension of compound 19-4 (110.0 mg, 0.30 mmol) in toluene (3 mL) was added DIEA (392.0 mg, 3.03 mmol) and POCl$_3$ (233.0 mg, 1.52 mmol) at 0° C. The resultant suspension was heated to 100° C. for 2 hrs, then cooled to room temperature. A mixture of DIEA (392.0 mg, 3.03 mmol) and prop-2-yn-1-amine (167.0 mg, 3.03 mmol) in NMP (1 mL) was added and stirred at 50° C. for 1 h. The mixture was diluted with DCM (5 mL) and water (15 mL), extracted with DCM (10 mL×3), the combined organic phases were washed with water (10 mL×3), brine, dried over anhydrous Na$_2$SO$_4$ and concentrated. The residue was purified by gel column chromatography to afford compound 19. LCMS: 399.0 [M+H]$^+$. $^1$H NMR (400 MHz, DMSO-d$_6$) δ 8.82 (t, J=5.6 Hz, 1H), 8.60 (dd, J=4.8 Hz, 1.6 Hz, 1H), 7.72 (dd, J=8.0 Hz, 1.2 Hz, 1H), 7.46 (dd, J=8.0 Hz, 4.8 Hz, 1H), 7.10 (d, J=1.6 Hz, 1H), 5.97 (d, J=1.6 Hz, 1H), 7.37-7.24 (m, 2H), 4.05 (s, 3H), 3.15 (t, J=2.8 Hz, 1H), 2.16 (s, 3H).

Example 20: Synthesis of 7-chloro-5-methoxy-4-(prop-2-yn-1-ylamino)-1-(pyridin-3-yl)quinazolin-2(1H)-one

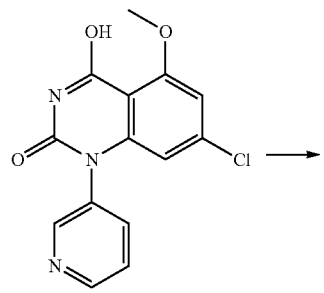

Intermediate A

⟶

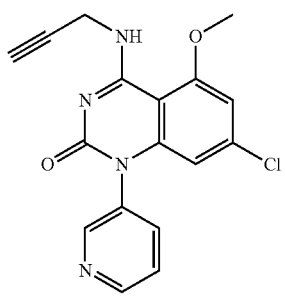

Compound 20

To a solution of compound Intermediate A (100 mg, 0.37 mmol) in DMF (2.5 mL) was added prop-2-yn-1-amine (36.3 mg, 0.74 mmol), PyAOP (253.0 mg, 0.49 mmol) and DBU (175.5 mg, 1.15 mmol). The reaction mixture was stirred at room temperature for 2 hrs. Water (25 mL) was added, extracted with DCM (20 mL×3), the organic layer was washed by brine, dried by Na$_2$SO$_4$, filtered, concentrated, and purified by prep-HPLC to give compound 20 (41.2 mg, 36.7% yield). LCMS: 341.0[M+H]$^+$. $^1$H NMR (400 MHz, DMSO-d$_6$) δ 8.81 (t, J=5.2 Hz, 1H), 8.70 (dd, J=4.8 Hz, 1.6 Hz, 1H), 8.53 (d, J=2.0 Hz, 1H), 7.87-7.80 (m, 1H), 7.63 (dd, J=8.0 Hz, 4.8 Hz, 1H), 6.98 (d, J=1.6 Hz, 1H), 5.91 (d, J=1.6 Hz, 1H), 4.31-4.29 (m, 2H), 4.05 (s, 3H), 3.13 (t, J=2.4 Hz, 1H).

TABLE 3

Compounds in Table 3 below were prepared in accordance with the synthetic sequence in Example 20 using the corresponding starting materials.

| Example | Structure | MW [M + H]$^+$ | $^1$H NMR |
|---|---|---|---|
| 65 | (structure shown) | 355.1 | $^1$H NMR (400 MHz, DMSO-d$_6$) δ 8.70 (dd, J = 4.4 Hz, 1.2 Hz, 1H), 8.53 (s, 1H), 8.38 (d, J = 7.6 Hz, 1H), 7.85-7.83 (m, 1H), 7.65-7.61 (m, 1H), 7.00 (d, J = 2.0 Hz, 1H), 5.92 (d, J = 2.0 Hz, 1H), 5.23-5.19 (m, 1H), 4.08 (s, 3H), 3.29 (s, 1H), 1.54 (d, J = 7.2 Hz, 3H). |

TABLE 3-continued

Compounds in Table 3 below were prepared in accordance with the synthetic sequence in Example 20 using the corresponding starting materials.

| Example | Structure | MW [M + H]+ | 1H NMR |
|---|---|---|---|
| 66 | 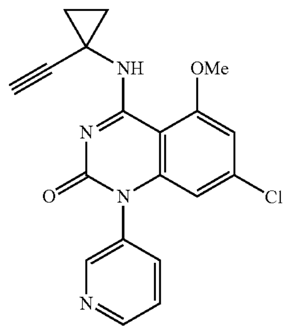 | 367.1 | 1H NMR (400 MHz, DMSO-d6) δ 8.73 (s, 1H), 8.71 (dd, J = 4.8 Hz, 1.6 Hz, 1H), 8.54 (d, J = 2.4 Hz, 1H), 7.87-7.84 (m, 1H), 7.64 (dd, J = 8.0 Hz, 4.8 Hz, 1H), 6.96 (d, J = 1.6 Hz, 1H), 5.91 (d, J = 1.6 Hz, 1H), 4.05 (s, 3H), 3.02 (s, 1H), 1.29-1.23 (m, 4H). |
| 73 | 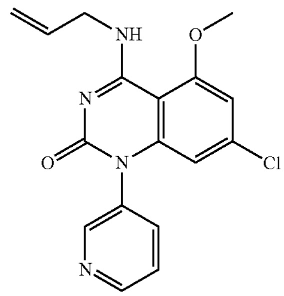 [SMILES: C=CCNc1nc(=O)n(-c2cccnc2)c2cc(Cl)cc(OC)c12] | 343.0 | 1H NMR (400 MHz, DMSO-d6) δ 8.70-8.65 (m, 2H), 8.51 (d, J = 2.4 Hz, 1H), 7.84-7.81 (m, 1H), 7.62 (dd, J = 8.0 Hz, 4.8 Hz, 1H), 6.98 (d, J = 2.0 Hz, 1H), 6.04-5.91 (m, 1H), 5.90 (s, 1H), 5.23-5.13 (m, 2H), 4.18 (t, J = 3.6 Hz, 2H), 4.06 (s, 3H). |

Example 21: Synthesis of 7-chloro-5-methoxy-4-(prop-2-yn-1-ylamino)-1-(pyrazin-2-yl)quinazolin-2(1H)-one

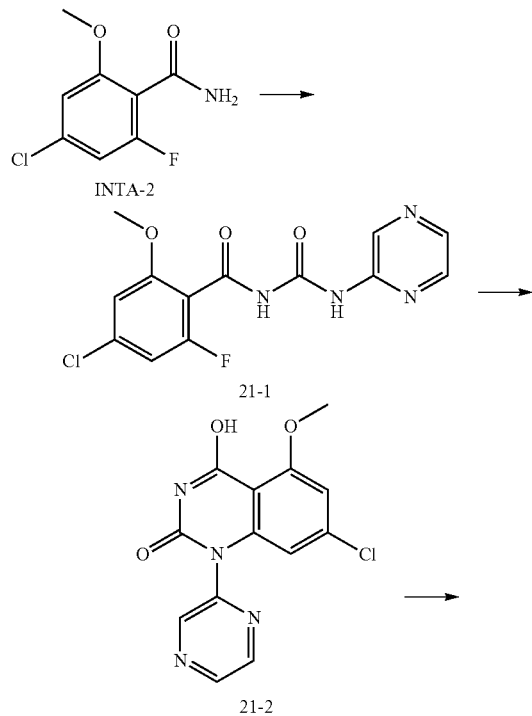

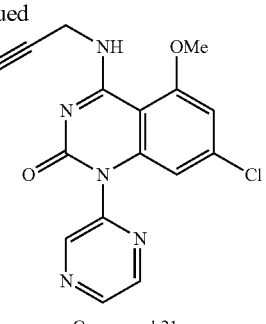

Compound 21

Step 1: To a solution of compound INTA-2 (1.0 g, 4.91 mmol) in DCE (10 mL) was added oxalyl dichloride (686.0 mg, 5.40 mmol) at room temperature, then the mixture was stirred at 80° C. for 1 h. The mixture was cooled to room temperature, pyrazin-2-amine (935.0 mg, 9.82 mmol) was added. The precipitate was formed, and the mixture was stirred at room temperature for another 1 h. then cooled to 0° C. The precipitate was collected by filtration, washed with water, and dried to afford compound 21-1 (800.0 mg, 50.3% yield). LCMS: 325.0 [M+H]+.

Step 2: To a solution of compound 21-1 (300.0 mg, 0.92 mmol) in THF (5 mL) was added KHMDS (2.0 mL, 2.03 mmol, 1M in THF) at −20° C., then the mixture was stirred at 40° C. for 4 hrs. The mixture was concentrated, diluted with water, and adjusted pH to 6~7 with aqueous 4M HCl. The precipitate was collected by filtration, washed with water and Et2O, and dried to afford compound 21-2 (220.0 mg, 78.2% yield). LCMS: 305.0 [M+H]+;

Steps 3: To a stirred solution of compound 21-2 (150.0 mg, 0.49 mmol) in ACN (3 mL) was added DIEA (190.8 mg, 1.48 mmol) and POCl₃ (226.0 mg, 1.48 mmol) at 0° C. The suspension was heated to 80° C. for 2 hrs. After cooling to room temperature, a solution of prop-2-yn-1-amine (272.0 mg, 4.92 mmol) and DIEA (636.0 mg, 4.92 mmol) in ACN (1 mL) was added. The reaction was stirred at room temperature for 16 hrs and concentrated. The crude as diluted with water (30 mL), extracted by DCM (50 mL×3), the combined organic layer was further washed with water (50 mL×2), brine, dried over anhydrous Na₂SO₄ and concentrated. The residue was purified by column chromatography to afford compound 21 (75.0 mg, 42.9% yield). LCMS: 342.0 [M+H]⁺. ¹H NMR (400 MHz, DMSO-d₆) δ 8.93 (brs, 1H), 8.82-8.79 (m, 3H), 7.01 (d, J=1.6 Hz, 1H), 6.06 (d, J=1.6 Hz, 1H), 4.31 (s, 2H), 4.05 (s, 3H), 3.15 (s, 1H).

Example 22: Synthesis of 7-chloro-5-methoxy-1-(2-methylpyridin-3-yl)-4-(prop-2-yn-1-ylamino)quinazolin-2(1H)-one

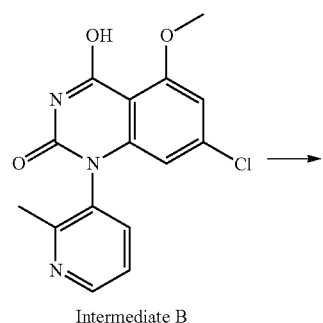

Intermediate B

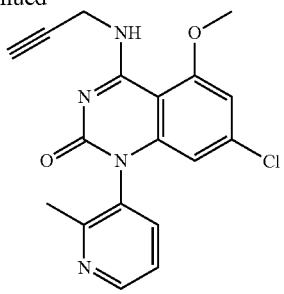

Compound 22

To a stirred solution of compound Intermediate B (200.0 mg, 0.63 mmol) in toluene (3 mL) was added POCl₃ (482.5 mg, 3.15 mmol) and DIPEA (813.5 mg, 6.29 mmol) at 0° C. The suspension was heated to 100° C. for 2 hrs. After cooling to room temperature, a mixture of DIPEA (813.5 mg, 6.29 mmol) and prop-2-yn-1-amine (346.7 mg, 6.29 mmol) in NMP (2 mL) was added. The resulting mixture was stirred at room temperature for 16 hrs. The mixture was concentrated and the residue was diluted with DCM (20 mL) and water (20 mL), extracted by DCM (50 mL×3), the combined organic phases were washed with water (50 mL×3), brine, dried over anhydrous Na₂SO₄ and concentrated. The residue was purified by gel column chromatography to afford compound 22 (65.5 mg, 29.3% yield). LCMS: 355.1 [M+H]⁺. ¹H NMR (400 MHz, DMSO-d₆) δ 8.81 (t, J=5.2 Hz, 1H), 8.59 (dd, J=4.8 Hz, 1.6 Hz, 1H), 7.72 (dd, J=8.0 Hz, 1.6 Hz, 1H), 7.46 (dd, J=8.0 Hz, 4.8 Hz, 1H), 6.99 (d, J=1.6 Hz, 1H), 5.83 (d, J=2.0 Hz, 1H), 4.24-4.40 (m, 2H), 4.06 (s, 3H), 3.15 (t, J=2.0 Hz, 1H), 2.16 (s, 3H).

TABLE 4

Compounds in Table 4 below were prepared in accordance with the synthetic sequence in Example 22 using the corresponding starting materials.

| Example | Structure | MW [M + H]⁺ | ¹H NMR |
|---|---|---|---|
| 26 | 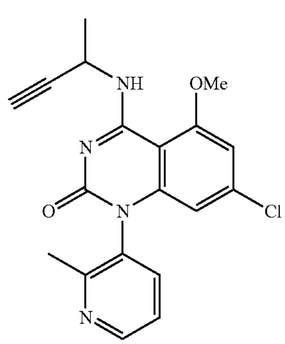 [SMILES: C#CC(C)Nc1nc(=O)n(-c2cccnc2C)c2cc(Cl)cc(OC)c12] | 369.0 | ¹H NMR (400 MHz, CD₃OD) δ 8.60 (d, J = 4.4 Hz, 1H), 7.73 (t, J = 6.8 Hz, 1H), 7.51 (dd, J = 7.6 Hz, 4.8 Hz, 1H), 7.02 (d, J = 0.8 Hz, 1H), 6.01 (d, J = 1.2 Hz, 1H), 5.35-5.30 (m, 1H), 4.13 (s, 3H), 2.79 (dd, J = 6.4 Hz, 2.4 Hz, 1H), 2.35-2.25 (m, 1H), 1.58 (dd, J = 6.8 Hz, 3.2 Hz, 3H). |

TABLE 4-continued

Compounds in Table 4 below were prepared in accordance with the synthetic sequence
in Example 22 using the corresponding starting materials.

| Example | Structure | MW [M + H]+ | 1H NMR |
|---|---|---|---|
| 28 | 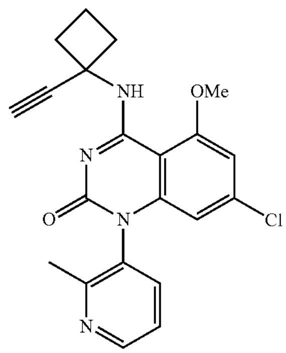 [SMILES: C#CC1(Nc2nc(=O)n(-c3cccnc3C)c3cc(Cl)cc(OC)c23)CCC1] | 395.1 | 1H NMR (400 MHz, DMSO-d6) δ 8.59 (dd, J = 4.8 Hz, 1.2 Hz, 1H), 8.46 (s, 1H), 7.73 (d, J = 8.0 Hz, 1H), 7.45 (dd, J = 8.0 Hz, J = 4.8 Hz, 1H), 7.00 (d, J = 1.6 Hz, 1H), 5.84 (d, J = 1.6 Hz, 1H), 4.08 (s, 3H), 3.32-3.30 (m, 1H), 2.57-2.54 (m, 4H), 2.21 (s, 3H), 2.06-1.93 (m, 2H). |
| 74 | 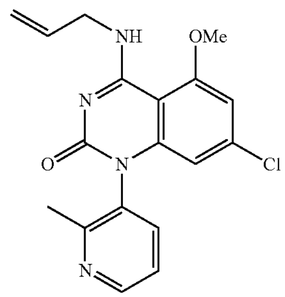 [SMILES: C=CCNc1nc(=O)n(-c2cccnc2C)c2cc(Cl)cc(OC)c12] | 357.1 | 1H NMR (400 MHz, DMSO-d6) δ 8.66 (t, J = 2.4 Hz, 1H), 8.58 (dd, J = 4.8 Hz, 1.6 Hz, 1H), 7.70 (dd, J = 8.0 Hz, 1.2 Hz, 1H), 7.45 (dd, J = 8.0 Hz, 4.8 Hz, 1H), 6.99 (d, J = 2.0 Hz, 1H), 6.06-5.94 (m, 1H), 5.82 (d, J = 1.6 Hz, 1H), 5.25-5.12 (m, 2H), 4.25-4.12 (m, 2H), 4.06 (s, 3H), 2.15 (s, 3H). |

Example 23: Synthesis of 7-chloro-5-methoxy-1-(3-methylpyrazin-2-yl)-4-(prop-2-yn-1-ylamino)quinazolin-2(1H)-one

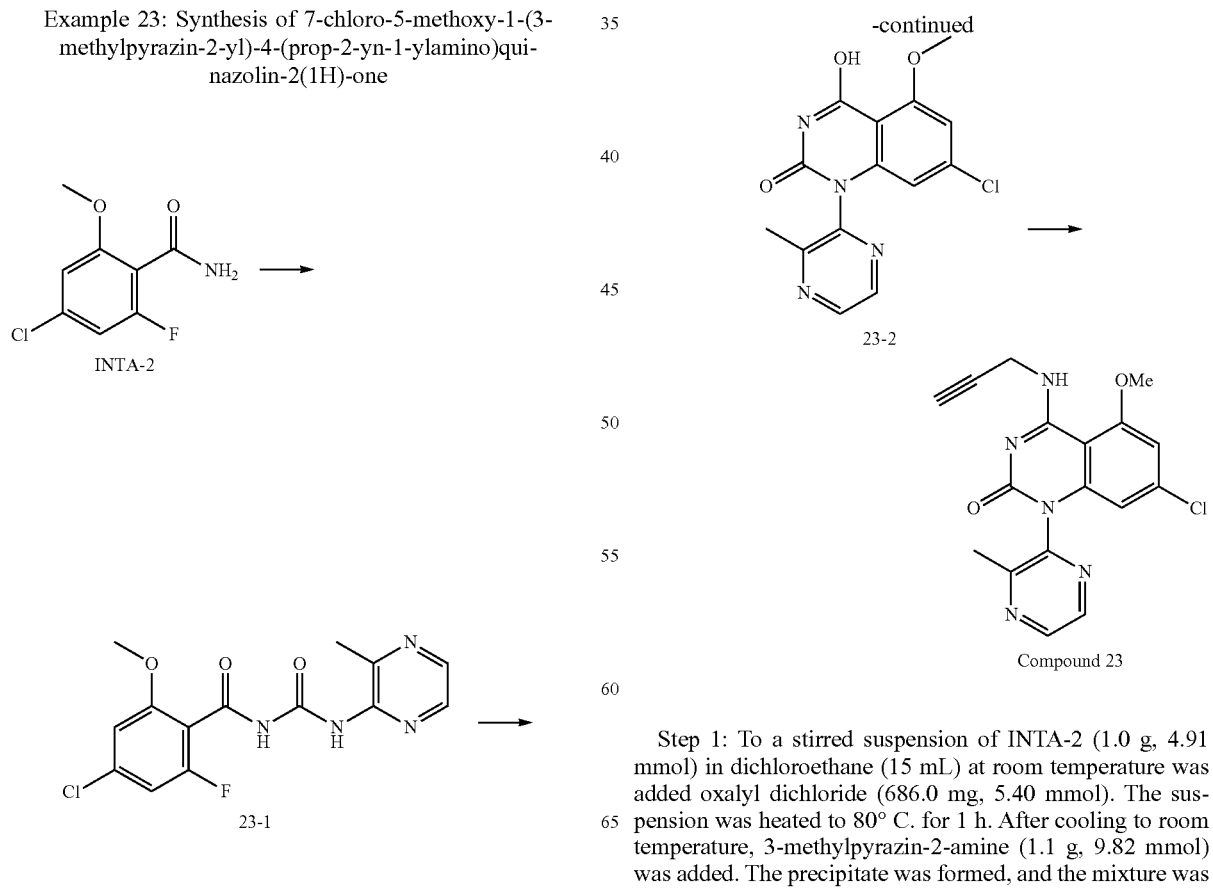

Step 1: To a stirred suspension of INTA-2 (1.0 g, 4.91 mmol) in dichloroethane (15 mL) at room temperature was added oxalyl dichloride (686.0 mg, 5.40 mmol). The suspension was heated to 80° C. for 1 h. After cooling to room temperature, 3-methylpyrazin-2-amine (1.1 g, 9.82 mmol) was added. The precipitate was formed, and the mixture was stirred at room temperature for another 1 h. The precipitate was collected by filtration, washed with water, and dried to afford compound 23-1 (940 mg, 56.5%). LCMS: 339.0 [M+H]⁺.

Step 2: To a solution of compound 23-1 (900.00 mg, 2.66 mmol) in THF (15 mL) was added NaH (319.0 mg, 7.98 mmol, 60% oil dispersion) at −20° C., then the resulting mixture was allowed to heat to 40° C. for 16 hrs. The mixture was concentrated, poured into ice-water (20 mL) and adjusted pH to 6~7 with aqueous 4M HCl. The precipitate was collected by filtration, washed with water and Et$_2$O, and dried to afford compound 23-2 (500.0 mg, 59.0% yield). LCMS: 319.0 [M+H]⁺.

Steps 3: To a stirred solution of compound 23-2 (150.0 mg, 0.47 mmol) in ACN (3 mL) was added DIEA (182.5 mg, 1.41 mmol) and POCl$_3$ (217.0 mg, 1.41 mmol) at 0° C. The resultant suspension was heated to 80° C. for 2 hrs. After cooling to room temperature, a solution of prop-2-yn-1-amine (255.0 mg, 4.71 mmol) and DIEA (608.0 mg, 4.71 mmol) in ACN (1 mL) was added. The mixture was stirred at room temperature for 16 hrs and then concentrated. The mixture was added to water (50 mL) and extracted by DCM (50 mL×3). The combined organic layer was washed with water (50 mL×2), brine, dried over anhydrous Na$_2$SO$_4$ and concentrated. The residue was purified by column chromatography to afford compound 23. LCMS: 356.0 [M+H]⁺. ¹H NMR (400 MHz, DMSO-d$_6$) δ 8.89 (t, J=5.6 Hz, 1H), 8.71 (d, J=2.8 Hz, 1H), 8.60 (d, J=2.4 Hz, 1H), 7.02 (d, J=1.6 Hz, 1H), 5.96 (d, J=1.6 Hz, 1H), 4.34-4.31 (m, 2H), 4.06 (s, 3H), 3.15 (t, J=2.4 Hz, 1H), 2.30 (s, 3H).

Example 24: Synthesis of 7-chloro-4-((1-ethynylcyclopropyl)amino)-5-methoxy-1-(pyrazin-2-yl)quinazolin-2(1H)-one

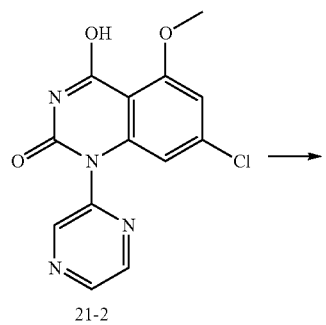

21-2

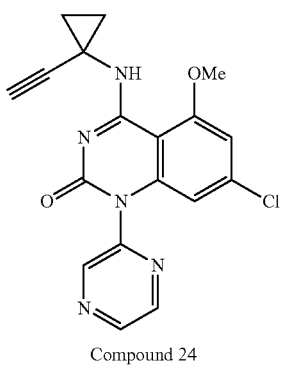

Compound 24

To a stirred solution of compound 21-2 (100.0 mg, 0.32 mmol) in MeCN (2 mL) was added DIEA (127.5 mg, 0.98 mmol) and POCl$_3$ (151.2 mg, 0.98 mmol) at 0° C. The suspension was heated to 80° C. for 2 hrs. After cooling to room temperature, a mixture of 1-ethynylcyclopropanamine hydrochloride (193.3 mg, 1.64 mmol) and DIEA (425.0 mg, 3.28 mmol) in NMP (1 mL) was added. The mixture was stirred at room temperature for 16 hrs and concentrated. The crude was added to the water (30 mL), extracted by DCM (50 mL×3), and the combined organic layer was further washed with water (50 mL×2), brine, dried over anhydrous Na$_2$SO$_4$ and concentrated. The residue was purified by column chromatography to afford compound 24. LCMS: 368.1 [M+H]⁺. ¹H NMR (400 MHz, DMSO-d$_6$) δ 8.83-8.79 (m, 4H), 6.98 (d, J=1.6 Hz, 1H), 6.05 (d, J=1.6 Hz, 1H), 4.05 (s, 3H), 3.03 (s, 1H), 1.29-1.28 (m, 2H), 1.25-1.24 (m, 2H).

Example 25: Synthesis of 7-chloro-4-((1-ethynylcyclopropyl)amino)-5-methoxy-1-(3-methylpyrazin-2-yl)quinazolin-2(1H-one

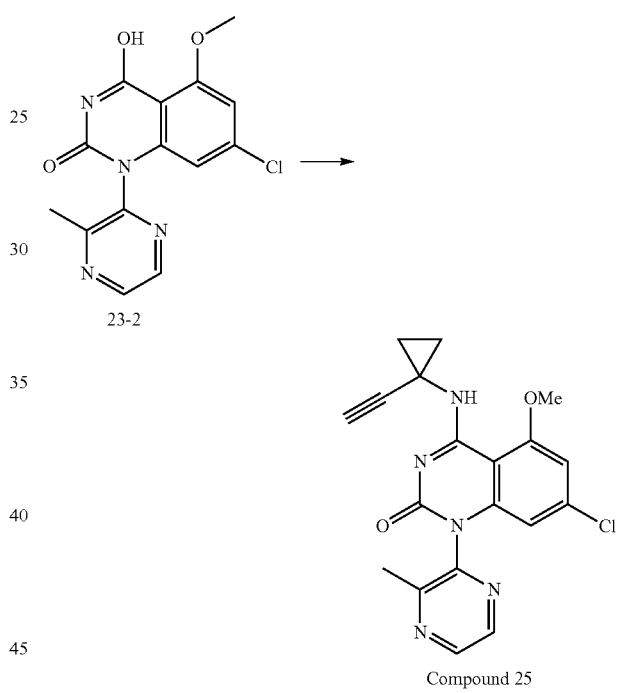

Compound 25

To a stirred mixture of compound 23-2 (100.0 mg, 0.31 mmol) in toluene (1 mL) was added DIEA (406.4 mg, 3.14 mmol) and POCl$_3$ (241.0 mg, 1.57 mmol) at 0° C. The suspension was heated to 100° C. for 2 hrs, and then cooled to room temperature. A solution of 1-ethynylcyclopropan-1-amine hydrochloride (184.0 mg, 1.57 mmol) and DIEA (406.4 mg, 3.14 mmol) in NMP (1 mL) was added. The mixture was stirred at room temperature for 16 hrs and concentrated. The mixture was diluted with DCM (30 mL) and water (30 mL), and further extracted with DCM (30 mL×2). The combined organic phases were washed with water (30 mL×3), brine, dried over anhydrous Na$_2$SO$_4$ and concentrated. The residue was purified by column chromatography to afford compound 25 (80.9 mg, 67.5% yield). LCMS: 382.0 [M+H]⁺. ¹H NMR (400 MHz, DMSO-d$_6$) δ 8.81 (s, 1H), 8.72 (d, J=2.4 Hz, 1H), 8.60 (d, J=2.4 Hz, 1H), 6.99 (d, J=1.6 Hz, 1H), 5.96 (d, J=1.6 Hz, 1H), 4.05 (s, 3H), 3.03 (s, 1H), 2.30 (s, 3H), 1.31-1.28 (m, 2H), 1.26-1.23 (m, 2H).

Example 27: Synthesis of 7-chloro-4-((1-ethynylcyclopropyl)amino)-5-methoxy-1-(2-methylpyridin-3-yl)quinazolin-2(1H)-one

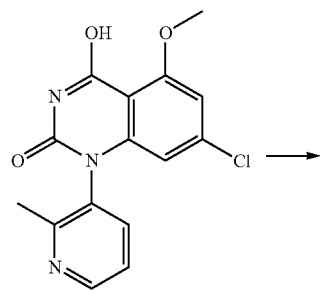

Intermediate B

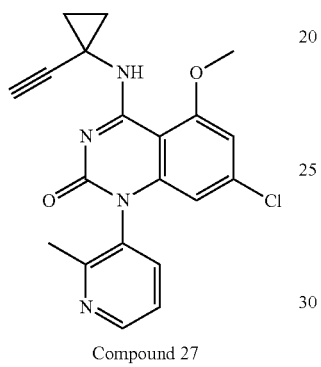

Compound 27

To a stirred solution of Intermediate B (2.0 g, 6.30 mmol) in toluene (20 mL) was added POCl$_3$ (4.8 g, 31.47 mmol) and DIEA (8.1 g, 62.95 mmol) at 0° C. The suspension was heated to 100° C. for 2 hrs. After cooling to room temperature, a mixture of 1-ethynylcyclopropanamine hydrochloride (2.6 g, 31.47 mmol) and DIEA (8.1 g, 62.95 mmol) in NMP (50 mL) was added. The mixture was stirred at room temperature for 16 hrs. After concentration, the residue was diluted with DCM (200 mL) and water (200 mL), extracted by DCM (50 mL×3). The organic phases were washed with water, brine, dried over Na$_2$SO$_4$ and concentrated. The residue was purified by gel column chromatography to afford compound 27 (500.3 mg). LCMS: 381.0 [M+H]$^+$. $^1$H NMR (400 MHz, DMSO-d$_6$) δ 8.74 (s, 1H), 8.61 (dd, J=4.8 Hz, 1.6 Hz, 1H), 7.74 (dd, J=8.0 Hz, 1.6 Hz, 1H), 7.47 (dd, J=8.0 Hz, 4.8 Hz, 1H), 6.97 (d, J=2.0 Hz, 1H), 5.84 (d, J=1.6 Hz, 1H), 4.05 (s, 3H), 3.03 (s, 1H), 2.17 (s, 3H), 1.31-1.27 (m, 2H), 1.25-1.22 (m, 2H).

Example 29: Synthesis of 7-chloro-5-fluoro-4-(prop-2-yn-1-ylamino)-1-(pyridin-3-yl)quinazolin-2(1H)-one

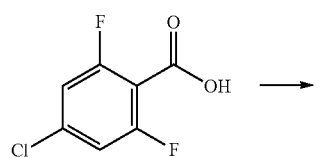

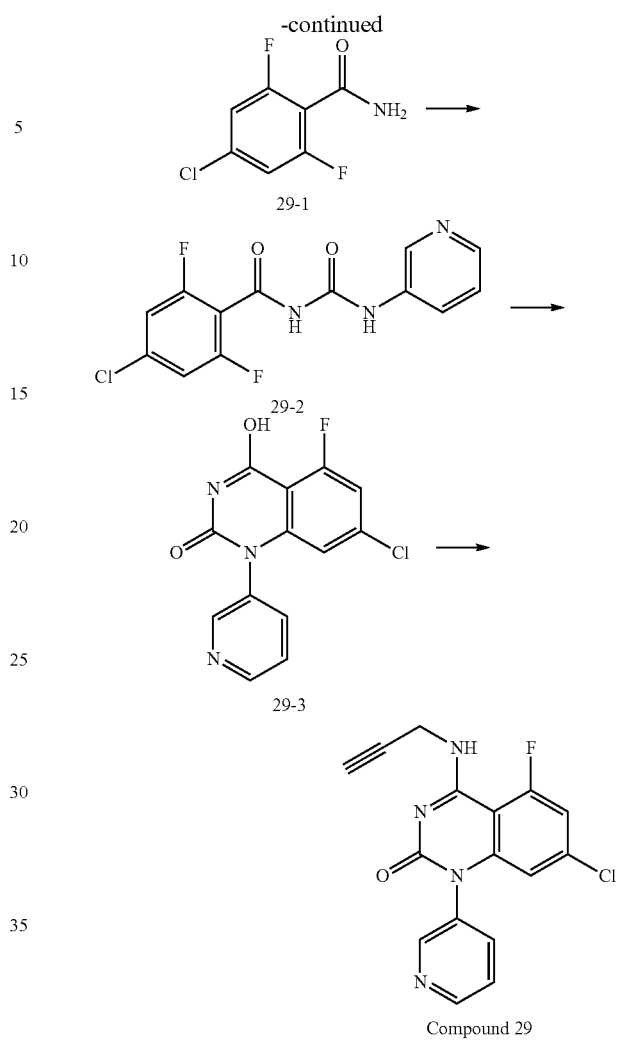

Step 1: A solution of 4-chloro-2, 6-difluorobenzoic acid (23.0 g, 119.45 mmol) in SOCl$_2$ (100.0 mL) was stirred at 80° C. for 3 hrs. The mixture was concentrated and the residue was dissolved in dioxane (60 mL), then NH$_4$OH solution (60 mL) was added at 0° C. dropwise. The mixture was then stirred at 25° C. for 0.5 h and concentrated. The crude was diluted with water while stirring until a white solid was precipitated. The solid product was filtered, washed with water, and dried to afford compound 29-1 (15.0 g, 65.6% yield). $^1$H NMR (400 MHz, DMSO-d$_6$) δ 8.17 (brs, 1H), 7.92 (brs, 1H), 7.49-7.42 (m, 2H).

Step 2: To a stirred suspension of compound 29-1 (350.0 mg, 1.83 mmol) in DCE (5 mL) was added oxalyl dichloride (255.0 mg, 2.01 mmol) and the mixture was heated to 80° C. for 1 h. After cooling to room temperature, pyridin-3-amine (344.0 mg, 3.65 mmol) was added. The resultant mixture was stirred at room temperature for 1 h, then cooled to 0° C. The precipitate was collected by filtration, washed with water, and dried to afford compound 29-2 (400.0 mg, 70.2% yield). LCMS: 312.0 [M+H]$^+$.

Step 3: To a solution of compound 29-2 (400.0 mg, 1.28 mmol) in THF (10 mL) was added KHMDS (2.8 mL, 2.82 mmol, 1.0 M in THF) at −20° C., and the resulting mixture was warmed to room temperature over 3 hrs. The mixture was concentrated, diluted with water, and adjusted pH to 6~7 with aqueous 4.0 M HCl. The precipitate was collected by filtration, washed with water, and dried to afford compound 29-3 (250.0 mg, 66.8% yield). LCMS: 292.0 [M+H]+.

Step 4: To a stirred mixture of compound 29-3 (230.0 mg, 0.79 mmol) in toluene (3 mL) was added POCl$_3$ (604.5 mg, 3.94 mmol) and DIPEA (1.0 g, 7.89 mmol) at 0° C. The suspension was heated to 100° C. for 2 hrs, then cooled to room temperature. A mixture of DIPEA (1.0 g, 7.89 mmol) and prop-2-yn-1-amine (434.3 mg, 7.89 mmol) in NMP (3 mL) was added. The resulting mixture was stirred at room temperature for 16 hrs and concentrated. The residue was diluted with water (20 mL), extracted by DCM (50 mL×3). The combined organic phases were washed with water, brine, dried over Na$_2$SO$_4$ and concentrated. The residue was purified by gel column chromatography to afford compound 29. LCMS: 329.1 [M+H]+. $^1$H NMR (400 MHz, DMSO-d$_6$) δ 8.72 (dd, J=4.8 Hz, 1.2 Hz, 1H), 8.57 (d, J=2.4 Hz, 1H), 8.38 (s, 1H), 7.87 (dd, J=6.4 Hz, 2.0 Hz, 1H), 7.64 (dd, J=8.0 Hz, 4.8 Hz, 1H), 7.37 (dd, J=12.0 Hz, 1.6 Hz, 1H), 6.21 (s, 1H), 4.29 (s, 2H), 3.15 (t, J=2.0 Hz, 1H).

Example 30: Synthesis of 7-chloro-5-fluoro-1-(2-methylpyridin-3-yl)-4-(prop-2-yn-1-ylamino)quinazolin-2(1H)-one

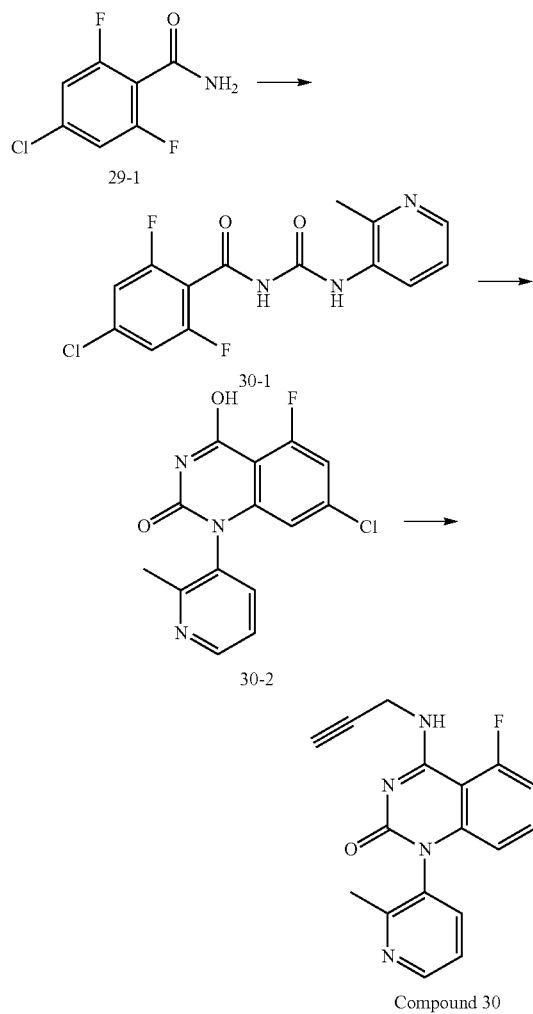

Compound 30

Step 1: To a solution of compound 29-1 (500.0 mg, 191.56 mmol) in DCE (10 mL) was added oxalyl dichloride (370.1 mg, 2.87 mmol) at room temperature, the mixture was stirred at 80° C. for 1 h. After cooling to room temperature, 2-methylpyridin-3-amine (564.5 mg, 5.22 mmol) was added. The mixture was stirred at room temperature for another 40 mins. The reaction mixture was filtered and the filter cake was washed with water (20 mL×3) and dried to afford compound 30-1 (560.0 mg, 63.5% yield). LCMS: 326.0 [M+H]+.

Step 2: To a solution of compound 30-1 (560.0 mg, 1.66 mmol) in THF (10 mL) was added KHMDS (3.8 mL, 3.78 mmol, 1M in THF) at −20° C., then the mixture was stirred at room temperature for 7 hrs. The mixture was concentrated, diluted with water, and adjusted pH to 6~7 with aqueous 4.0 M HCl. The precipitate was collected by filtration, washed with water, and dried to afford compound 30-2 (350.0 mg, 66.6% yield). LCMS: 306.0 [M+H]+.

Step 3: A mixture of compound 30-2 (150.0 mg, 0.49 mmol), POCl$_3$ (376.2 mg, 2.45 mmol) and DIPEA (634.2 mg, 4.91 mmol) in toluene (2 mL) was stirred at 100° C. for 2 hrs. After cooling to room temperature, a mixture of DIPEA (634.2 mg, 4.91 mmol) and prop-2-yn-1-amine (270.3 mg, 4.91 mmol) in NMP (2 mL) was added. The resulting mixture was stirred at room temperature for 2 hrs and concentrated. The residue was diluted with DCM (20 mL) and H$_2$O (20 mL), extracted by DCM (20 mL×3), the combined organic phases were washed with water, brine, dried over Na$_2$SO$_4$ and concentrated. The residue was purified by gel column chromatography to afford compound 30 (30.0 mg, 17.8% yield). LCMS: 343.1 [M+H]+. $^1$H NMR (400 MHz, DMSO-d$_6$) δ 8.61 (dd, J=4.8 Hz, 1.6 Hz, 1H), 8.41-8.36 (m, 1H), 7.78-7.74 (m, 1H), 7.47 (dd, J=7.6 Hz, 4.8 Hz, 1H), 7.39 (dd, J=12.0 Hz, 2.0 Hz, 1H), 6.13 (s, 1H), 4.33-4.27 (m, 2H), 3.16 (t, J=2.4 Hz, 1H), 2.19 (s, 3H).

Example 31: Synthesis of 7-chloro-4-((1-ethynylcyclopropyl)amino)-5-fluoro-1-(2-methylpyridin-3-yl)quinazolin-2(1H)-one

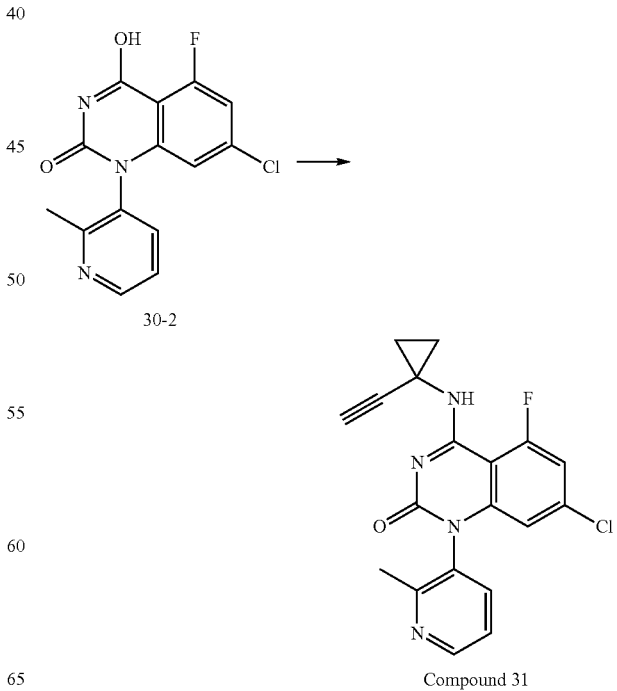

Compound 31

To a stirred solution of compound 30-2 (150.0 mg, 0.49 mmol) in toluene (3 mL) was added DIEA (634.2 mg, 4.91 mmol) and POCl₃ (376.2 mg, 2.45 mmol) at 0° C. The suspension was heated to 100° C. for 2 hrs. After cooling to room temperature, a solution of 1-ethynylcyclopropan-1-amine hydrochloride (346.2 mg, 2.94 mmol) and DIEA (634.2 mg, 4.91 mmol) in NMP (2 mL) was added. The mixture was stirred at room temperature for 16 hrs and concentrated. Water (50 mL) was added and the suspension was extracted by DCM (50 mL×3), the combined organic layer was washed with water, brine, dried over Na₂SO₄ and concentrated. The residue was purified by column chromatography to afford compound 31 ((29.6 mg, 16.3% yield). LCMS: 369.0 [M+H]⁺. ¹H NMR (400 MHz, DMSO-d₆) δ 8.61 (dd, J=4.8 Hz, 1.6 Hz, 1H), 8.38 (d, J=11.6 Hz, 1H), 7.76 (dd, J=8.0 Hz, 1.2 Hz, 1H), 7.47 (dd, J=8.0 Hz, 4.8 Hz, 1H), 7.37 (dd, J=12.0 Hz, 2.0 Hz, 1H), 6.12 (s, 1H), 3.04 (s, 1H), 2.18 (s, 3H), 1.29-1.26 (m, 4H).

Example 32: Synthesis of 5-fluoro-4-(prop-2-yn-1-ylamino)-1-(pyrazin-2-yl)-7-(trifluoromethyl)quinazolin-2(1H)-one

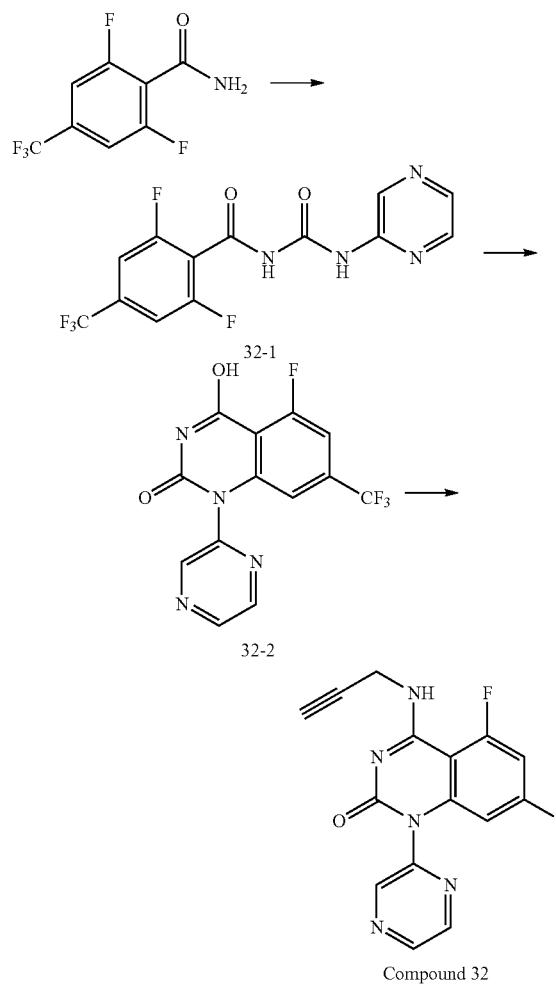

Step 1: To a solution of 2,6-difluoro-4-(trifluoromethyl)benzene-1-carboxamide (400.0 mg, 1.78 mmol) in DCE (10 mL) was added oxalyl dichloride (250.0 mg, 1.95 mmol) at room temperature, the mixture was stirred at 80° C. for 2 hrs. After cooling to room temperature, pyrazin-2-amine (337.9 mg, 3.55 mmol) was added and the solution was stirred at room temperature for 40 mins. The precipitate was collected by filtration, washed with water, and dried to afford compound 32-1 (350.0 mg, 56.9% yield). LCMS: 347.1 [M+H]⁺.

Step 2: To a solution of compound 32-1 (350.0 mg, 1.01 mmol) in THF (10 mL) was added KHMDS (2.3 mL, 2.22 mmol, 1M in THF) at −20° C., then the mixture was stirred at room temperature for 2 hrs. The mixture was quenched by H₂O (20 mL) and concentrated to remove THF. The water layer was washed with EtOAc (10 mL), and acidified with 1.0 M HCl to pH=6~7. The precipitate formed was filtered, washed with water (20 mL), dried to afford compound 32-2 (250.0 mg, 75.8% yield). LCMS: 327.0 [M+H]⁺.

Step 3: To a solution of compound 32-2 (150.0 mg, 0.46 mmol) in MeCN (2 mL) was added POCl₃ (211.5 mg, 1.38 mmol) and DIPEA (178.3 mg, 1.38 mmol), and the reaction was stirred at 80° C. for 2 hrs. After cooling to room temperature, prop-2-yn-1-amine (253.3 mg, 4.59 mmol) and DIPEA (594.3 mg, 4.59 mmol) in MeCN (2 mL) was added, the reaction was stirred at room temperature for 16 hrs. The mixture was diluted with DCM (20 mL) and H₂O (20 mL), extracted with DCM (20 mL×2), the combined organic phases were washed with water, dried over anhydrous Na₂SO₄ and concentrated. The residue was purified by silica gel column to afford compound 32 (52.8 mg, 31.7% yield). LCMS: 364.0 [M+H]⁺. ¹H NMR (400 MHz, DMSO-d₆) δ 8.86-8.79 (m, 3H), 8.65 (t, J=6.0 Hz, 1H), 7.65 (d, J=11.6 Hz, 1H), 6.63 (s, 1H), 4.33 (d, J=3.2 Hz, 2H), 3.18 (t, J=2.4 Hz, 1H).

Example 33: Synthesis of 1-(2-methylpyridin-3-yl)-4-(prop-2-yn-1-ylamino)-7-(trifluoromethyl)quinazolin-2(1H)-one

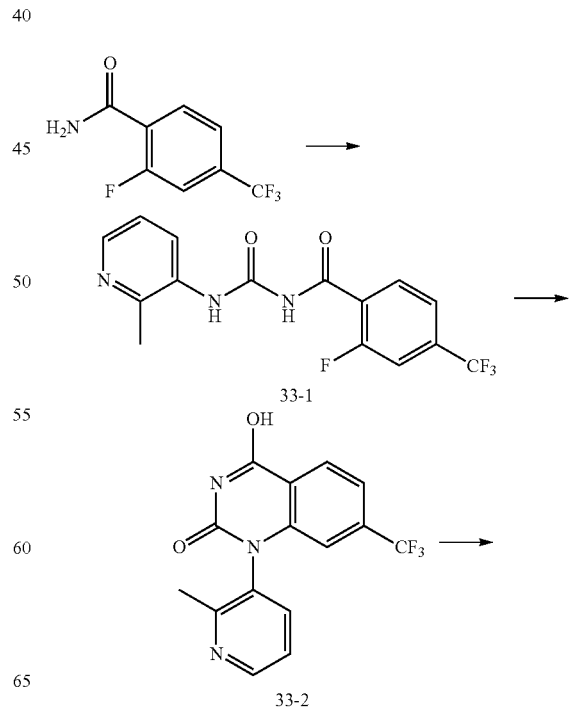

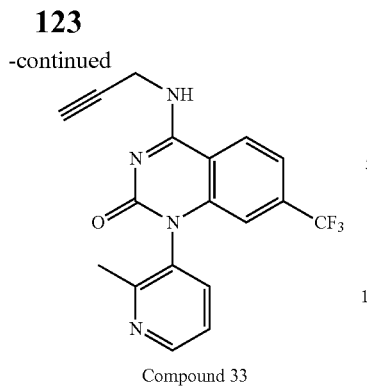

Compound 33

Step 1: To a solution of 2-fluoro-4-(trifluoromethyl)benzene-1-carboxamide (2.0 g, 9.66 mmol) in dichloroethane (50 mL) was added oxalyl dichloride (1.4 g, 10.62 mmol) at room temperature, the mixture was stirred at 80° C. for 1 h. After cooling to room temperature, 2-methylpyridin-3-amine (2.1 g, 19.30 mmol) was added. The precipitate formed was collected, washed with water, and dried to afford compound 33-1 (3.0 g, 91.0% yield). LCMS: 342.0 [M+H]+.

Step 2: KHMDS (19.3 mL, 19.30 mmol, 1M in THF) was added to a mixture of compound 33-1 (3.0 g, 8.79 mmol) in THF (50 mL) at −20° C. and the mixture was stirred at room temperature for 2 hs. The reaction mixture was concentrated, diluted with water, and adjusted pH to 6~7 with aqueous 4M HCl. The precipitate was collected, washed with water and Et₂O, dried to afford compound 33-2 (2.7 g, 95.6% yield). LCMS: 322.1 [M+H]+.

Step 3: To a stirred suspension of compound 33-2 (200.0 mg, 0.62 mmol) in toluene (3 mL) was added POCl₃ (477.0 mg, 3.11 mmol) and DIPEA (805.0 mg, 6.23 mmol) at 0° C. The resultant suspension was heated to 100° C. for 2 hs. After cooling to room temperature. A mixture of DIPEA (805.0 mg, 6.23 mmol) and prop-2-yn-1-amine (342.0 mg, 6.22 mmol) in NMP (2 mL) was added. The mixture was stirred at room temperature for 16 hs. The reaction mixture was diluted with DCM (20 mL) and water (20 mL), extracted with DCM (30 mL×3), the combined organic phases were washed with water, brine, dried over anhydrous Na₂SO₄ and concentrated. The residue was purified by silica gel column to afford compound 33 (72.6 mg, 32.5% yield). LCMS: 359.2 [M+H]+. ¹H NMR (400 MHz, DMSO-d₆) δ 9.32 (t, J=5.2 Hz, 1H), 8.63 (dd, J=4.8 Hz, 1.6 Hz, 1H), 8.45 (d, J=8.4 Hz, 1H), 7.79 (dd, J=8.0 Hz, 1.6 Hz, 1H), 7.65 (d, J=8.0 Hz, 1H), 7.49 (dd, J=8.0 Hz, 4.8 Hz, 1H), 6.47 (s, 1H), 4.43-4.29 (m, 2H), 3.31-3.24 (m, 1H), 2.08 (s, 3H)

Example 34: Synthesis of 5-methoxy-4-(prop-2-yn-1-ylamino)-1-(pyridin-3-yl)-7-(trifluoromethyl)quinazolin-2(1H)-one

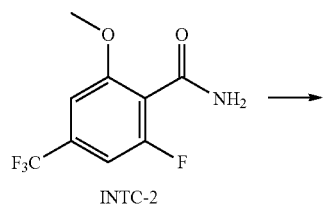

INTC-2

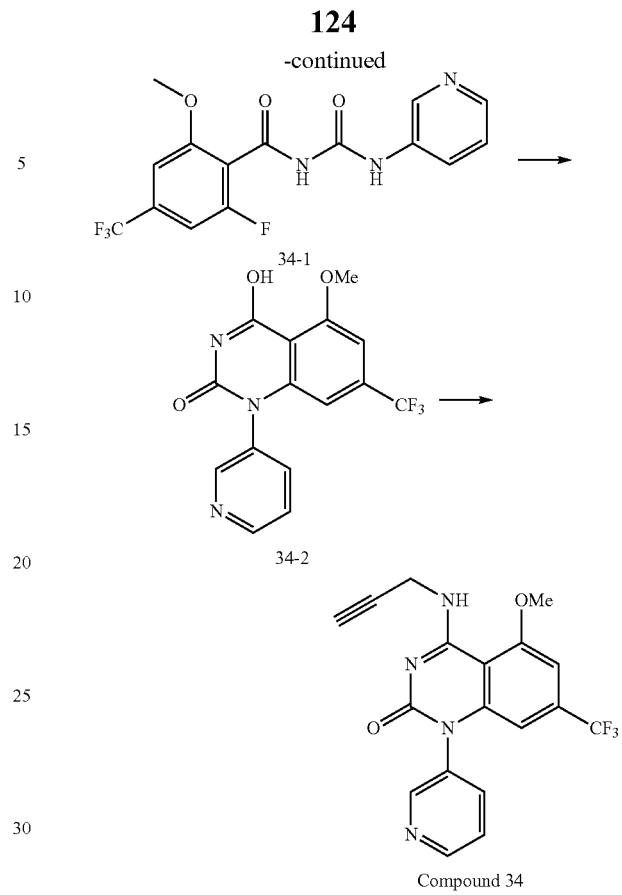

Compound 34

Step 1: To a stirred suspension of compound INTC-2 (450.0 mg, 1.89 mmol) in dichloroethane (5 mL) at room temperature was added oxalyl dichloride (264.9 mg, 2.08 mmol). The resultant suspension was heated to 80° C. for 1 h. After cooling to room temperature, pyridin-3-amine (357.2 mg, 3.79 mmol) was added to the reaction mixture. The resultant reaction mixture was stirred at room temperature for 16 h. The precipitate was collected, washed with water, and dried to afford compound 34-1 (512 mg, 75.3% yield). LCMS: 358.0 [M+H]+.

Step 2: KHMDS (3.07 mL, 3.07 mmol) was added to a mixture of compound 34-1 (500.0 mg, 1.40 mmol) in THF (5 mL) at −20° C., and the resulting mixture was warmed to room temperature over 3 hs. The reaction mixture was concentrated, diluted with water, and adjusted pH value to 6~7 with aqueous 4.0 M HCl. The precipitate was collected, washed with water, and dried to afford compound 34-2 (503 mg, 96.5%). LCMS: 338.0 [M+H]+.

Step 3: To a stirred suspension of compound 34-2 (100.0 mg, 0.29 mmol) in toluene (1 mL) was added DIPEA (383.2 mg, 2.96 mmol) and POCl₃ (227.3 mg, 1.48 mmol) at 0° C. The resultant suspension was heated to 100° C. for 2 hs. After cooling to room temperature, a solution of DIPEA (383.2 mg, 2.96 mmol) and prop-2-yn-1-amine (163.3 mg, 2.96 mmol) in NMP (1 mL) was added. The mixture was stirred at 50° C. for 1 h. Water (10 mL) was added, extracted by dichloromethane (5 mL×3), the organic layer was washed by brine, dried over anhydrous Na₂SO₄, filtered, concentrated, and purified by column chromatography to afford compound 34. LCMS: 375.1 [M+H]+. ¹H NMR (400 MHz, DMSO-d₆) δ 8.96 (t, J=5.6 Hz, 1H), 8.72 (d, J=4.4, 1.2 Hz, 1H), 8.58 (d, J=2.4 Hz, 1H), 7.88 (d, J=8.4 Hz, 1H), 7.65 (dd, J=8.0, 4.8 Hz, 1H), 7.14 (s, 1H), 6.13 (s, 1H), 4.34-4.30 (m, 2H), 4.12 (s, 3H), 3.15 (t, J=2.4 Hz, 1H).

Example 35: Synthesis of 4-(but-3-yn-2-ylamino)-5-methoxy-1-(pyridin-3-yl)-7-(trifluoromethyl)quinazolin-2(1H)-one

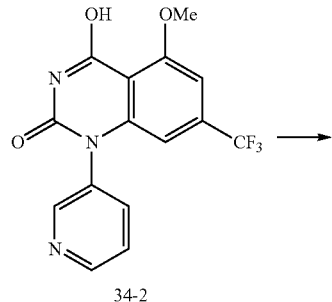

34-2

Example 36: Synthesis of 5-methoxy-1-(2-methylpyridin-3-yl)-4-(prop-2-yn-1-ylamino)-7-(trifluoromethyl)quinazolin-2(1H)-one

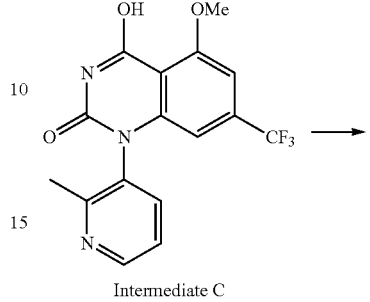

Intermediate C

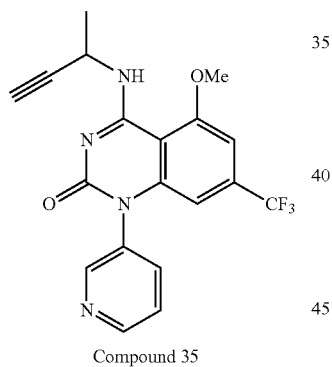

Compound 35

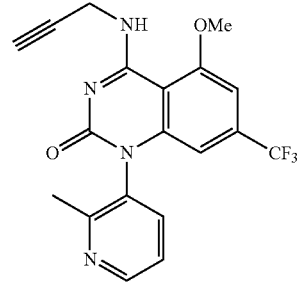

Compound 36

To a stirred solution of compound 34-2 (140.0 mg, 0.42 mmol) in toluene (2 mL) was added DIEA (536.5 mg, 4.15 mmol) and POCl$_3$ (319.0 mg, 2.08 mmol) at 0° C. The resultant suspension was heated to 100° C. for 2 h. After cooling to room temperature, a solution of but-3-yn-2-amine hydrochloride (263.0 mg, 2.49 mmol) and DIEA (536.51 mg, 4.15 mmol) in NMP (2 mL) was added. The mixture was stirred at room temperature for 16 h. Water was added, extracted by DCM, and the combined organic layer was washed with water, brine, dried over anhydrous Na$_2$SO$_4$ and concentrated. The residue was purified by column chromatography to afford compound 35. LCMS: 389.1 [M+H]$^+$. $^1$H NMR (400 MHz, DMSO-d$_6$) δ 8.72 (dd, J=4.8 Hz, 1.6 Hz, 1H), 8.57-8.53 (m, 2H), 7.89 (s, 1H), 7.67-7.64 (m, 1H), 7.16 (s, 1H), 6.13 (s, 1H), 5.25-5.21 (m, 1H), 4.15 (s, 3H), 3.36-3.32 (m, 1H), 1.54 (d, J=6.8 Hz, 3H).

To a stirred suspension of compound Intermediate C (70.0 mg, 0.20 mmol) in toluene (1 mL) was added DIPEA (257.0 mg, 1.99 mmol) and POCl$_3$ (153.0 mg, 1.00 mmol) at 0° C. The resultant suspension was heated at 100° C. for 2 hs. After cooling to room temperature, a solution of DIPEA (257.0 g, 1.99 mmol) and prop-2-yn-1-amine (109.6 mg, 1.99 mmol) in NMP (0.5 mL) was added. The mixture was stirred at 50° C. for 1 h. Water (10 mL) was added, extracted by dichloromethane (5 mL×3), the organic layer was washed by brine, dried over anhydrous Na$_2$SO$_4$, filtered, concentrated, and purified by column chromatography to give compound 36 (29.0 mg, 37.9% yield). LCMS: 389.1 [M+H]$^+$. $^1$H NMR (400 MHz, DMSO-d$_6$) δ 8.96 (t, J=5.2 Hz, 1H), 8.61 (dd, J=4.8, 1.6 Hz, 1H), 7.75 (dd, J=8.0, 1.6 Hz, 1H), 7.47 (dd, J=7.6, 4.8 Hz, 1H), 7.15 (s, 1H), 6.03 (s, 1H), 4.39-4.26 (m, 2H), 4.13 (s, 3H), 3.16 (t, J=2.4 Hz, 1H), 2.16 (s, 3H)

TABLE 5

Compounds in Table 5 below were prepared in accordance with the synthetic sequence in Example 36 using the corresponding starting materials.

| Example | Structure | MW [M + H]+ | 1H NMR |
|---|---|---|---|
| 37 | 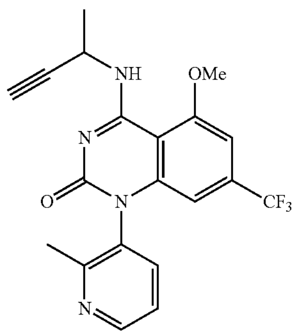 [SMILES: C#CC(C)Nc1nc(=O)n(-c2cccnc2C)c2cc(C(F)(F)F)cc(OC)c12] | 403.1 | 1H NMR (400 MHz, DMSO-d6) δ 8.62 (dd, J = 4.8 Hz, 1.6 Hz, 1H), 8.55 (dd, J = 8.0 Hz, 4.0 Hz, 1H), 7.80 (dd, J = 13.2 Hz, 8.0 Hz, 1H), 7.51-7.47 (m, 1H), 7.17 (s, 1H), 6.05 (s, 1H), 5.25 (dd, J = 7.2 Hz, 2.0 Hz), 4.15 (s, 3H), 3.32-3.31 (m, 1H), 2.17 (d, J = 6.0 Hz, 3H), 1.54 (dd, J = 6.8 Hz, 4.8 Hz, 1H). |
| 49 | 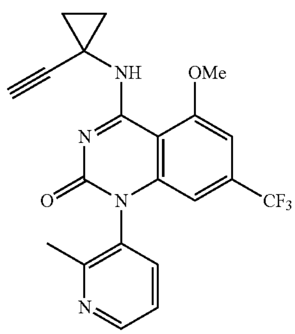 [SMILES: C#CC1(Nc2nc(=O)n(-c3cccnc3C)c3cc(C(F)(F)F)cc(OC)c23)CC1] | 415.1 | 1H NMR (400 MHz, DMSO-d6) δ 8.88 (s, 1H), 8.62 (d, J = 3.6 Hz, 1H), 7.79 (d, J = 7.6 Hz, 1H), 7.48 (dd, J = 7.6 Hz, 4.8 Hz, 1H), 7.13 (s, 1H), 6.03 (s, 1H), 4.12 (s, 3H), 3.05 (s, 1H), 2.17 (s, 3H), 1.33-1.24 (m, 4H). |
| 50 | 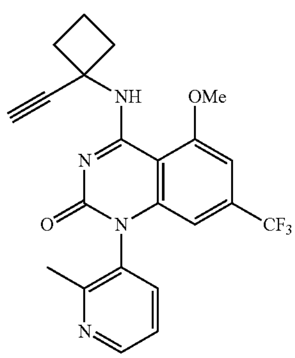 [SMILES: C#CC1(Nc2nc(=O)n(-c3cccnc3C)c3cc(C(F)(F)F)cc(OC)c23)CCC1] | 429.1 | 1H NMR (400 MHz, DMSO-d6) δ 8.62-8.60 (m, 2H), 7.77 (d, J = 7.6 Hz, 1H), 7.46 (dd, J = 7.6 Hz, 4.8 Hz, 1H), 7.16 (s, 1H), 6.03 (s, 1H), 4.15 (s, 3H), 3.32 (s, 1H), 2.59-2.53 (m, 4H), 2.16 (s, 3H), 2.08-1.94 (m, 2H). |
| 77 | 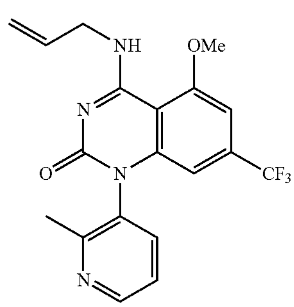 [SMILES: C=CCNc1nc(=O)n(-c2cccnc2C)c2cc(C(F)(F)F)cc(OC)c12] | 391.1 | 1H NMR (400 MHz, DMSO-d6) δ 8.84 (t, J = 5.6 Hz, 1H), 8.61 (d, J = 4.8 Hz, 1H), 7.75 (d, J = 7.6 Hz, 1H), 7.46 (dd, J = 8.0 Hz, 4.8 Hz, 1H), 7.15 (s, 1H), 6.06-5.97 (m, 2H), 5.25-5.15 (m, 2H), 4.31-4.16 (m, 2H), 4.13 (s, 3H), 2.15 (s, 3H). |

TABLE 5-continued

Compounds in Table 5 below were prepared in accordance with the synthetic sequence in Example 36 using the corresponding starting materials.

| Example | Structure | MW [M + H]+ | 1H NMR |
|---|---|---|---|
| 78 | 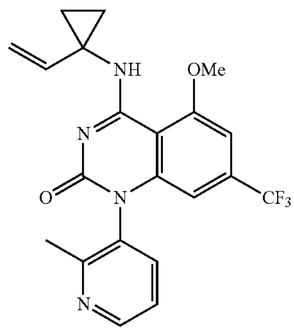 [SMILES: C=CC1(Nc2nc(=O)n(-c3cccnc3C)c3cc(C(F)(F)F)cc(OC)c23)CC1] | 417.1 | 1H NMR (400 MHz, DMSO-$d_6$) δ 8.74 (s, 1H), 8.61 (dd, J = 4.8 Hz, 1.6 Hz, 1H), 7.76 (dd, J = 8.0 Hz, 1.2 Hz, 1H), 7.46 (dd, J = 7.6 Hz, 4.8 Hz, 1H), 7.15 (d, J = 0.8 Hz, 1H), 6.03 (s, 1H), 5.72-5.64 (m, 1H), 4.99-4.94 (m, 2H), 4.13 (s, 3H), 2.14 (s, 3H), 1.23-1.21 (m, 2H), 1.13-1.11 (m, 2H). |

Example 38: Synthesis of 5-(fluoromethoxy)-4-(prop-2-yn-1-ylamino)-1-(pyridin-3-yl)-7-(trifluoromethyl)quinazolin-2(1H)-one

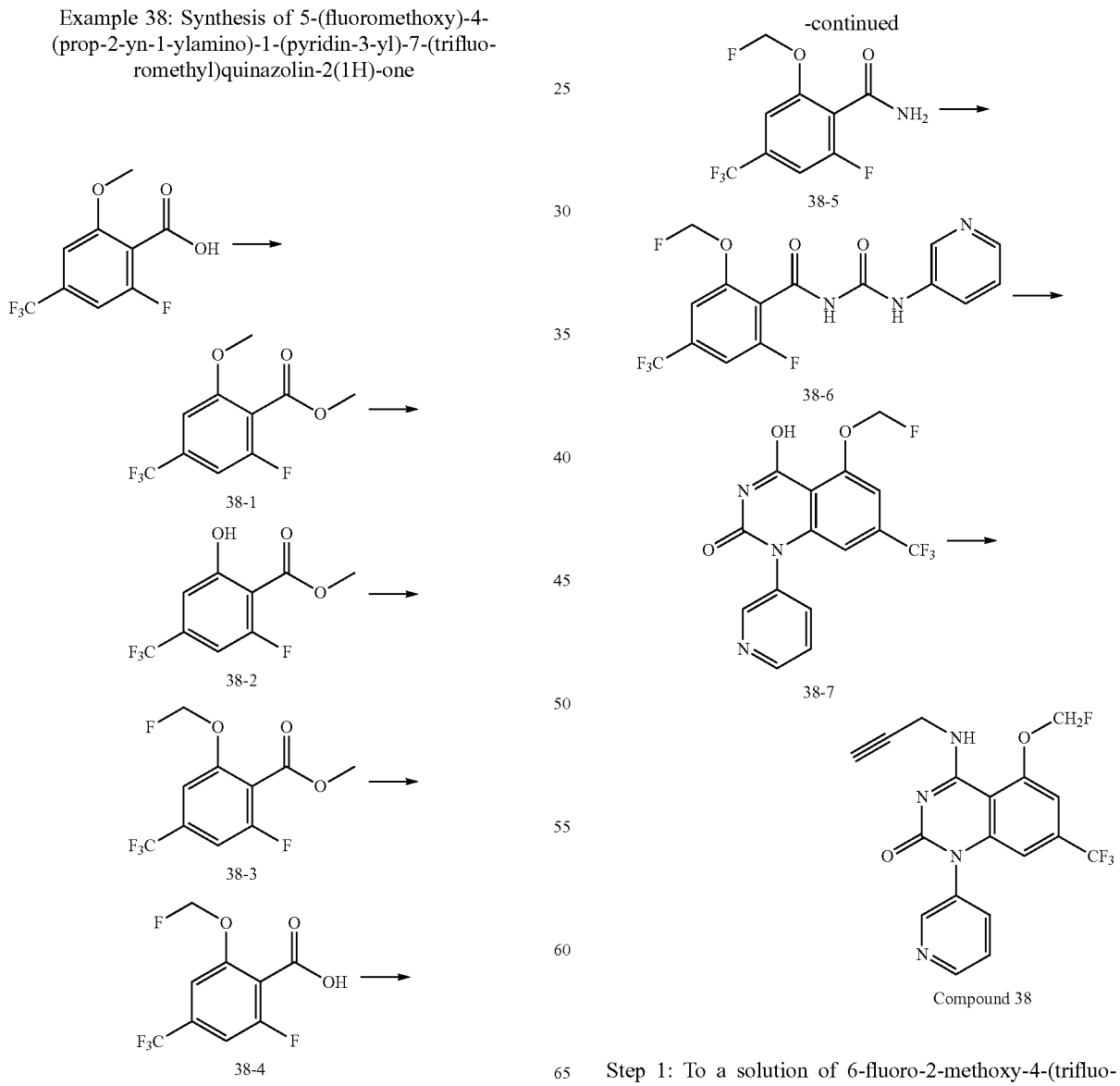

Step 1: To a solution of 6-fluoro-2-methoxy-4-(trifluoromethyl)benzoic acid (5.0 g, 20.99 mmol) in DMF (50 mL) were added $K_2CO_3$ (3.2 g, 23.09 mmol), and the reaction was stirred at room temperature for 15 min. Then MeI (3.2 g, 23.09 mmol) was added, and the reaction was stirred at 40° C. for 2 hrs. The mixture was cooled to room temperature and then diluted with EA (500 mL) and water (500 mL). The organic layer was separated, washed with brine, and concentrated in vacuo. The residue was purified by silica gel column to provide compound 38-1 (4.92 g, 92.6% yield). LCMS: 253.1 [M+H]$^+$.

Step 2: To a solution of compound 38-1 (4.9 g, 19.43 mmol) in DCM (50 mL) was added BBr$_3$ (5.3 g, 21.37 mmol) at −78° C., then the mixture was stirred at −78° C. for 30 min. The mixture was quenched with methanol and concentrated. The residue was purified by silica gel column to afford compound 38-2 (4.50 g, 97.2% yield). $^1$H NMR (400 MHz, CDCl$_3$) δ 11.42 (s, 1H), 7.06 (s, 1H), 6.86 (dd, J=10.8 Hz, 1.6 Hz, 1H), 4.02 (s, 3H).

Step 3: To a solution of compound 38-2 (1.0 g, 4.20 mmol) in MeCN (10 mL) was added fluoroiodomethane (806.3 mg, 5.04 mmol) and Cs$_2$CO$_3$ (1.64 g, 5.04 mmol) at room temperature, then the mixture was stirred at room temperature for 6 hrs. The mixture was filtered, and the filtrate was concentrated and purified by silica gel column to afford compound 38-3 (968.0 mg, 85.3% yield). $^1$H NMR (400 MHz, CDCl$_3$) δ 7.24 (s, 1H), 7.18 (d, J=8.4 Hz, 1H), 5.75 (d, 2H), 3.96 (s, 3H).

Step 4: To a solution of compound 38-3 (948.0 mg, 3.51 mmol) in THF (5 mL) and water (5 mL) was added LiOH (740.0 mg, 17.54 mmol) at room temperature, then the mixture was stirred at room temperature for 16 hrs. EA (10 mL) and H$_2$O (10 mL) was added. The water layer was adjusted to pH to 2-3 with aqueous 4M HCl. The precipitate was collected, washed with water, and dried to afford compound 38-4 (805.0 mg, 89.6% yield). $^1$H NMR (400 MHz, DMSO-d$_6$) δ 14.14 (brs, 1H), 7.59 (d, J=8.8 Hz, 1H), 7.45 (s, 1H), 6.03 (d, 2H).

Step 5: A solution of compound 38-4 (805.0 mg, 3.14 mmol) in SOCl$_2$ (6 mL) was stirred at 80° C. for 2 hs. The mixture was concentrated and dioxane (9 mL) was added, followed by NH$_4$OH (40%, 9.0 mL). The resulting solution was stirred at room temperature for 1 h. Water was added and the solid product was collected, washed with water to give compound 38-5 (703.0 mg, 85.6% yield). $^1$H NMR (400 MHz, DMSO-d$_6$) δ 8.07 (s, 1H), 7.84 (s, 1H), 7.55 (d, J=8.4 Hz, 1H), 7.40 (s, 1H), 6.00 (d, 2H).

Step 6: To a stirred suspension of compound 38-5 (150.0 mg, 0.59 mmol) in dichloroethane (3 mL) at room temperature was added oxalyl dichloride (82.0 mg, 0.65 mmol). The resultant suspension was heated to 80° C. for 1 h. After cooling to room temperature, pyridin-3-amine (110.7 mg, 1.18 mmol) was added to the reaction mixture. The mixture was stirred at room temperature for 16 hrs, and then cooled to 0° C. After 10 min, the precipitate was collected, washed with water, and dried to afford compound 38-6 (168.0 mg, 76.3% yield). LCMS: 376.0 [M+H]$^+$.

Step 7: KHMDS (1.0 mL, 0.98 mmol, 1M in THF) was added to a mixture of compound 38-6 (168.0 mg, 0.44 mmol) in THF (2 mL) at −20° C., and the resulting mixture was warmed to room temperature over 3 h. The reaction mixture was concentrated, diluted with water, and adjusted pH to 6~7 with 4M HCl. The precipitate was collected, washed with water, and dried to afford compound 38-7 (127.0 mg, 79.8% yield). LCMS: 356.0 [M+H]$^+$.

Step 8: To a stirred suspension of compound 38-7 (100.0 mg, 0.28 mmol) in MeCN (1 mL) was added DIEA (109.0 mg, 0.84 mmol) and POCl$_3$ (129.0 mg, 0.84 mmol) at 0° C. The resultant suspension was heated to 80° C. for 2 hrs, and then cooled to room temperature. A solution of DIEA (366.3 mg, 2.84 mmol) and prop-2-yn-1-amine (156.2 mg, 2.84 mmol) in NMP (1 mL) was added. The mixture was stirred at 50° C. for 1 h. Water (30 mL) was added, extracted by dichloromethane (50 mL×3), the organic layer was washed by brine, dried over Na$_2$SO$_4$, filtered, concentrated, and purified by column chromatography to afford compound 38 (18.5 mg, 16.8% yield). LCMS: 393.1 [M+H]$^+$. $^1$H NMR (400 MHz, DMSO-d$_6$) δ 8.96 (t, J=5.6 Hz, 1H), 8.72 (dd, J=4.8 Hz, 1.6 Hz, 1H), 8.59 (d, J=2.0 Hz, 1H), 7.91-7.88 (m, 1H), 7.66 (dd, J=8.0 Hz, 4.8 Hz, 1H), 7.27 (s, 1H), 6.29-6.16 (m, 3H), 4.33 (dd, J=6.4 Hz, 2.0 Hz, 2H), 3.15 (t, J=2.0 Hz, 1H).

Example 39: Synthesis of 5-(difluoromethoxy)-4-(prop-2-yn-1-ylamino)-1-(pyridin-3-yl)-7-(trifluoromethyl)quinazolin-2(1H)-one

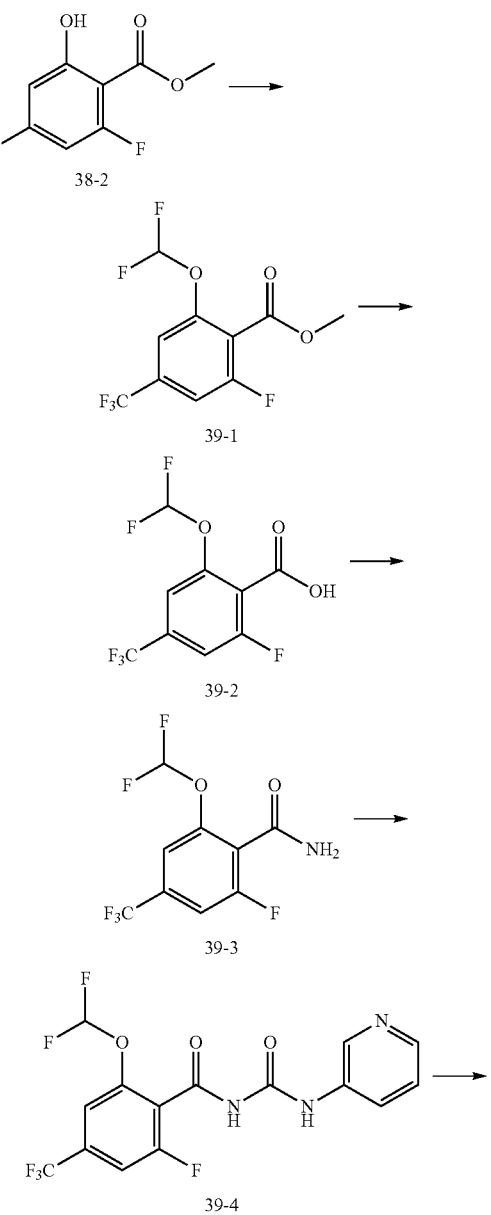

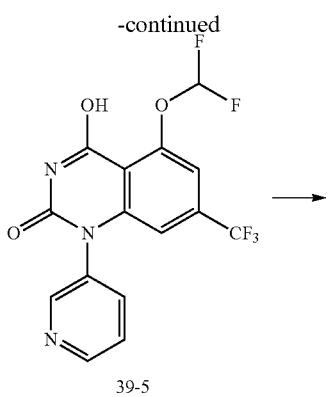

39-5

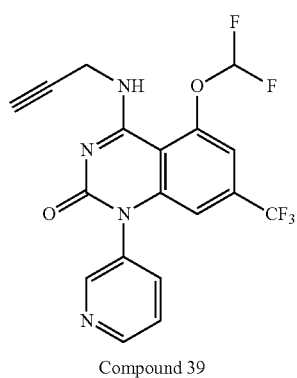 [SMILES: C#CCNc1nc(=O)n(-c2cccnc2)c2cc(C(F)(F)F)cc(OC(F)F)c12]

Compound 39

Step 1: To a solution of compound 38-2 (1.0 g, 4.19 mmol) in ACN (10 mL) was added diethyl (bromodifluoromethyl)phosphonate (1.1 g, 4.19 mmol) and KF (0.5 g, 8.39 mmol) at room temperature, then the mixture was stirred at 30° C. for 8 hrs. The mixture was concentrated and purified by silica gel column to afford compound 39-3 (283.00 mg, 23.3% yield). $^1$H NMR (400 MHz, CDCl$_3$) δ 7.32-7.28 (m, 2H), 6.58 (t, J=72.4 Hz, 1H), 3.97 (s, 3H).

Step 2: To a solution of compound 39-3 (600.0 mg, 2.08 mmol) in THF/H$_2$O (5 mL) was added LiOH (437.4 mg, 10.41 mmol) at room temperature, then the mixture was stirred at room temperature for 16 hrs. The reaction was diluted with EA (200 mL) and H$_2$O (200 mL). Collected aqueous layer and adjusted pH value to 1-2 with HCl. The solid was collected and dried to afford compound 39-4 (562.00 mg, 98.9% yield).

Step 3: A solution of compound 39-4 (562.0 mg, 2.05 mmol) in SOCl$_2$ (5.0 mL) was stirred at 80° C. for 2 hrs. Concentrated and diluted with dioxane (5 mL). Then the mixture was added to NH$_4$OH (10 mL) for 30 min. The mixture was extracted with EA (200 mL×2), washed with water (200 mL), dried over Na$_2$SO$_4$, concentrated to afford compound 39-5 (403.00 mg, 71.9% yield). LCMS: 274.1 [M+H]$^+$.

Step 4: To a solution of compound 39-5 (180.0 mg, 0.66 mmol) in DCE (5 mL) was added oxalyl dichloride (0.36 mL, 0.72 mmol, 2M in DCM) at room temperature, the mixture was stirred at 80° C. for 2 hrs. The mixture was cooled to room temperature and then pyridin-3-amine (124.1 mg, 1.32 mmol) was added, the solution was stirred at room temperature for 16 hs. The solid was collected and washed with H$_2$O (10 mL×2), dried to afford compound 39-6 (140.0 mg, 54.0% yield). LCMS: 394.0 [M+H]$^+$.

Step 5: To a solution of compound 39-6 (135.0 mg, 0.34 mmol) in THF (5 mL) was added KHMDS (0.76 mL, 0.76 mmol, 1M in THF) at −20° C., then the mixture was stirred at room temperature for 16 hrs. The reaction mixture was quenched by H$_2$O (20 mL). After concentration, the water layer was washed with EA (10 mL), and acidified with 1M HCl to pH=6~7. The solid formed was collected and washed with H$_2$O (20 mL), dried to afford compound 39-7 (100.0 mg, 78.1% yield). LCMS: 374.0 [M+H]$^+$.

Step 6: A mixture of compound 39-7 (120.0 mg, 0.32 mmol), POCl$_3$ (0.09 mL, 0.96 mmol) and DIEA (0.16 mL, 0.96 mmol) in MeCN (2 mL) was stirred at 80° C. for 2 hrs. Then the mixture was cooled to room temperature, a mixture of prop-2-yn-1-amine (177.1 mg, 3.22 mmol) and DIEA (402.7 mg, 3.22 mmol) in MeCN (2 mL) was added. The mixture was stirred at room temperature for 2 h. After concentration, DCM (20 mL) and H$_2$O (20 mL) was added. The organic layer was washed with H$_2$O, brine, dried over Na$_2$SO$_4$ and concentrated. The residue was purified by silica gel column to afford compound 39 (32.0 mg, 24.3% yield). LCMS: 411.0 [M+H]$^+$. $^1$H NMR (400 MHz, DMSO-d$_6$) δ 8.74 (dd, J=4.8 Hz, 1.2 Hz, 1H), 8.60 (d, J=2.4 Hz, 1H), 8.38 (t, J=5.2 Hz, 1H), 7.94-7.88 (m, 1H), 7.80-7.31 (m, 2H), 7.32 (s, 1H), 6.41 (s, 1H), 4.36-4.34 (m, 2H), 3.23 (t, J=2.0 Hz, 1H).

Example 40: Synthesis of 5-(difluoromethoxy)-1-(2-methylpyridin-3-yl)-4-(prop-2-yn-1-ylamino)-7-(trifluoromethyl)quinazolin-2(1H)-one

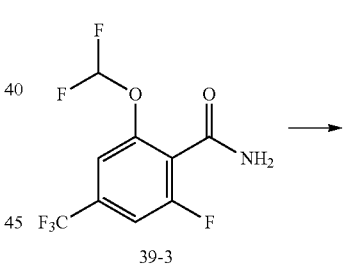

39-3

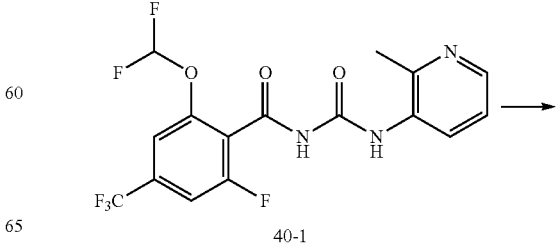

40-1

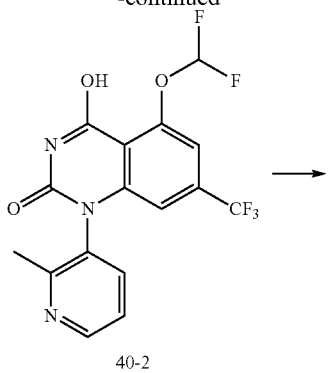

40-2

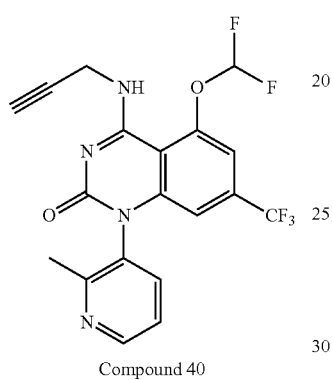

Compound 40

Step 1: To a solution of compound 39-3 (200.0 mg, 0.73 mmol) in dichloroethane (5 mL) was added oxalyl dichloride (102.2 mg, 0.80 mmol) at room temperature, then the mixture was stirred at 80° C. for 1 h. After cooling to room temperature 2-methylpyridin-3-amine (158.3 mg, 1.46 mmol) was added. The solid formed was collected, washed with water, and dried afford compound 40-1 (251.00 g, 84.2% yield). LCMS: 408.0 [M+H]+.

Step 2: KHMDS (1.35 mL, 1.35 mmol, 1M in THF) was added to a mixture of compound 40-1 (250.0 mg, 0.61 mmol) in THF (5 mL) at −20° C., then the mixture was stirred at room temperature for 2 hs. After concentration, water was added and adjusted pH to 6~7 with aqueous 4M HCl. The solid was collected and washed with water and Et₂O, dried to afford compound 40-2 (212.00 mg, 90.4% yield). LCMS: 388.0 [M+H]+.

Steps 3: To a stirred suspension of compound 40-2 (100.0 mg, 0.25 mmol) in toluene (1 mL) was added POCl₃ (197.9 mg, 1.29 mmol) and DIEA (333.7 mg, 2.58 mmol) at 0° C. The mixture was heated to 100° C. for 2 hrs, and cooled to room temperature. A mixture of DIEA (333.4 mg, 2.58 mmol) and prop-2-yn-1-amine (142.1 mg, 2.58 mmol) in NMP (1 mL) was added. The mixture was stirred at 50° C. for 1 h and diluted with DCM (50 mL) and water (50 mL), extracted with DCM (30 mL×3). The combined organic phases were washed with water (20 mL×3), brine, dried over Na₂SO₄ and concentrated. The residue was purified by silica gel column to afford compound 40 (25.60 mg, 21.1% yield). LCMS: 425.1 [M+H]+. ¹H NMR (400 MHz, DMSO-d₆) δ 8.63 (dd, J=4.8 Hz, 1.2 Hz, 1H), 8.36 (t, J=4.8 Hz, 1H), 7.80-7.33 (m, 3H), 7.32 (s, 1H), 6.32 (s, 1H), 4.38-4.35 (m, 2H), 3.24 (t, J=2.4 Hz, 1H), 2.18 (s, 3H).

Example 41: Synthesis of 5-(difluoromethoxy)-4-((1-ethynylcyclopropyl)amino)-1-(2-methylpyridin-3-yl)-7-(trifluoromethyl)quinazolin-2(1H)-one

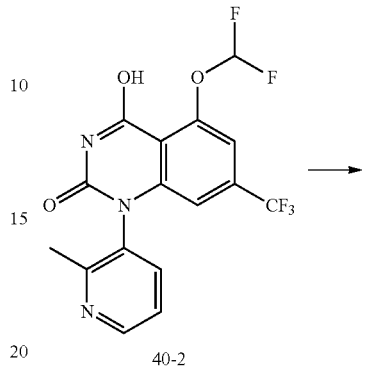

40-2

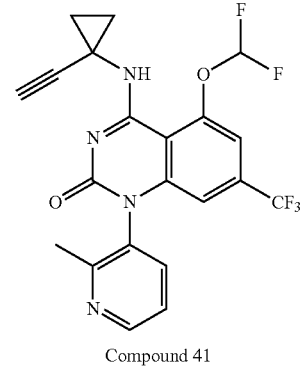

Compound 41

To a stirred suspension of compound 40-2 (100.0 mg, 0.25 mmol) in ACN (1 mL) was added POCl₃ (118.7 mg, 0.77 mmol) and DIEA (100.1 mg, 0.77 mmol) at 0° C. The mixture was heated to 80° C. for 2 hrs. After cooling to room temperature, a mixture of 1-ethynylcyclopropan-1-amine hydrochloride (104.6 mg, 1.29 mmol) and DIEA (333.4 mg, 2.58 mmol) in ACN (1 mL) was added. The mixture was stirred at 50° C. for 1 h and diluted with DCM (50 mL) and water (50 mL), extracted with DCM (30 mL×3). The combined organic phases were washed with water, brine, dried over Na₂SO₄ and concentrated. The residue was purified by silica gel column to afford compound 41 (76.1 mg, 65.4% yield). LCMS: 451.1 [M+H]+. ¹H NMR (400 MHz, DMSO-d₆) δ 8.64 (dd, J=4.8 Hz, 1.6 Hz, 1H), 8.39 (s, 1H), 7.81 (dd, J=8.0 Hz, 1.2 Hz, 1H), 7.72-7.37 (m, 2H), 7.29 (s, 1H), 6.33 (s, 1H), 3.08 (s, 1H), 2.18 (s, 3H), 1.36-1.31 (m, 2H), 1.27-1.20 (m, 2H).

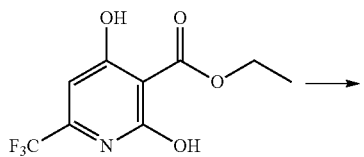

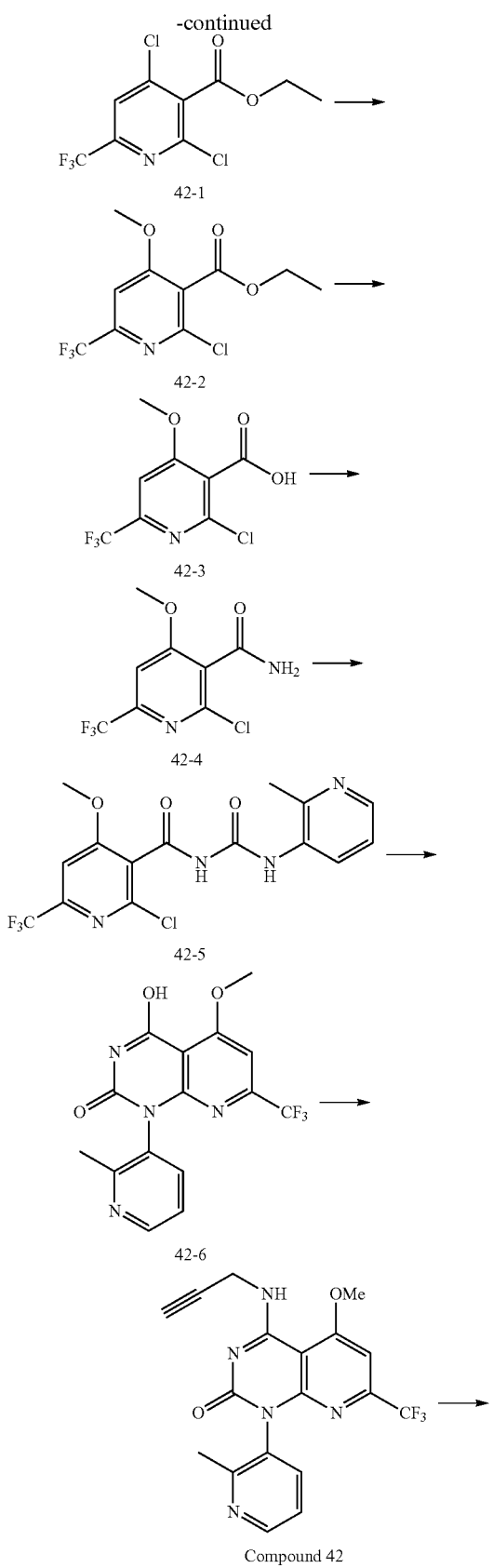

Compound 42

Step 1: A solution of ethyl 2,4-dihydroxy-6-(trifluoromethyl)pyridine-3-carboxylate (2.0 g, 7.96 mmol) in DMF (2.3 g, 31.85 mmol) and POCl₃ (5.5 g, 35.83 mmol) was stirred at 90° C. for 72 hrs. The mixture was concentrated. The residue was diluted with DCM (50 mL) and H₂O (50 mL), the mixture was treated with saturated aqueous NaHCO₃ until pH=5~6, extracted with DCM (100 mL×3). The organic layer was concentrated and the residue was purified by silica gel column to afford compound 42-1 (1.9 g, 82.9% yield). LCMS: 288.0 [M+H]⁺.

Step 2: To a solution of compound 42-1 (2.0 g, 6.94 mmol) in MeOH (20 mL) was added MeONa (412.5 mg, 7.64 mmol) at 0° C., then the mixture was stirred at room temperature for 18 hrs. The reaction mixture was quenched with H₂O (50 mL) at 0° C., extracted with EA (50 mL×3). The organic layer was concentrated and the residue was purified by silica gel column to afford compound 42-2 (1.8 g, 91.4% yield). LCMS: 284.0 [M+H]⁺.

Step 3: To a solution of compound 42-2 (1.9 g, 6.70 mmol) in THF (20 mL) and H₂O (20 mL) was added LiOH (1.4 g, 33.49 mmol) at room temperature, the solution was stirred at 80° C. for 8 hrs. The reaction mixture was acidified with 1.0 M HCl to pH=2-3, extracted with EA (50 mL×2). The combined organic layer was concentrated to afford compound 42-3 (1.6 g, 98.8% yield). LCMS: 256.0 [M+H]⁺.

Step 4: A solution of compound 42-3 (4.9 g, 20.58 mmol) in SOCl₂ (50.0 mL) was stirred at 80° C. for 2 hrs. The reaction mixture was concentrated and the residue was dissolved in dioxane (10 mL). NH₄OH (10 mL) was added at 0° C. The mixture was stirred at 25° C. for 0.5 h. After concentration, water was added and the solid product was collected, washed with water, and dried to afford compound 42-4 (4.0 g, 84.4% yield). LCMS: 255.0 [M+H]⁺.

Step 5: To a solution of compound 42-4 (500.0 mg, 1.97 mmol) in DCE (5 mL) was added oxalyl dichloride (275.0 mg, 2.17 mmol) at room temperature, the mixture was stirred at 80° C. for 2 hrs. After cooling to room temperature, 2-methylpyridin-3-amine (424.8 mg, 3.93 mmol) was added, and the solution was stirred at room temperature for 16 h. The precipitate was collected, washed with water, and dried to afford compound 42-5 (440.0 mg, 51.4% yield). LCMS: 389.1 [M+H]⁺.

Step 6: To a solution of compound 42-5 (440.0 mg, 1.13 mmol) in THF (10 mL) was added KHMDS (2.5 mL, 2.50 mmol, 1.0 M in THF) at −20° C., the mixture was stirred at room temperature for 2 hrs. The reaction mixture was quenched by H₂O (20 mL). After concentration, the water layer was extracted with EtOAc (10 mL), and acidified with 1.0 M HCl to pH=6~7. The precipitate was collected and washed with H₂O, dried to afford compound 42-6 (250.0 mg, 62.7% yield). LCMS: 353.1 [M+H]⁺.

Step 7: A mixture of compound 42-6 (100.0 mg, 0.28 mmol), POCl₃ (130.6 mg, 0.85 mmol) and DIPEA (110.1 mg, 0.85 mmol) in MeCN (2 mL) was stirred at 80° C. for 2 hrs. After cooling to room temperature, a mixture of DIPEA (366.9 mg, 2.84 mmol) and prop-2-yn-1-amine (156.4 mg, 2.84 mmol) in MeCN (2 mL) was added. The mixture was stirred at room temperature for 16 hrs and concentrated. The residue was diluted with DCM (20 mL) and H₂O (20 mL) and extracted by DCM (30 mL×2). The combined organic layer was washed with water, brine, dried and concentrated. The residue was purified by silica gel column to afford compound 42 (70.0 mg, 63.3% yield). LCMS: 390.1 [M+H]⁺. ¹H NMR (400 MHz, DMSO-d₆) δ 8.90 (t, J=5.2 Hz, 1H), 8.63 (dd, J=4.8 Hz, 1.2 Hz, 1H), 7.79 (dd, J=8.0 Hz, 1.6 Hz, 1H), 7.48 (dd, J=8.0 Hz, 4.8 Hz, 1H), 6.19 (s, 1H), 4.43-4.26 (m, 2H), 4.14 (s, 3H), 3.18 (t, J=2.0 Hz, 1H), 2.20 (s, 3H).

Example 43: Synthesis of 4-((1-ethynylcyclopropyl)amino)-5-methoxy-1-(2-methylpyridin-3-yl)-7-(trifluoromethyl)pyrido[2,3-d]pyrimidin-2(1H)-one

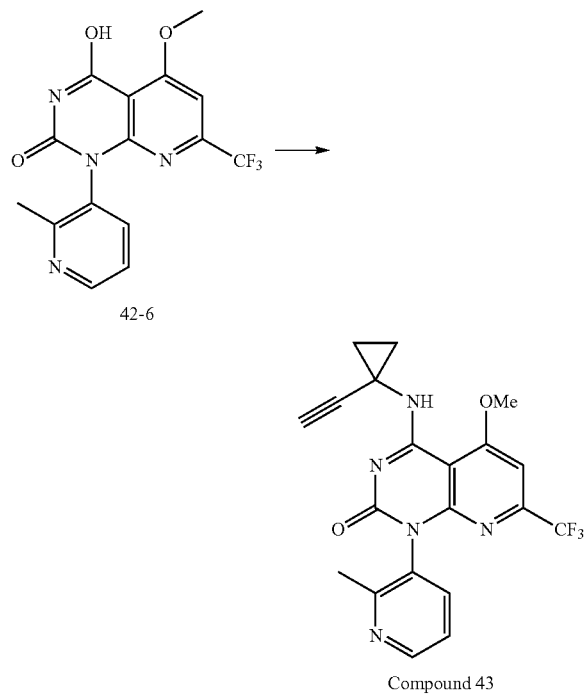

Compound 43

A mixture of compound 42-6 (100.0 mg, 0.28 mmol), POCl$_3$ (130.6 mg, 0.85 mmol) and DIEA (110.1 mg, 0.85 mmol) in MeCN (2 mL) was stirred at 80° C. for 2 hrs. After cooling to room temperature, a mixture of DIEA (366.9 mg, 2.84 mmol) and 1-ethynylcyclopropanamine hydrochloride (166.9 mg, 1.42 mmol) in MeCN (2 mL) was added. The mixture was stirred at room temperature for 16 h. After concentration, the residue was diluted with DCM (20 mL) and water (20 mL), extracted by DCM (30 mL×2). The combined organic layer was washed with water, brine, dried over Na$_2$SO$_4$ and concentrated. The residue was purified by silica gel column to afford compound 43 (36.5 mg, 31.2% yield). LCMS: 416.0 [M+H]$^+$. $^1$H NMR (400 MHz, DMSO-d$_6$) δ 8.81 (s, 1H), 8.63 (dd, J=4.8 Hz, 1.2 Hz, 1H), 7.79 (dd, J=8.0 Hz, 1.6 Hz, 1H), 7.48 (dd, J=8.0 Hz, 4.8 Hz, 1H), 6.18 (s, 1H), 4.12 (s, 3H), 3.07 (s, 1H), 2.20 (s, 3H), 1.34-1.31 (m, 2H), 1.27-1.25 (m, 2H).

Example 44: Synthesis of 1-(2,5-dimethylpyridin-3-yl)-4-(prop-2-yn-1-ylamino)-7-(trifluoromethyl)quinazolin-2(1H)-one

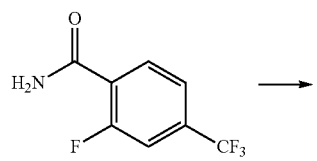

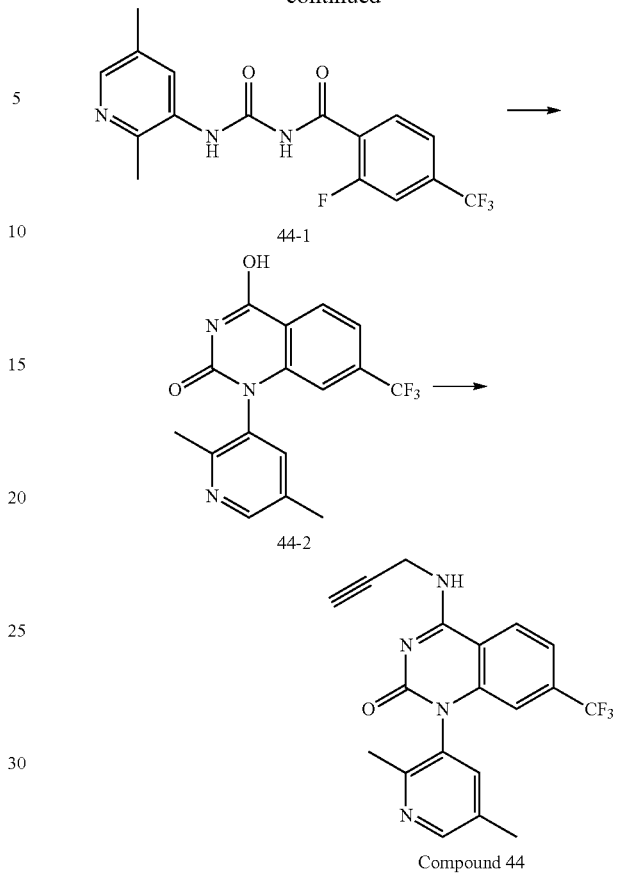

Compound 44

Step 1: To a stirred suspension of 2-fluoro-4-(trifluoromethyl)benzamide (2.0 g, 9.66 mmol) in dichloroethane (20 mL) at room temperature was added oxalyl dichloride (1.3 g, 10.62 mmol). The mixture was heated to 80° C. for 1 h. After cooling to room temperature, 2,5-dimethylpyridin-3-amine (2.4 g, 19.31 mmol) was added. The mixture was stirred at room temperature for 1 h. The precipitate was collected, washed with water, and dried to afford compound 44-1 (1.7 g, 50.7% yield). LCMS: 356.0 [M+H]$^+$.

Step 2: To a solution of compound 44-1 (1.7 g, 4.90 mmol) in THF (25.0 mL) was added NaH (978.0 mg, 24.48 mmol, 60% oil dispersion) at room temperature, and the mixture was stirred for 5 hrs. After concentration, the residue was poured into ice-water (50 mL) and adjusted pH to 6~7 with aqueous 4M HCl. The precipitate was collected, washed with water and Et$_2$O, and dried to afford compound 44-2 (1.2 g, 74.7% yield). $^1$H NMR (400 MHz, DMSO-d$_6$) δ 12.10 (s, 1H), 8.51 (d, J=0.8 Hz, 1H), 8.28 (d, J=8.0 Hz, 1H), 7.72 (s, 1H), 7.64 (d, J=8.0 Hz, 1H), 6.50 (s, 1H), 2.35 (s, 3H), 2.12 (s, 3H).

Step 3: To a stirred mixture of compound 44-2 (200.0 mg, 0.60 mmol) in toluene (2 mL) was added DIEA (771.0 mg, 5.96 mmol) and POCl$_3$ (458.0 mg, 2.98 mmol) at 0° C. The mixture was heated to 100° C. for 2 hrs. After cooling to room temperature, a solution of prop-2-yn-1-amine (328.6 mg, 5.96 mmol) and DIEA (771.0 mg, 5.96 mmol) in NMP (1 mL) was added. The mixture was stirred at room temperature for 16 h. Water (50 mL) was added, extracted by DCM (50 mL×3), the combined organic layer was washed with water, brine, dried over Na$_2$SO$_4$ and concentrated. The residue was purified by column chromatography to afford compound 44 (43.3 mg, 19.5% yield). LCMS: 373.1 [M+H]+. 1H NMR (400 MHz, DMSO-d6) δ 9.29 (t, J=5.2 Hz 1H), 8.47 (s, 1H), 8.45 (s, 1H), 7.64 (d, J=8.4 Hz, 1H), 7.62 (s, 1H), 6.49 (s, 1H), 4.43-4.29 (m, 2H), 3.25 (s, 1H), 2.35 (s, 3H), 2.12 (s, 3H).

Example 45: Synthesis of 1-(2-isopropylpyridin-3-yl)-4-(prop-2-yn-1-ylamino)-7-(trifluoromethyl)quinazolin-2(1H)-one

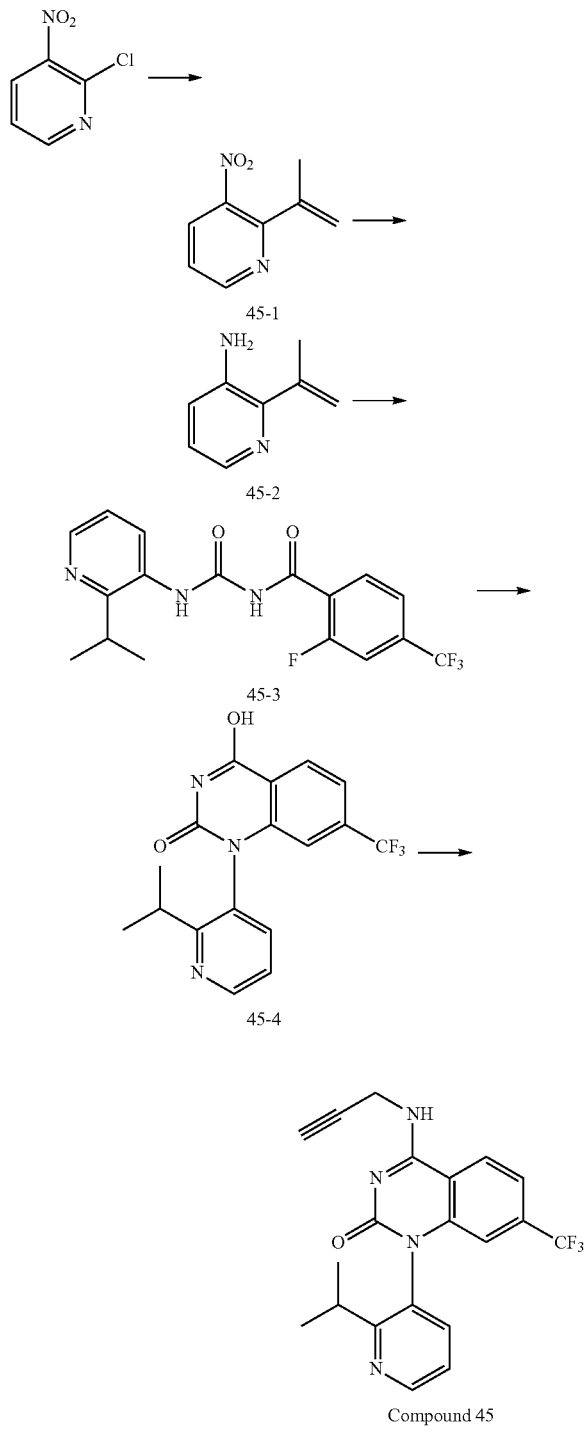

Step 1: To a stirred suspension of 2-chloro-3-nitropyridine (3.0 g, 18.92 mmol) and 4,4,5,5-tetramethyl-2-(prop-1-en-2-yl)-1,3,2-dioxaborolane (9.5 g, 56.77 mmol) in dioxane (20 mL) and H2O (4 mL) was added Pd(PPh3)4 (2.2 g, 1.89 mmol) and Na2CO3 (4.0 g, 37.84 mmol), then the mixture was stirred at 100° C. for 2 hrs. After cooling to room temperature, water (60 mL) was added, extracted with EtOAc (60 mL×3). The combined organic layers were washed with brine, dried over Na2SO4, and concentrated and purified by column chromatography to afford compound 45-1 (1.5 g). 1H NMR (400 MHz, DMSO-d6) δ 8.82 (dd, J=4.8 Hz, 1.2 Hz, 1H), 8.36-8.34 (m, 1H), 7.62 (dd, J=8.0 Hz, 4.8 Hz, 1H), 5.33 (s, 1H), 5.06 (s, 1H), 2.14 (s, 3H).

Step 2: A solution of compound 45-1 (1.0 g, 6.09 mmol) and Pd/C (100.0 mg, 10% on activated carbon, 5% wet) in MeOH (10 mL) was stirred at room temperature for 6 hrs using hydrogen balloon. The mixture was filtered, washed with EtOAc and the filtrate was concentrated and purified by column chromatography to afford compound 45-2 (500.0 mg, 60.3% yield). 1H NMR (400 MHz, DMSO-d6) δ 7.74 (d, J=4.0 Hz, 1H), 6.89-6.87 (m, 2H), 5.01 (s, 2H), 3.15-3.09 (m, 1H), 1.15 (d, J=6.4 Hz, 6H).

Step 3: To a stirred suspension of 2-fluoro-4-(trifluoromethyl)benzamide (650.0 mg, 3.14 mmol) in dichloroethane (8 mL) at room temperature was added oxalyl dichloride (438.0 mg, 3.45 mmol). The mixture was heated to 80° C. for 1 h. After cooling to room temperature, compound 45-2 (854.0 mg, 6.27 mmol) was added. The mixture was stirred at room temperature for 1 h. The precipitate was collected, washed with water, and dried to afford compound 45-3 (600.0 mg, 51.8% yield). LCMS: 370.2 [M+H]+.

Step 4: KHMDS (3.3 mL, 3.33 mmol, 1M in THF) was added to a mixture of compound 45-3 (560.0 mg, 1.51 mmol) in THF (5 mL) at −20° C., and the mixture was warmed to room temperature. The mixture was concentrated, diluted with water, and adjusted pH to 6~7 with aqueous 4M HCl. The precipitate was collected, washed with water, and dried to afford compound 45-4 (450.0 mg, 84.9% yield). LCMS: 350.0 [M+H]+.

Step 5: To a stirred solution of compound 45-4 (200.0 mg, 0.57 mmol) in toluene (2 mL) was added DIEA (740.5 mg, 5.73 mmol) and POCl3 (440.0 mg, 2.87 mmol) at 0° C. The mixture was heated to 100° C. for 2 hrs. After cooling to room temperature, a solution of but-3-yn-2-amine (315.0 mg, 5.73 mmol) and DIEA (740.5 mg, 5.73 mmol) in NMP (2 mL) was added. The mixture was stirred at room temperature for 16 h. The mixture was diluted with DCM (50 mL) and water (50 mL), extracted with DCM (30 mL×3). The combined organic phases were washed with water, brine, dried over Na2SO4 and concentrated. The residue was purified to afford compound 45 (93.3 mg, 42.1% yield). LCMS: 387.1 [M+H]+. 1H NMR (400 MHz, DMSO-d6) δ 9.29 (t, J=5.2 Hz, 1H), 8.73 (dd, J=4.8 Hz, 1.2 Hz, 1H), 8.44 (d, J=8.4 Hz, 1H), 7.73 (dd, J=8.0 Hz, 1.6 Hz, 1H), 7.64 (d, J=8.4 Hz, 1H), 7.47 (dd, J=8.0 Hz, 4.8 Hz, 1H), 6.44 (s, 1H), 4.36-4.29 (m, 2H), 3.22 (s, 1H), 2.74-2.67 (m, 1H), 1.11 (d, J=6.4 Hz, 3H), 0.98 (d, J=6.8 Hz, 3H).

Example 46: Synthesis of 4-((1-ethynylcyclopropyl)amino)-1-(2-methylpyridin-3-yl)-7-(trifluoromethyl)quinazolin-2(1H)-one

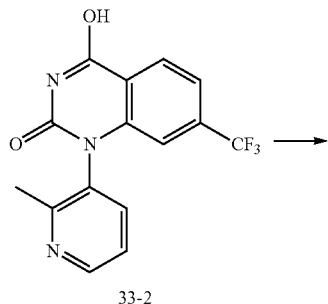

33-2

Example 47: Synthesis of 4-((1-ethynylcyclopropyl)amino)-5-methoxy-1-(pyridin-3-yl)-7-(trifluoromethyl)quinazolin-2(1H)-one

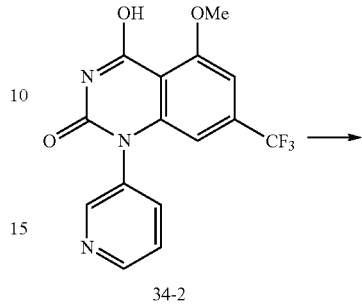

34-2

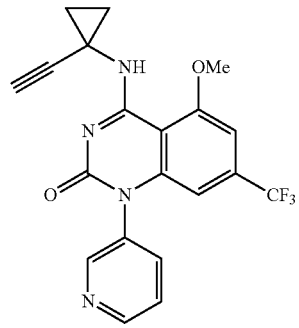

Compound 47

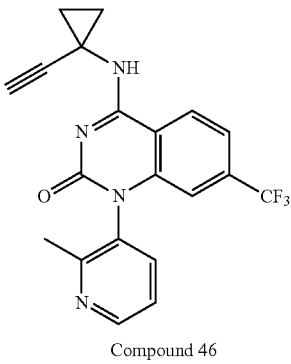

Compound 46

To a stirred suspension of compound 33-2 (200.0 mg, 0.62 mmol) in toluene (2 mL) was added POCl₃ (477.6 mg, 3.11 mmol) and DIEA (805.0 mg, 6.23 mmol) at 0° C. The resultant suspension was heated to 100° C. for 2 hrs. After cooling to room temperature, a mixture of 1-ethynylcyclopropanamine hydrochloride (366.0 mg, 3.11 mmol) and DIEA (805.0 mg, 6.23 mmol) in NMP (2 mL) was added. The resulting mixture was stirred at 50° C. for 1 h. The mixture was diluted with DCM (50 mL) and water (50 mL), extracted with DCM (50 mL×3). The combined organic phases were washed with water, brine, dried over Na₂SO₄ and concentrated. The residue was purified by silica gel column to afford compound 46 (128.0 mg, 53.5% yield). LCMS: 385.1 [M+H]⁺. ¹H NMR (400 MHz, DMSO-d₆) δ 9.33 (s, 1H), 8.65 (dd, J=4.8 Hz, 1.2 Hz, 1H), 8.41 (d, J=8.4 Hz, 1H), 7.84 (d, J=7.2 Hz, 1H), 7.61 (d, J=8.0 Hz, 1H), 7.52 (dd, J=8.0 Hz, 4.8 Hz, 1H), 6.49 (s, 1H), 3.07 (s, 1H), 2.19 (s, 3H), 1.32-1.30 (m, 2H), 1.26-1.23 (m, 2H).

To a stirred solution of compound 34-2 (150.0 mg, 0.44 mmol) in toluene (3 mL) was added DIPEA (574.8 mg, 4.45 mmol) and POCl₃ (341.0 mg, 2.22 mmol) at 0° C. The resultant suspension was heated to 100° C. for 2 hrs, then cooled to room temperature. A solution of 1-ethynylcyclopropanamine hydrochloride (313.8 mg, 2.67 mmol) and DIPEA (574.8 mg, 4.45 mmol) in NMP (2 mL) was added to the mixture. The reaction mixture was stirred at room temperature for 16 hrs. Water (30 mL) was added, extracted by DCM (50 mL×3), and the combined organic phases were washed with water (50 mL×3), brine, dried over Na₂SO₄ and concentrated. The residue was purified by gel column chromatography to afford compound 47. LCMS: 401.1 [M+H]⁺. ¹H NMR (400 MHz, DMSO-d₆) δ 8.88 (s, 1H), 8.73 (dd, J=4.8 Hz, 1.6 Hz, 1H), 8.58 (d, J=2.0 Hz, 1H), 7.91-7.88 (m, 1H), 7.66 (dd, J=8.0 Hz, 4.8 Hz, 1H), 7.12 (s, 1H), 6.12 (s, 1H), 4.12 (s, 3H), 3.04 (s, 1H), 1.33-1.30 (m, 2H), 1.26-1.23 (m, 2H).

Example 48: Synthesis of 5-methoxy-1-(3-methylpyrazin-2-yl)-4-(prop-2-yn-1-ylamino)-7-(trifluoromethyl)quinazolin-2(1H)-one

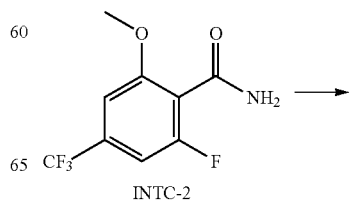

INTC-2

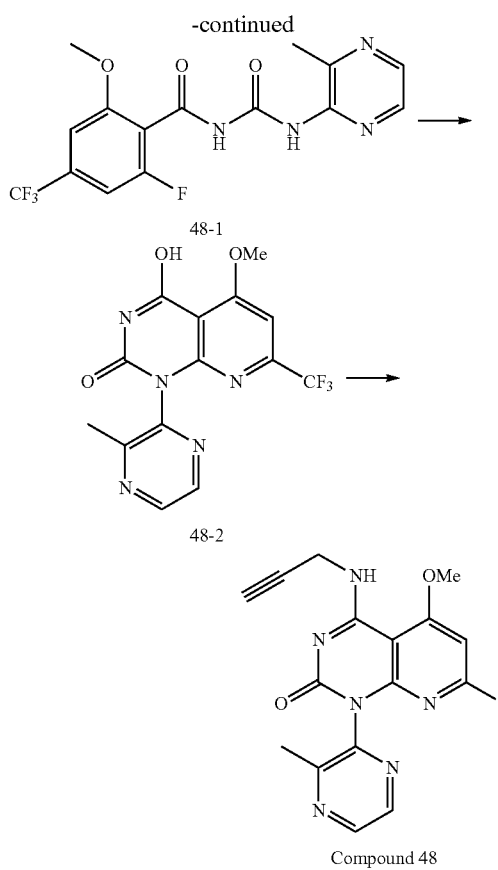

Compound 48

Step 1: To a stirred suspension of compound INTC-2 (300.0 mg, 1.27 mmol) in dichloroethane (6 mL) at room temperature was added oxalyl chloride (177.0 mg, 1.39 mmol). The resultant suspension was heated to 80° C. for 1 h. After cooling to room temperature, 3-methylpyrazin-2-amine (276.0 mg, 2.53 mmol) was added. The mixture was stirred at room temperature for 16 hrs. The precipitate was collected by filtration, washed with water, and dried to afford compound 48-1 (400.0 mg, 77.2% yield). LCMS: 373.1 [M+H]$^+$.

Step 2: NaH (116.0 mg, 2.91 mmol, 60% oil dispersion) was added to a mixture of compound 48-1 (360.0 mg, 0.97 mmol) in THF (5 mL) at −20° C. The mixture was warmed to room temperature and stirred at 40° C. for 16 hrs. The reaction mixture was poured into iced water (3 mL) and adjusted pH to 6~7 with aqueous 4.0 M HCl. The precipitate was collected, washed with water, and dried to afford compound 48-2 (220 mg, 64.7% yield). LCMS: 353.1 [M+H]$^+$.

Step 3: To a stirred suspension of compound 48-2 (100.0 mg, 0.28 mmol) in acetonitrile (2 mL) was added DIPEA (110.0 mg, 0.85 mmol) and POCl$_3$ (130.0 mg, 0.85 mmol) at 0° C. The mixture was heated to 80° C. for 2 hrs. After cooling to room temperature, a mixture of DIPEA (362.0 mg, 2.80 mmol) and prop-2-yn-1-amine (154.0 mg, 2.80 mmol) in NMP (1 mL) was added. The mixture was stirred at 50° C. for 1 h. The mixture was diluted with DCM (5 mL) and water (15 mL), extracted with DCM (10 mL×3). The combined organic phases were washed with water, brine, dried over Na$_2$SO$_4$ and concentrated. The residue was purified by gel column chromatography to afford compound 48 (63.4 mg, 57.3% yield). LCMS: 390.1 [M+H]$^+$. $^1$H NMR (400 MHz, DMSO-d$_6$) δ 9.06 (m, 1H), 8.74 (m, 1H), 8.63 (s, 1H), 7.18 (s, 1H), 6.12 (s, 1H), 4.35 (s, 2H), 4.13 (s, 3H), 3.17 (s, 1H), 2.31 (s, 3H).

Example 52: Synthesis of 1-(2,4-dimethylpyridin-3-yl)-4-(prop-2-yn-1-ylamino)-7-(trifluoromethyl)quinazolin-2(1H)-one

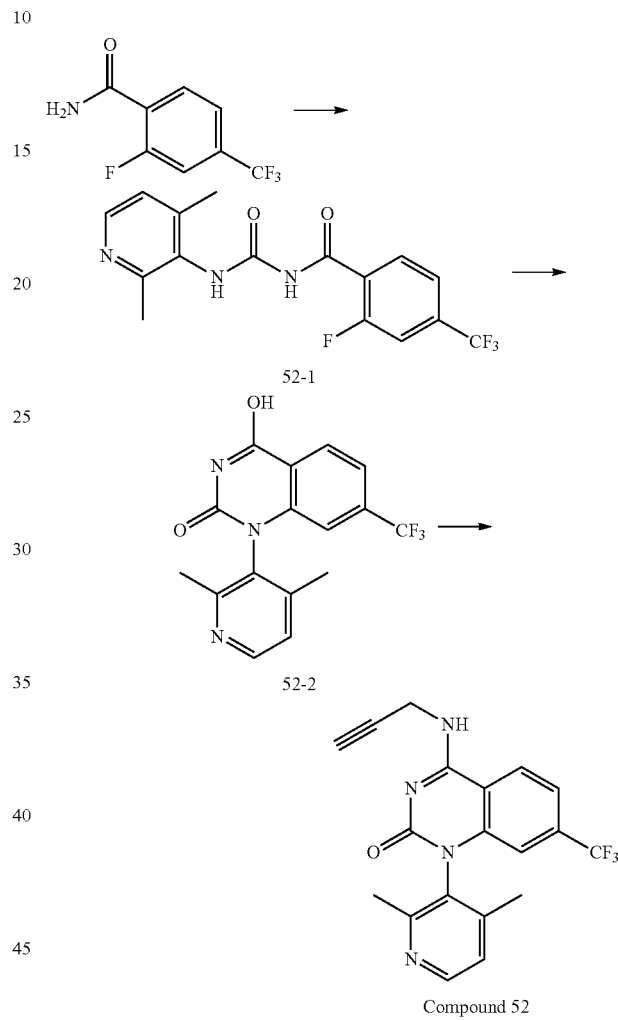

Compound 52

Step 1: To a stirred suspension of 2-fluoro-4-(trifluoromethyl)benzamide (2.0 g, 9.66 mmol) in dichloroethane (20 mL) at room temperature was added oxalyl dichloride (1.3 g, 10.67 mmol). The mixture was heated to 80° C. for 1 h. After cooling to room temperature, 2,4-dimethylpyridin-3-amine (2.4 g, 19.31 mmol) was added. The mixture was stirred at room temperature for 16 hrs, then cooled to 0° C. The precipitate was collected by filtration, washed with water and Et$_2$O, dried to afford compound 52-1 (2.2 g, 64.1% yield). LCMS: 356.1 [M+H]$^+$.

Step 2: NaH (743.0 mg, 18.58 mmol, 60% oil dispersion) was added to a mixture of compound 52-1 (2.2 g, 6.19 mmol) in THF (20 mL) at −20° C., and the resulting mixture was allowed to warm to room temperature over 3 hrs. The reaction mixture was concentrated, diluted with water, and adjusted pH to 6~7 with aqueous 4M HCl. The precipitate was collected by filtration, washed with water, and dried to afford compound 52-2 (2.0 g, 96.3% yield). $^1$H NMR (400

MHz, DMSO-d$_6$) δ 12.18 (s, 1H), 8.53 (d, J=5.2 Hz, 1H), 8.33 (d, J=8.4 Hz, 1H), 7.69 (d, J=8.0 Hz, 1H), 7.41 (d, J=4.8 Hz, 1H), 6.46 (s, 1H), 2.22 (s, 3H), 2.07 (s, 3H).

Step 3: To a solution of compound 52-2 (200.0 mg, 0.60 mmol) in toluene (2 mL) was added DIEA (771.0 mg, 5.96 mmol) and POCl$_3$ (457.3 mg, 2.98 mmol) at 0° C. The resultant suspension was heated to 100° C. for 2 hrs. After cooling to room temperature, prop-2-yn-1-amine (328.6 mg, 5.96 mmol) and DIEA (771.0 mg, 5.96 mmol) in NMP (1.5 mL) was added. The mixture was stirred at room temperature for 16 hrs. Water (50 mL) was added, extracted by DCM (50 mL×3). The combined organic layer was washed with water, brine, dried over Na$_2$SO$_4$ and concentrated. The residue was purified by column chromatography to afford compound 52 (48.1 mg, 21.6% yield). LCMS: 373.1[M+H]$^+$. $^1$H NMR (400 MHz, DMSO-d$_6$) δ 9.38 (t, J=5.2 Hz, 1H), 8.50-8.47 (m, 2H), 7.67 (d, J=7.6 Hz, 1H), 7.38 (d, J=4.8 Hz, 1H), 6.44 (s, 1H), 4.38 (dd, J=5.2 Hz, 2.4 Hz, 2H), 3.27 (t, J=2.4 Hz, 1H), 2.11 (s, 3H), 1.96 (s, 3H).

Example 53: Synthesis of 4-(prop-2-yn-1-ylamino)-1-(pyrazin-2-yl)-7-(trifluoromethyl)quinazolin-2(1H)-one

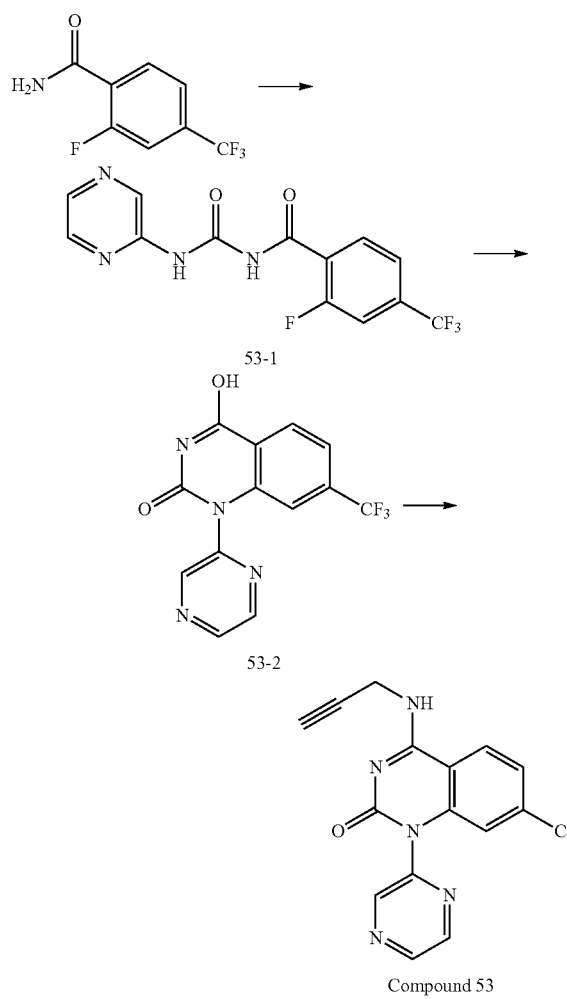

Compound 53

Step 1: To a stirred suspension of 2-fluoro-4-(trifluoromethyl)benzamide (3.0 g, 14.49 mmol) in dichloroethane (30 mL) at room temperature was added oxalyl dichloride (2.0 g, 15.94 mmol). The mixture was heated to 80° C. for 1 h. After cooling to room temperature, pyrazin-2-amine (2.7 g, 28.98 mmol) was added. The mixture was stirred at room temperature for 16 hrs. The precipitate was collected by filtration, washed with water, and dried to afford compound 53-1 (4.5 g, 95.7% yield). $^1$H NMR (400 MHz, DMSO-d$_6$) δ 11.58 (s, 1H), 10.81 (s, 1H), 9.26 (s, 1H), 8.44 (s, 2H), 7.96-7.90 (m, 2H), 7.76 (d, J=8.0 Hz, 1H).

Step 2: KHMDS (30.0 mL, 30.18 mmol) was added to a mixture of compound 53-1 (4.5 g, 13.72 mmol) in DMF (30 mL) at −20° C., and the resulting mixture was warmed to room temperature over 1 h. The mixture was concentrated, diluted with water, and adjusted pH to 6~7 with aqueous 4M HCl. The precipitate was collected, washed with water, and dried to afford compound 53-2 (3.0 g, 71.0% yield). $^1$H NMR (400 MHz, DMSO-d$_6$) δ 12.21 (s, 1H), 8.97 (s, 1H), 8.91 (d, J=2.4 Hz, 1H), 8.86-8.85 (m, 1H), 8.30 (d, J=8.4 Hz, 1H), 7.68 (d, J=8.0 Hz, 1H), 6.86 (s, 1H).

Step 3: To a solution of compound 53-2 (100.0 mg, 0.32 mmol) in toluene (1 mL) was added DIEA (419.3 mg, 3.24 mmol) and POCl$_3$ (249.0 mg, 1.62 mmol) at 0° C. The mixture was heated to 100° C. for 2 hrs. After cooling to room temperature, a solution of prop-2-yn-1-amine (89.5 mg, 1.62 mmol) and DIEA (168.0 mg, 1.30 mmol) in NMP (1 mL) was added. The mixture was stirred at room temperature for 16 hrs. The reaction mixture was diluted with DCM (30 mL) and water (20 mL), extracted with DCM (30 mL×2), the combined organic phases were washed with water, brine, dried over Na$_2$SO$_4$ and concentrated. The residue was purified by prep-HPLC to afford compound 53 (27.5 mg, 24.5% yield). LCMS: 346.0[M+H]$^+$. $^1$H NMR (400 MHz, DMSO-d$_6$) δ 9.40 (d, J=5.2 Hz, 1H), 8.89 (d, J=0.8 Hz, 1H)), 8.83 (d, J=2.4 Hz, 1H), 8.81 (d, J=1.2 Hz, 1H), 8.44 (d, J=8.8 Hz, 1H), 7.67 (d, J=8.0 Hz, 1H), 6.80 (s, 1H), 4.36 (d, J=2.4 Hz, 2H), 3.25 (t, J=2.4 Hz, 1H).

Example 54: Synthesis of 5-methoxy-4-(prop-2-yn-1-ylamino)-1-(pyrazin-2-yl)-7-(trifluoromethyl)quinazolin-2(1H)-one

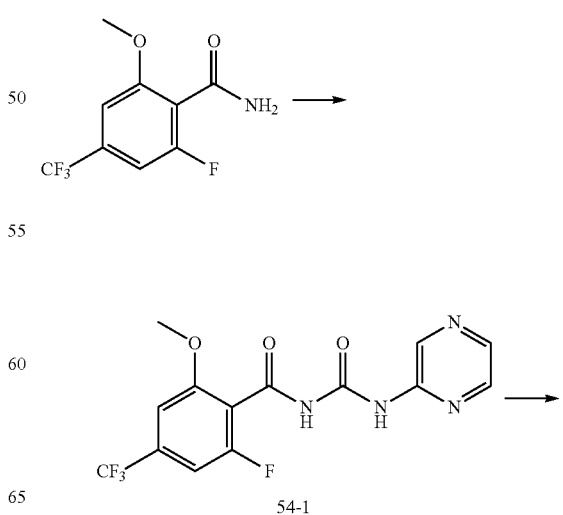

54-1

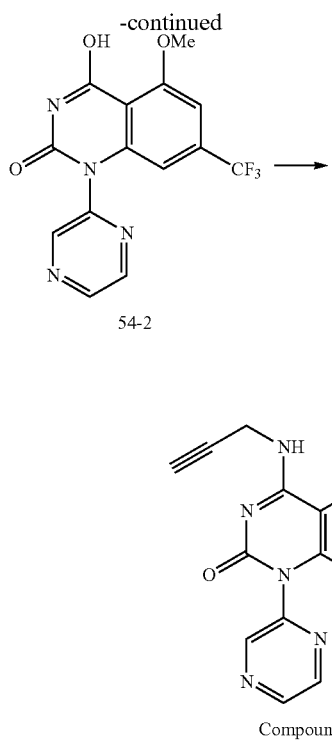

54-2

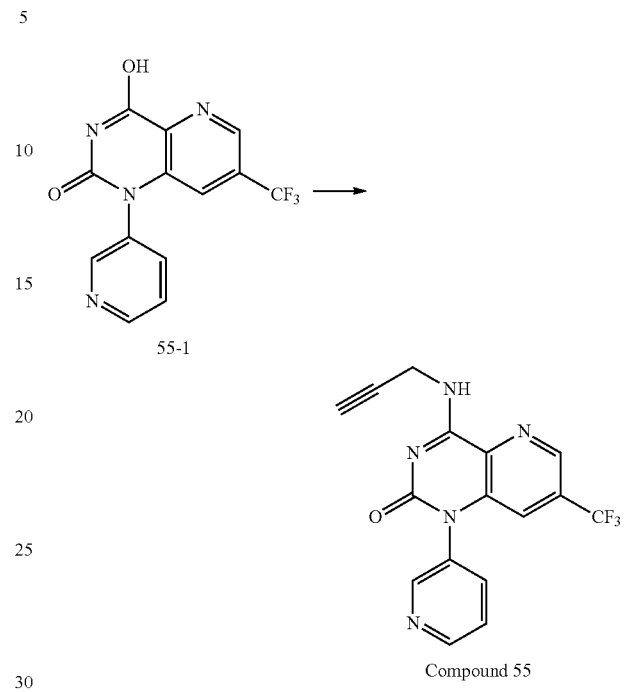

Compound 54

Step 1: To a stirred suspension of compound INTC-2 (300.0 mg, 1.27 mmol) in dichloroethane (6 mL) at room temperature was added oxalyl chloride (177.0 mg, 1.39 mmol). The mixture was heated to 80° C. for 1 h. After cooling to room temperature, pyrazin-2-amine (240.6 mg, 2.53 mmol) was added. The mixture was stirred at room temperature for 1 h, then cooled to 0° C. and stirred for 10 min. The precipitate was collected, washed with water, and dried to afford compound 54-1 (300.0 mg, 66.2% yield). LCMS: 359.1 [M+H]$^+$.

Step 2: NaH (87.0 mg, 2.26 mmol, 60% oil dispersion) was added to a mixture of compound 54-1 (270.00 mg, 0.75 mmol) in THF (5 mL) at −20° C., and the resulting mixture was heated to 40° C. over 16 hrs. The reaction mixture was concentrated, poured into ice-water (20 mL) and adjusted pH to 6~7 with aqueous 4M HCl. The precipitate was collected, washed with water and Et$_2$O, and dried to afford compound 54-2 (150.0 mg, 58.8% yield). LCMS: 339.1 [M+H]$^+$.

Steps 3: To a stirred mixture of compound 54-2 (130.0 mg, 0.38 mmol) in ACN (2 mL) was added DIEA (149.0 mg, 1.15 mmol) and POCl$_3$ (177.0 mg, 1.15 mmol) at 0° C. The resultant suspension was heated to 80° C. for 2 hrs. After cooling to room temperature, a solution of prop-2-yn-1-amine (212.0 mg, 3.84 mmol) and DIEA (497.0 mg, 3.84 mmol) in ACN (2 mL) was added. The mixture was stirred at room temperature for 16 hrs. Water (50 mL) was added, and extracted with DCM (50 mL×3). The combined organic layer was washed with water, brine, dried over Na$_2$SO$_4$ and concentrated. The residue was purified by column chromatography to afford compound 54 (57.8 mg, 40.1% yield). LCMS: 376.0 [M+H]$^+$. $^1$H NMR (400 MHz, DMSO-d$_6$) δ 9.07 (t, J=5.2 Hz, 1H), 8.86 (s, 1H), 8.83 (d, J=2.4 Hz, 1H), 8.81 (d, J=1.2 Hz, 1H), 7.17 (s, 1H), 6.23 (s, 1H), 4.34 (dd, J=5.6 Hz, 2.0 Hz, 2H), 4.13 (s, 3H), 3.16 (t, J=2.4 Hz, 1H).

Example 55: Synthesis of 4-(prop-2-yn-1-ylamino)-1-(pyridin-3-yl)-7-(trifluoromethyl)pyrido[3,2-d]pyrimidin-2(1H)-one A mixture of compound 55-1 (100.0 mg, 0.32 mmol), POCl$_3$ (248.7 mg, 1.62 mmol) and DIEA (209.7 mg, 1.62 mmol) in acetonitrile (2 mL) was stirred at 80° C. for 2 hrs. After cooling to room temperature, a mixture of DIEA (419.5 mg, 3.24 mmol) and prop-2-yn-1-amine (179.0 mg, 3.24 mmol) in acetonitrile (2 mL) was added. The mixture was stirred at room temperature for 16 hrs. Water (30 mL) was added, extracted by DCM (50 mL×3). The combined organic layer was washed with water (50 mL×3), brine, dried over anhydrous Na$_2$SO$_4$ and concentrated. The residue was purified by column chromatography to afford compound 55. LCMS: 346.1 [M+H]$^+$. $^1$H NMR (400 MHz, DMSO-d$_6$) δ 9.41 (t, J=6.0 Hz, 1H), 8.82 (d, J=1.2 Hz, 1H), 8.73 (dd, J=4.8 Hz, 1.2 Hz, 1H), 8.63 (d, J=2.0 Hz, 1H), 7.94-7.91 (m, 1H), 7.66 (dd, J=8.4 Hz, 4.8 Hz, 1H), 7.11 (d, J=1.2 Hz, 1H), 4.30 (dd, J=6.0 Hz, 2.4 Hz, 2H), 3.17-3.16 (m, 1H).

Example 56: Synthesis of 4-((1-ethynylcyclopropyl)amino)-1-(pyridin-3-yl)-7-(trifluoromethyl)pyrido[3,2-d]pyrimidin-2(1H)-one

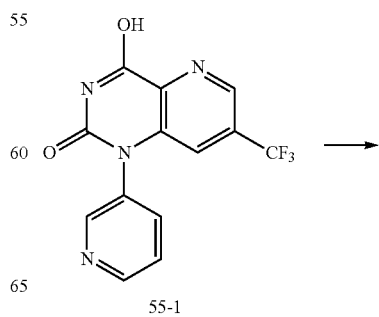

55-1

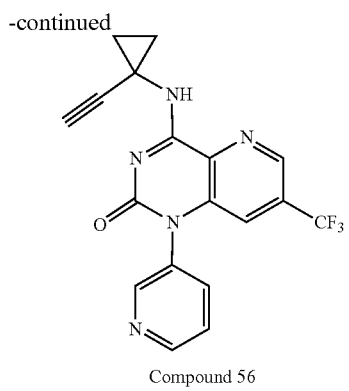

Compound 56

A mixture of compound 55-1 (100.0 mg, 0.32 mmol), POCl₃ (248.9 mg, 1.62 mmol) and DIEA (209.8 mg, 1.62 mmol) in MeCN (2 mL) was stirred at 80° C. for 2 hrs. After cooling to room temperature, a mixture of DIEA (419.6 mg, 2.84 mmol) and 1-ethynylcyclopropanamine hydrochloride (229.0 mg, 1.95 mmol) in MeCN (2 mL) was added. The resulting mixture was stirred at room temperature for 16 hrs. After concentration, the residue was diluted with DCM (20 mL) and water (20 mL), extracted by DCM (30 mL×2). The combined organic layer was washed with water, brine, dried over Na₂SO₄ and concentrated. The residue was purified by silica gel column to afford compound 56 (21.4 mg, 17.6% yield). LCMS: 372.1 [M+H]⁺. ¹H NMR (400 MHz, DMSO-d₆) δ 9.57 (s, 1H), 8.76 (d, J=1.2 Hz, 1H), 8.74 (dd, J=4.8 Hz, 1.2 Hz, 1H), 8.64 (d, J=2.4 Hz, 1H), 7.94-7.91 (m, 1H), 7.66 (dd, J=8.0 Hz, 4.8 Hz, 1H), 7.09 (s, 1H), 3.04 (s, 1H), 1.28-1.23 (m, 4H).

Example 57: Synthesis of 4-(prop-2-yn-1-ylamino)-1-(pyridin-3-yl)-7-(trifluoromethyl)pyrido[2,3-d]pyrimidin-2(1H)-one

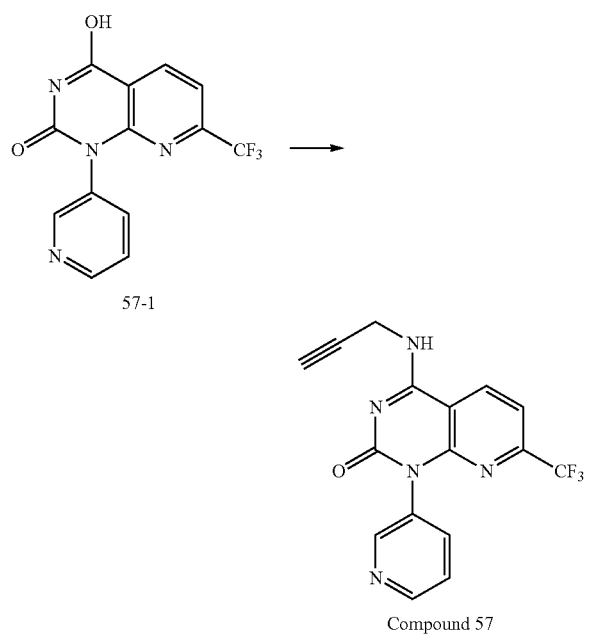

To a stirred mixture of compound 57-1 (100.0 mg, 0.32 mmol) in toluene (1 mL) was added DIEA (419.6 mg, 3.24 mmol) and POCl₃ (248.9 mg, 1.62 mmol) at 0° C. The mixture was heated to 100° C. for 2 hrs. After cooling to room temperature. A solution of prop-2-yn-1-amine (178.5 mg, 3.24 mmol) and DIEA (419.6 mg, 3.24 mmol) in NMP (1 mL) was added. The mixture was stirred at room temperature for 16 h. The reaction mixture was diluted with DCM (20 mL) and water (30 mL), extracted with DCM (30 mL×2). The combined organic phases were washed with water, brine, dried over Na₂SO₄ and concentrated. The residue was purified by column chromatography to afford compound 57. LCMS: 346.1 [M+H]⁺. ¹H NMR (400 MHz, DMSO-d₆) δ 9.45 (t, J=5.2 Hz, 1H), 8.84 (d, J=8.0 Hz, 1H), 8.60 (dd, J=4.8 Hz, 1.2 Hz, 1H), 8.51 (d, J=2.0 Hz, 1H), 7.81-7.78 (m, 2H), 7.57-7.54 (m, 1H), 4.36 (dd, J=5.2 Hz, 2.4 Hz, 2H), 3.27 (t, J=2.0 Hz, 1H).

Example 58: Synthesis of 4-(prop-2-yn-1-ylamino)-1-(pyridin-3-yl)-7-(trifluoromethyl)pyrido[4,3-d]pyrimidin-2(1H)-one

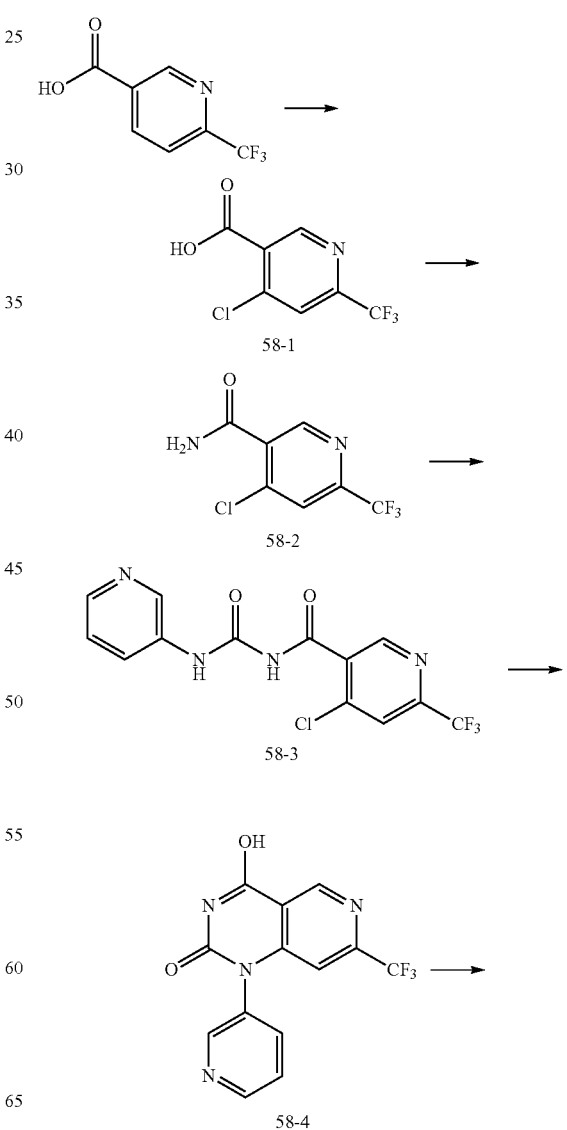

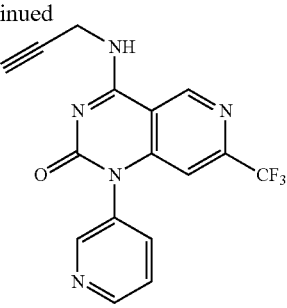

Compound 58

Step 1: To a mixture of TEMP (54.3 g, 384 mmol) in THF (250 mL) was added n-BuLi (2.5 M, 153 mL) dropwise at −78° C. under N₂, the mixture was stirred at −78° C. for 0.5 hr, then a solution of 6-(trifluoromethyl)nicotinic acid (24.5 g, 128 mmol) in THF (250 mL) was added dropwise at −78° C. The mixture was stirred at −78° C. for 1 hr, and 1,1,1,2,2,2-hexachloroethane (60.7 g, 256 mmol) in THF (250 mL) was added and stirred at −78° C. for 3 hrs. Aqueous ammoniumchloride (250 mL) was added slowly at −78° C. and the mixture was stirred at 25° C. for 20 min. The mixture was extracted with ethyl acetate (250 mL×3). The combined organic layer was concentrated to give compound 58-1 (42.0 g, crude). LCMS: 226.0 [M+H]⁺.

Step 2: Compound 58-1 (40.0 g) was dissolved in DCM (240 mL), and then DMF (77.1 mg, 1.06 mmol) was added at 0° C. followed by oxalyl chloride (34.5 g, 271 mmol). The mixture was stirred at 25° C. for 2 hrs. After concentration, the reside was dissolved in THF (24 mL), and added to NH₄OH (108.0 g, 28.0% purity) under ice cooling. The mixture was poured into H₂O (250 mL), and extracted with DCM (300 mL×3). The combined organic layers were dried over Na₂SO₄, concentrated to give compound 58-2 (32.0 g, crude). LCMS: 225.1 [M+H]⁺.

Step 3: To a stirred suspension of compound 58-2 (29.0 g, 59.3% purity) in DCE (290 mL) at 25° C. was added oxalyl chloride (10.6 g, 84.2 mmol). The mixture was heated to 80° C. for 1 hr. The mixture was allowed to cool to 25° C., pyridin-3-amine (8.65 g, 91.8 mmol) was added. The mixture was stirred at 25° C. for 30 min. The precipitate was collected by filtration, washed with DCM, and dried to give compound 58-3 (26.0 g, crude). LCMS: 345.1 [M+H]⁺.

Step 4: A slurry of compound 58-3 (10.0 g, 29.0 mmol) in DME (5 mL) was cooled to 0° C. and treated with NaH (3.60 g, 89.9 mmol, 60% oil dispersion). The reaction mixture was warmed to 25° C. for 3 hrs and poured into aq. NH₄Cl (40 mL). Extracted with EtOAc (50 mL×3). The combined organic layers were dried over Na₂SO₄, filtered and concentrated to give compound 58-4. LCMS: 309.1 [M+H]⁺. 1HNMR: (400 MHz, DMSO-d₆) δ 12.36 (s, 1H), 9.22 (s, 1H), 8.87 (d, 1H), 8.79 (d, 1H), 8.12 (s, 1H), 7.83 (m, 1H), 6.82 (s, 1H).

Steps 5: To a stirred suspension of compound 58-4 (100.0 mg, 0.32 mmol) in MeCN (1 mL) was added POCl₃ (149.2 mg, 0.97 mmol) and DIPEA (125.8 mg, 0.97 mmol) at 0° C. The mixture was heated to 80° C. for 2 hrs. After cooling to room temperature, a mixture of DIPEA (419.3 mg, 3.24 mmol) and prop-2-yn-1-amine (178.7 mg, 3.24 mmol) in MeCN (1 mL) was added. The mixture was stirred at 50° C. for 1 h and diluted with DCM (10 mL) and water (10 mL), extracted with DCM (30 mL×2). The combined organic phases were washed with water, brine, dried over Na₂SO₄ and concentrated. The residue was purified by silica gel column to afford compound 58 (33.80 mg, 30.1% yield). LCMS: 346.1 [M+H]⁺. ¹H NMR (400 MHz, DMSO-d₆) δ 9.54 (t, J=4.8 Hz, 1H), 9.43 (s, 1H), 8.74 (dd, J=4.8 Hz, 1.2 Hz, 1H), 8.62 (d, J=2.0 Hz, 1H), 7.93-7.90 (m, 1H), 7.66 (dd, J=8.0 Hz, 3.2 Hz, 1H), 6.65 (s, 1H), 4.38 (m, 2H), 3.28 (m, 1H).

Example 59: Synthesis of 4-(but-3-yn-2-ylamino)-1-(pyridin-3-yl)-7-(trifluoromethyl)pyrido[4,3-d]pyrimidin-2(1H)-one

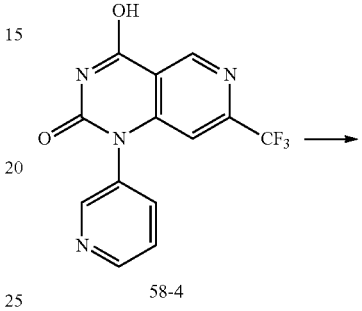

58-4

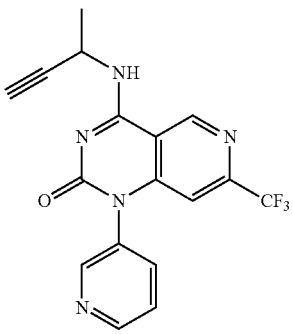

Compound 59

To a stirred suspension of compound 58-4 (200.0 mg, 0.64 mmol) in MeCN (2 mL) was added POCl₃ (298.4 mg, 1.94 mmol) and DIPEA (251.6 mg, 1.94 mmol) at 0° C. The mixture was heated to 80° C. for 2 hrs. After cooling to room temperature, a mixture of DIPEA (838.6 mg, 6.48 mmol) and but-3-yn-2-amine hydrochloride (224.2 mg, 3.24 mmol) in MeCN (1 mL) was added. The mixture was stirred at 50° C. for 1 h and diluted with DCM (50 mL) and water (30 mL). Extracted with DCM (50 mL×2). The combined organic phases were washed with water, brine, dried over anhydrous Na₂SO₄ and concentrated. The residue was purified by silica gel column to afford compound 59 (78.20 mg, 32.5% yield). LCMS: 360.1 [M+H]⁺. ¹H NMR (400 MHz, DMSO-d₆) δ 9.51 (s, 1H), 9.36 (d, J=7.6 Hz, 1H), 8.74 (dd, J=4.8 Hz, 1.2 Hz, 1H), 8.62 (s, 1H), 7.91 (s, 1H), 7.67 (m, 1H), 6.64 (s, 1H), 5.31-5.27 (m, 1H), 3.37 (d, J=2.0 Hz, 1H), 1.54 (d, J=6.8 Hz, 3H).

Example 60: Synthesis of 4-((1-ethynylcyclopropyl)amino)-1-(pyridin-3-yl)-7-(trifluoromethyl)pyrido[4,3-d]pyrimidin-2(1H)-one

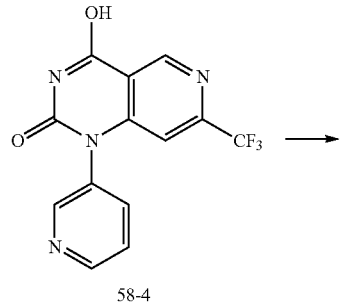

58-4

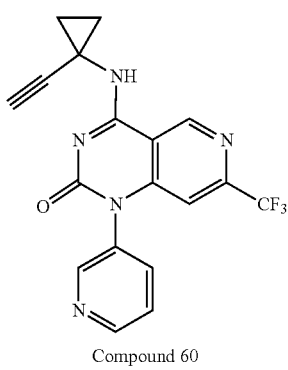

Compound 60

To a stirred suspension of compound 58-4 (200.0 mg, 0.65 mmol) in acetonitrile (2 mL) was added DIPEA (251.0 mg, 1.95 mmol) and POCl$_3$ (298.0 mg, 1.95 mmol) at 0° C. The mixture was heated to 80° C. for 2 hrs. After cooling to room temperature, a mixture of DIPEA (838.0 mg, 6.50 mmol) and 1-ethynylcyclopropanamine hydrochloride (457.0 mg, 3.89 mmol) in NMP (2 mL) was added. The mixture was stirred at room temperature for 16 hrs, and diluted with DCM (10 mL) and water (15 mL). Extracted with DCM (20 mL×3). The combined organic phases were washed with water, brine, dried over Na$_2$SO$_4$ and concentrated. The residue was purified by gel column chromatography to afford compound 60 (94.3 mg, 39.3% yield). LCMS: 372.0 [M+H]$^+$. $^1$H NMR (400 MHz, DMSO-d$_6$) δ 9.56 (s, 1H), 9.37 (s, 1H), 8.75 (d, J=4.0 Hz, 1H), 8.64 (d, J=1.6 Hz, 1H), 7.94 (d, J=8.0 Hz, 1H), 7.67 (dd, J=4.8 Hz, 1.2 Hz, 1H), 6.63 (s, 1H), 3.11 (s, 1H), 1.34-1.26 (m, 4H).

Example 61: Synthesis of 4-(prop-2-yn-1-ylamino)-1-(pyridin-3-yl)-7-(trifluoromethyl)pyrimido[4,5-d]pyrimidin-2(1H)-one

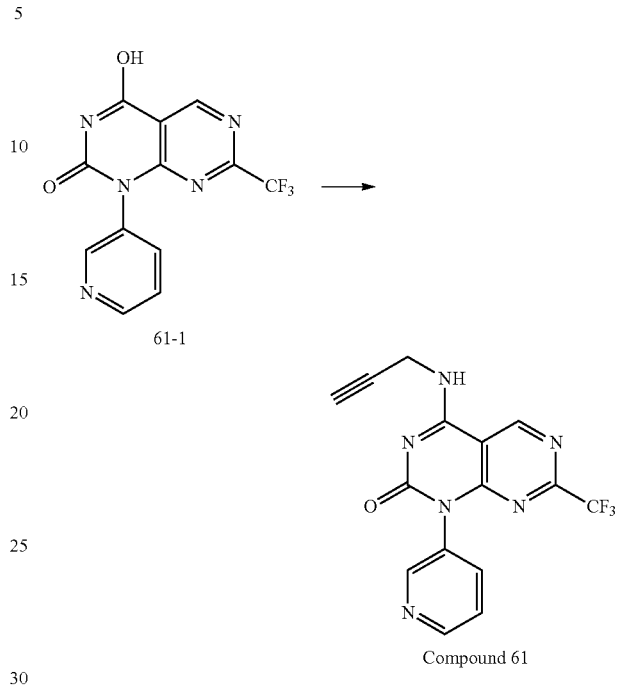

61-1

Compound 61

To a stirred solution of compound 61-1 (120.0 mg, 0.39 mmol) in MeCN (2 mL) was added DIEA (150.5 mg, 1.16 mmol) and POCl$_3$ (178.5 mg, 1.16 mmol) at 0° C. The mixture was heated to 80° C. for 2 hrs. After cooling to room temperature, a solution of prop-2-yn-1-amine (214.0 mg, 3.88 mmol) and DIEA (501.5 mg, 3.88 mmol) in MeCN (2 mL) was added. The mixture was stirred at room temperature for overnight. Water (50 mL) was added and extracted by DCM (50 mL×3). The combined organic layer was washed with water, brine, dried over Na$_2$SO$_4$ and concentrated. The residue was purified by column chromatography to afford compound 61 (18.8 mg, 14.0% yield). LCMS: 347.1 [M+H]$^+$. $^1$H NMR (400 MHz, DMSO-d$_6$) δ 9.70 (t, J=5.2 Hz, 1H), 9.57 (s, 1H), 8.64 (dd, J=4.8 Hz, 1.2 Hz, 1H), 8.54 (d, J=2.0 Hz, 1H), 7.83-7.80 (m, 1H), 7.59 (dd, J=8.0 Hz, 4.8 Hz, 1H), 4.38 (dd, J=4.8 Hz, 2.4 Hz, 2H), 3.28 (t, J=2.4 Hz, 1H).

Example 62: Synthesis of 4-((1-ethynylcyclopropyl)amino)-1-(pyridin-3-yl)-7-(trifluoromethyl)pyrimido[4,5-d]pyrimidin-2(1H)-one

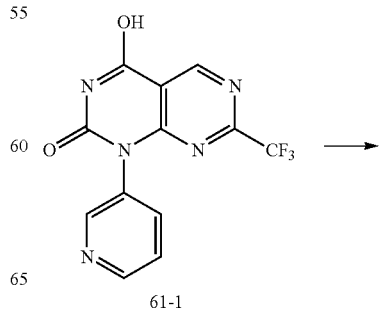

61-1

-continued

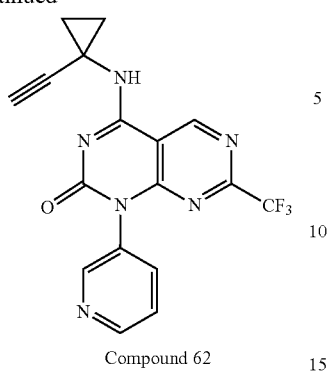

Compound 62

To a stirred solution of compound 61-1 (100.0 mg, 0.32 mmol) in MeCN (2 mL) was added DIEA (125.4 mg, 0.97 mmol) and $POCl_3$ (149.0 mg, 0.97 mmol) at 0° C. The mixture was heated to 80° C. for 2 hrs. After cooling to room temperature, a solution of 1-ethynylcyclopropanamine hydrochloride (228.0 mg, 1.94 mmol) and DIEA (418.0 mg, 3.23 mmol) in MeCN (2 mL) was added. The mixture was stirred at room temperature for 16 hrs. Water (50 mL) was added and extracted by DCM (50 mL×3). The combined organic layer was washed with water, brine, dried over anhydrous $Na_2SO_4$ and concentrated. The residue was purified by column chromatography to afford compound 62 (30.5 mg, 25.3% yield). LCMS: 373.0 $[M+H]^+$. $^1H$ NMR (400 MHz, DMSO-$d_6$) δ 9.71 (s, 1H), 9.51 (s, 1H), 8.64 (dd, J=4.8 Hz, 2.4 Hz, 1H), 8.55 (d, J=2.4 Hz, 1H), 7.84-7.81 (m, 1H), 7.59 (dd, J=8.0 Hz, 4.8 Hz, 1H), 3.14 (s, 1H), 1.38-1.35 (m, 2H), 1.27-1.24 (m, 2H).

Example 63: Synthesis of 4-(prop-2-yn-1-ylamino)-1-(pyridazin-3-yl)-7-(trifluoromethyl)pyrido[2,3-d]pyrimidin-2(1H)-one

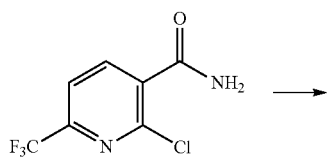

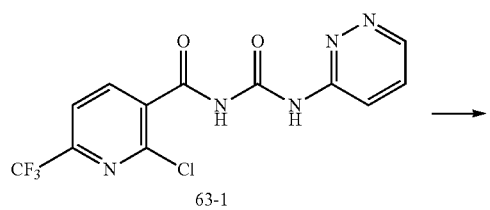

63-1

-continued

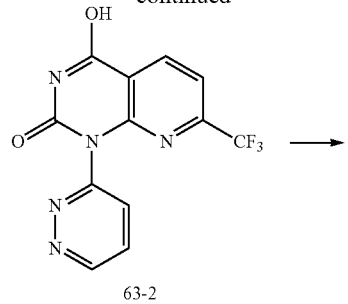

63-2

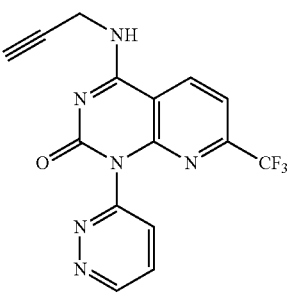

Compound 63

Step 1: To a stirred suspension of 2-chloro-6-(trifluoromethyl)nicotinamide (7.08 g, 31.5 mmol) in DCE (70 mL) at 25° C. was added $(COCl)_2$ (4.40 g, 34.7 mmol). The mixture was heated to 80° C. for 1 hr. After cooling to 25° C., pyridazin-3-amine (3.60 g, 37.8 mmol) was added. The mixture was stirred at 25° C. for 30 min. The precipitate was collected by filtration, washed with DCM, and dried to give compound 63-1 (8.20 g, 75.2% yield). LCMS: 346.1 $[M+H]^+$.

Step 2: A slurry of compound 63-1 (8.20 g, 23.7 mmol) in DME (82 mL) was cooled to 0° C. and treated with NaH (2.94 g, 73.5 mmol, 60.0%). The reaction mixture was warmed to 25° C. for 3 hrs. The mixture was poured into aq. $NH_4Cl$ (40 mL), and extracted with ethyl acetate (50 mL×3). The combined organic layers were dried over $Na_2SO_4$, and concentrated to give compound 63-2 (5.50 g, 75.0% yield). LCMS: 310.2 $[M+H]^+$. $^1HNMR$: (400 MHz, DMSO-$d_6$) δ 12.33 (br s, 1H), 9.41 (dd, J=4.8, 1.2 Hz, 1H), 8.68 (d, J=8.0 Hz, 1H), 8.06-7.99 (m, 1H), 7.97-7.91 (m, 1H), 7.81 (d, J=8.0 Hz, 1H).

Step 3: A mixture of compound 63-2 (200.0 mg, 0.65 mmol), $POCl_3$ (297.5 mg, 1.94 mmol), DIPEA (250.8 mg, 1.94 mmol) in MeCN (2 mL) was stirred at 80° C. for 2 hrs. After cooling to room temperature, a mixture of DIPEA (835.9 mg, 6.47 mmol) and prop-2-yn-1-amine (356.3 mg, 6.47 mmol) in MeCN (2 mL) was added. The resulting mixture was stirred at room temperature for 16 hrs. The mixture was diluted with DCM (20 mL) and $H_2O$ (20 mL), and extracted by DCM (20 mL×3). The combined organic phases were washed with water, brine, dried over anhydrous $Na_2SO_4$ and concentrated. The residue was purified by prep-TLC to afford compound 63. LCMS: 347.1 $[M+H]^+$. $^1H$ NMR (400 MHz, DMSO-$d_6$) δ 9.62-9.51 (m, 1H), 9.35 (dd, J=4.8 Hz, 1.2 Hz, 1H), 8.90 (d, J=8.0 Hz, 1H), 7.96 (dd, J=8.8 Hz, 4.8 Hz, 1H), 7.90-7.81 (m, 2H), 4.38 (d, J=1.2 Hz, 2H), 3.29 (t, J=2.4 Hz, 1H).

Example 68: Synthesis of 4-((1-ethynylcyclopropyl)amino)-1-(pyridin-3-yl)-7-(trifluoromethyl)pyrido[2,3-d]pyrimidin-2(1H)-one

Example 69: Synthesis of 4-((1-ethynylcyclopropyl)amino)-1-(pyrazin-2-yl)-7-(trifluoromethyl)quinazolin-2(1H)-one

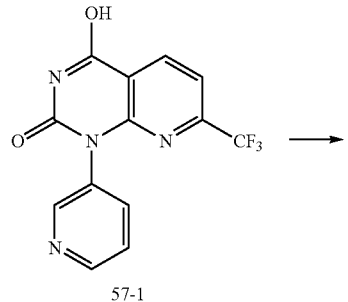

57-1

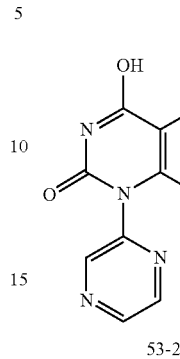

53-2

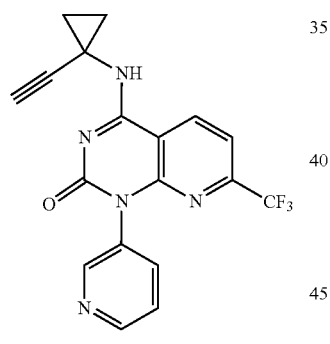

Compound 68

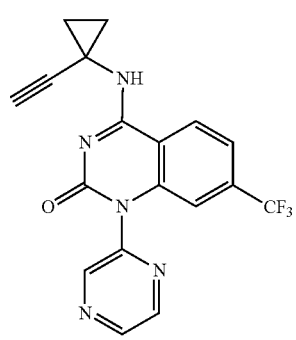

Compound 69

To a mixture of compound 57-1 (100.0 mg, 0.32 mmol) in toluene (1 mL) was added DIEA (419.6 mg, 3.24 mmol) and $POCl_3$ (248.9 mg, 1.62 mmol) at 0° C. The mixture was heated to 100° C. for 2 hrs. After cooling to room temperature, a solution of 1-ethynylcyclopropan-1-amine hydrochloride (189.9 mg, 1.62 mmol) and DIEA (419.6 mg, 3.24 mmol) in NMP (1 mL) was added. The mixture was stirred at room temperature for 16 hrs. The mixture was diluted with DCM (30 mL) and water (30 mL), and extracted with DCM (30 mL×2). The combined organic phases were washed with water, brine, dried over $Na_2SO_4$ and concentrated. The residue was purified by prep-TLC to afford compound 68. LCMS: 372.1 [M+H]$^+$. $^1$H NMR (400 MHz, DMSO-$d_6$) δ 9.46 (s, 1H), 8.78 (d, J=8.4 Hz, 1H), 8.61 (dd, J=4.8 Hz, 1.6 Hz, 1H), 8.52 (d, J=2.4 Hz, 1H), 7.82-7.77 (m, 2H), 7.57-7.54 (m, 1H), 3.09 (s, 1H), 1.35-1.32 (m, 2H), 1.25-1.22 (m, 2H).

To a mixture of compound 53-2 (200.0 mg, 0.65 mmol) in toluene (2 mL) was added DIEA (841.3 mg, 6.51 mmol) and $POCl_3$ (499.0 mg, 3.25 mmol) at 0° C. The mixture was heated to 100° C. for 2 hrs. After cooling to room temperature, a solution of 1-ethynylcyclopropan-1-amine hydrochloride (382.7 mg, 3.25 mmol) and DIEA (841.3 mg, 6.51 mmol) in NMP (2 mL) was added. The mixture was stirred at room temperature for 16 h. The mixture was diluted with DCM (50 mL) and water (50 mL), and extracted with DCM (50 mL×2). The combined organic phases were washed with water, brine, dried over $Na_2SO_4$ and concentrated. The residue was purified by prep-TLC to afford compound 69 (100.2 mg, 41.5% yield). LCMS: 372.1 [M+H]$^+$. $^1$H NMR (400 MHz, DMSO-$d_6$) δ 9.41 (s, 1H), 8.91 (d, J=1.2 Hz, 1H), 8.84 (d, J=2.4 Hz, 1H), 8.81 (dd, J=2.4 Hz, 1.2 Hz, 1H), 8.40 (d, J=8.0 Hz, 1H), 7.64 (d, J=7.6 Hz, 1H), 6.77 (s, 1H), 3.08 (s, 1H), 1.35-1.30 (m, 2H), 1.28-1.23 (m, 2H).

Example 70: Synthesis of 4-((1-ethynylcyclopropyl)amino)-1-(pyridazin-3-yl)-7-(trifluoromethyl)pyrido[2,3-d]pyrimidin-2(1H)-one

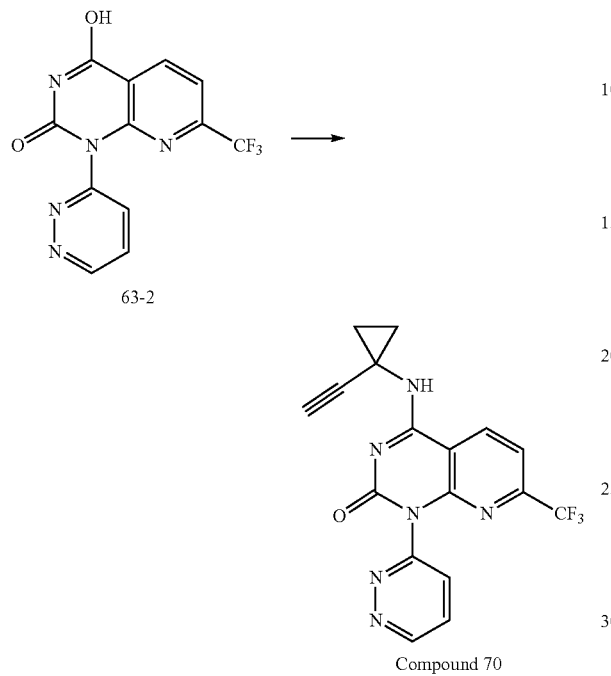

To a mixture of compound 63-2 (100.0 mg, 0.32 mmol) in MeCN (2 mL) was added DIEA (125.5 mg, 0.97 mmol) and POCl₃ (149.0 mg, 0.97 mmol). The mixture was heated to 100° C. for 2 hrs. After cooling to room temperature, a solution of 1-ethynylcyclopropanamine hydrochloride (228.0 mg, 1.94 mmol) and DIEA (418.0 mg, 3.23 mmol) in NMP (1 mL) was added. The mixture was stirred at room temperature for 16 hrs. Water (50 mL) was added, extracted by DCM (50 mL×3). The combined organic layer was washed with water, brine, dried over Na₂SO₄ and concentrated. The residue was purified by column chromatography to afford compound 70. LCMS: 373.0 [M+H]⁺. ¹H NMR (400 MHz, DMSO-d₆) δ 9.59 (s, 1H), 9.35 (d, J=4.8 Hz, 1H), 8.84 (d, J=7.6 Hz, 1H), 7.99-7.95 (m, 1H), 7.89 (d, J=8.4 Hz, 1H), 7.83 (d, J=8.0 Hz, 1H), 3.11 (s, 1H), 1.35-1.23 (m, 4H).

Example 71: Synthesis of 7-chloro-4-(prop-2-yn-1-ylamino)-1-(pyrimidin-5-yl)quinazolin-2(1H)-one

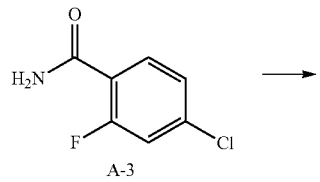

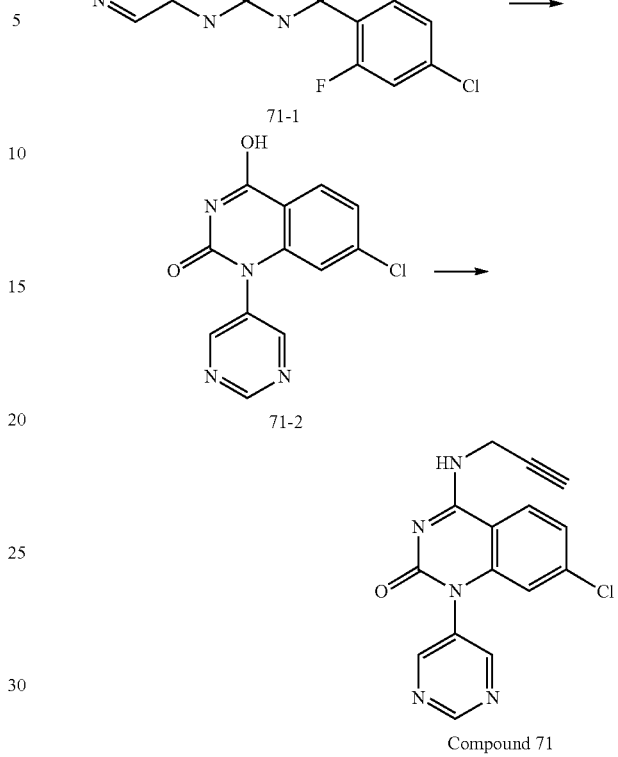

Step 1: To a solution of compound A-3 (500.0 mg, 2.88 mmol) in DCE (10 mL) was added oxalyl dichloride (402.0 mg, 3.17 mmol) at room temperature. The mixture was stirred at 80° C. for 1 h. After cooling to room temperature, pyrimidin-5-amine (548.0 mg, 5.76 mmol) was added and stirred at room temperature for 16 hrs. The precipitate was collected by filtration, washed with water, and dried to afford compound 71-1 (510.0 mg, 76.4% yield). LCMS: 295.1 [M+H]⁺.

Step 2: To a solution of compound 71-1 (510.0 mg, 1.73 mmol) in DMF (8 mL) was added KHMDS (3.8 mL, 3.81 mmol, 1M in THF) at −20° C. The mixture was stirred at room temperature for 16 hrs. The mixture was diluted with water (80 mL) and adjusted pH to 6~7 with aqueous 4M HCl. The precipitate was collected by filtration, washed with water, and dried to afford compound 71-2 (390 mg, 81.9% yield). LCMS: 275.0 [M+H]⁺.

Step 3: To a solution of compound 71-2 (100.0 mg, 0.36 mmol) in toluene (1 mL) was added POCl₃ (279.0 mg, 1.82 mmol) and DIEA (470.5 mg, 3.64 mmol). The mixture was heated to 100° C. for 2 hrs. After cooling to room temperature, a mixture of prop-2-yn-1-amine (200.5 mg, 3.64 mmol) and DIEA (188.0 mg, 1.46 mmol) in NMP (1 mL) was added. The mixture was stirred at room temperature for 16 hrs. After concentration, the residue was diluted with DCM (20 mL) and water (20 mL). Extracted by DCM (20 mL×3). The combined organic phases were washed with water, brine, dried over Na₂SO₄ and concentrated. The residue was purified by prep-TLC to afford compound 71. LCMS: 312.0 [M+H]⁺. ¹H NMR (400 MHz, DMSO-d₆) δ 9.32 (s, 1H), 9.23 (t, J=5.2 Hz, 1H), 8.92 (s, 2H), 8.23 (d, J=8.4 Hz, 1H), 7.36 (dd, J=4.8 Hz, 1.6 Hz, 1H), 6.67 (d, J=2.0 Hz, 1H), 4.32 (dd, J=4.8 Hz, 2.0 Hz, 2H), 3.22 (t, J=2.4 Hz, 1H).

Example 72: Synthesis of 1-(1-methyl-1H-pyrazol-4-yl)-4-(prop-2-yn-1-ylamino)-7-(trifluoromethyl)quinazolin-2(1H)-one

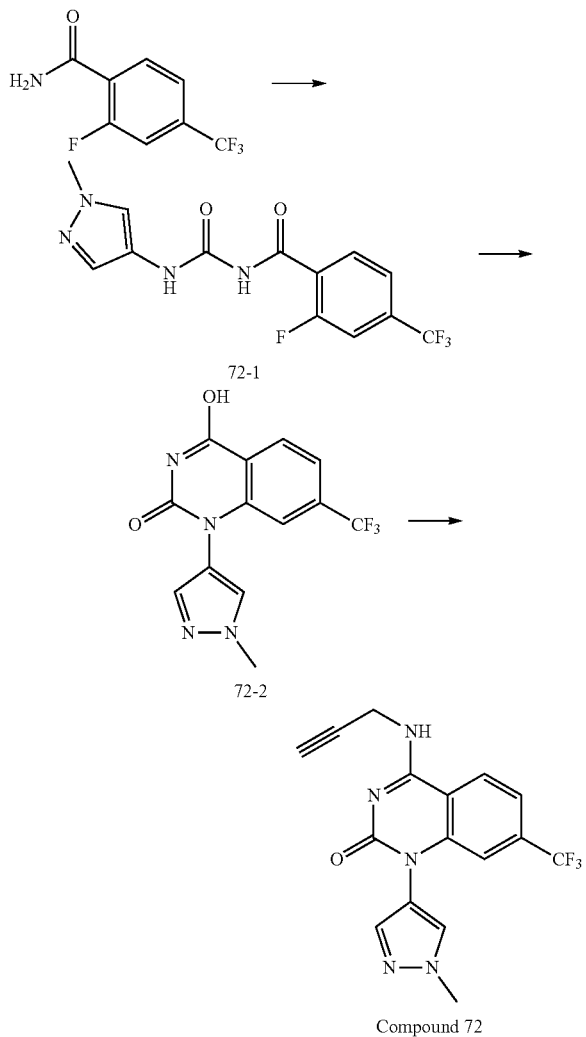

Step 1: To a solution of 2-fluoro-4-(trifluoromethyl)benzamide (2.0 g, 9.66 mmol) in DCE (20 mL) was added oxalyl dichloride (1.4 g, 10.62 mmol) at room temperature. The mixture was stirred at 80° C. for 1 hr. After cooling to room temperature, 1-methylpyrazol-4-amine (1.8 g, 19.31 mmol) was added. The mixture was stirred at room temperature for 1 h. The solid was collected and washed with water and dried to afford compound 72-1 (2.6 g, 81.5% yield). LCMS: 331.1 [M+H]+.

Step 2: KHMDS (17.3 mL, 17.30 mmol, 1M in THF) was added to a mixture of compound 72-1 (2.6 g, 7.87 mmol) in THF (30 mL) at −20° C. The mixture was stirred at room temperature for 2 hrs. After concentration, the residue was diluted with water and adjusted pH to 6~7 with aqueous 4M HCl. The solid was collected, washed with water and Et$_2$O, dried to afford compound 72-2 (1.5 g, 61.4% yield). $^1$H NMR (400 MHz, DMSO-d$_6$) δ 11.9 (s, 1H), 8.21 (d, J=8.0 Hz, 1H), 7.99 (s, 1H), 7.61-7.54 (m, 2H), 6.97 (s, 1H), 3.95 (s, 3H).

Steps 3: To a suspension of compound 72-2 (200.0 mg, 0.64 mmol) in toluene (2 mL) was added POCl$_3$ (494.2 mg, 3.22 mmol) and DIEA (833.2 mg, 6.44 mmol) at 0° C. The mixture was heated to 100° C. for 2 hrs. After cooling to room temperature, a mixture of DIEA (833.2 mg, 6.44 mmol) and prop-2-yn-1-amine (355.1 mg, 6.44 mmol) in NMP (2 mL) was added. The mixture was stirred at 50° C. for 1 h. The mixture was diluted with DCM (50 mL) and water (50 mL), extracted with DCM (30 mL×3). The combined organic phases were washed with water, brine, dried over Na$_2$SO$_4$ and concentrated. The residue was purified by prep-TLC to afford compound 72 (53.3 mg, 23.8% yield). LCMS: 348.1 [M+H]+. $^1$H NMR (400 MHz, DMSO-d$_6$) δ 9.17 (brs, 1H), 8.35 (d, J=8.0 Hz, 1H), 7.93 (s, 1H), 7.59 (d, J=8.4 Hz, 1H), 7.52 (s, 1H), 6.99 (s, 1H), 4.31 (s, 2H), 3.93 (s, 3H), 3.21 (t, J=2.4 Hz, 1H).

Example 75: Synthesis of 7-chloro-5-methoxy-1-(2-methylpyridin-3-yl)-4-((1-vinylcyclopropyl)amino)quinazolin-2(1H)-one

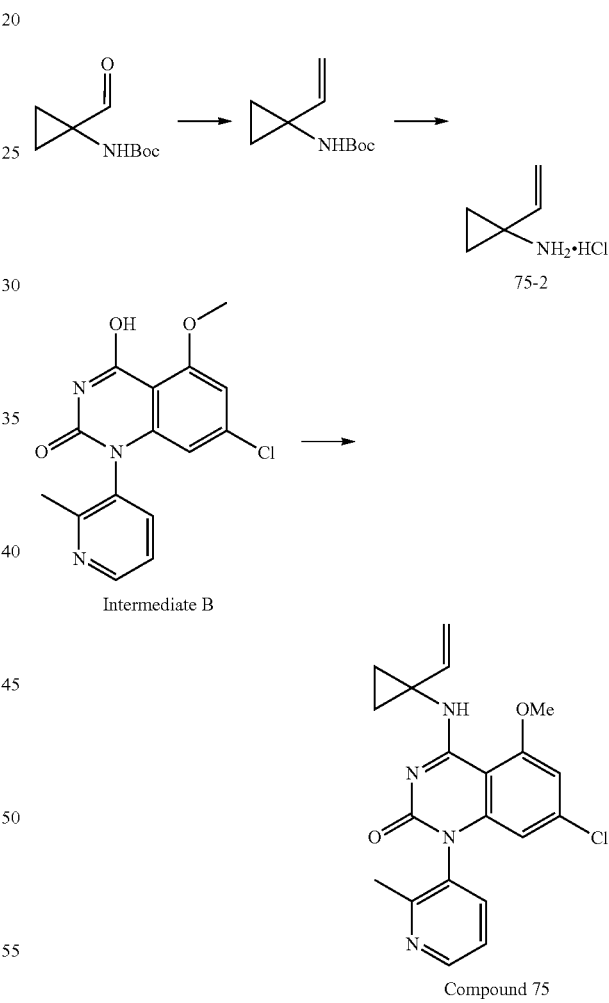

Step 1: To a solution of methyl triphenylphosphonium bromide (11.6 g, 32.39 mmol) in THF (50 mL) was added KHMDS (32.4 mL, 32.39 mmol) at 0° C. The mixture was stirred at room temperature for 30 min, and tert-butyl (1-formylcyclopropyl)carbamate (2.0 g, 10.79 mmol) was added at 0° C. After stirring at room temperature for 1 h, the reaction mixture was diluted with EA (100 mL) and H$_2$O (100 mL). The organic layer was washed with H$_2$O (100 mL×2) and concentrated. The residue was purified by silica gel column to afford compound 75-1 (1.6 g, 80.8% yield). $^1$H NMR (400 MHz, DMSO-d$_6$) δ 7.31 (s, 1H), 5.51-5.42 (m, 1H), 4.96-4.91 (m, 2H), 1.43 (s, 9H), 0.95-0.82 (m, 4H).

Step 2: To a solution of compound 75-1 (1.6 g, 8.73 mmol) in EA (10 mL) were added HCl/EA (10 mL, 3M in EA). The mixture was stirred at room temperature for 18 hrs. The reaction mixture was concentrated in vacuo to afford compound 75-2 (900.0 mg, 96.4% yield). $^1$H NMR (400 MHz, DMSO-d$_6$) δ 8.86 (brs, 3H), 5.69-5.59 (m, 1H), 5.24-5.11 (m, 2H), 1.27-1.23 (m, 2H), 0.96-0.91 (m, 2H).

Steps 3: A mixture of compound Intermediate B (60.0 mg, 0.19 mmol), POCl$_3$ (144.8 mg, 0.94 mmol) and DIEA (244.1 mg, 1.89 mmol) in toluene (2 mL) was stirred at 100° C. for 2 hrs. After cooling to room temperature, a mixture of compound 75-2 (205.9 mg, 1.89 mmol) and DIEA (244.1 mg, 1.89 mmol) in NMP (2 mL) was added. The mixture was stirred at room temperature for 16 hrs. After concentration, the residue was diluted with DCM (20 mL) and H$_2$O (20 mL). The organic layer was washed with H$_2$O (20 mL×3), brine (20 mL), dried over Na$_2$SO$_4$ and concentrated. The residue was purified by silica gel column to afford compound 75 (27.0 mg, 37.4% yield). LCMS: 383.1 [M+H]$^+$. $^1$H NMR (400 MHz, DMSO-d$_6$) δ 8.58 (t, J=5.2 Hz, 2H), 7.71 (dd, J=8.0 Hz, 1.6 Hz, 1H), 7.45 (dd, J=8.0 Hz, 4.8 Hz, 1H), 6.99 (d, J=2.0 Hz, 1H), 5.83 (d, J=1.6 Hz, 1H), 5.71-5.64 (m, 1H), 4.97-4.91 (m, 2H), 4.07 (s, 3H), 2.15 (s, 3H), 1.23-1.07 (m, 4H).

Example 79: Synthesis of (E)-4-((4-aminobut-2-en-1-yl)amino)-1-(pyridin-3-yl)-7-(trifluoromethyl)quinazolin-2(1H)-one

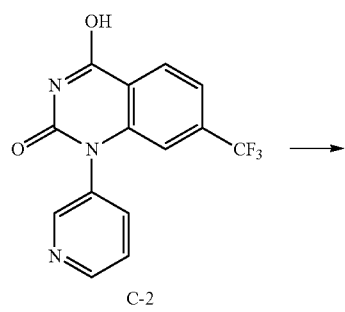

C-2

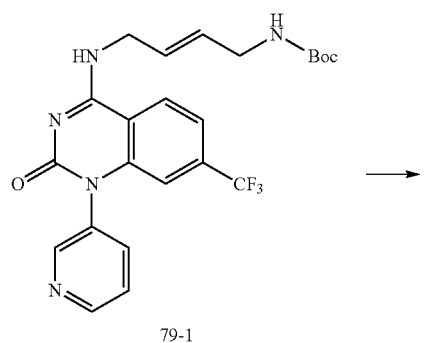

79-1

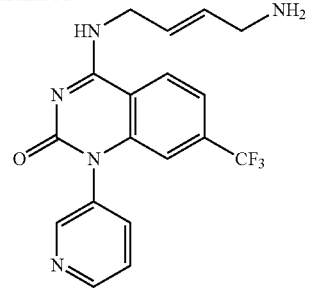

Compound 79

Step 1: To a solution of compound C-2 (200.0 mg, 0.65 mmol) in toluene (3 mL) was added DIEA (841.0 mg, 6.51 mmol) and POCl$_3$ (500.0 mg, 3.25 mmol) at 0° C. The mixture was heated to 100° C. for 2 hrs. After cooling to room temperature, a solution of tert-butyl (E)-(4-aminobut-2-en-1-yl)carbamate (727.5 mg, 3.91 mmol) and DIEA (841.0 mg, 6.51 mmol) in NMP (3 mL) was added. The mixture was stirred at room temperature for 16 hrs. The mixture was diluted with DCM (50 mL) and water (30 mL), extracted with DCM (30 mL×2). The combined organic phases were washed with water (50 mL×3), brine, dried over Na$_2$SO$_4$ and concentrated. The residue was purified by column chromatography to provide compound 79-1 (140.0 mg, 45.2% yield). LCMS: 476.2 [M+H]$^+$.

Step 2: To a solution of compound 79-1 (140.0 mg, 0.29 mmol) in DCM (3 mL) and MeOH (3 mL) was added HCl/EtOAc (0.5 mL, 3.0 M in EtOAc) at room temperature. The reaction mixture was stirred at room temperature for 2 hrs. The mixture was concentrated and the residue was purified by prep-HPLC to provide compound 79 (74.6 mg, 67.5% yield). LCMS: 376.1 [M+H]$^+$. $^1$H NMR (400 MHz, DMSO-d$_6$) δ 9.03 (brs, 1H), 8.72 (d, J=3.6 Hz, 1H), 8.59 (d, J=2.4 Hz, 1H), 8.44 (d, J=8.0 Hz, 1H), 7.89 (d, J=7.6 Hz, 1H), 7.70-7.55 (m, 2H), 6.56 (s, 1H), 5.83-5.65 (m, 2H), 4.16 (s, 2H), 3.19 (t, J=4.0 Hz, 2H).

Example A: MAT2A Biochemical Assay

Compounds described herein were tested as follows:
Enzyme Reaction (1). Prepared 1× Assay buffer.

(2). Preparation of compound concentration gradient: the compounds test condition were 1 uM start, 3-fold dilution, 10 doses, singlet or duplicate. 100× concentration compounds were prepared in 384-well plate. Then used Echo 550 to transfer 250 nl to a 384-reaction plate for later use. Added 250 nl of 100% DMSO to the negative and positive control wells.

(3). Prepared 1.67× final concentration enzyme solution with 1× Assay buffer.

(4). Added 15 μl of 1.67× Enzyme solution to the compound wells and positive control wells; added 15 μl of 1× Assay buffer to the negative control wells.

(5). Centrifuged at 1000 rpm for 30 seconds and incubate for 15 minutes.

(6). Prepared 2.5× final concentration Substrate mix solution with 1× Assay buffer.

(7). Added 10 μl of 2.5× final concentration Substrate mix solution to start the reaction.

(8). Centrifuged at 1000 rpm for 30 seconds and incubate for 150 minutes.

(9). Added 50 µl Biomol Green to stop the reaction, centrifuge at 1000 rpm for 30 seconds and incubate for 15 minutes, read O.D.620, process data.

Data Analysis (1) Using GraphPad Prism 5.

(2) % Inh=(Max signal−Compound signal)/(Max signal−Min signal)*100.

(3) Max signal was obtained from the positive control wells.

(4) Min signal was obtained from the negative control wells.

The data from Example A is shown in Table 6.

TABLE 6

| Example # | MAT2A enzymatic $IC_{50}$ |
|---|---|
| 1 | A |
| 2 | A |
| 3 | B |
| 4 | A |
| 5 | A |
| 6 | A |
| 7 | A |
| 8 | A |
| 9 | C |
| 10 | A |
| 11 | C |
| 12 | C |
| 13 | E |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | B |
| 33 | A |
| 34 | A |
| 35 | A |
| 36 | A |
| 37 | A |
| 38 | A |
| 39 | B |
| 40 | A |
| 41 | B |
| 42 | A |
| 43 | B |
| 44 | C |
| 45 | A |
| 46 | A |
| 47 | A |
| 48 | A |
| 49 | A |
| 50 | A |
| 51 | A |
| 52 | A |
| 53 | A |
| 54 | A |
| 55 | D |
| 56 | E |
| 57 | A |
| 58 | C |
| 59 | C |
| 60 | C |
| 61 | A |
| 62 | B |

TABLE 6-continued

| Example # | MAT2A enzymatic $IC_{50}$ |
|---|---|
| 63 | A |
| 64 | A |
| 65 | A |
| 66 | A |
| 67 | A |
| 68 | A |
| 69 | A |
| 70 | A |
| 71 | C |
| 72 | C |
| 73 | A |
| 74 | A |
| 75 | A |
| 76 | A |
| 77 | A |
| 78 | B |
| 79 | C |

$IC_{50}$ (nM): $0 < A \leq 50$; $50 < B \leq 100$; $100 < C \leq 500$; $500 < D \leq 1{,}000$; $1{,}000 < E$

What is claimed is:

1. A compound of Formula (I) or Formula (II), or a pharmaceutically acceptable salt thereof:

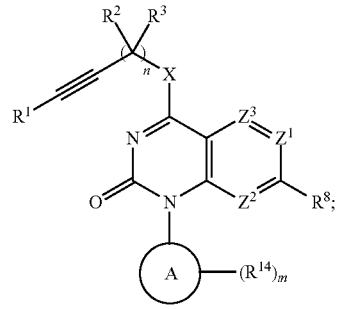

Formula (I)

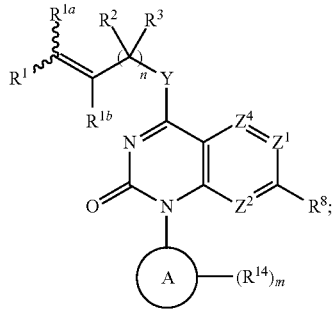

Formula (II)

wherein:

is selected from pyridyl, pyrazinyl, pyrimidyl, and pyridazinyl;

$Z^1$ is $CR^7$;

$Z^2$ is $CR^9$;

$Z^3$ is $CR^6$;

$Z^4$ is $CR^6a$;

X is —N(R$^4$)—;

Y is —N(R$^{4a}$);

R[1] is hydrogen;

R[1a] and R[1b] are hydrogen;

R[2] and R[3] are each independently selected from hydrogen and $C_{1-6}$alkyl;

or R[2] and R[3], together with the carbon to which they are attached, form a $C_{3-6}$cycloalkyl;

R[4] is hydrogen;

R[4a] is hydrogen;

R[6] is selected from hydrogen, halogen, and —OR[10];

R[6a] is selected from hydrogen and —OR[10];

R[7] is hydrogen;

R[8] is selected from hydrogen, halogen, and $C_{1-6}$haloalkyl;

R[9] is hydrogen;

each R[10] is independently selected from hydrogen, $C_{1-6}$alkyl, and $C_{1-6}$haloalkyl;

each R[14] is independently $C_{1-6}$alkyl;

m is 0, 1, or 2; and n is 1.

2. The compound of claim 1, or a pharmaceutically acceptable salt thereof, wherein R[10] is $C_{1-6}$alkyl.

3. The compound of claim 1, or a pharmaceutically acceptable salt thereof, wherein R[2] is hydrogen and R[3] is hydrogen.

4. The compound of claim 1, or a pharmaceutically acceptable salt thereof, wherein R[2] and R[3], together with the carbon to which they are attached, form a $C_{3-6}$cycloalkyl.

5. The compound of claim 1, or a pharmaceutically acceptable salt thereof, having the structure of Formula (Ia):

Formula (Ia)

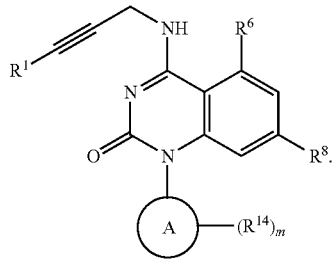

6. The compound of claim 1, or a pharmaceutically acceptable salt thereof, wherein

A is pyridyl.

7. The compound of claim 1, or a pharmaceutically acceptable salt thereof, wherein m is 1.

8. The compound of claim 1, or a pharmaceutically acceptable salt thereof, wherein R[8] is halogen or $C_{1-6}$haloalkyl.

9. The compound of claim 1 selected from the group consisting of:

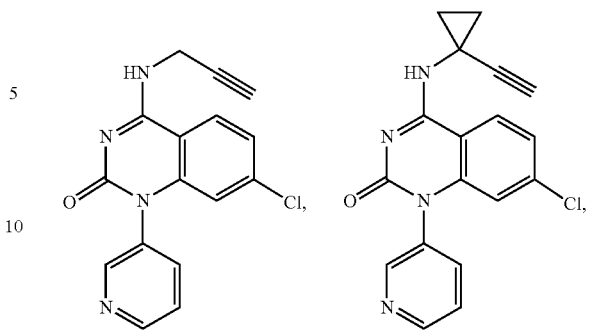

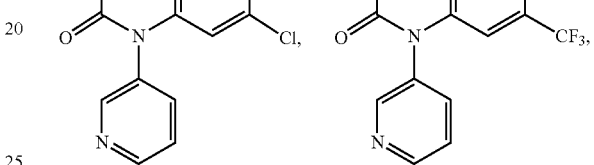

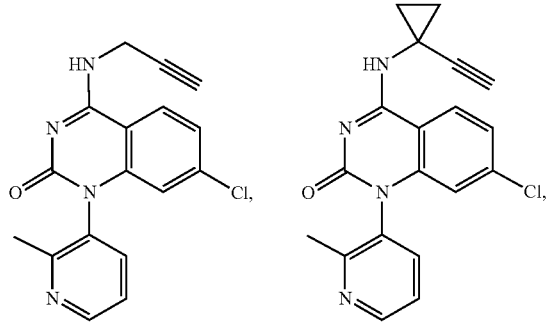

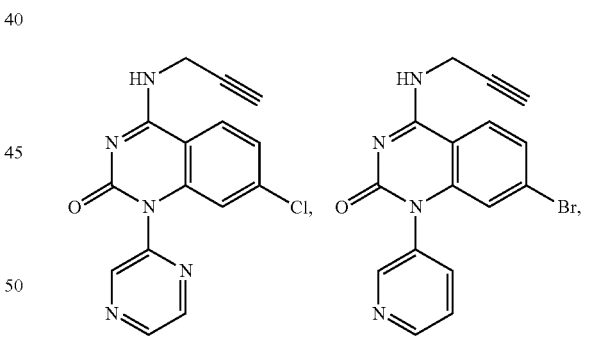

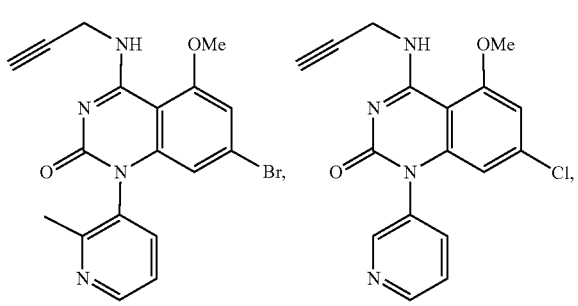

171
-continued
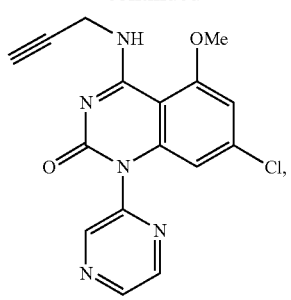
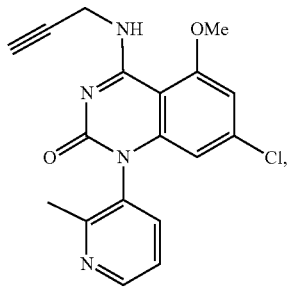
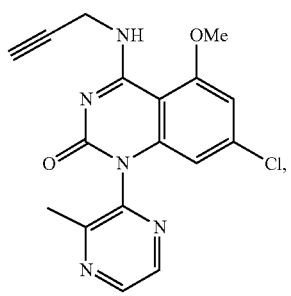
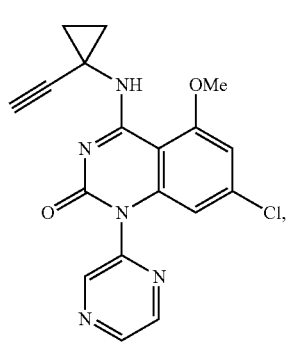
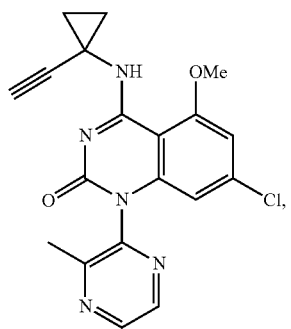
172
-continued
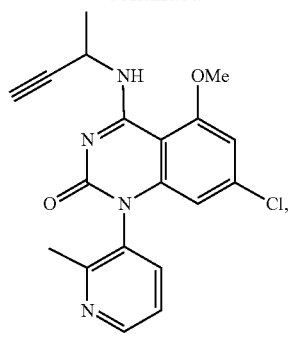
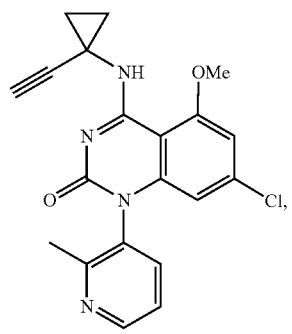
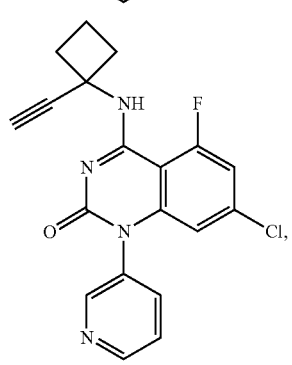
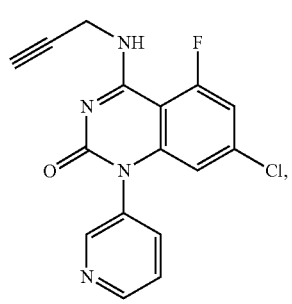
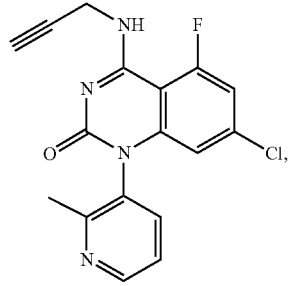

173
-continued
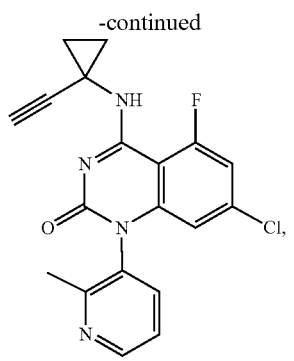
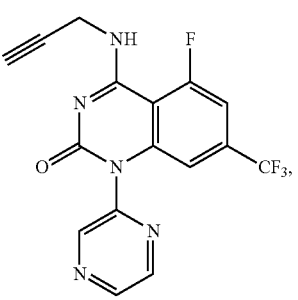
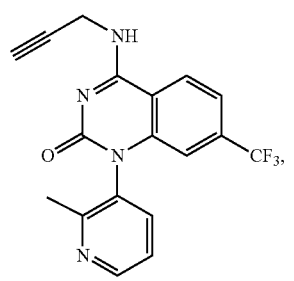
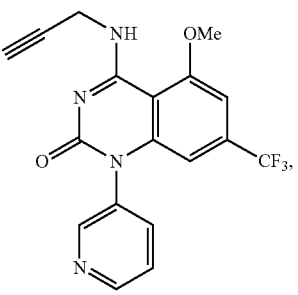
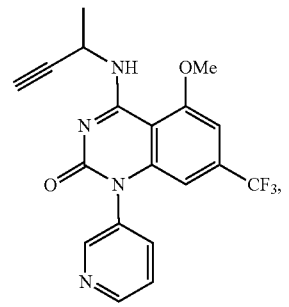
174
-continued
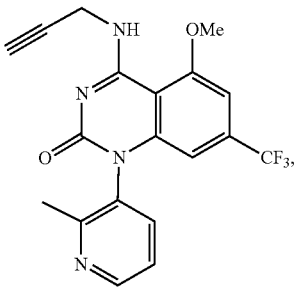
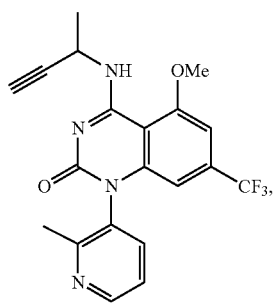
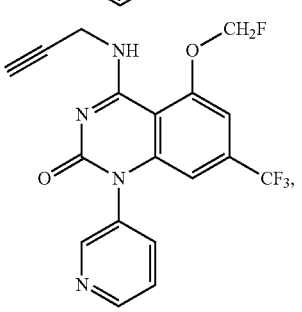
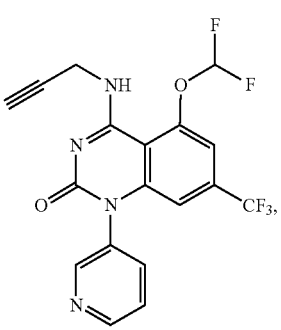
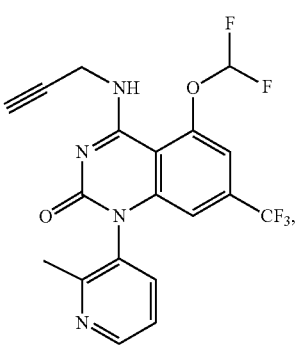

-continued
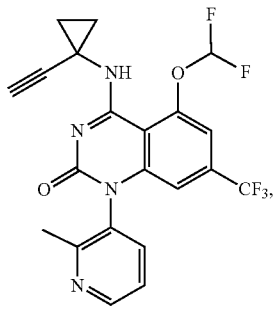
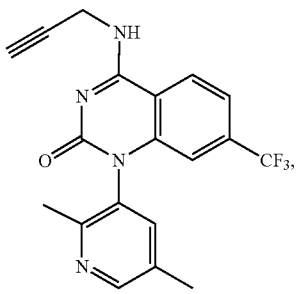
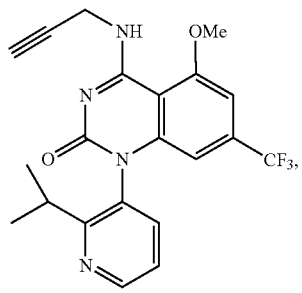
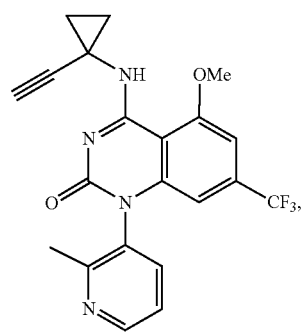
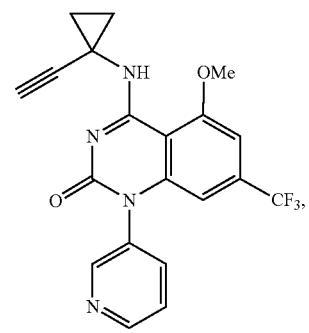
-continued
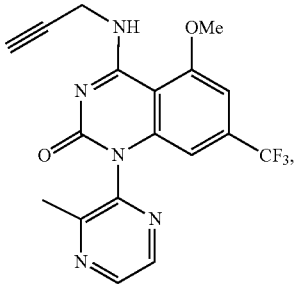
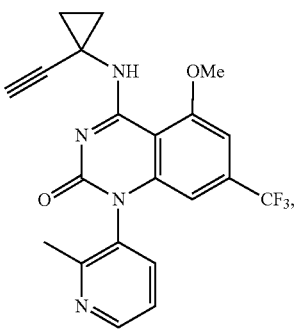
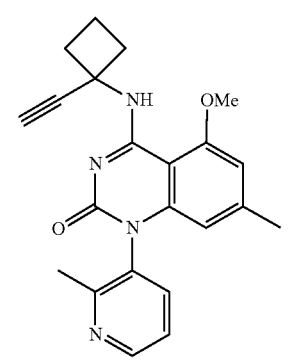
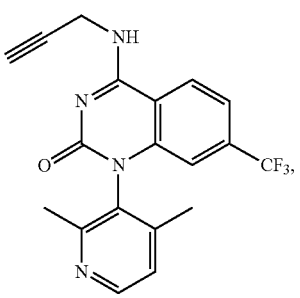
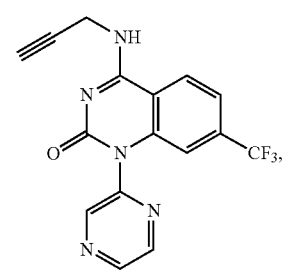

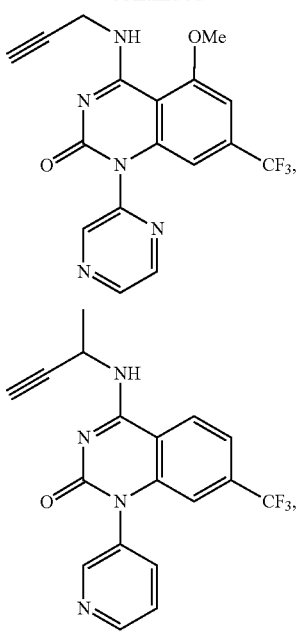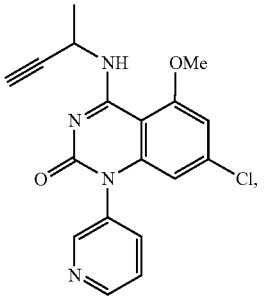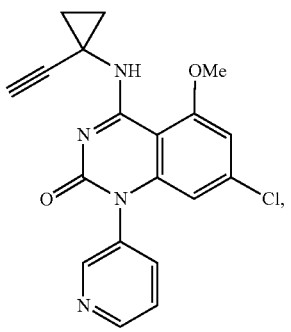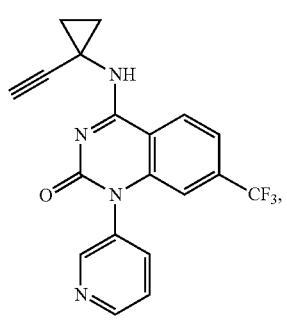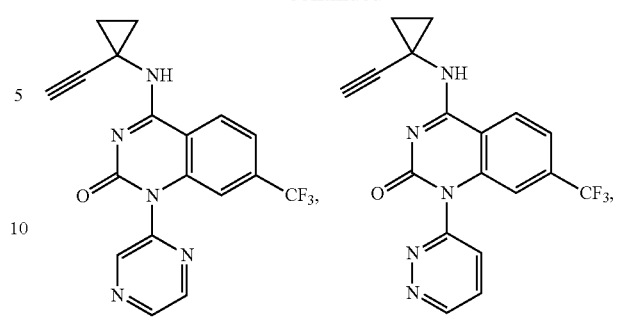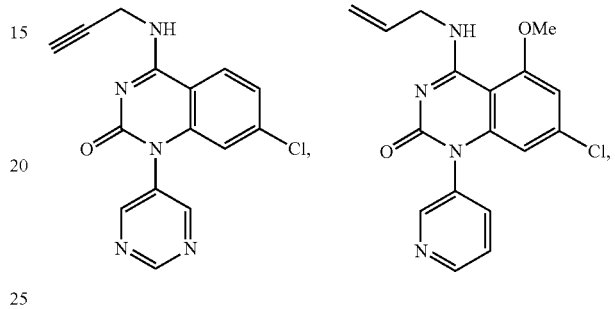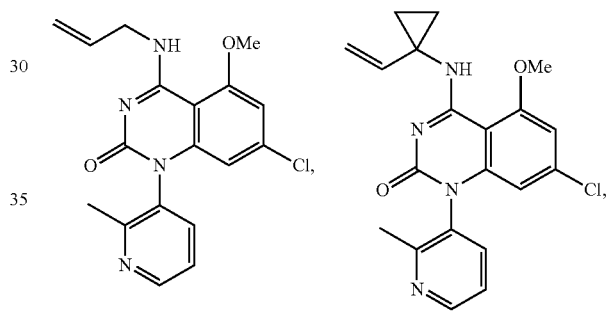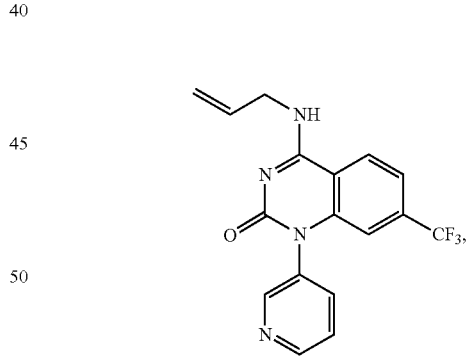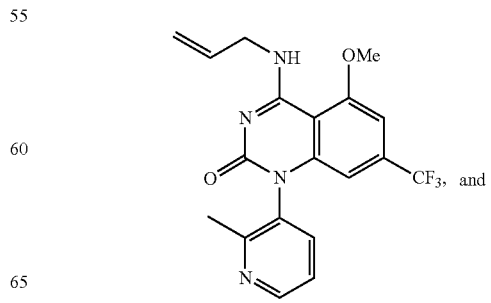

-continued

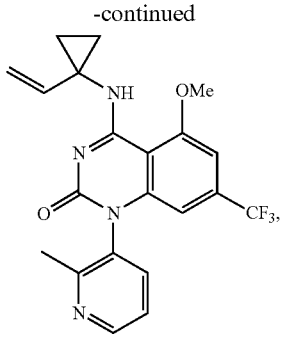

or a pharmaceutically acceptable salt thereof.

10. The compound of claim 1 that is

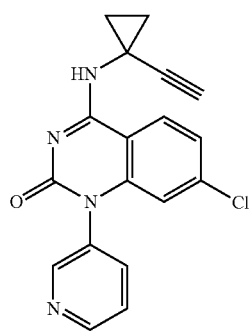 [SMILES: C#CC1(Nc2nc(=O)n(-c3cccnc3)c3cc(Cl)ccc23)CC1]

or a pharmaceutically acceptable salt thereof.

11. The compound of claim 1 that is

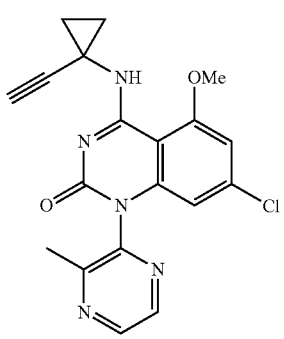

or a pharmaceutically acceptable salt thereof.

12. The compound of claim 1 that is

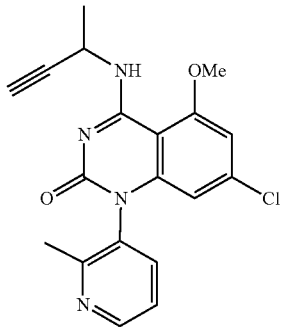 [SMILES: C#CC(C)Nc1nc(=O)n(-c2cccnc2C)c2cc(Cl)cc(OC)c12]

or a pharmaceutically acceptable salt thereof.

13. The compound of claim 1 that is

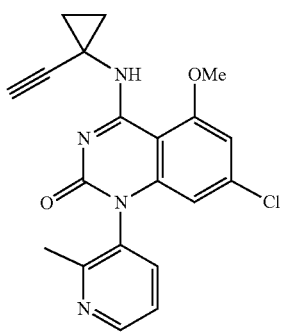 [SMILES: C#CC1(Nc2nc(=O)n(-c3cccnc3C)c3cc(Cl)cc(OC)c23)CC1]

or a pharmaceutically acceptable salt thereof.

14. The compound of claim 1 that is

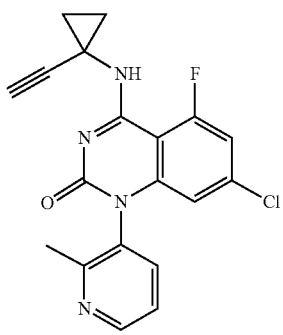 [SMILES: C#CC1(Nc2nc(=O)n(-c3cccnc3C)c3cc(Cl)cc(F)c23)CC1]

or a pharmaceutically acceptable salt thereof.

15. The compound of claim 1 that is

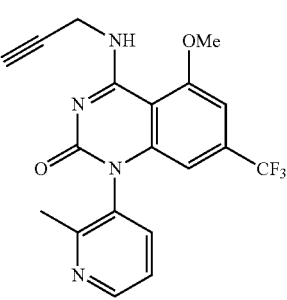

or a pharmaceutically acceptable salt thereof.

16. The compound of claim 1 that is

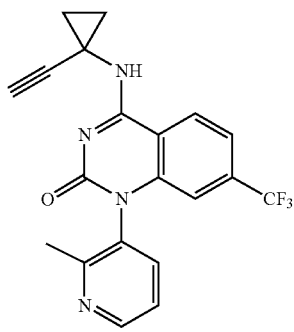 [SMILES: C#CC1(Nc2nc(=O)n(-c3cccnc3C)c3cc(C(F)(F)F)ccc23)CC1]

or a pharmaceutically acceptable salt thereof.

17. The compound of claim 1 that is

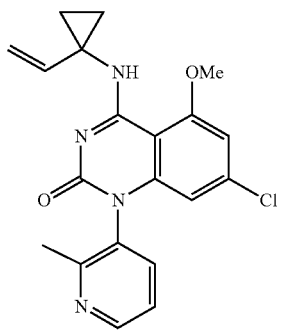 [SMILES: C=CC1(Nc2nc(=O)n(-c3cccnc3C)c3cc(Cl)cc(OC)c23)CC1]

or a pharmaceutically acceptable salt thereof.

18. The compound of claim 1 that is

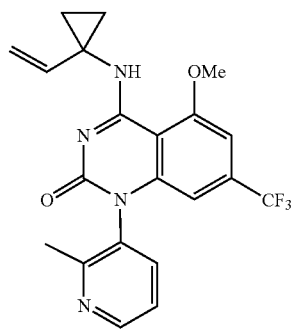 [SMILES: C=CC1(Nc2nc(=O)n(-c3cccnc3C)c3cc(C(F)(F)F)cc(OC)c23)CC1]

or a pharmaceutically acceptable salt thereof.

19. A pharmaceutical composition comprising a compound of claim 1, or a pharmaceutically acceptable salt thereof, and at least one pharmaceutically acceptable excipient.

20. A method of treating cancer in a mammal in need thereof, comprising administering to the mammal a compound of Formula (I) or Formula (II), or a pharmaceutically acceptable salt thereof:

Formula (I)

Formula (II)

wherein:

A is selected from pyridyl, pyrazinyl, pyrimidyl, and pyridazinyl;
$Z^1$ is $CR^7$;
$Z^2$ is $CR^9$;
$Z^3$ is $CR^6$;
$Z^4$ is $CR^6a$;
X is —N($R^4$)—;
Y is —N($R^{4a}$)—;
$R^1$ is hydrogen;
$R^{1a}$ and $R^{1b}$ are hydrogen;
$R^2$ and $R^3$ are each independently selected from hydrogen and $C_{1-6}$alkyl;
or $R^2$ and $R^3$, together with the carbon to which they are attached, form a $C_{3-6}$cycloalkyl;
$R^4$ is hydrogen;
$R^{4a}$ is hydrogen;
$R^6$ is selected from hydrogen, halogen, and —$OR^{10}$;
$R^{6a}$ is selected from hydrogen and —$OR^{10}$;
$R^7$ is hydrogen;
$R^8$ is selected from hydrogen, halogen, and $C_{1-6}$haloalkyl;
$R^9$ is hydrogen;
each $R^{10}$ is independently selected from hydrogen, $C_{1-6}$alkyl, and $C_{1-6}$haloalkyl;
each $R^{14}$ is independently $C_{1-6}$alkyl;
m is 0, 1, or 2; and
n is 1.

* * * * *

UNITED STATES PATENT AND TRADEMARK OFFICE
CERTIFICATE OF CORRECTION

PATENT NO. : 11,999,713 B2
APPLICATION NO. : 18/509658
DATED : June 4, 2024
INVENTOR(S) : Chiachun Chen et al.

Page 1 of 2

It is certified that error appears in the above-identified patent and that said Letters Patent is hereby corrected as shown below:

In the Claims

Column 168, Line 67:
In Claim 1, replace "Y is —N($R^{4a}$)" with --Y is —N($R^{4a}$)— --

Column 172, Lines 27-40:

In Claim 9, replace " 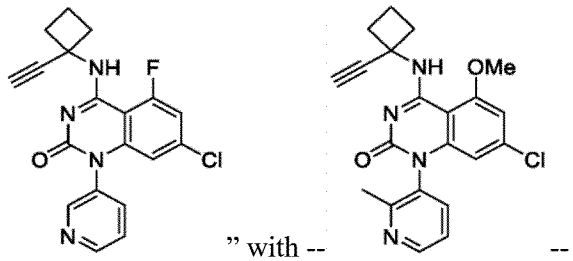 " with -- --

Column 175, Lines 25-35:

In Claim 9, replace " 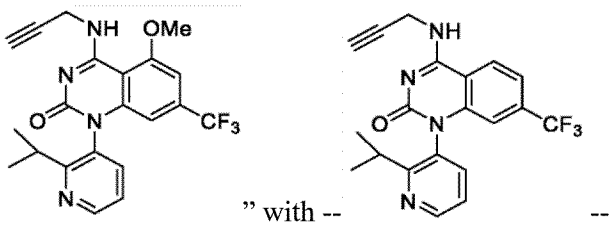 " with -- --

Signed and Sealed this
Twenty-sixth Day of November, 2024

*Katherine Kelly Vidal*

Katherine Kelly Vidal
*Director of the United States Patent and Trademark Office*

CERTIFICATE OF CORRECTION (continued)
U.S. Pat. No. 11,999,713 B2

Column 175, Lines 37-50:

In Claim 9, replace " 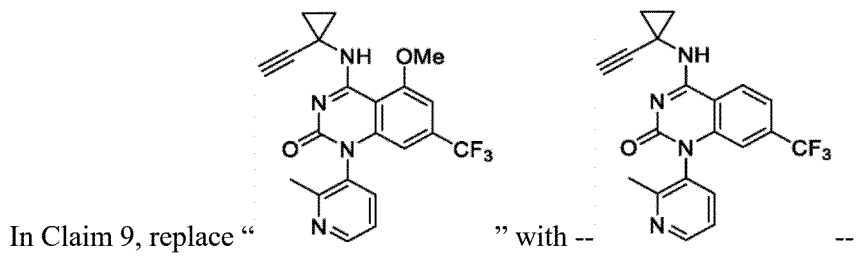 " with -- --

Column 176, Lines 26-38:

In Claim 9, replace " 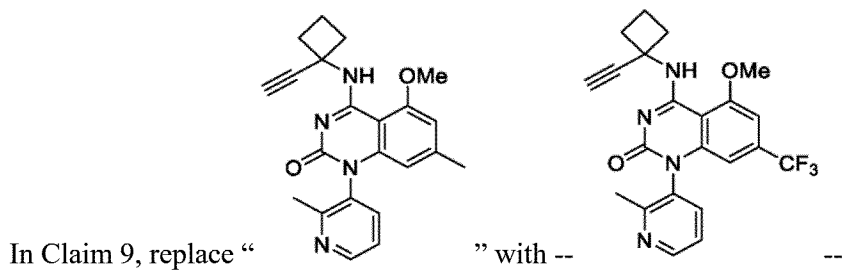 " with -- --

Column 178, Lines 1-14 (second compound):

In Claim 9, delete " 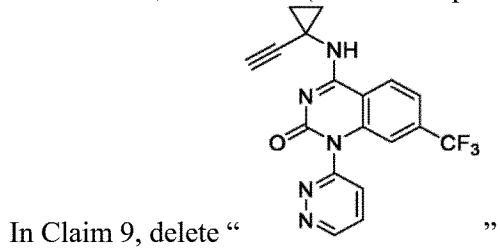 "